US007879840B2

(12) United States Patent
Marks et al.

(10) Patent No.: US 7,879,840 B2
(45) Date of Patent: *Feb. 1, 2011

(54) AGENTS FOR PREVENTING AND TREATING DISORDERS INVOLVING MODULATION OF THE RYR RECEPTORS

(75) Inventors: Andrew Robert Marks, Larchmont, NY (US); Donald W. Landry, New York, NY (US); Shixian Deng, White Plains, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 681 days.

This patent is subject to a terminal disclaimer.

(21) Appl. No.: 11/506,285

(22) Filed: Aug. 17, 2006

(65) Prior Publication Data

US 2007/0173482 A1 Jul. 26, 2007

Related U.S. Application Data

(63) Continuation-in-part of application No. 11/212,309, filed on Aug. 25, 2005.

(51) Int. Cl.
*A61P 9/00* (2006.01)
*A61K 31/553* (2006.01)
*A61K 31/554* (2006.01)
*C07D 281/02* (2006.01)

(52) U.S. Cl. ............... 514/211.05; 514/211.09; 540/490; 540/552

(58) Field of Classification Search ............ 514/211.05, 514/211.09; 540/490, 552
See application file for complete search history.

(56) References Cited

U.S. PATENT DOCUMENTS

| 3,367,930 A | 2/1968 | Schmutz et al. |
| 3,519,647 A | 7/1970 | Krapcho |
| 4,330,446 A | 5/1982 | Miyosawa |
| 4,407,899 A | 10/1983 | Hara et al. |
| 4,567,254 A | 1/1986 | Kataoka et al. |
| 4,658,055 A | 4/1987 | Onuki et al. |
| 4,659,394 A | 4/1987 | Hara et al. |
| 4,723,012 A | 2/1988 | Matsumoto et al. |
| 4,775,600 A | 10/1988 | Adaniya et al. ............ 428/623 |
| 4,841,055 A | 6/1989 | Matsumoto et al. |
| 4,845,065 A | 7/1989 | Sugimori et al. |
| 4,849,535 A | 7/1989 | Naora et al. |
| 4,888,418 A | 12/1989 | Kawai et al. |
| 4,889,775 A | 12/1989 | Adaniya et al. ............ 428/62 |
| 4,963,671 A | 10/1990 | Krapcho |
| 4,990,707 A | 2/1991 | Mais et al. |
| 5,064,810 A | 11/1991 | Askanazi et al. |
| 5,075,293 A | 12/1991 | Reifschneider et al. |
| 5,142,647 A | 8/1992 | Nakagawa et al. |
| 5,153,184 A | 10/1992 | Reifschneider et al. |
| 5,166,347 A | 11/1992 | Izawa et al. |
| 5,179,125 A | 1/1993 | Mimura et al. |
| 5,180,720 A | 1/1993 | Husa et al. |
| 5,182,272 A | 1/1993 | Hallinan et al. |
| 5,204,462 A | 4/1993 | Kobayashi et al. |
| 5,210,266 A | 5/1993 | Mimura et al. |
| 5,213,846 A | 5/1993 | Tsuneta et al. ............ 427/386 |
| 5,214,056 A | 5/1993 | Haruta et al. |
| 5,221,681 A | 6/1993 | Kabbe et al. |
| 5,223,508 A | 6/1993 | Izawa et al. |
| 5,260,286 A | 11/1993 | Lawson et al. |
| 5,272,164 A | 12/1993 | Izawa et al. |
| 5,304,380 A | 4/1994 | Miyajima et al. |
| 5,304,558 A | 4/1994 | Kaneko et al. |
| 5,304,644 A | 4/1994 | Husa et al. |
| 5,324,722 A | 6/1994 | Hagen et al. |
| 5,332,734 A | 7/1994 | Kobayashi et al. |
| 5,354,747 A | 10/1994 | Hansen, Jr. et al. |
| 5,354,758 A | 10/1994 | Lawson et al. |
| 5,387,684 A | 2/1995 | Inoue et al. |
| 5,397,638 A | 3/1995 | Miki et al. |
| 5,413,929 A | 5/1995 | Ishizaki et al. |
| 5,416,066 A | 5/1995 | Kaneko et al. |
| 5,437,937 A | 8/1995 | Cayless |

(Continued)

FOREIGN PATENT DOCUMENTS

DE          3837575          5/1990

(Continued)

OTHER PUBLICATIONS

Bidasee et al., "Chronic Diabetes Increases Advanced Glycation End Products on Cardiac Ryanodine Receptors/Calcium-Release Channels," Diabetes, vol. 52, pp. 1825-1836, 2003.

(Continued)

*Primary Examiner*—Brenda L Coleman
(74) *Attorney, Agent, or Firm*—Winston & Strawn LLP

(57) ABSTRACT

The present invention provides compounds of Formula I

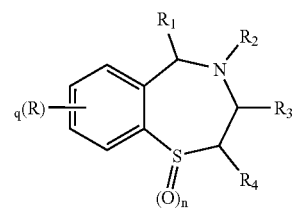

and salts, hydrates, solvates, complexes, and prodrugs thereof. The present invention further provides methods for synthesizing compounds of Formula I. The invention additionally provides pharmaceutical compositions comprising the compounds of Formula I and methods of using the pharmaceutical compositions of Formula I to treat and prevent disorders and diseases associated with the RyR receptors that regulate calcium channel functioning in cells.

38 Claims, 50 Drawing Sheets

U.S. PATENT DOCUMENTS

| | | |
|---|---|---|
| 5,449,675 A | 9/1995 | Chandrakumar et al. |
| 5,453,282 A | 9/1995 | Kanauchi et al. |
| 5,457,182 A | 10/1995 | Wiederrecht et al. |
| 5,461,047 A | 10/1995 | Hansen, Jr. et al. |
| 5,476,780 A | 12/1995 | Watanabe |
| 5,478,832 A | 12/1995 | Inoue et al. |
| 5,508,293 A | 4/1996 | Okawara et al. |
| 5,514,483 A | 5/1996 | Sujita et al. ............... 428/623 |
| 5,523,410 A | 6/1996 | Kagara et al. |
| 5,580,866 A | 12/1996 | Housley et al. |
| 5,593,988 A | 1/1997 | Tahara et al. |
| 5,624,961 A | 4/1997 | Ban et al. |
| 5,654,001 A | 8/1997 | Kanauchi et al. |
| 5,665,881 A | 9/1997 | Inoue et al. |
| 5,719,155 A | 2/1998 | Cho et al. |
| 5,723,210 A | 3/1998 | Sujita et al. ............... 428/219 |
| 5,723,458 A | 3/1998 | Brieaddy et al. |
| 5,750,696 A | 5/1998 | Shibata et al. |
| 5,753,649 A | 5/1998 | Tahara et al. |
| 5,767,247 A | 6/1998 | Kaneko et al. |
| 5,780,441 A | 7/1998 | Higa et al. |
| 5,792,655 A | 8/1998 | Watanabe |
| 5,807,850 A | 9/1998 | Nakamura et al. |
| 5,817,652 A | 10/1998 | Brieaddy et al. |
| 5,824,862 A | 10/1998 | Hiyoshi et al. |
| 5,859,240 A | 1/1999 | Brieaddy |
| 5,866,341 A | 2/1999 | Spinella et al. |
| 5,906,819 A | 5/1999 | Kaibuchi et al. |
| 5,910,494 A | 6/1999 | Brieaddy |
| 5,969,019 A | 10/1999 | Kanai et al. |
| 6,013,499 A | 1/2000 | Narumiya et al. |
| 6,090,873 A | 7/2000 | Okibe et al. |
| 6,096,139 A | 8/2000 | Shimakura et al. |
| 6,111,072 A | 8/2000 | Narumiya et al. |
| 6,130,060 A | 10/2000 | Nakamura et al. |
| 6,143,784 A | 11/2000 | Greenhaff et al. |
| 6,180,177 B1 | 1/2001 | Nagashima et al. |
| 6,184,352 B1 | 2/2001 | Nakamura et al. |
| 6,235,730 B1 | 5/2001 | Sato et al. |
| 6,241,830 B1 | 6/2001 | Shimakura et al. |
| 6,255,472 B1 | 7/2001 | Tokino et al. |
| 6,271,353 B1 | 8/2001 | Nakamura et al. |
| 6,309,477 B1 | 10/2001 | Shimakura et al. |
| 6,313,113 B1 | 11/2001 | Lohray et al. |
| 6,316,485 B1 | 11/2001 | Nakamura et al. |
| 6,338,955 B2 | 1/2002 | Oguri et al. |
| 6,348,334 B1 | 2/2002 | Nagata et al. |
| 6,362,231 B1 | 3/2002 | Sakai et al. |
| 6,391,595 B1 | 5/2002 | Kato et al. |
| 6,403,830 B2 | 6/2002 | Webber et al. |
| 6,410,561 B1 | 6/2002 | Shinkai et al. |
| 6,426,365 B1 | 7/2002 | Shinkai et al. |
| 6,447,589 B2 | 9/2002 | Sasaki et al. |
| 6,465,518 B2 | 10/2002 | Hansen, Jr. et al. |
| 6,465,686 B2 | 10/2002 | Grapperhaus et al. |
| 6,475,300 B2 | 11/2002 | Shimakura et al. |
| 6,475,621 B1 | 11/2002 | Kohli et al. |
| 6,489,125 B1 | 12/2002 | Marks et al. |
| 6,495,544 B2 | 12/2002 | Moormann et al. |
| 6,500,816 B1 | 12/2002 | Ekimoto et al. |
| 6,506,745 B1 | 1/2003 | Aisaka et al. |
| 6,538,092 B1 | 3/2003 | Terry et al. |
| 6,545,170 B2 | 4/2003 | Pitzele et al. |
| 6,562,618 B1 | 5/2003 | Tamatani et al. |
| 6,562,828 B1 | 5/2003 | Katoh et al. |
| 6,572,983 B2 | 6/2003 | Shimakura et al. |
| 6,583,157 B2 | 6/2003 | McGee et al. |
| 6,586,474 B2 | 7/2003 | Webber et al. |
| 6,632,976 B1 | 10/2003 | Tomizuka et al. |
| 6,649,366 B2 | 11/2003 | Tavares et al. |
| 6,660,837 B1 | 12/2003 | Kaibuchi et al. |
| 6,673,904 B2 | 1/2004 | Nishikawa et al. |
| 6,683,083 B1 | 1/2004 | Kaneko et al. |
| 6,719,836 B2 | 4/2004 | Nederlof et al. |
| 6,727,309 B1 | 4/2004 | Paiva et al. |
| 6,750,255 B2 | 6/2004 | Sakai et al. |
| 6,753,346 B2 | 6/2004 | Shinkai et al. |
| 6,756,406 B2 | 6/2004 | Durley et al. |
| 6,780,608 B1 | 8/2004 | Hakamata et al. |
| 6,787,668 B2 | 9/2004 | Pitzele et al. |
| 6,803,039 B2 | 10/2004 | Tsuji et al. |
| 6,808,873 B2 | 10/2004 | Murphy et al. |
| 6,812,252 B2 | 11/2004 | Ikawa et al. |
| 6,821,987 B2 | 11/2004 | Kubo et al. |
| 6,824,973 B2 | 11/2004 | Tang et al. |
| 6,828,456 B2 | 12/2004 | Hansen, Jr. et al. |
| 6,830,896 B2 | 12/2004 | Kaneko et al. |
| 6,852,753 B2 | 2/2005 | Koeller et al. |
| 6,869,975 B2 | 3/2005 | Abe et al. |
| 6,890,531 B1 | 5/2005 | Horie et al. |
| 6,897,295 B1 | 5/2005 | Nagata et al. |
| 6,906,072 B1 | 6/2005 | Yamamoto et al. |
| 6,914,158 B2 | 7/2005 | Webber et al. |
| 6,939,895 B2 | 9/2005 | Sakai et al. |
| 6,951,889 B2 | 10/2005 | Hansen, Jr. et al. |
| 6,962,926 B2 | 11/2005 | Laborde et al. |
| 6,964,975 B2 | 11/2005 | Ueno et al. |
| 6,977,252 B1 | 12/2005 | Kaneko et al. |
| 6,989,275 B2 | 1/2006 | Waggoner |
| 6,998,469 B2 | 2/2006 | Tandon et al. |
| 7,005,450 B2 | 2/2006 | Durley et al. |
| 7,029,671 B1 | 4/2006 | Koezuka et al. |
| 7,030,225 B1 | 4/2006 | Tamatani et al. |
| 7,041,870 B2 | 5/2006 | Tomizuka et al. |
| 7,045,615 B2 | 5/2006 | Tamatani et al. |
| 7,064,194 B2 | 6/2006 | Misawa et al. |
| 7,102,013 B2 | 9/2006 | Webber et al. |
| 7,112,655 B1 | 9/2006 | Tamatani et al. |
| 7,135,466 B2 | 11/2006 | Sakai et al. |
| 7,163,952 B2 | 1/2007 | Inaba et al. |
| 7,312,044 B2 | 12/2007 | Marks |
| 7,393,652 B2 | 7/2008 | Marks |
| 2001/0020066 A1 | 9/2001 | Sasaki et al. |
| 2001/0042491 A1 | 11/2001 | Shimakura et al. |
| 2001/0054455 A1 | 12/2001 | Shimakura et al. |
| 2001/0056157 A1 | 12/2001 | Terry et al. |
| 2002/0042405 A1 | 4/2002 | Schuh |
| 2002/0052358 A1 | 5/2002 | Chubinskaya et al. |
| 2002/0107406 A1 | 8/2002 | Sakai et al. |
| 2002/0115831 A1 | 8/2002 | Tamatani et al. |
| 2002/0132001 A1 | 9/2002 | Garthwaite et al. |
| 2002/0151685 A1 | 10/2002 | Tamatani et al. |
| 2002/0156242 A1 | 10/2002 | Tamatani et al. |
| 2002/0199213 A1 | 12/2002 | Tomizuka et al. |
| 2003/0022911 A1 | 1/2003 | Smith et al. |
| 2003/0032721 A1 | 2/2003 | Terry et al. |
| 2003/0044845 A1 | 3/2003 | Jenkins et al. |
| 2003/0054531 A1 | 3/2003 | Gretarsdottir et al. |
| 2003/0055027 A1 | 3/2003 | Schun |
| 2003/0055087 A1 | 3/2003 | Shinkai et al. |
| 2003/0064406 A1 | 4/2003 | Kaneko et al. |
| 2003/0083472 A1 | 5/2003 | Tamatani et al. |
| 2003/0087907 A1 | 5/2003 | Kubo et al. |
| 2003/0092708 A1 | 5/2003 | Shinkai et al. |
| 2003/0124637 A1 | 7/2003 | Kaneko et al. |
| 2003/0134331 A1 | 7/2003 | Marks et al. |
| 2003/0144526 A1 | 7/2003 | Sakai et al. |
| 2003/0176485 A1 | 9/2003 | Sakai et al. |
| 2003/0181764 A1 | 9/2003 | Ikawa et al. |
| 2003/0186885 A1 | 10/2003 | Tandon et al. |
| 2003/0191323 A1 | 10/2003 | Ikawa et al. |
| 2003/0195218 A1 | 10/2003 | Koeller et al. |
| 2003/0199482 A1 | 10/2003 | Seibert et al. |
| 2003/0199701 A1 | 10/2003 | Webber et al. |

| | | |
|---|---|---|
| 2003/0220310 A1 | 11/2003 | Schuh |
| 2003/0220312 A1 | 11/2003 | Schuh |
| 2003/0232855 A1 | 12/2003 | Iwamura et al. |
| 2004/0006099 A1 | 1/2004 | Katoh et al. |
| 2004/0009300 A1 | 1/2004 | Shimakura et al. |
| 2004/0017409 A1 | 1/2004 | Mizutani et al. |
| 2004/0022950 A1 | 2/2004 | Jung et al. |
| 2004/0048780 A1 | 3/2004 | Marks |
| 2004/0053919 A1 | 3/2004 | Chubinskaya et al. |
| 2004/0054044 A1 | 3/2004 | Bittner et al. |
| 2004/0062873 A1 | 4/2004 | Jung et al. |
| 2004/0068035 A1 | 4/2004 | Paiva et al. |
| 2004/0073012 A1 | 4/2004 | Tamatani et al. |
| 2004/0073957 A1 | 4/2004 | Tomizuka et al. |
| 2004/0082653 A1 | 4/2004 | Nonaka et al. |
| 2004/0120945 A1 | 6/2004 | Tamatani et al. |
| 2004/0132658 A1 | 7/2004 | Tamatani et al. |
| 2004/0132727 A1 | 7/2004 | Sakai et al. |
| 2004/0146506 A1 | 7/2004 | Tamatani et al. |
| 2004/0146991 A1 | 7/2004 | Tsuji et al. |
| 2004/0151669 A1 | 8/2004 | Tamatani et al. |
| 2004/0151718 A1 | 8/2004 | Tamatani et al. |
| 2004/0151720 A1 | 8/2004 | Tamatani et al. |
| 2004/0171613 A1 | 9/2004 | Iwamura et al. |
| 2004/0173802 A1 | 9/2004 | Yukimoto |
| 2004/0175814 A1 | 9/2004 | Kato et al. |
| 2004/0180052 A1 | 9/2004 | Tsuji et al. |
| 2004/0186178 A1 | 9/2004 | Webber et al. |
| 2004/0192584 A1 | 9/2004 | McMahon et al. |
| 2004/0198719 A1 | 10/2004 | Laborde et al. |
| 2004/0209871 A1 | 10/2004 | Fox et al. |
| 2004/0220193 A1 | 11/2004 | Yamamoto et al. |
| 2004/0224368 A1 | 11/2004 | Marks |
| 2004/0225018 A1 | 11/2004 | Sunami et al. |
| 2004/0229781 A1 | 11/2004 | Marks et al. |
| 2004/0229788 A1 | 11/2004 | Tamatani et al. |
| 2004/0229790 A1 | 11/2004 | Tezuka et al. |
| 2004/0229803 A1 | 11/2004 | Stephenson et al. |
| 2004/0229876 A1 | 11/2004 | Kubo et al. |
| 2004/0229957 A1 | 11/2004 | Shinkai et al. |
| 2004/0235162 A1 | 11/2004 | Sato |
| 2004/0242683 A1 | 12/2004 | Urata et al. |
| 2005/0009733 A1 | 1/2005 | Stephenson et al. |
| 2005/0020668 A1 | 1/2005 | Urata et al. |
| 2005/0032210 A1 | 2/2005 | Sato et al. |
| 2005/0035939 A1 | 2/2005 | Akiyama |
| 2005/0051181 A1 | 3/2005 | Okamoto |
| 2005/0059655 A1 | 3/2005 | Garvey et al. |
| 2005/0059810 A1 | 3/2005 | Maeda et al. |
| 2005/0070543 A1 | 3/2005 | Stephenson |
| 2005/0070545 A1 | 3/2005 | Fox et al. |
| 2005/0074762 A1 | 4/2005 | Nakamura et al. |
| 2005/0113451 A1 | 5/2005 | Hansen et al. |
| 2005/0159365 A1 | 7/2005 | Serizawa et al. |
| 2005/0159403 A1 | 7/2005 | Stephenson et al. |
| 2005/0165106 A1 | 7/2005 | Webber et al. |
| 2005/0171196 A1 | 8/2005 | Fujii et al. |
| 2005/0177884 A1 | 8/2005 | Tomizuka et al. |
| 2005/0186640 A1 | 8/2005 | Marks et al. |
| 2005/0187221 A1 | 8/2005 | Matsuda et al. |
| 2005/0187386 A1 | 8/2005 | Marks et al. |
| 2005/0192259 A1 | 9/2005 | Garthwaite et al. |
| 2005/0213426 A1 | 9/2005 | Midas et al. |
| 2005/0215540 A1 | 9/2005 | Marks et al. |
| 2005/0255546 A1 | 11/2005 | Nishikawa |
| 2005/0256199 A1 | 11/2005 | Durley et al. |
| 2005/0277649 A1 | 12/2005 | DeGraffenreid et al. |
| 2006/0011375 A1 | 1/2006 | Sugimoto et al. |
| 2006/0014768 A1 | 1/2006 | Kawasaki et al. |
| 2006/0026698 A1 | 2/2006 | Tomizuka et al. |
| 2006/0030565 A1 | 2/2006 | Shinkai et al. |
| 2006/0035882 A1 | 2/2006 | Koga et al. |
| 2006/0037093 A1 | 2/2006 | Tomizuka et al. |
| 2006/0041945 A1 | 2/2006 | Robl et al. |
| 2006/0059575 A1 | 3/2006 | Kusunoki et al. |
| 2006/0078992 A1 | 4/2006 | Misawa et al. |
| 2006/0084658 A1 | 4/2006 | Yamamoto et al. |
| 2006/0100195 A1 | 5/2006 | Maruyama et al. |
| 2006/0122181 A1 | 6/2006 | Ikemoto et al. |
| 2006/0123490 A1 | 6/2006 | Kakitani et al. |
| 2006/0135506 A1 | 6/2006 | Stephenson et al. |
| 2006/0167043 A1 | 7/2006 | Iwakubo et al. |
| 2006/0185025 A1 | 8/2006 | Oshimura et al. |
| 2006/0189603 A1 | 8/2006 | Garvey et al. |
| 2006/0194767 A1 | 8/2006 | Marks et al. |
| 2006/0205731 A1 | 9/2006 | Kodama et al. |
| 2006/0211717 A1 | 9/2006 | Sakai et al. |
| 2006/0217426 A1 | 9/2006 | Eto et al. |
| 2006/0223133 A1 | 10/2006 | Tamatani et al. |
| 2006/0233902 A1 | 10/2006 | Yajima et al. |
| 2006/0258701 A1 | 11/2006 | Mitsuya et al. |
| 2006/0270705 A1 | 11/2006 | Yonemori et al. |
| 2006/0293266 A1 | 12/2006 | Marks |
| 2007/0010571 A1 | 1/2007 | Garvey et al. |
| 2007/0010670 A1 | 1/2007 | Hirata et al. |
| 2007/0049572 A1 | 3/2007 | Marks et al. |
| 2007/0173482 A1 | 7/2007 | Marks et al. |

FOREIGN PATENT DOCUMENTS

| | | |
|---|---|---|
| EP | 0467325 | 1/1992 |
| EP | 0565721 | 10/1993 |
| EP | 0718261 | 6/1996 |
| EP | 1147772 | 10/2001 |
| EP | 1369129 | 12/2003 |
| EP | 1439221 A1 | 7/2004 |
| EP | 1447096 | 8/2004 |
| EP | 1743895 | 1/2007 |
| FR | 2709753 | 3/1995 |
| JP | 59116381 | 7/1984 |
| JP | 3093419 | 4/1991 |
| JP | 4230681 | 8/1992 |
| JP | 05271208 | 10/1993 |
| JP | 10045706 | 2/1998 |
| JP | 11199574 | 7/1999 |
| WO | WO-91/04328 | 4/1991 |
| WO | WO-92/12148 | 7/1992 |
| WO | WO-92/19617 | 11/1992 |
| WO | WO-9300095 | 1/1993 |
| WO | WO 93/04053 | 3/1993 |
| WO | WO 93/09104 | 5/1993 |
| WO | WO-93/13082 | 7/1993 |
| WO | WO-94/11360 | 5/1994 |
| WO | WO 94/18183 | 8/1994 |
| WO | WO-94/29286 | 12/1994 |
| WO | WO-96/08228 | 3/1996 |
| WO | WO 96/18629 | 6/1996 |
| WO | WO-97/03986 | 2/1997 |
| WO | WO-97/17344 | 5/1997 |
| WO | WO 98/01417 | 1/1998 |
| WO | WO-98/05657 | 2/1998 |
| WO | WO-98/45291 | 10/1998 |
| WO | WO-99/16758 | 4/1999 |
| WO | WO-99/26921 | 6/1999 |
| WO | WO-99/32115 | 7/1999 |
| WO | WO-01/00185 | 1/2001 |
| WO | WO-01/47510 | 7/2001 |
| WO | WO-02/08211 A1 | 1/2002 |
| WO | WO-02/14245 | 2/2002 |
| WO | WO-02/14246 | 2/2002 |
| WO | WO-02/051232 | 7/2002 |
| WO | WO-02/051838 | 7/2002 |
| WO | WO-02/053548 | 7/2002 |
| WO | WO-02056790 | 7/2002 |
| WO | WO-02/072145 | 9/2002 |
| WO | WO-03/034980 | 5/2003 |

| WO | WO-03/043655 | 5/2003 |
| WO | WO-2004/022057 | 3/2004 |
| WO | WO-2004/023030 | 3/2004 |
| WO | WO-2004/042389 A2 | 5/2004 |
| WO | WO-2004/080283 | 9/2004 |
| WO | WO 2004/104895 | 12/2004 |
| WO | WO-2005/002518 | 1/2005 |
| WO | WO 2005/026177 | 3/2005 |
| WO | WO-2005/037195 | 4/2005 |
| WO | WO-2005/094457 | 10/2005 |
| WO | WO-2005/105793 | 11/2005 |
| WO | WO-2006/071603 | 7/2006 |
| WO | WO-2006/101496 | 9/2006 |
| WO | WO-2006/101497 | 9/2006 |
| WO | WO-2007/024717 | 3/2007 |
| WO | WO-2007/127145 | 11/2007 |
| WO | WO-2007/143112 | 12/2007 |
| WO | WO-2008/021432 | 2/2008 |
| WO | WO-2008/021439 | 2/2008 |
| WO | WO-2008/060332 | 5/2008 |
| WO | WO-2008/140592 | 11/2008 |

OTHER PUBLICATIONS

Bidasee et al., "Diabetes Increases Formation of Advanced Glycation End Products on Sarco (endo) plasmic Reticulum Ca2+-ATPase," Diabetes, vol. 53, pp. 463-473 (2004).
Bruton et al., "Ryanodine receptors of pancreatic β-cells mediate a distinct context-dependent signal for insulin secretion," the FASEB Journal, vol. 17, pp. 301-303 (2003).
Buijs et al., "β-Adrenergic activation reveals impaired cardia calcium handling at early stage of diabetes," Life Sciences, vol. 76, pp. 1083-1098 (2005).
Dyachok et al., "Ca2+-induced Ca2+ release by activation of inositol 1,4,5-trisphosphate receptors in primary pancreatic β-cells," Cell Calcium, vol. 36, pp. 1-9 (2004).
Dyachok et al., "Ca2+-induced Ca2+ Release via Inositol 1,4,5-trisphosphate Receptors is Amplified by Protein Kinase and Triggers Exocytosis in Pancreatic β-Cells," The Journal of Biological Chemistry, vol. 279, No. 44, pp. 45455-45461 (2004).
Eisner et al., "The Ryanodine Receptor: Cause or Consequence of Diabetic Heart Failure?," J. Moll Cell Cardiol, vol. 32, pp. 1377-1378 (2000).
Gailly, "New Aspects of Calcium signaling in skeletal muscle cells: implications in Duchenne muscular Dystrophy," Biochimica et Biophysica Acta, vol. 1600, pp. 38-44 (2002).
Holz et al., " cAMP-dependent Mobilization of Intracellular Ca2+ Stores by Activation of Ryanodine Receptors in Pancreatic β-Cells," The Journal of Biological Chemistry, vol. 274, pp. 14147-14156 (1999).
International Preliminary Report on Patentability from International Application PCT/US2005/010055, mailed Oct. 4, 2007.
International Preliminary Report on Patentability from International Application PCT/US2005/010056, mailed Oct. 4, 2007.
International Preliminary Report on Patentability from International Application PCT/US2005/045914, mailed Jun. 28, 20073.
International Search Report and Written Opinion from International Patent Application No. PCT/US06/32405, Dec. 7, 2007.
International Search Report and Written Opinion from PCT/US2005/10056, Jun. 5, 2007.
Islam et al., "Effects of caffeine on cytoplasmic free Ca2+ concentration in pancreatic β-cells are mediated by interaction with ATP-sensitive K+ channels and L-type voltage-gated Ca2+ channels but not ryanodine receptor," Biochem. J., vol. 306, pp. 679-686 (1995).
Islam et al., "In situ activation of the type 2 ryanodine receptor in pancreatic beta cells requires cAMP-dependent phosphorylation," Proc. Natl. Acad. Sci. USA, vol. 95, pp. 6145-6150 (1998).
Islam S., "Perspectives in Diabetes. The Ryanodine Receptor Calcium Channel of β-Cells. Molecular Regulation and Physiological Significance," Diabetes, vol. 51, pp. 1299-1309 (2002).
Johnson et al., "Ryanodine receptors in human pancreatic β cells: localization and effects on insulin secretion1," the FASEB Journal, vol. 18, pp. 878-880 (2004).

Johnson et al., "RyR2 and Calpain-10 Delineate a Novel Apoptosis Pathway in Pancreatic Islets " The Journal of Biological Chemistry, vol. 279, pp. 24794-24802 (2004).
Kang et al., "A cAMP and Ca2+ coincidence detector in support of Ca2+-induced Ca2+ release in mouse pancreatic β cells," J. Physiol, vol. 566, pp. 173-188 (2005).
Kang et al., "cAMP-regulated guanine nucleotide exchange factor II (Epac2) mediates Ca2+- induced Ca2+ release in INS-1 pancreatic β-cells," Journal of Physiology, vol. 536.2, pp. 375-385 (2001).
LaFerla, "Calcium Dyshomeostasis and Intracellular signalling in Alzheimer's disease," Nature Reviews, vol. 3, pp. 862-872 (Nov. 2002).
Lehnart et al., "Phosphodiesterase 4D associates with the cardiac calcium release channel (Ryanodine Receptor) and protects from Hypertrophy and heart failure", Circulation, vol. 110, No. 17 Suppl. S, pp. 227-228 (Oct. 26, 2004).
Liu et al., "Crosstalk between the cAMP and Inositol Trisphosphate-Signalling Pathways in Pancreatis β-Cells," Archives of Biochemistry and Biophysics, vol. 334, pp. 295-302 (1996).
Mackenzie et all, "The Role of inositol 1,4,5-trisphosphate receptors in Ca2+ signalling and the generation of arrhythmias in rat atrila myocytes," J. Physiol., vol. 541, pp. 395-409 (2002).
Mitchell et al., "Ryanodine Receptor Type I and Nicotinic Acid Adenine Dinucleotide Phosphate Receptors Mediate Ca2+ Release from Insulin-containing Vesicles in Living Pancreatic β-Cells (MIN6)," The Journal of Biological Chemistry, vol. 278, pp. 11057-11064 (2003).
Pereira et al., "Mechanisms of (Ca2+)i Transient Decrease in Cardiomyopathy of db/db Type 2 Diabetic Mice," Diabetes, vol. 55, pp. 608-615 (2006).
Shao et al., "Dyssynchronous (non-uniform) Ca2+ release in myocytes from streptozotocin-induced diabetic rats," Journal of Molecular and Cellular Cardiology, vol. 42, pp. 234-246 (2007).
Takasawa et al., "Cyclic ADP-ribose and Inositol 1,4,5-Trisphosphate as Alternate Second Messengers for Intracellular Ca2+ Mobilization in Normal and Diabetic β-Cells," The Journal of Biological Chemistry, vol. 273, pp. 2497-2500 (1998).
Taur et al., "The Cardiac Ryanodine Receptor (RyR2) and its Role in Heart Disease," Cardiology in Review, vol. 13, No. 3, pp. 142-146 (2005).
Varadi et al., "Dynamic Imaging of Endoplasmic Reticulm Ca2+ Concentration in Insulin-Secreting MIN6 Cells Using Recombinant Target Cameleons. Role of Sarco (endo) plasmic Reticulum Ca2+-ATPase (SERCA)-2 and Ryanodine Receptors," Diabetes, vol. 51, Suppl. 1, pp. S190-S201 (2002).
Woolcott et al., "Arachidonic acid is a physiological activator of the ryanodine receptor in pancreatic β-cells," Cell Calcium, vol. 39, pp. 529-537 (2006).
Yaras et al., "Effects of Diabetes on Ryanodine Receptor Ca Release Channel (RyR2) and Ca2+Homeostasis in Rat Heart," Diabetes, vol. 54, pp. 3082-3088 (2005).
Yaras et al., "Restoration of Diabetes-induced abnormal local Ca2+ release in cardiomyocytes by angiotensin II receptor blockade," Am J. Physiol Heart Circ Physiol, vol. 292, pp. H912-H920 (2007).
Zhang et al., "Growth Hormone Promotes Ca+2-induces Ca2+ Release in Insulin-Secreting Cells by Ryanodine Receptor Tyrosine Phosphorylation," Molecular Endocrinology, vol. 18, pp. 1658-1669 (2004).
International Search Report and Written Opinion for International Patent Application No. PCT/US04/06971, mailed Jun. 25, 2008.
International Search Report and Written Opinion for International Patent Application No. PCT/US07/09715, mailed Aug. 21, 2008.
International Search Report and Written Opinion for International Patent Application No. PCT/US07/18138, mailed Aug. 26, 2008.
International Search Report and Written Opinion for International Patent Application No. PCT/US07/18147, mailed Sep. 8, 2008.
International Search Report and Written Opinion mailed Oct. 28, 2008 for International Patent Application No. PCT/US07/12936 filed Jun. 1, 2007.
Non Final Office Action mailed Oct. 20, 2008 for U.S. Appl. No. 11/212,309, filed Aug. 25, 2005.
Non Final Office action mailed Oct. 20, 2008 for U.S. Appl. No. 11/212,413, filed Aug. 25, 2005.

Non Final Office action mailed on Sep. 4, 2008 for U.S. Appl. No. 10/809,089, filed on Mar. 25, 2004.
Salama et al., "Mouse models of long QT syndrome," J. Physiol 578 (1); pp. 43-53 (2006).
Tomaselli et al., "What causes Sudden Death in Heart Failure ?," Circulation Research, vol. 95 (8), pp. 754-763 (2004).
Giordano et al., "Rapamycin antagonizes NF-KappaB nuclear translocation activated by TNF-alpha in primary vascular smooth muscle cells and enhances apoptosis," Am J. Physiol Heart circu Physiol, vol. 290, pp. 2459-2465, (2006).
Zahradka et al., "Activation of MMP-2 in response to vascular injury is mediated by phosphatidylinositol 3-kinase-Dependent expression of MT1-Mmp," Am J. Physiol Heart Circ. Physiol, vol. 287, pp. H2861-H2870 (2004).
International Search Report an Written opinion mailed Aug. 14, 2008, for International Application no. PCT/US07/09289 filed Apr. 13, 2007.
International Search Report and Written Opinion mailed Jan. 10, 2008 for International Patent Application no. PCT/US07/12969 filed Jun. 1, 2007.
Non Final Office Action mailed Sep. 17, 2008 for U.S. Appl. No. 11/305,528, filed Dec. 16, 2005.
Loughrey et al., "K201 modulates excitation-contraction coupling and spontaneous Ca2+ release in normal adult rabbit ventricular cardiomyocytes," Cardiovascular Research, vol. 76, pp. 236-246 (2007).
Supplementary European Search Report for European Patent Application No. 04756121.2.
Non Final Office Action mailed Aug. 7, 2001 for U.S. Appl. No. 09/568,474, filed on May 10, 2000.
Non Final Office Action mailed Jan. 14, 2002 for U.S. Appl. No. 09/568,474, filed on May 10, 2000.
Non Final Office Action mailed on May 4, 2004 for U.S. Appl. No. 10/288,606, filed on Nov. 5, 2002.
Final Office Action mailed on Nov. 22, 2004 for U.S. Appl. No. 10/288,606, filed on Nov. 5, 2002.
Non Final Office Action Mailed on Jul. 11, 2005 for U.S. Appl. No. 10/288,606, filed on Nov. 5, 2002.
Final Office Action mailed on Jan. 5, 2006 for U.S. Appl. No. 10/288,606, filed on Nov. 5, 2002.
Non Final Office Action mailed on Jan. 26, 2007 for U.S. Application no. 10/288,606 filed on Nov. 5, 2002.
Final Office Action mailed on Oct. 5, 2007 for U.S. Appl. No. 10/288,606, filed on Nov. 5, 2002.
Non Final Office Action mailed on Mar. 25, 2008 for U.S. Appl. No. 10/288,606, filed on Nov. 5, 2002.
Non Final Office Action mailed on Feb. 27, 2007 for U.S. Appl. No. 10/680,988, filed on Oct. 7, 2003.
Final Office Action mailed Nov. 29, 2007 for U.S. Appl. No. 10/680,988, filed on Oct. 7, 2003.
Non Final Office Action mailed on Mar. 19, 2008 for U.S. Appl. No. 10/680,988, filed on Oct. 7, 2003.
Non Final Office Action mailed on Apr. 27, 2005 for U.S. Appl. No. 10/608,723, filed on Jun. 26, 2003.
Final Office Action mailed on Dec. 29, 2005 for U.S. Appl. No. 10/608,723, filed Jun. 26, 2003.
Non Final Office Action mailed on Aug. 23, 2006 for U.S. Appl. No. 10/608,723, filed Jun. 26, 2003.
Final Office Action mailed on Feb. 16, 2007 for U.S. Appl. No. 10/608,723, filed Jun. 26, 2003.
Non Final Office Action mailed on Oct. 30, 2007 for U.S. Appl. No. 10/608,723, filed on Jun. 26, 2003.
Final office Action mailed on Mar. 20, 2008 for U.S. Appl. No. 10/608,723, filed on Jun. 26, 2003.
Non Final Office Action mailed on Nov. 27, 2007 for U.S. Appl. No. 10/809,089, filed on Mar. 25, 2004.
Non Final Office Action mailed on May 3, 2005 for U.S. Appl. No. 10/794,218, filed on Mar. 5, 2004.
Non Final Office Action mailed on Jan. 9, 2006 for U.S. Appl. No. 10/794,218, filed on Mar. 5, 2004.
Final Office Action mailed on Aug. 23, 2006 for U.S. Appl. No. 10/794,218, filed on Mar. 5, 2004.
Non Final Office Action mailed on Aug. 29, 2006 for U.S. Appl. No. 11/088,123, filed Mar. 23, 2005.
Final Office Action mailed on Mar. 27, 2007 for U.S. Appl. No. 11/088,123, filed on Mar. 23, 2005.
U.S. Appl. No. 10/763,498, filed Jan. 22, 2004, Marks et al.
Ackerman, MJ, "Cardiac channelopathies: it's in the genes," Nat. Med., vol. 10, pp. 463-464 (2004).
Ahern et al., "Intramembrane Charge Movements and Excitation-Contraction Coupling Expressed by Two-Domain Fragments of the Ca2+ Channel" Proc Natl Acad Sci USA, vol. 98, No. 12, pp. 6935-6940, (2001).
Ahern et al., "Subconductance States in Single-Channel Activity of Skeletal Muscle Ryanodine Receptors After Removal of FKBP12." Biophys J, vol. 72, pp. 146-162. (1997).
Ahmmed, G.U. et al., "Changes in Ca(2+) Cycling Proteins Underlie Cardiac Action Potential Prolongation in a Pressure-Overloaded Guinea Pig Model with Cardiac Hypertrophy and Failure." Circ. Res., vol. 86, No. 5, pp. 558-570. (2000).
Alvarez et al. "Late Post Myocardial Infarcation Induces a Tetrodotoxin-Resistant Na+ Current in Rat Cardiomyocytes." J. Mol. Cell Cardiol, vol. 32, pp. 1169-1179. (2000).
Antos et al. "Dilated Cardiomyopathy and Sudden Death Resulting from Constitute Activiation of Protein Kinase A." Circ. Res., vol. 89, pp. 997-1004. (2001).
Baillie, et al., "beta-Arrestin-mediated PDE4 cAMP phosphodiesterase recruitment regulates beta-adrenoceptor switching from Gs to Gi," Proc. Natl. Acada. Sci. USA 100, 940-945 (2003).
Bangur, et al., "Mutational analysis of the D1/E1 core helices and the conserved N-terminal region of yeast transcription factor IIb (TFIIB): identification of an N-terminal mutant that stabilizes TATA-binding protein-TFIIB-DNA complexes," Mol. Cell Biol., vol. 17, pp. 6784-6793 (1997).
Barbone et al. "Comparison of Right and Left Ventricular Responses to Left Ventricular Assist Device Support in Patients with Severe Heart Failure: A Primary Role of Mechanical Unloading Underlying Reverse Remodeling." Circulation, vol. 104, pp. 670-675. 2001.
Barnes, P.J., "Theophylline: new perspectives for an old drug," Am. J. Respir. Crit. Care Med. 167, 813-8 (2003).
Basso, C. et al., "Arrhythmogenic Right Ventricular Cardiomyopathy Causing Sudden Cardiac Death in Boxer Dogs: A New Animal Model of Human Disease." Circulation, vol. 109, No. 9, pp. 1180-1185. (2004).
Behr, et al., "Cardiological assessment of first-degree relatives in sudden arrhythmic death syndrome," The Lancet, vol. 362, 1457-59 (2003).
Bennett et al. "The Pattern of Onset and Spontaneous Cessation of Atrial Fibrillation in Man." Circulation, vol. 41, pp. 981-988. (1970).
Bennett et al., "Synthesis of 2-methoxydibenzo [b,f](1,4)-thiazepin-11 (10H)-one 5,5-dioxide." Organic Preparations and Procedures International, vol. 6, No. 6, pp. 287-293. (1974).
Bennett, J.A. et al. "Identification and Characterization of the Murine FK506 Binding Protein (FKBP) 12.6 gene." Mamm. Genome, vol. 9, pp. 1069-1071. (1998).
Beuckelmann, D. et al. "Intracellular Calcium Handling in Isolated Ventricular Myocytes from Patients with Terminal Heart Failure." Circulation vol. 85, pp. 1046-1055 (1992).
Bezprozvanny, I. et al. "Bell-shaped Calcium Response Curves of Ins (1,4,5) P3- and Calcium-gated Channels from Endoplasic Reticulum of Cerebellum." Nature, vol. 351, pp. 751-754. (1991).
Bittar, et al., "The arrhythmogeneicity of theophylline. A multivariate analysis of clinical determinants," Chest 99, 1415-1420 (1991).
Bohm, M. et al. "cAMP Concentrations, cAMP Dependent Protein Kinase Activity, and Phospholamban in Non-Failing and Failing Myocardium." Cardivasc. Res., vol. 28, No. 11, pp. 1713-1719. (1994).
Bolger, et al., "Characterization of five different proteins produced by alternatively spliced mRNAs from the human cAMP-specific phosphodiesterase PDE4D gene," Biochem. J. 328 (Pt 2), 539-48 (1997).
Boyden et al., "2APB- and JTV519 (K201)-Sensitive Micro Ca 2+ Waves in Arrhythmogenic Purkinje Cells that Survive in Infarcted Canine Heart." Heart Rhythm, vol. 1, pp. 218-226. (2004).

Brillantes, Anne-Marie B. et al., "Stabilization of Calcium Release Channel (Ryanodine Receptor) Function by FK506-Binding Protein." Cell, vol. 77, pp. 513-523. (May 20, 1994).

Brillantes, et al., "Developmental and tissue-specific regulation of rabbit skeletal and cardiab muscle calcium channels involved in excitation-contraction coupline, " Circ. Res., vol. 75, pp. 503-510 (1994).

Brillantes, et al., "Differences in cardiac calcium release channel (ryanodine receptor) expression in myocardium from patients with end-state heart failure caused by ischemic versus dilated cardiomyopathy," Circ. Res., vol. 71, pp. 18-26 (1992).

Bristow, et al., "Beta 1- and beta 2-adrenergic-receptor subpopulations in nonfailing and failing human ventricular myocardium: coupling of both receptor subtypes to muscle contraction and selective beta 1-receptor down-regulation in heart failure," Circulation Research, vol. 59, no. 3, pp. 297-309. (1986).

Bristow, et al., "Carvedilol Produces Dose-Related Improvements in left Ventricular Function and Survival in Subjects with Chronic Heart Failure." Circulation, vol. 94, pp. 2807-2816. (1996).

Bristow, Michael R. et al. "Beta-Adrenergic Neuroeffector Abnormalities in the Failing Human Heart are Produced by Local Rather Than Systemic Mechanisms." J. Clin. Invest, vol. 89, pp. 803-815 (Mar. 1992).

Bristow, Michael R., M.D., Ph.D. et al., "Decreased Catecholamine Sensitivity and B-Adrenergic-Receptor Density in Failing Human Hearts." The New England Journal of Medicine, vol. 307, No. 4, pp. 205-211 (Jul. 22, 1982).

Burashnikov et al. "Reinduction of Atrial Fibrillation Immediately After Termination of the Arrhythmia is Mediated by Late Phase 3 Early Afterdepolarization-Induced Triggered Activity." Circulation, vol. 107, pp. 2355-2360. (2003).

Callaway, C. et al., "Localization of the High and Low Affinity [3H] Ryanodine Binding Sites on the Skeletal Muscle Ca2+ Release Channel." The Journal of Biological Chemistry, vol. 269, No. 22, pp. 15876-15884. (1994).

Cameron, Andrew M. et al. "FKBP12 Binds the Inositol 1,4,5-Trisphosphate Receptor at Leucine-Proline (1400-1401) and Anchors Calcineurin to this FK506-like Domain." Journal of Biological Chemistry, vol. 272, No. 44, pp. 27582-27588, (Oct. 31, 1997).

Carlisle Michel, et al., "PKA-phosphorylation of PDE4D3 facilitates recruitment of the mAKAP signaling complex," Biochem. J., vol. 381, pp. 587-592 (2004).

Catsoulacos, "Synthesis of Substituted Dihydrobenzothiazepines and Related Compounds." J Heterocyclic Chemistry, vol. 7, No. 2: pp. 409-411. (1970).

Cerrone, M. et al., "Bidirectional Ventricular Tachycardia and Fibrillation Elicited in a Knock-in Mouse Model Carrier of a Mutation in the Cardiac Ryanodine Receptor." Circ. Res., vol. 96, pp. e77-e82. (2005).

Chatrath, et al., "Beta-blocker therapy failures in symptomatic probands with genotyped long-QT syndrome," Pediatr. Cardiol., vol. 25, pp. 459-465 (2004).

Che. et al., "Reversal of P-glycoprotein mediated multidrug resistance by a newly synthesized 1,4-benzothiazipine derivative, JTV-519," Cancer Lett., vol. 187, pp. 111-119 (2002).

Chen, Ye-Guang et al., "Mechanism of TGFbeta Receptor Inhibition by FKBP12." The EMBO Journal, vol. 16, No. 13, pp. 3866-3876. (1997).

Cheng, H. et al., "Amplitude Distribution of Calcium Sparks in Confocal Images: Theory and Studies with an Automatic Detection Method." Biophys J., vol. 76, pp. 606-617. (1999).

Chidsey et al. "Augmentation of Plasma Nor-epinephrine Response to Exercise in Patients with Congestive Heart Failure." N. Engl. J. Med. vol. 267, No. 13, pp. 650-654. (1962).

Choi, et al., "Spectrum and frequency of cardiac channel defects in swimming-triggered arrhythmia syndromes," Circulation, vol. 110, pp. 2119-2124 (2004).

Choi, et al., "Sudden cardiac death and channelopathies: a review of implantable defibrillator therapy," Pediatr. Clin. North Am., vol. 51, pp. 1289-1303 (2004).

Chugh et al. "Epidemiology and Natural History of Atrial Fibrillation: Clinical Implications." J. Am. Coll. Cardiol., vol. 37, no. 2, pp. 371-378. (2001).

CIBIS-II, The Cardiac Insufficiency Bisoprolol Study II (CIBIS-II): A Randomized Trial. The Lancet, vol. 353, pp. 9-13, (1999).

Cohn, J.N. et al. "Plasma Norepinephrine as a Guide to Prognosis in Patients with Chronic Congestive Heart Failure." N. Eng. J. Med., vol. 311, No. 13, pp. 819-823 (1984).

Conti, et al., "Cyclic AMP-specific PDE4 phosphodiesterases as critical components of cyclic AMP signaling," J. Biol. Chem., vol. 278, No. 8, pp. 5493-5496. (2003).

Cranefield, P.F. "Action Potentials, Afterpotentials and Arrhythmias." Circ. Res., vol. 41, No. 4, pp. 415-423. (1977).

Culligan, et al., "Drastic reduction of calsequestrin-like proteins and impaired calcium binding in dystrophic mdx muscle," J. Appl. Physiol., vol. 92, pp. 435-445 (2002).

Daoud et al. "Effect of Verapamil and Procainamide on Atrial Fibrillation-Induced Electrical Remodeling in Humans." Circulation, Vol. 96, pp. 1542-1550. (1997).

Dietz et al., "Epinephrine Regulation of Skeletal Muscle Glydogen Metabolism :Studies Utilizing the Perfused Rat Hindlimb Preparation." J. Biol. Chem., vol. 255, No. 6, pp. 2301-2307. (1980).

Dodge K.L., et al. "mAKAP Assembles a Protein Kinase A/PDE4 Phosphodiesterase cAMP Signaling Module." EMBO J. vol. 20, No. 8, pp. 1921-1930. (2001).

Doi et al., "Propranolol prevents the Develepment of Heart Failure by Restoring FKBP12.60-Mediated Stabilization of Ryanodine Receptor." Circulation vol. 105, pp. 1374-1379. (2002). .

Dorian, P., "Antiarrhythmic action of beta-blockers: potential mechanisms," J. Cardiovasc. Pharmacol. Therapeut., vol. 10, pp. S15-S22 (2005).

Drexler et al. "Contrasting Peripheral Short-Term and Long-Term Effects of Coverting Enzyme Inhibition in Patients with Congestive Heart Failure. A Double-Blind, Placebo-Controlled Trial." Circulation, vol. 79, pp. 491-502. (1989).

Dun et al. "Chronic Atrial Fibrillation Does Not Further Decrease Outward Currents. It Increases Them." Am. J. Physiol. Heart Circ. Physiol., vol. 285, pp. H1378-H1384. (2003).

Echt et al., "Mortality and morbidity in patients receiving encainide, flecainide, or placebo," The Cardiac Arrhythmia Suppression Trial, N. Engl. J. Med., vol. 324, pp. 781-788. (1991).

Eichhorn et al. "Medical Therapy can Improve the Biological Properties of the Chronically Failing Heart. A New Era in the Treatment of Heart Failure." Circulation, vol. 94, pp. 2285-2296. (1996).

Elvan et al. "Pacing-induced Chronic Atrial Fibrillation Impairs Sinus Node Function in Dogs: Electrophysiological Remodeling." Circulation, vol. 94, pp. 2953-2960. (1996).

Exhibit A: Chemical Structures 2006.

Fabiato. A. "Calcium-induced Release of Calcium from the Cardiac Sarcoplasmic Reticulum." Am. J. Physiol., vol. 245, pp. C1-C14. (1983).

Falk, R.H. "Atrial Fibrillation." N. Engl. J. Med., vol. 344, No. 14, pp. 1067-1078. (2001).

Farr, et al., "Sparking the failing heart," N. Engl. J. Med., vol. 351, pp. 185-187 (2004).

Feldman, et al., "Deficient production of cyclic AMP: pharmacologic evidence of an important cause of contractile dysfunction in patients with end-stage heart failure," Circulation, vol. 75, No. 2, pp. 331-339 (1987).

Fisher, J.D. et al. "Familial Polymorphic Ventricular Arrhythmias: A Quarter Century of Successful Medical Treatment Based on Serial Exercise-Pharmacologic Testing." J. Am. Coll. Cardiol., vol. 34, No. 7, pp. 2015-2022. (1999).

Fitzgerald, et al., "Reduced ryanodine receptor content in isolated neonatal cardiomyocytes compared with the intact tissue," J. Mol. Cell, Cardiol., vol. 26, pp. 1261-1265 (1994).

Fodor et al. "New Convenient Synthesis of 1,4-benzothiazepines." Tetrahedron Letters, vol. 36, No. 5, pp. 753-756. (1995).

Fox, P.R., ."Spontaneously Occurring Arrhythmogenic Right Ventricular Cardiomyopathy in the Domestic Cat: A New Animal Model Similar to the Human Disease." Circulation, vol. 102, No. 15, pp. 1863-1870. (2000).

Fozzard, H.A. "Afterdepolarizations and triggered activity." Basic Res. Cardiol., vol. 87, pp. 105-113. (1992).

Franzen, P. et al. "Cloning of a TGFbeta Type I Receptor That Forms a Heteromeric Complex with the TGF beta type II receptor." Cell, vol. 75, pp. 681-692. (1993).

Franzini-Armstrong et al., "Alternate Disposition of Tetrads in Peripheral Couplings of Skeletal Muscle." Journal of Muscle Research & Cell Motility. vol. 16, pp. 319-324. (1995).

Fraser, I.D. et al. "Modulation of Ion Channels: a "current" view of AKAPs." Neuron, vol. 23, pp. 423-426. (1999).

Frazier, O.H. et al. "First Use of an Untethered, Vented Electric Left Ventricular Assist Device for Long-Term Support." Circulation, vol. 89, pp. 2908-2914. (1994).

Gaburjakova, M. et al. "FKBP12 Binding Modulates Ryanodine Receptor Channel Gating." J. Biol. Chem., vol. 276, No. 20, pp. 16931-16935. (2001).

Gaspo et al. "Functional Mechanisms Underlying Tachycardia-induced Sustained Atrial Fibrillation in a Chronic Dog Model." Circulation, vol. 96, pp. 4027-4035. (1997).

Giembycz, M.A., "Development status of second generation PDE4 inhibitors for asthma and COPD: the story so far," Monaldi, Arch. Chest Dis., vol. 57, pp. 48-64. (2002).

Gillian, et al., "Analysis of expression of the human ryanodine receptor gene in malignant hyperthermia skeletal muscle tissue," Biochem. Soc. Trans., vol. 19, pp. 46S (1991).

Gillo et al. "Calcium Influx in Induced Differentiation of Murine Erythroleukemia Cells." Blood, vol. 81, No. 3, pp. 783-792. (1993).

Go, Loewe O. et al., "Differential Regulation of Two Types of Intracellular Calcium Release Channels during End-Stage Heart Failure." J. Clin. Invest., vol. 95, pp. 888-894. (Feb. 1995).

Goette et al. "Electrical Remodeling in Atrial Fibrillation: Time Course and Mechanisms." Circulation, vol. 94, pp. 2968-2974. (1996).

Gomez, A.M. et al. "Defective Excitation-Contraction Coupling in Experimental Cardiac Hypertrophy and Heart Failure." Science, vol. 276, pp. 800-806. (May 2, 1997).

Gong, et al., "Persistent improvement in synaptic and cognitive functions in an Alzheimer mouse model after rolipram treatment," J. Clin. Invest., vol. 114, pp. 1624-1634. (2004).

Gonzalez et al. "Involvement of Multiple Intracellular Release Channels in Calcium Sparks of Skeletal Muscle." Proc. Natl Acad Sci USA, vol. 97, No. 8, pp. 4380-4385. (2000).

Gretarsdottir et al.. "The gene encodina phosphodiesterase 4D confers risk of ischemic stroke,"Nat. Genet., vol. 35, pp. 131-138. (2003).

Gullestad et al., "Effect of Metoprolol CR/XL on Exercise Tolerance in Chronic Heart Failure—a Substudy to the MERIT-HF Trial. " Eur. J. Heart Fail, vol. 3, pp. 463-468. (2001).

Gwathmey et al. "Abnormal Intracellular Calcium Handling in Myocardium From Patients with End-Stage Heart Failure." Circ. Res., vol. 61, pp. 70-76. (1987).

Hachida et al. "Protective effect of JTV519 on Prolonged Myocardial Preservation." Transplant Proc., vol. 31, pp. 1094. (1999).

Hachida et al. "Significant Effect of 1,4-Benzothiazepine Derivative (K2) in Improving Myocardial Preservation." Transplantation Proceedings, vol. 29, pp. 1346-1348. (1997).

Hachida, et al., "Protective Effect of JTV519 (K201), a New 1, 4-Benzothiazepine Derivative, on Prolonged Myocardia Preservation." Transplantation Proceedings, vol. 31, pp. 996-1000. (1999).

Hachida, M. et al. "Protective Effect of JT-519, a new 1, 4-Benzothiazepine Derivative, on Prolonged Myocardial Preservation." J. Card. Surg., vol. 14, pp. 187-193. (1999).

Hain, J. et al., "Phosphorylation Modulates the Function of the Calcium Release Channel of Sarcoplasmic Reticulum from Skeletal Muscle." Biophys. J., vol. 67, pp. 1823-1833. (1994).

Hain, Jurgen et al. "Phosphorylation Modulates the Function of the Calcium Release Channel of Sarcoplasmic Reticulum from Cardiac Muscle." The Journal of Biological Chemistry, vol. 270, No. 5, pp. 2074-2081. (Feb. 3, 1995).

Hara et al., "Steady-state and nonsteady State Action Potentials in Fibrillating Canine Atrium: Abnormal Rate Adaption and Its Possible Mechanisms." Cardiovasc. Res., vol. 42, pp. 455-469. (1999).

Harnick, D.J. et al. "The Human Type 1 Inositol 1,4,5-trisphosphate receptor from T Lymphocytes: Structure, Localization, and Tyrosine Phosphorylation." J. Biol. Chem., vol. 270, No. 6, pp. 2833-2840. (1995.).

Harrington, D. et al. "Mechanisms of Exercise Intolerance in Congestive Heart Failure." Current. Opinion in Cardiology, vol. 12, No. 3, pp. 224-232. (1997).

Hasenfuss et al., "Treatment of Heart Failure Through Stabilization of the Cardiac Ryanodine Receptor." Circulation, vol. 107, pp. 378-380. (2003).

Haut, Donahue, et al., "Annexin V Disruption Impairs Mechanically Induced Calcium Signaling in Osteoblistic Cells," Bone, vol. 35, No. 3) pp. 656-663, (2004).

Houslay, et al., "PDE4 cAMP phosphodiesterases: modular enzymes that orchestrate signaling cross-talk, desensitization and compartmentalization," Biochem. J., vol. 370, pp. 1-18. (2003).

Huse, M. et al. "Crystal Structure of the Cytoplasmic Domain of the Type 1 TGFbeta Receptor in Complex With FKBP12." Cell, vol. 96, pp. 425-436. (1999).

Ikemoto, et al., "Regulation of calcium release by interdomain interaction within ryanodine receptors," Front Biosci., vol. 7, pp. d671-d683 (2002).

Inagaki et al. "Anti-ischemic Effect of a Novel Cardioprotective Agent, JTV 519, is mediated through Specific Activation of d-Isoform of Protein Kinase C in Rat Ventricular Myocardium." Circulation, vol. 101, pp. 797-804. (2000).

Inagaki et al. "The Cardioprotective Effects of a new 1,4-benzothiazepine Derivative, JTV 519, on ischemia/reperfusion-induced Ca2+ Overload in Isolated Rat Hearts." Cardiovasc Drugs Ther., vol. 14, pp. 489-495. (2000).

International Search Report and Written Opinion from PCT/US04/20474, Aug. 30, 2005.

International Search Report and Written Opinion from PCT/US04/32550, Oct. 18, 2005.

International Search Report and Written Opinion from PCT/US05/009495, Mar. 14, 2006.

International Search Report and Written Opinion from PCT/US05/10055, Oct. 27, 2005.

International Search Report and Written Opinion from PCT/US05/45914, Aug. 31, 2006.

Ishii, et al., "JTV-519, a new cardioprotective drug, and cariporide, synergistically improved post-ischemic contractile recovery in rat," Journal of Molecular and Cellular Cardiology, vol. 35, Issue 6, p. A29 (2002).

Isselbacher, Kurt J. et al. "Harrison's Principles of Internal Medicine." 13th Edition, vol. 1, pp. 1022-1024. (1994).

Ito et al. "JTV-519, a Novel Cardioprotective Agent, Improves the Contractile Recovery after Ischaemia Reperfusion in Coronary Perfused Guinea Pig Ventricular Muscles." Br. J. Pharmacol., vol. 130, No. 4, pp. 767-776. (2000).

Jayaraman, T. et al. "Regulation of the Inositol 1,4,5-Trisphosphate Receptor by Tyrosine Phosphorylation." Science, vol. 272, pp. 1492-1494. (1996.).

Jayaraman, Thottala et al. "FK506 Binding Protein Associated with the Calcium Release Channel (Ryanodine Receptor)." The Journal of Biological Chemistry, vol. 267, No. 14, pp. 9474-9477. (May 15, 1992).

Jiang et al., "Abnormal Ca2+ Release, but Normal Ryanodine Receptors, in Canine and Human Heart Failure." Circulation Research, vol. 91, pp. 1015-1022. (Nov. 29, 2002).

Jiang, D. et al. "Enhanced Basal Activity of a Cardiac Ca2+ Release Channel (Ryanodine Receptor) Mutant Asssociated with Ventricular Tachycardia and Sudden Death." Circ. Res., vol. 91, pp. 218-225. (2002).

Jin, et al., "Impaired growth and fertility of cAMP-specific phosphodiesterase PDE4D-deficient mice," Proc. Natl. Acad. Sci. USA 96, pp. 11998-12003. (1999).

Kaftan, Edward et al. "Effects of Rapamycin on Ryanodine Receptor/Ca2+ -Release Channels from Cardiac Muscle." Circulation Research, vol. 78, No. 6, pp. 990-997. (Jun. 1996).

Kaneko et al., "Crystal Structure of Annexin V with Its Ligand K-201 as a Calcium Channel Activity Inhibitor." Journal of Molecular Biology, vol. 274, pp. 16-20. (1997).

Kaneko et al., "Inhibition of Annexin V-dependent Ca2 Movement in Large Unilamellar Vesicles by K201, a New 1,4 benzothiazepine derivative," Biochimica et Biophysica Acta, vol. 1330, pp. 1-7. (1997).

Kaneko, N. "New 1,4-benzothiazepine Derivative, K201, Demonstrates Cardioprotective Effects Against Sudden Cardiac Cell Death and Intracellular Calcium Blocking Action." Drug Dev. Res., vol. 33: pp. 429-438 (1994).

Kapiloff, M.S. et al. "mAKAP and the ryanodine receptor are part of a multi-component signaling complex on the cardiomyocyte nuclear envelope," Journal of Cell Science, vol. 114, pp. 3167-3176 (2001).

Kapiloff, M.S. et al. "mAKAP:an A-kinase Anchoring Protein Targeted to the Nuclear Membrane of Differentiated Myocytes."J Cell Sci., vol. 112, pp. 2725-2736. (1999).

Katritzky, et al., "1H and 13C NMR study of tetrahydro-1, 4-benzothiazepine conformations," J. Chem. Soc. 5, pp. 1816-1822 (2002).

Katritzky, et al., "Convenient syntheses of 2, 3, 4, 5-tetrahydro-1, 4-benzothiazepines, -1, 4- benzoxazepines and -1, 4-benzodiazepines, " J. Chem. Soc. 11, Perkin Trans. I, pp. 592-598 (2002).

Katz et al., "Lactate Turnover at Rest and During Submaximal Excercise in Patients with Heart Failure." J. Appl. Physiol., vol. 75, No. 5, pp. 1974-1979. (1993).

Kawabata et al. "A Novel Cardioprotective Agent, JTV-519, is abolished by Nitric Oxide Synthase Inhibitor on Myocardial Metabolism in Ischemia-Reperfused Rabbit Hearts." Hypertens Res., vol. 25, pp. 303-309. (2002).

Kawabata et al. "Effect of a Novel Cardioprotective Agent, JTV-519, on Metabolism, Contraction and Relaxation in the Ischemia-Reperfused Rabbit Heart." Jpn Circ. J., vol. 64, pp. 772-776. (2000).

Kimura, J. et al. "Effects of a Novel Cardioprotective Drug, JTV-519 on Membrane Currents of Guinea Pig Ventricular Myocytes." Jpn. J. Pharmacol., vol. 79, pp. 275-281. (1999).

Kirchhefer, U. et al. "Activity of cAMP-dependent Protein Kinase and Ca2+/calmodulin-dependent Protein Kinase in Failing and Nonfailing Human Hearts." Cardiovasc. Res., vol. 42, pp. 254-261 (1999).

Kiriyama et al. "Effects of JTV-519, a Novel Anti-Ischaemic Drug, on the Delayed Rectifier K+ Current in Guinea-Pig Ventricular Myocytes." Naunyn Schmiedebergs Arch Pharmacol. vol. 361, No. 6, pp. 646-653. (2000).

Kirsch et al., "Spark and Ember-Like Elementary Ca2+ Release Events in Skinned Fibre of Adult Mammalian Skeletal Muscle." J. Physiol., vol. 537, No. 2, pp. 379-389. (2001).

Kirsch, et al., "The roles of annexins and types II and X collagen in matrix vesicle-mediated mineralization of growth plate cartilage," J. Biol. Chem., vol. 275, pp. 35577-35583 (2000).

Kiryu, K. et al. "Pathologic and Electrocardiographic Findings in Sudden Cardiac Death in Racehorses." J. Vet. Med. Sci., vol. 61, No. 8, pp. 921-928. (1999).

Kittleson, M.D. et al., "Familial Hypertrophic Cardiomyopathy in Maine Coon Cats: An Animal Model of Human Disease." Circulation, vol. 99, No. 24, pp. 3172-3180. (1999).

Klein et al., "Voltage Dependence of the Pattern and Frequency of Discrete Ca2+ Release Events After Brief Repriming in Frog Skeletal Muscle." Proc. Natl. Acad. Sci. USA, vol. 94, pp. 11061-11066. (1997).

Kneller et al. "Remodeling of Ca2+ -handling by Atrial Tachycardia: Evidence for a Role in Loss of Rate-Adaption." Cardiovasc. Res., vol. 54., pp. 416-426. (2002).

Kobrinsky, et al., "Expressed ryanodine receptor can substitute for the inositol 1,4,5-trisphosphate receptor in *Xenopus laevis* oocytes during progesterone-induced maturation," Dev. Biol., vol. 172, pp. 531-540 (1995).

Kohno et al., "A New Cardioprotective Agent, JTV-519, Improves Defective Channel Gating of Ryanodine Receptor in Heart Failure. " Am. J. Physiol Heart Circ. Physiol., vol. 284, No. 3, pp. H1035-H1042. First published Nov. 14, 2002. (Mar. 2003).

Kukin, M.L. et al. "Prospective, Randomized Comparison of Effect of Long-Term Treatment with Metoprolol or Carvedilol on Symptoms, Excercise, Ejection Fraction, and Oxidative Stress in Heart Failure." Circulation, vol. 99, pp. 2645-2651. (1999).

Kumagai et al. "Antiarrhythmic Effects of JTV-519, a novel Cardioprotective Drug, on Atrial Fibrillation/Flutter in a Canine Sterile Pericarditis Model." J. Cardiovasc. Electrophysiol. vol. 14, No. 8, pp. 880-884. (2003).

Lacampagne, A. et al., "Modulation of the Frequency of Spontaneous Sarcoplasmic Reticulum Ca2+ Release Events (Ca2+ Sparks) by Myoplasmic (Mg2+ ) Frog Skeletal Muscle." J. Gen. Physiol. 111, pp. 207-224. (1998).

Laflamme, M.A. et al. "Gs and Adenylyl Cyclase in Transverse Tubules of Heart: Implications for cAMP-dependent signaling." Am. J. Phys., vol. 277, pp. H1841-H1848. (1999).

Lai, F.A., et al., "The Ryanodine Receptor-Ca2+ Release Channel Complex of Skeletal Muscle Sarcoplasmic Reticulum. Evidence for a Cooperatively Coupled, Negatively Charged Homotetramer." J. Biol. Chem., vol. 264, No. 28, pp. 16776-16785. (1989).

Laitinen, P.J. et al. "Mutations of the Cardiac Ryanodine Receptor (RyR2) Gene in Familial Polymorphic Ventricular Tachycardia." Circulation, vol. 103, pp. 485-490. (2001).

Lamb et al., "Effects of FK506 and Rapamycin on Excitation-Contraction Coupling in Skeletal Muscle Fibres of the Rat." J Phys, vol. 494, No. 2, pp. 569-576. (1996).

Lauffenburger et al. , "Receptors." Oxford University Press, Chapter 2, pp. 9-12. (1996).

Laver et al., "Inactivation of Ca2+ Release Channels (Ryanodine Receptors RyR1 and RyR2) with Rapid Steps in [Ca2+] and Voltage." Biophys J., vol. 74, pp. 2352-2364. (1998).

Lee, et al., "Sudden unexplained death: evaluation of those left behind." The Lancet. vol. 362. pp. 1429-1431 (2003).

Leenhardt, A. et al. "Catecholaminergic Polymorphic Ventricular Tachycardia in Children: a 7-year follow-up of 21 patients." Circulation, vol. 91, pp. 1512-1519. (1995).

Lehnart et al. "Cardiac Ryanodine Receptor Function and Regulation in Heart Disease." Ann NY Acad Sci., vol. 1015, pp. 144-159. (2004).

Lehnart et al. "Defective Ryanodine Receptor Interdomain Interactions May Contribute to Intracellular Ca2+ Leak: A Novel Therapeutic Target in Heart Failure." Circulation, vol. 111, No. 25, pp. 3342-3346. (2005).

Lehnart et al., "Phosphodiesterase 4D Deficiency in the Ryanodine-Receptor Complex Promotes Heart Failure and Arrhythmias." Cell, vol. 123, No. 1, pp. 25-35. (Oct. 7, 2005).

Lehnart et al. "Sudden Death in Familial Polymorphic Ventricular Tachycardia Associated with Calcium Release Channel (Ryanodine Receptor) Leak." Circulation, vol. 109, pp. 3208-3214. (2004).

Lehnart, et al., "Calstabin deficiency, ryanodine receptors, and sudden cardiac death, " Biochem. Biophys. Res. Commun., vol. 322, pp. 1267-1279 (2004).

Lehnart, et al., "Immunophilins and coupled gating of ryanodine receptors, "Curr. Top. Med. Chem., vol. 3, pp. 1383-1391 (2003).

Leistad et al. "Atrial Contractile Dysfunction After Short-Term Atrial Fibrillation is Reduced by Verapamil But Increased by BAY K8644." Circulation, vol. 93, pp. 1747-1754. (1996).

Lesh, et al., "Anti-ryanodine receptor antibody binding sites in vascular and endocardial endothelium," Cir., Res., vol. 72, pp. 481-488 (1993).

Levin, H.R. et al. "Reversal of Chronic Ventricular Dilation in Patients with End-Stage Cardiomyopathy by Prolonged Mechanical Unloading." Circulation, vol. 91, pp. 2717-2720. (1995).

Levy et al. "Long-Term Trends in the Incidence of the Survival with Heart Failure." N. Engl. J. Med., vol. 347, No. 18, pp. 1397-1402. (2002).

Lisy et al., "New Cardioprotective Agent K201 is Natriuretic and Glomerular Filtration Rate Enhancing." Circulation, vol. 113, pp. 246-251. (2006).

Lorenz, M.C. et al. "TOR Mutations Confer Rapamycin Resistance by Preventing Interaction with FKBP12-Rapamycin." J. Biol. Chem., vol. 270, No. 46, pp. 27531-27537. (1995).

Lunde et al., "Contraction and Intracellular Ca2+ Handling in Isolated Skeletal Muscle of Rats with Congestive Heart Failure." Circ. Res., vol. 88, pp. 1299-1305. (2001).

Lunde, et al. "Contractile Properties of in Situ Perfused Skeletal Muscles from Rats with Congestive Heart Failure." J. Physiol, vol. 540, pp. 571-580. (2002).

MacDougall, L.K. et al. "Identification of the Major Protein Phosphatases in Mammalian Cardiac Muscle Which Dephosphorylate Phospholamban." Eur. J. Biochem., vol. 196, pp. 725-734. (1991).

MacFarlane et al. "Cellular Basis for Contractile Dysfunction in the Diaphragm from a Rabbit Infarct Model of Heart Failure." Am. J. Physiol. Cell Physiol., vol. 278. pp. C739-C746. (2000).

Mancini et al., "Contribution of a Skeletal Muscle Atrophy to Exercise Intolerance and Altered Muscle Metabolism in Heart Failure." Circulation, vol. 85, pp. 1364-1373 (1992).

Manzur, et al., "A severe clinical and pathological variant of central core disease with possible autosomal recessive inheritance," Neur. Disorders, vol. 8, pp. 467-473 (1998).

Marban, E. et al. "Mechanisms of Arrhythmogenic Delayed and Early Afterpolarizations in Ferret Ventricular Muscle." J. Clin. Invest., vol. 78, pp. 1185-1192. (1986).

Marks et al. "Clinical Implications of Cardiac Ryanodine Receptor/Calcium Release Channel Mutation Linked to Sudden Cardiac Death." Circulation, vol. 106, pp. 8-10. (Jul. 2, 2002).

Marks et al. "Involvement of the Cardiac Rvanodine Receptor/Calcium Release Channel in Catecholaminegric Polymorphic Ventricular Tachycardia."J. Cell. Physiol., vol. 190, pp. 1-6. First published Oct. 26, 2001 (2002).

Marks et al. "Progression of Heart Failure: Is Protein Kinase a Hyerphosphorylation of the Ryanodine Receptor a Contributing. Factor?" Circulation, vol. 105, pp. 272-275 (2002).

Marks et al. "Ryanodine Receptors, FKBP12, and Heart Failure." Frontiers in Bioscience, vol. 7, pp. 970-977. (2002).

Marks et al., "A Guide for the Perplexed: Towards an Understanding of the Molecular Basis of Heart Failure." Circulation. vol. 107, pp. 1456-1459. (2003).

Marks, A.R. "Cardiac Intracellular Calcium Release Channels: Role in Heart Failure." Circ. Res., vol. 87, pp. 8-11. (2000).

Marks, A.R. "Cellular Functions of Immunophilins." Physiol. Rev., vol. 76, no. 3, pp. 631-649. (1996).

Marks, Andrew. "Ryanodine Receptors/Calcium Release Channels in Heart Failure and Sudden Cardiac Death," Journal of Molecular Cell Cardiology, vol. 33, pp. 615-624. (2001).

Marks, AR, "Arrhythmias of the heart: beyond ion channels," Nat. Medicine, vol. 9, pp. 263-264, (2003).

Marks, AR, "Calcium and the heart: a question of life and death," J. Clin. Investigation, vol. 111, pp. 597-600, (2003).

Marks, AR, "Calcium channels expressed in vascular smooth muscle," Circulation, vol. 86, pp. III61-III67 (1992).

Marks, AR, "Immunophilin modulation of calcium channel gating," Methods., vol. 9, pp. 177-187 (1996).

Marks, AR, "Intracellular calcium-release channels: regulators of cell life and death," Am. J. Phsiol., vol. 272, pp. H597-H605 (1997).

Marks, et al., "Molecular cloning and characterization of the Ryanodine receptor/junctional channel complex cDNA from skeletal muscle sarcoplasmic reticulum," Proc. Natl. Acad. Sci. U.S.A., vol. 86, pp. 8683-8687 (1989).

Marks, et al., "Regulation of ryanodine receptors via macromolecular complexes: a novel role for leucine/isoleucine zippers," Tends Cardiovasc. Med., vol. 12, pp. 166-170 (2002).

Marks, et al., "Surface topography analysis of the ryanodine receptor/junctional channel complex based on proteolysis sensitivity mapping," J. Biol. Chem., vol. 265, pp. 13143-13149 (1990).

Marks, et al., "The ryanodine receptor/junctional channel complex is regulated by growth factors in a myogenic cell line," J. Cell. Biol., vol. 114, pp. 303-312, (1991).

Maron, et al., "Recommendations for physical activity and recreational sports participation for young patients with genetic cardiovascular diseases," Circulation, vol. 109, pp. 2807-2816 (2004).

Marx et al. "Requirement of a Macromolecular signaling complex for Beta-Adrenergic Receptor Modulation of the KCNQ1/KCNE1 Potassium Channel," Science, vol. 295, pp. 496-499. (2002).

Marx et al., "Coupled Gating Between Cardiac Calcium Release Channels (Ryanodine Receptors)" Circ. Res., vol. 88, pp. 1151-1158. (2001).

Marx S.O et al., "Regulation of the Ryanodine Receptor in Heart Failure." Basic Res. Cardiol., vol. 97, Suppl. 1, pp. 1/49-1/51. (2002).

Marx, S.O. et al. "Phosphorylation-dependent Regulation of Ryanodine Receptors: A Novel Role for Leucine/Isoleucine Zippers." J. Cell. Biol., vol. 153, No. 4, pp. 699-708. (2001).

Marx, S.O. et al. "PKA Phosphorylation Dissociates FKBP12.6 from the Calcium Release Channel (Rvanodine Receptor): Defective Regulation in Failing Hearts." Cell. vol. 101. pp. 365-376. (2000).

Marx, Steven O. et al. "Coupled Gating Between Individual Skeletal Muscle Ca2+ Release Channels (Ryanodine Receptors)." Science, vol. 281, pp. 818-821. (Aug. 7, 1998).

Masumiya et al., "Localization of the 12.6 kDa FK506-binding Protein (FKBP12.6) Binding Site to the NH2- Terminal Domain of the Cardiac Ca2+ Release Channel. (Ryanodine Receptor)." The Journal of Biological Chemistry, vol. 278, pp. 3786-3792. (2003).

McCartney, S. et al. "Cloning and Characterization of A-Kinase Anchor Protein 100 (AKAP100). A Protein That Targets A-Kinase to the Sarcoplasmic Reticulum." J. Biol. Chem., vol. 270, No. 16, pp. 9327-9333. (1995).

McPhie, et al., "Structure of the hormone binding domain of human beta 1 thyroid hormone nuclear receptor: is is an alpha/beta barrel?" Biochemistry, vol. 32, pp. 7460-7465 (1993).

Meissner, G., "Ryanodine Receptor/Ca2+ Release Channels and Their Regulation by Endogenous Effectors." Annu. Rev. Physiol., vol. 56, pp. 485-508. (1994).

Merit-HF Study Group. "Effect of Metoprolol CR/XL in Chrohic Heart Failure: Metoprolol CR/XL Randomised Intervention Trial in Congestive Heart Failure (MERIT-HF)," The Lancet, vol. 353, pp. 2001-2007. (Jun. 12, 1999).

Meurs, K.M. et al., "A Cardiac Myosin Binding Protein C Mutation in the Maine Coon Cat with Familial Hypertrophic Cardiomyopathy." Hum Mol Genet, vol. 14, No. 23, pp. 3587-3593. (2005).

Meurs, KM. "Boxer Dog Cardiomyopathy: An Update." Vet Clin North Am Small Anim Pract., vol. 34, pp. 1235-1244. (2004).

Miller, K.B., "Manganese Alters Mitochodrial Integrity in the Hearts of Swine Marginally Deficient in Magnesium." Biofactors, vol. 20, No. 2, pp. 85-96. (2004).

Minotti et al., "Impaired Skeletal Muscle Function in Patients with Congestive Heart Failure. Relationship to Systemic Excercise Performance." J. Clin. Invest., vol. 88, pp. 2077-2082. (1991).

Mitchell, G.F. et al. "Measurement of Heart Rate and Q-T Interval in the Conscious Mouse." Am. J. Physiol., vol. 274, pp. H747-H751. (1998).

Moghadam, H.K. "Heritability of Sudden Death Syndrome and Its Associated Correlations to Ascites and Body Weight in Broilers." Br Poult Sci, vol. 46, No. 1, pp. 54-57. (2005).

Mohler, P.J. et al. "Ankyrin-B Mutation Causes Type 4 long-QT Cardiac Arrhythmia and Sudden Cardiac Death." Nature, vol. 421, pp. 634-639. (2003).

Moise, N. S., "Inherited Arrhythmias in the Dog: Potential Experimental Models of Cardiac Disease." Cardiovasc Res, vol. 44, No. 1, pp. 37-46. (1999).

Mongillo, et al., "Fluorescence resonance energy transfer-based analysis of cAMP dynamics in live neonatal rat cardiac myocytes revelas distinct functions of compartmentalized phosphodiesterases," Cir. Res., 95, 67-75 (2004).

Morgan, J. et al. "Abnormal Intracellular Calcium Handling: A Major Cause of Systolic and Diastolic Dysfunction in Ventricular Myocardium from Patients with heart failure." Circulation, vol. 81 (Suppl. 3), pp. III21-III32. (1990).

Morillo et al. "Chronic Rapid Atrial Pacing: Structural, Functional, and Electrophysiological Characteristics of a New Model of Sustained Atrial Fibrillation." Circulation, vol. 91, pp. 1588-1595. (1995).

Morita, et al., "Ca channel blocking activity of JTV-519, a novel protective drug to cytotoxicity," Neuroscience Research, vol. 31, Supp. 1, p. S65 (1998).

Moschella, M.C. et al., "Inositol 1,4,5-trisphosphate Receptor Expression in Cardiac Myocytes." J. Cell. Biol., vol. 120, No. 5, pp. 1137-1146. (1993).

Nabauer, M. et al. "Regulation of Calcium Release is Gated by Calcium Current, Not Gating Charge, in Cardiac Myocytes." Science, vol. 244, pp. 800-803. (1989).

Nair, et al., "Synthesis and reactions of 1, 4-benzothiazepine derivatives," Indian Jour. of Chemist, vol. 7, No. 9, pp. 862-865. (1969).

Nakai, et al., "Functional Nonequality of the Cardiac and Skeletal Ryanodine Receptors," Proc. Natl. Acad. Sci. USA, vol. 94, pp. 1019-1022, Feb. 1997.

Nakamura, et al., "Reversal of cisplatin resistance by the 1,4-benzothiazepine derivative, JTV-519," Jpn. J. Cancer Res., vol. 92, pp. 597-602 (2001).

Nakamura, Y. et al., "Parasitic Females of Strongyloides Papillosus as a Pathogenetic Stage for Sudden Cardiac Death in Infected Lambs." J. Vet Med. Sci., vol. 56, No. 4, pp. 723-727. (1994).

Nakaya et al. "Inhibitory Effects of JTV-519, a Novel Cardioprotective Drug, on Potassium Currents and Experimental Atrial Fibrillation in Guinea-Pig Hearts," British Journal of Pharmacology, vol. 131, pp. 1363-1372. (2000).

Neumann, J. et al. "Increased Expression of Cardiac Phosphatases in Patients with End-Stage Heart Failure." J. Mol. Cell. Cardiol., vol. 29, pp. 265-272. (1997).

Ondrias, et al., "FKBP12 modulates gating of the ryanodine receptor/calcium release channel," Ann. N.Y. Acad. Sci., vol. 853, pp. 149-156 (1998).

Ondrias, et al., Single channel properties and calcium conductance of the cloned expressed ryanodine receptor/calcium-release channel, Soc. Gen. Physiol. Serv., vol. 51, pp. 29-45 (1996).

Ono et al. "Altered Interaction of FKBP12.6 with Ryanodine Receptor as a Case of Abnormal Ca2+ Release in Heart Failure." Cardiovasc. Res., Vol. 48, pp. 323-331. (2000).

Otsu, K. et al. "Molecular Cloning of cDNA encoding the Ca2+ release channel (Ryanodine Receptor) of Rabbit Cardiac Muscle Sarcoplasmic Reticulum." J. Biol. Chem., vol. 265, No. 23, pp. 13472-13483. (1990).

Oyama, Mark A. et al., "Genomic Expression Patterns of Cardiac Tissues from Dogs with Dilated Cardiomyopathy." AJVR, vol. 66, No. 7, pp. 1140-1155. (Jul. 2005).

Packer, et al., "Effect of oral milrinone on mortality in severe chronic heart failure," The Promise Study Research Group, N. Engl. J. Med., vol. 325, pp. 1468-1475 (1991).

Paul-Pletzer, et al., "Identification of a dantrolene-binding sequence on the skeletal muscle ryanodine receptor," J. Biol. Chem., vol. 277, pp. 34918-34923 (2002).

Perreault et al., "Alterations in Contractility and Intracellular Ca2+ Transients in Isolated Bundles of Skeletal Muscle Fibers from Rats with Chronic Heart Failure." Circ. Res., vol. 73, No. 2, pp. 405-412. (1993).

Perry, et al., "Targeting of cyclic AMP degradation to beta 2-adrenergic receptors by betaarrestins," Science 298, 834-6 (2002).

Pieske, et al., "Ca2+ handling and sarcoplasmic reticulum Ca2+ content in isolated failing and nonfailing human myocardium," Circ. Res., vol. 85, pp. 38-46 (1999).

Pogwizd, S.M. et al. "Mechanisms Underlying Spontaneous and Induced Ventricular Arrhythmias in Patients with Idiopathic Dilated Cardiomyopathy." Circulation, vol. 98, pp. 2404-2414. (1998).

Pogwizd, S.M. et al. "Arrhythmogenesis and Contractile Dysfunction in Heart Failure: Roles of Sodium-Calcium Exchange, Inward Rectifier Potassium Current, and Residual Beta-Adrenergic Responsiveness." Circ. Res., vol. 88, pp. 1159-1167. (2001).

Priori, S.G. et al. "Clinical and Molecular Characterization of Patients with Catecholaminergic Polymorphic Ventricular Tachycardia." Circulation, vol. 106, pp. 69-74. (2002).

Priori, S.G. et al. "Mutations in the Cardiac Ryanodine Receptor Gene (hRyR2) Underlie Catecholaminergic Polymorphic Ventricular Tachycardia." Circulation, vol. 103, pp. 196-200. (2001).

Protas. L. et al.. "Regional Dispersion of L-type Calcium Current in Ventricular Myocytes of German Shepherd Dogs with Lethal Cardiac Arrhythmias." Heart Rhythm, vol. 2, Issue. 2, pp. 172-176. (2005).

Ramirez et al., "Mathematical Analysis of Canine Atrial Action Potentials: Rate, Regional Factors and Electrical Remodeling." Am. J. Physiol. Heart Circ. Physiol., vol. 279, pp. H1767-H1785. (2000).

Regitz-Zagrosek, et al. "Myocardial Cyclic AMP and Norepinephrine Content in Human Heart Failure." Eur. Heart J, vol. 15 Suppl. D: pp. 7-13. (1994).

Reiken et al. "PKA Phosphorylation Activates the Calcium Release Channel (Ryanodine Receptor) in Skeletal Muscle: Defective Regulation in Heart Failure." J. Cell. Biol., vol. 160, No. 6, pp. 919-928. (2003).

Reiken et al. "Protein Kinase A Phosphorylation of the Cardiac Calcium Release Channel (Ryanodine Receptor) in Normal and Failing Hearts. Role of Phosphatases and Response to Isoproterenol." J. Biol. Chem., vol. 278, No. 1, pp. 444-453. (2003).

Reiken et al., "A Novel Excitation-Contraction (EC) Coupling Myopathy in Heart Failure Involving Both Cardiac and Skeletal Muscles." Circulation, vol. 104, No. 17 Supplement, pp. II.131. (Oct. 23, 2001).

Reiken et al., "Beta-Blockers Restore Calcium Release Channel Function and Improve Cardiac Muscle Performance in Human Heart Failure." Circulation, vol. 107, pp. 2459-2466. (2003).

Reiken et al., "Defective Skeletal Muscle Calcium Release Channel Function during Heart Failure." Circulation, vol. 106, No. 19 Supplement, pp. 11-225. (2002).

Reiken, S. et al. "Beta-Adrenergic Receptor Blockers Restore Cardiac Calcium Release Channel (Ryanodine Receptor) Structure and Function in Heart Failure." Circulation, vol. 104, pp. 2843-2848. (2001).

Reiken, S. et al. "PKA Phosphorylation of the Cardiac Calcium Release Channel (Ryanodine Receptor) in Normal and Failing Hearts: Role of Phosphatases and Response to Isoproterenol." J. Biol. Chem. (2002).

Reiner, G. et al., "Skeletal Muscle Sarcoplasmic Calcium Regulation' And Sudden Death Syndrome in Chickens." Br Poult Sci., vol. 36, No. 4, pp. 667-675. (1995).

Rensma et al. "Length of Excitation Wave and Susceptibility to Reentrant Atrial Arrhythmias in Normal Conscious Dogs." Circ. Res., vol. 62, pp. 395-410. (1988).

Richter, et al., "Splice variants of the cyclic nucleotide phosphodiesterase PDE4D are differentially expressed and regulated in rat tissue," Biochem., vol. 388, pp. 803-811 (2005).

Rios et al., "Charge Movement and the Nature of Signal Transduction in Skeletal Muscle Excitation-Contraction Coupling." Annu Rev Physiol, vol. 54, pp. 109-133. (1992).

Rios et al., "Involvement of Dihydropyridine Receptors in Excitation-Contraction Coupling in Skeletal Muscle." Nature, vol. 325, pp. 717-720. (1987).

Rosemblit, et al., "Intracellular calcium release channel expression during embryogenesis," Dev. Biol., vol. 206, pp: 163-177 (1999).

Ruehr, et al., "Targeting the protein kinase a by muscle a kinase-anchoring protein (mAKAP) regulates phosphorylation and function of the skeletal muscle ryanodine receptor," J. Biol. Chem., vol. 278, pp. 24831-24836 (2003).

Schneider et al., "Voltage Dependent Charge Movement in Skeletal Muscle: A Possible Step in Excitation-Contraction Coupling." Nature, vol. 242, pp. 244-246. (1973).

Schoenmakers et al., "CHELATOR: An Improved Method for Computing Metal Ion Concentrations in Physiological Solutions." Biocomputing, vol. 12, pp. 870-879. (1992).

Schotten et al., "Electrical and contractile remodeling during the first days of atrial fibrillation go hand in hand," Circulation, vol. 107, pp. 1433-1439. (2003).

Semsarian et al., "The L-Type Calcium Channel Inhibitor Diltiazem Prevents Cardiomyopathy in a Mouse Model." J. Clin. Invest., vol. 109, No. 8, pp. 1013-1020. (2002).

Sen, L.Y. et al. "Inotropic and Calcium Kinetic Effects of Calcium Channel Agonist and Antagonist in Isloated Cardiac Myocytes from Cardiomyopathic Hamsters." Circ Res, vol. 67, No. 3, pp. 599-608. (1990).

Sette, et al., "Phosphorylation and activation of a cAMP-specific phosphodiesterase by the cAMP-dependent protein kinase. Involvement of serine 54 in the enzyme activation," J. Biol. Chem., vol. 271, pp. 16526-16534 (1996).

Sette, et al., "The ratPDE3/Ivd phosphodiesterase gene codes for multiple proteins differentially activated by cAMP-dependent protein kinase," J. Biol. Chem., vol. 269, pp. 18271-18274 (1994).

Shannon, et al., "Elevated sarcoplasmic reticulum Ca2+ leak in intact ventricular myocytes from rabbits in heart failure," Circ. Res., vol. 93, pp. 592-594 (2003).

Shibata, "264 W94" Current Opinion in Cardiovascular, Pulmonary, and Renal Investigational Drugs., vol. 1, No. 2, pp. 276-278. (1999).
Shinohara, "A Synthesis of Mono-and Dimethoxy -1,2,3,4—Tetrahydroisoquinolines via Pummerer Reaction: Effects of Methoxyl Groups on Intramolecular Cyclization." Chemical and Pharmaceutical Bulletin, vol. 46, No. 6, pp. 918-927. (1998).
Shirokova, N. et al., "Local Calcium Release in Mammalian Skeletal Muscle." J. Physiol, vol. 512, No. 2, pp. 377-384. (1998).
Shiroshita-Takeshita et al., "Atrial fibrillation: basic mechanisms, remodeling and triggers," J. Interv. Card. Electrophysiol, vol. 13, pp. 181-193. (2005).
Shou, W. et al. "Cardiac Defects and Altered Ryanodine Receptor Function in Mice Lacking FKBP12." Nature, vol. 391, pp. 489-492. (1998).
Shtifman, et al., "Interdomain interactions within ryanodine receptors regulate Ca2+ spark frequency in skeletal muscle," J. Gen. Physiol., vol. 119, pp. 15-31 (2002).
Song, Y. et al. "ATP Promotes Development of Afterdepolarizations and Triggered Activity in Cardiac Myocytes." Am. J. Physiol., vol. 267, pp. H2005-H2011. (1994).
Sonnleitner et al., "Gating of the Skeletal Calcium Release Channel by ATP is Inhibited by Protein Phosphatase 1 but not by Mg2+," Cell Calcium 21, No. 4, pp. 283-290. (1997).
Sorensen et al., "Excercised Blood Flow and Microvascular Distensibility in Skeletal Muscle Normalize After Heart Transplantation." Clin. Transplant, vol. 13, pp. 410-419. (1999).
Special Report "Preliminary Report: Effect of Encainide and Flecainide on mortality in a randomized trial of arrhythmia suppression after myocardial infraction," The New England Jour. of Med., vol. 321, No. 6, pp. 406-412. (1989).
Stevenson, W.G. et al., "Sudden death prevention in patients with advanced ventricular dysfunction," Circulation, vol. 88, pp. 2953-2961. (1993).
Stratton et al., "Effects of Cardiac transplantation on Bioenergetic Abnormalities of Skeletal Muscle in Congestive Heart Failure." Circulation, vol. 89, pp. 1624-1631. (1994).
Suissa, et al., "Bronchodilators and acute cardiac death," Am. J. Respir. Grit. Care Med., vol. 154, pp. 1598-1602 (1996).
Suko et al., "Phosphorylation of Serine 2843 in Ryanodine Receptor-Calcium Release Channel of Skeletal Muscle by cAMP-, cGMP- and CaM-Dependent Protein Kinase." Bioch Biophys. Acta., vol. 1175, pp. 193-206. (1993).
Sullivan et al., "Exercise Intolerance in Patients with Chronic Heart Failure." Prog. Cardiovasc. Dis., vol. 38, No. 1, pp. 1-22. (1995).
Sun et al., "Cellular Mechanisms of Atrial Contractile Dysfunction Caused by Sustained Atrial Tachycardia." Circulation, vol. 98, pp. 719-727. (1998).
Swan, et al., "Calcium channel antagonism reduces exercise-induced ventricular arrhythmias in catecholaminergic polymorphic ventricular tachycardia patients with RyR2 mutations," J. of Card. Electrophysiology, vol, 16, No. 2, pp. 162-166, (2005).
Swan, H. et al. "Arrhythmic Disorder Mapped to Chromosome 1q42-q43 Causes Malignant Polymorphic Ventricular Tachycardia in Structurally Normal Hearts." J. Am. Coll. Cardiol., vol. 34, No. 7, pp. 2035-2042. (1999).
Szabo et al. "Synthesis and Spectroscopic Investigation of 1,4-Benzothiazepine Derivatives." Magyar Kemiai Folyoirat, vol. 93, No. 6. pp. 269-276. (1987). (in Hungarian and English).
Szabo et al. "Synthesis and Transformation of 4,5-dihydro-1,4-benzothiazepin-3(2H)—one derviatives." Magyar Kemiai Folyoirat, vol. 93, No. 3, pp. 139-144. (1987). (in Hungarian and English).
Szabo et al. "Synthesis and Transformations of 4,5-Dihydro-1,4-benzothiazepin-3(2H)-one Derivatives1,2)." Chemische Berichte., vol. 119, No. 9, pp. 2904-2913. (1986).
Szabo, Janos et al., "Synthesis and Spectroscopic Investigations of 1,4-benzothiazepine derivatives." Can. J. Chem, vol. 65, pp. 175-181. (1987).
Takeshima, H. et al. "Primary Structure and Expression from Complementary DNA of Skeletal Muscle Ryanodine Receptor." Nature, vol. 339, pp. 439-445. (1989).
Tanabe, T. et al., "Regions of the Skeletal Muscle Dihydropyridine Receptor Critical for Excitation-Contraction Coupling." Nature, vol. 346, pp. 567-569. (1990).
Tasken, et al., "Phosphodiesterase 4D and protein kinase a type II constitue a signaling unit in the centrosomal area," J. Biol. Chem., vol. 276, pp. 21999-22002 (2001).
Tester, et al., "Compendium of cardiac channel mutations in 541 consecutive unrelated patients referred for long QT syndrome genetic testing," Heart Rhythm. vol. 2, pp. 507-517 (2005).
Tester, et al., "Targeted mutational analysis of the RyR2-encoded cardiac ryanodine receptor in sudden unexplained death: a molecular authopsy of 40 medical examiner/coroner's cases," May Clin. Proc., vol. 79, pp. 1380-1384 (2004).
Tieleman et al. "Verapamil Reduces Tachycardia-Induced Electrical Remodeling of the Atria." Circulation, vol. 95, pp. 1945-1953. (1997).
Timerman, Anthony P. et al., "The Calcium Release Channel of Sarcoplasmic Reticulum is Modulated by FK-506- binding Protein." J. Bio. Chem., vol. 268, No. 31, pp. 22992-22999. (1993).
Timerman, et al., "The ryanodine receptor from canine heart sacroplasmic reticulum is associated with a novel FK-506 binding protein," Biochem. Biophys. Res. Commun., vol. 198, pp. 701-706 (1994).
Timmermans et al., "Immediate Reinitiation of Atrial Fibrillation Following Internal Atrial Defibrillation." J. Cardiovasc. Electrophysiol., vol. 9, pp. 122-128. (1998).
Tipton, et al., "My child just fainted: no big deal or sudden-death warning?" Emerg. Med. Serv., vol. 33, pp. 41-45 (2004).
Tse et al. "JTV-519 Japan. Tobacco." Curr. Opin. Investig. Drugs. vol. 2, No. 7, pp. 936-939. (2001).
Tsuji, N. et al., "Sudden Cardiac Death in Calves with Experimental Heavy Infection of Strongyloides Papillosus." J. Vet. Med. Sci., vol. 54, No. 6, pp. 1137-1143. (1992).
Tunwell et al., "H. Sapiens mRNA for Ryanodine Receptor 2." GenBank Database, Accession No. X98330. Sep. 9, 1996.
Tunwell et al., "The Human Cardiac Muscle Ryanodine Receptor-Calcium Release Channel: Identification, Primary Structure and Topological Analysis." Biochem. J., vol. 318, pp. 477-487. (1996).
Valdivia, Hector H. et al. "Rapid Adaptation of Cardiac Ryanodine Receptors: Modulation by Mg2+ and Phosphorylation." Science, vol. 267, pp. 1997-2000. (Mar. 31, 1995).
van Rooij, et al., "MCIPI overexpression suppresses left ventricular remodeling and sustains cardiac function after myocardial infarction," Circ. Res., vol. 94, pp. e18-e26 (2004).
Verde, et al., "Characterization of the cyclic nucleotide phosphodiesterase subtypes involved in the regulation of the L-type Ca2+ current in rat ventricular myocytes," Br. J. Pharmacol. vol. 127, pp. 65-74 (1999).
Vest, J.A. et al., "Defective Cardiac Ryanodine Receptor Regulation During Atrial Fibrillation." Circulation. vol. 111, No. 16, pp. 2025-2032. (2005).
Vignola, A.M., "PDE4 inhibitors in COPD-a more selective approach to treatment," Respir. Med., vol. 98, pp. 495-503 (2004).
von Altrock, A., "Sudden Deaths in Fattening Herds on taking Blood Samples—Experiences from the Practice." Berl Munch Tierarztl Wschr, vol. 112, pp. 86-90. (1999).
Wang et al. "Regional and Functional Factors Determining Induction and Maintenance of Atrial, Fibrillation in Dogs." Am. J. Physiol., vol. 271, pp. H148-H158. (1996).
Wang, et al., "Cloning and characterization of novel PDE4D isoforms PDE4D6 and PDE4D7," Cell. Signal., vol. 15, pp. 883-891 (2003).
Wang, et al., "Retinoic acid stimulates annexin-mediated growth plate chondrocyte mineralization," J. Cell Biol., vol. 157, pp. 1061-1069 (2002).
Wang, J. et al. "Physical Training Alters the Pathogenesis of Pacing-Induced Heart Failure Through Endothelium-Mediated Mechanisms in Awake Dogs." Circulation, vol. 96, pp. 2683-2692. (1997).
Wang, W., et al., "Annexin-mediated Ca2+ influx regulates growth plate chondrocyte maturation and apoptosis," J. Biol Chem, vol. 278, pp. 3762-3769 (2003).
Wang, ZG et al., "Effects of Flecainide and Quinidine on Human Atrial Action Potentials. Role of rate-dependence and comparison with guinea pig, rabbit, and dog tissues," Circulation, Journal of the American Heart Association, vol. 82, pp. 274-283. 1990.

Ward, et al., "Defects in ryanodine receptor calcium release in skeletal muscle from postmyocardial infarct rats, "Faseb J. , vol, 17, pp. 1517-1519 (2003).

Wehrens et al. "Ca2+/Calmodulin-Dependent Protein Kinase II Phosphorylation Regulates the Cardiac Ryanodine Receptor." Circ. Res., vol. 94, No. 6. pp. e61-e70. (Apr. 2004).

Wehrens et al. "Enhancing Calstabin Binding to Ryanodine Receptors Improves Cardiac and Skeletal Muscle Function in Heart Failure." Proc Natl Acad Sci USA, vol. 102, No. 27, pp. 9607-9612. (Jul. 5, 2005).

Wehrens et al. "FKBP12.6 Deficiency and Defective Calcium Release Channel (Ryanodine Receptor) Function Linked to Exercise Induced Sudden Cardiac Death." Cell, vol. 113, pp. 829-840. (2003).

Wehrens et al., "Molecular Determinants of Altered Contractility in Heart Failure." Ann Med., vol. 36, Suppl. 1, pp. 70-80. (2004).

Wehrens et al., "Novel Therapeutic Approaches for Heart Failure by Normalizing Calcium Cycling." Nature Reviews Drug Discovery., vol. 3, pp. 565-573. (2004).

Wehrens et al., "Protection from Cardiac Arrhythmia Through Ryanodine Receptor-Stabilizing Protein Calstabin2." Science, vol. 304, pp. 292-296. (Apr. 2004).

Wehrens et al., "Ryanodine Receptor-Targeted Anti-Arrhythmic Therapy." Ann N. Y Acad. Sci., vol. 1047, pp. 366-375. (2005).

Wehrens et al., "Sudden Unexplained Death Caused by Cardiac Ryanodine Receptor (RyR2) Mutations." Mayo Clin Proc., vol. 79, No. 11, pp. 1367-1371. (Nov. 2004).

Wehrens, et al., "Altered function and regulation of cardiac ryanodine receptors in cardiac disease, "Trends Biochem. Sci., vol. 28, pp. 671-678 (2003).

Wehrens, et al.. "Intracellular Calcium Release Channels and Cardiac Disease." Annu. Rev. Physiol, vol. 67, pp. 69-98. First published on Jul. 21, 2004 (2005).

Wehrens, et al., "Myocardial disease in failing hearts: defective excitation-contraction coupling," Cold Spring Harb. Symp. Quant. Biol., vol. 67, pp. 533-541 (2002).

Wellen et al.; "Atrioverter: An Implantable Device for the Treatment of Atrial fibrillation." Circulation, vol. 98, pp. 1651-1656. (1998).

Westphal, R.S. et al. "Regulation of NMDA Receptors by an Associated Phosphatase-Kinase Signaling Complex." Science, vol. 285, pp. 93-96. (1999).

Wijffels et al. "Atrial Fibrillation Begets Atrial Fibrillation: A Study in Awake Chronically Instrumented Goats." Circulation, vol. 92, pp. 1954-1968. (1995).

Wilde et al., "Ion Channels, the QT interval, and arrhythmias," Pacing Clin Electrophysiol, vol. 20, pp. 2048-2051. 1997.

Wilson, et al. "Exertional Fatigue Due to Skeletal Muscle Dysfunction in Patients with Heart Failure." Circulation, vol. 87, pp. 470-475. (1993).

Wilson, J.R. "Exercise Intolerance in Heart Failure. Importance of Skeletal Muscle." Circulation, vol. 91, pp. 559-561. (1995).

Wit, A.L. et al. "Pathophysiologic Mechanisms of Cardiac Arrhythmias." Am. Heart. J., vol. 106, pp. 798-811. (1983).

Xiang, Y. et al., "Phosphodiesterase 4D is required for β2 adrenoceptor subtype-specific signaling in cardiac myocytes" PNAS, Jan. 18, 2005, vol. 102, No. 3, pp. 909-914.

Xin, H.B. et al. "Oestrogen Protects FKBP12.6 Null Mice from Cardiac Hypertrophy." Nature, vol. 416, pp. 334-337. (2002).

Yamamoto et al. "Abnormal Ca2+ Release from Cardiac Sarcoplasmic Reticulum in Tachycardia-Induced Heart Failure." Cardiovasc. Res., vol. 44, pp. 146-155. (1999).

Yamamoto, et al., "Ca2+-dependent dual function of peptice C. The peptide corresponding to the Glu724-Pro760 region (the so-called determinant of excitation-contraction coupling) of the dihydropyridine receptor alpha 1 subunit II-III loop," J. Biol. Chem., vol. 277, pp. 993-1001 (2002).

Yamamoto, et al., "Peptide probe study of the critical regulatory domain of the cardiac ryanodine receptor," Biochem, Biophys. Res. Commun., vol. 291, pp. 1102-1108 (2002).

Yamamoto, et al., "Spectroscopic monitoring of local conformational changes during the intramolecular domain-domain interaction of the ryanodine receptor," Biochemistry, vol, 41, pp. 1492-1501 (2002).

Yamamoto, et al., "T-tubule depolarization-induced local events in the ryanodine receptor, as monitored with the fluorescent conformational probe incorporated by mediation of peptide A," J. Biol. Chem. vol. 277, pp. 984-992 (2002).

Yamamoto-Nino, M. et al. "Cloning and Characterization of Human Type 2 and Type 3 Inositol 1,4,5-trisphosphate Receptors." Receptor Channels, vol. 2, pp. 9-22. (1994).

Yamawaza, et. al., "Subtype Specificity of the Ryanodine Receptor for Ca2+ Signal Amplification in the Excitation-Contraction Coupling," The EMBO Journal, vol. 15, No. 22, pp. 6172-6177, 1996.

Yang, Jiacheng et al. "A-kinase Anchoring Protein 100 (AKAP100) is Localized in Multiple Subcellular Compartments in the Adult Rat Heart." The Journal of Cell Biology, vol. 142, No. 2, pp. 511-522 (Jul. 27, 1998.).

Yano et al. "Altered Stoichiometry of FKBP12.6 Versus Ryanodine Receptor as a Cause of Abnormal Ca2+ Leak Through Ryanodine Receptor in Heart Failure." Circulation, vol. 102, pp. 2131-2136. (2000).

Yano et al., "RyR-Bound FKBP12.6 and the Modulation." Journal Clinical Calcium, vol. 11, No. 6, pp. 743-748. (Jun. 2001).

Yano, M. et al. "FKBP12.6-Mediated Stabilization of Calcium-Release Channel (Ryanodine Receptor) as a Novel Therapeutic Strategy against Heart Failure." Circulation, vol. 107, pp. 477-484. (2003).

Yu et al., "Tachycardia-induced Change of Atrial Refractory Period in Humans: Rate Dependency and Effects of Antiarrhythmic Drugs." Circulation, vol. 97, pp. 2331-2337. (1998).

Yue et al., "Ionic Remodeling Underlying Action Potential Changes in a Canine Model of Atrial Fibrillation." Circ. Res., vol. 81, pp. 512-525. (1997).

Zaccolo, et al., "Discrete micro domains with high concentration of cAMP in stimulated rat neonatal cardiac myocytes," Science, vol. 295, pp. 1711-1715 (2002).

Zucchi et al., "The Sarcoplasmic Reticulum Ca2+ Channel/ Ryanodine Receptor: Modulation by Endogenous Effectors, Drugs, and Disease States." Pharmacological Reviews, vol. 49, no. 1, pp. 1-51. (1997).

Czollner et al., "Synthesis of 1,4-benzothiazepines and investigation of their reactions," MAgyar Kemiai Folyoirat, Kiralyi Magy. Termtud. Tars. Chem. Szakoszt, Budapest, Hu, vol. 94, pp. 332-335 (1988).

Duddeck et al., "Oxazepines and thiazepines, XVI. Proton and Carbon-13 NMR studies of the structure of Benzothiazepinone derivative," Liebigs Annalen der Chemie, pp. 869-876 (1985).

Extended European Search Report for European Patent No. 09166965.5 Oct. 14, 2009.

Levai et al., "Oxazepines and thiazepines. VI. A convenient synthesis of benzothiazepines sulfoxides," Acta Chimica, Academia Scientiarum Hungarica, Budapest, HU, vol. 102, pp. 141-142 (1979).

Shridhar et al," Antiinflammatory agents. Part VII. Synthesis of some new Methyl 2,3-dihydro-1, 4- and-1, 5-benzothiazepinone-2-acetates," Indian Journal of Chemistry, Section B: Organic and Medicinal Chemistry Scientific Publishers, Jodhpur, In, vol. 22B, pp. 300-302 (1983).

Still et al., "Behavior of thiochromanone and isothiochromanone sulfoxides in the Schmidt reaction. Isolation of a novel azide product from thiochromone sulfone," Canadian Journal of Chemistry, pp. 276-282 (1975).

Wuensch et al., "Benzokondensierte 7-ring-Heterocyclen, I.2.3.4.5- Tetrahydro-1.4-benzothiazepin-one-(5) = Benzo condensed heterocycles with 7-membered rings. I. 2,3,4,5-Tetrahydro-1, 4-benzothiazepin-5-ones," Chemische Berichte, verlag Chemie GMBH. Weinheim, DE, vol. 102, pp. 1618-1625 (May 1969) (English Abstract).

Wuensch et al., "Benzokondensierte 7-ring-Heterocyclen, IV. Schmidt-Reaktion and 1-thio-chromanonen-(4) and 1-Thiochromanon-(4)-1.1-dioxiden=benzo-fused seven-membered heterocyclic compounds. IV. Schmidt reaction on 1-thio-4-chromanone and 1-thio-4-chromanone 1,1-dioxides," Chemische Berichte, verlag Chemie GMBH. Weinheim, DE, vol. 103, pp. 2302-2307 (Jul. 1970) (English Abstract).

Altamura et al.,"Investigation on the flexibility of chiral tricyclic derivatives," New J. Chem., 32, 1617-1627 (2008).

Final Office Action mailed on Aug. 5, 2009 for U.S. Appl. No. 10/809,089, filed on Mar. 25, 2004.

Final Office Action mailed on Jun. 22, 2009 for U.S. Appl. No. 11/212,309, filed Aug. 25, 2005.

Garofalo et a., "Polycondensed Heterocycles. X. Method for the Preparation of Pyrrolo[2,1-c][1,4]benzothiazepines by Intramolecular Mitsunobu Cyclisation," Tetrahedron 55:1479-1490 (1999).

Hirai et al., Reactivity of some benzodiazepine derivatives, Sankyo Kenkyusho Nenpo, 44: 141-50 (1992).

International Search Report and Written Opinion mailed Jan. 10, 2008 for International Patent Application No. PCT/US07/12969 filed Jun. 1, 2007.

Johansson B.W.,"Adams-Stokes Syndrome. A Review and follow-up Study of Forty-two cases," The American Journal of Cardiology, pp. 76-93 (Jul. 1961).

Most et al., "Sealing the leak, healing the heart," Nature Medicine, vol. 9, pp. 993-994 (Aug. 2003).

Non Final Office action mailed on Feb. 5, 2009 for U.S. Appl. No. 10/809,089, filed on Mar. 25, 2004.

Non Final Office Action mailed Sep. 17, 2008 for U.S. Appl. No. 11/305,528, filed Dec. 16, 2005.

Nousiainan et al., "Cardiac arrhythmias in the differential diagnosis of epilepsy," J. Neurol, vol. 236, pp. 93-96 (1989).

Pfammater et al., "Cardiac arrhythmias mimicking primary neurological disorders: a difficult diagnostic situation," Acta Paediatr, vol. 84, pp. 569-572 (1995).

Schott et al., "Cardiac Arrhythmias that masquerade as epilepsy," British Medical Journal, vol. 1, pp. 1454-1457 (1977).

Supplementary European Search Report mailed Dec. 12, 2008 for European Patent Application No. 04794052.3 filed Oct. 4, 2004.

Supplementary European Search Report mailed May 14, 2009 for European Patent Application No. 06801887.8, filed Aug. 17, 2006.

Supplementary European Search Report mailed on Mar. 27, 2009 for European Patent Application No. 05732932.8 filed Mar. 22, 2005.

Bellinger et al., "Remodeling of ryanodine receptor complex causes "leaky" channels: A molecular mechanism for decreases exercise capacity," PNAS, vol. 105, pp. 2198-2202 (Feb. 12, 2008).

Bellinger et al., "Hypernitrosylated ryanodine receptor calcium release channels are leaky in dystrophic muscle," Nature Medicine, Advance online publication; Received Jul. 2, 2008; accepted Dec. 9, 2008; published online Feb. 8, 2009, pp. 1-6.

Blayney et al., "Ryanodine receptor-mediated arrhythmias and sudden cardiac death," Pharmacol Ther, vol. 123(2), pp. 151-177 (Aug. 2009).

Ellison et al., "Acute β-Adrenergic overload produces Myocyte damage through Calcium Leakage from the Ryanodine Receptor 2 but Spares Cardiac Stem cells," The Journal of Biological Chemistry vol. 282, pp. 11397-11409 (Apr. 13, 2007).

Lehnart et al., "Leaky Ca2 release Channel/ryanodine receptor 2 causes seizures and sudden caridac death in mice," The Journal of Clinical Investigation, vol. 118, pp. 2230-2245 (Jun. 2008).

Oyama et al., "Arrhythmogenic right ventricular cardiomyopathy in boxer dogs is associated with calstabin2 deficiency," Journal of Veterinary Cardiology, vol. 10, pp. 1-10 (2008).

Wehrens et al., "Ryanodine receptor/calcium release channel Pka phosphorylation: A critical mediator of heart failure progression," PNAS, vol. 103, pp. 511-518 (Jan. 17, 2006).

Wehrens et al., "Regulation of RYRs by phosphorylation/ Dephosphorylation," Ryanodine Receptors. Structure, Function and dysfunction in clinical disease, Edited by Xander H.T. Wehrens and Andrew R. Marks, Springer, pp. 155-260 (2005).

Vest John et al. "Defective Cardiac Ryanodine receptor regulation during atrial fibrillation," Circulation vol. 111, pp. 2025-2032 (Apr. 26, 2005).

The Cardiac Arrhythmia Suppression Trial (CAST) investigators, Special Report "Preliminary Report: Effect of Encainide and Flecainide on mortality in a randomized trial of arrhythmia suppression after myocardial infraction," the New Encload Jour. of Med., vol. 321, No. 6, pp. 406-412 (1989).

Harrison's Principles of Internal Midicinae, 13$^{th}$ edition, vol. 1, published 1994 by McGraw-Hill, Inc. (NY), pp. 1022-1024.

Non-Final Office Action mailed Nov. 20, 2009 for U.S. Appl. No. 11/212,309, filed Aug. 25, 2005.

Non-Final Advisory Office Action mailed Sep. 22, 2009 for U.S. Appl. No. 11/212,309, filed Aug. 25, 2005.

Non-Final Advisory Office Action mailed Jun. 5, 2009 for U.S. Appl. No. 11/212,309, filed Aug. 25, 2005.

Non-Final Office Action (Restriction Requirement) mailed Jan. 9, 2008 for U.S. Appl. No. 11/088,058, filed Mar. 23, 2005.

Non-Final Office Action (Restriction Requirement) mailed Jul. 29, 2008 for U.S. Appl. No. 11/088,058, filed Mar. 23, 2005.

Non-Final Office Action (Restriction Requirement) mailed May 13, 2008 for U.S. Appl. No. 11/212,143, filed Aug. 23, 2005.

A

JTV-519

B

C

D

A

B

C

D

A

B

A

B

A

B

C

A

B

C

A

Control (Wild-type)
Po 0.001, To 1.4 ms, Tc 1425.1 ms

B

C

*mdx (dystrophin⁻ᐟ⁻)*
Po 0.107, To 2.9 ms, Tc 23.1 ms

D

E

F

A

B

A

B

A

B

C

D

A

B

A

B

A

B

A

B

C

US 7,879,840 B2

AGENTS FOR PREVENTING AND TREATING DISORDERS INVOLVING MODULATION OF THE RYR RECEPTORS

This application is a continuation-in-part of U.S. patent application Ser. No. 11/212,309, filed on Aug. 25, 2005.

This invention was made with government support under NIH Grant No. PO1 HL 67849-01. As such, the United States government may have certain rights in this invention.

FIELD OF THE INVENTION

This invention relates to compounds and their use to treat and prevent disorders and diseases associated with the RyR receptors that regulate calcium channel functioning in cells. More particularly, the invention discloses compounds that are related to 1,4-benzothiazepines and are useful to treat cardiac and skeletal muscular disorders. The invention also discloses pharmaceutical compositions comprising the compounds and articles of manufacture comprising the pharmaceutical compositions.

BACKGROUND OF THE INVENTION

The sarcoplasmic reticulum (SR) is a structure in cells that functions, among other things, as a specialized intracellular calcium ($Ca^{2+}$) store. Channels in the SR called ryanodine receptors (RyRs) open and close to regulate the release of $Ca^{2+}$ from the SR into the intracellular cytoplasm of the cell. Release of $Ca^{2+}$ into the cytoplasm from the SR increases cytoplasmic $Ca^{2+}$ concentration. Open probability (Po) of the RyR receptor refers to the likelihood that the RyR channel is open at any given moment, and therefore capable of releasing $Ca^{2+}$ into the cytoplasm from the SR.

There are three types of ryanodine receptors, all of which are highly-related $Ca^{2+}$ channels: RyR1, RyR2, and RyR3. RyR1 is found predominantly in skeletal muscle as well as other tissues, RyR2 is found predominantly in the heart as well as other tissues, and RyR3 is found in the brain as well as other tissues. The RyR channels are formed by four RyR polypeptides in association with four FK506 binding proteins (FKBPs), specifically FKBP12 (calstabin1) and FKBP12.6 (calstabin2). Calstabin1 binds to RyR1, calstabin2 binds to RyR2, and calstabin1 binds to RyR3. The FKBP proteins (calstabin1 and calstabin2) bind to the RyR channel (one molecule per RyR subunit), stabilize RyR-channel functioning, and facilitate coupled gating between neighboring RyR channels, thereby preventing abnormal activation of the channel during the channel's closed state.

Besides the calstabin binding proteins, protein kinase A (PKA) also binds to the cytoplasmic surface of the RyR receptors. PKA phosphorylation of the RyR receptors causes partial dissociation of calstabins from RyRs. Dissociation of calstabin from RyR causes increased open probability of RyR, and therefore increased $Ca^{2+}$ release from the SR into the intracellular cytoplasm.

$Ca^{2+}$ release from the SR in skeletal muscle cells and heart cells is a key physiological mechanism that controls muscle performance, because increased concentration of $Ca^{2+}$ in the intracellular cytoplasm causes contraction of the muscle.

Excitation-contraction (EC) coupling in skeletal muscles involves electrical depolarization of the plasma membrane in the transverse tubule (T-tubule), which activates voltage-gated L-type $Ca^{2+}$ channels (LTCCs). LTCCs trigger $Ca^{2+}$ release from the SR through physical interaction with RyR1. The resulting increase in cytoplasmic $Ca^{2+}$ concentration induces actin-myosin interaction and muscle contraction. To enable relaxation, intracellular $Ca^{2+}$ is pumped back into the SR via SR $Ca^{2+}$-ATPase pumps (SERCAs), which is regulated by phospholamban (PLB) depending on the muscle fiber type.

It has been shown that disease form's that result in sustained activation of the sympathetic nervous system and increased plasma catecholamine levels cause maladaptive activation of intracellular stress pathways resulting in destabilization of the RyR1 channel closed state and intracellular $Ca^{2+}$ leak. SR $Ca^{2+}$ leak via RyR1 channels was found to deplete intracellular SR calcium stores, to increase compensatory energy consumption, and to result in significant acceleration of muscle fatigue. The stress-induced muscle defect permanently reduces isolated muscle and in vivo performance particularly in situations of increased demand.

It also has been shown that destabilization of the RyR1 closed state occurs under pathologic conditions of increased sympathetic activation and involves depletion of the stabilizing calstabin1 (FKBP12) channel subunit. Proof-of-principle experiments have shown that PKA activation as an end effector of the sympathetic nervous systems increases RyR1 PKA phosphorylation at Ser-2843 which decreases the binding affinity of calstabin1 to RyR1and increases channel open probability.

In cardiac striated muscle, RyR2 is the major $Ca^{2+}$-release channel required for EC coupling and muscle contraction. During EC coupling, depolarization of the cardiac-muscle cell membrane during phase zero of the action potential activates voltage-gated $Ca^{2+}$ channels. $Ca^{2+}$ influx through the open voltage-gated channels in turn initiates $Ca^{2+}$ release from the SR via RyR2. This process is known as $Ca^{2+}$-induced $Ca^{2+}$ release. The RyR2-mediated, $Ca^{2+}$-induced $Ca^{2+}$ release then activates the contractile proteins in the cardiac cell, resulting in cardiac muscle contraction.

Phosphorylation of cardiac RyR2 by PKA is an important part of the "fight or flight" response that increases cardiac EC coupling gain by augmenting the amount of $Ca^{2+}$ released for a given trigger. This signaling pathway provides a mechanism by which activation of the sympathetic nervous system, in response to stress, results in increased cardiac output. PKA phosphorylation of RyR2 increases the open probability of the channel by dissociating calstabin2 (FKBP12.6) from the channel complex. This, in turn, increases the sensitivity of RyR2 to $Ca^{2+}$-dependent activation.

Despite advances in treatment, heart failure remains an important cause of mortality in Western countries. An important hallmark of heart failure is reduced myocardial contractility. In heart failure, contractile abnormalities result, in part, from alterations in the signaling pathway that allows the cardiac action potential to trigger $Ca^{2+}$ release via RyR2 channels and muscle contraction. In particular, in failing hearts, the amplitude of the whole-cell $Ca^{2+}$ transient is decreased and the duration prolonged.

Cardiac arrhythmia, a common feature of heart failure, results in many of the deaths associated with the disease. Atrial fibrillation (AF) is the most common cardiac arrhythmia in humans, and represents a major cause of morbidity and mortality. Structural and electrical remodeling—including shortening of atrial refractoriness, loss of rate-related adaptation of refractoriness, and shortening of the wavelength of re-entrant wavelets—accompany sustained tachycardia. This remodeling is likely important in the development, maintenance and progression of atrial fibrillation. Studies suggest that calcium handling plays a role in electrical remodeling in atrial fibrillation.

Approximately 50% of all patients with heart disease die from fatal cardiac arrhythmias. In some cases, a ventricular arrhythmia in the heart is rapidly fatal—a phenomenon referred to as "sudden cardiac death" (SCD). Fatal ventricular arrhythmias and SCD also occur in young, otherwise-healthy individuals who are not known to have structural heart disease. In fact, ventricular arrhythmia is the most common cause of sudden death in otherwise-healthy individuals.

Catecholaminergic polymorphic ventricular tachycardia (CPVT) is an inherited disorder in individuals with structurally normal hearts. It is characterized by stress-induced ventricular tachycardia—a lethal arrhythmia that causes SCD. In subjects with CPVT, physical exertion and/or stress induce bidirectional and/or polymorphic ventricular tachycardias that lead to SCD even in the absence of detectable structural heart disease. CPVT is predominantly inherited in an autosomal-dominant fashion. Individuals with CPVT have ventricular arrhythmias when subjected to exercise, but do not develop arrhythmias at rest. Studies have identified mutations in the human RyR2 gene, on chromosome 1 q42-q43, in individuals with CPVT.

Failing hearts (e.g., in patients with heart failure and in animal models of heart failure) are characterized by a maladaptive response that includes chronic hyperadrenergic stimulation. In heart failure, chronic beta-adrenergic stimulation is associated with the activation of beta-adrenergic receptors in the heart, which, through coupling with G-proteins, activate adenylyl cyclase and thereby increase intracellular cAMP concentration. CAMP activates cAMP-dependent PKA, which has been shown to induce hyperphosphorylation of RyR2. Thus, chronic heart failure is a chronic hyperadrenergic state that results in several pathologic consequences, including PKA hyperphosphorylation of RyR2.

The PKA hyperphosphorylation of RyR2 has been proposed as a factor contributing to depressed contractile function and arrhythmogenesis in heart failure. Consistent with this hypothesis, PKA hyperphosphorylation of RyR2 in failing hearts has been demonstrated, in vivo, both in animal models and in patients with heart failure undergoing cardiac transplantation.

In failing hearts, the hyperphosphorylation of RyR2 by PKA induces the dissociation of FKBP12.6 (calstabin2) from the RyR2 channel. This causes marked changes in the biophysical properties of the RyR2 channel, including increased open probability (Po) due to an increased sensitivity to $Ca^{2+}$-dependent activation; destabilization of the channel, resulting in subconductance states; and impaired coupled gating of the channels, resulting in defective EC coupling and cardiac dysfunction. Thus, PKA-hyperphosphorylated RyR2 is very sensitive to low-level $Ca^{2+}$ stimulation, and this manifests itself as a diastolic SR $Ca^{2+}$ leak through the PKA hyperphosphorylated RyR2 channel.

The maladaptive response to stress in heart failure results in depletion of FKBP12.6 from the channel macromolecular complex. This leads to a shift to the left in the sensitivity of RyR2 to $Ca^{2+}$-induced $Ca^{2+}$ release, resulting in channels that are more active at low-to-moderate $Ca^{2+}$ concentrations. Over time, the increased "leak" through RyR2 results in resetting of the SR $Ca^{2+}$ content to a lower level, which in turn reduces EC coupling gain and contributes to impaired systolic contractility.

Additionally, a subpopulation of RyR2 that are particularly "leaky" can release SR $Ca^{2+}$ during the resting phase of the cardiac cycle, diastole. This results in depolarizations of the cardiomyocyte membrane known as delayed after-depolarizations (DADs), which are known to trigger fatal ventricular cardiac arrhythmias.

In patients with CPVT mutations in their RyR2 and otherwise structurally-normal hearts, a similar phenomenon is at work. Specifically, it is known that exercise and stress induce the release of catecholamines that activate beta-adrenergic receptors in the heart. Activation of the beta-adrenergic receptors leads to PKA hyperphosphorylation of RyR2 channels. Evidence also suggests that the PKA hyperphosphorylation of RyR2 resulting from beta-adrenergic-receptor activation renders mutated RyR2 channels more likely to open in the relaxation phase of the cardiac cycle, increasing the likelihood of arrhythmias.

Cardiac arrhythmias are known to be associated with diastolic SR $Ca^{2+}$ leaks in patients with CPVT mutations in their RyR2 and otherwise structurally-normal hearts. In these cases, the most common mechanism for induction and maintenance of ventricular tachycardia is abnormal automaticity. One form of abnormal automaticity, known as triggered arrhythmia, is associated with aberrant release of SR $Ca^{2+}$, which initiates DADs. DADs are abnormal depolarizations in cardiomyocytes that occur after repolarization of a cardiac action potential. The molecular basis for the abnormal SR $Ca^{2+}$ release that results in DADs has not been fully elucidated. However, DADs are known to be blocked by ryanodine, providing evidence that RyR2 plays a key role in the pathogenesis of this aberrant $Ca^{2+}$ release.

U.S. Pat. No. 6,489,125 discusses JTV-519 (4-[3-(4-benzylpiperidin-1-yl)propionyl]-7-methoxy-2,3,4,5-tetrahydro-1,4-benzothiazepine monohydrochloride; also known as k201 or ICP-Calstan 100), a 1,4-benzothiazepine, as a new modulator of RyR calcium-ion channels.

Co-pending application U.S. Ser. No. 10/763,498 discusses RyR2 as a target for treating and preventing heart failure and cardiac arrhythmias, including atrial fibrillation and cardiac arrhythmias that cause exercise-induced sudden cardiac death (SCD). RyR2 channels with 7 different CPVT mutations (e.g., S2246L, R2474S, N4104K, R4497C, P2328S, Q4201R, V4653F) were found to have functional defects that resulted in channels that became leaky (i.e., a calcium leak) when stimulated during exercise. The mechanism for the VT in CPVT has been demonstrated to be the same as the mechanism for VT in heart failure.

It has been shown that exercise-induced arrhythmias and sudden death (in patients with CPVT) result from a reduced affinity or FKBP12.6 (calstabin2) for RyR2. Additionally, it has been demonstrated that exercise activates RyR2 as a result of phosphorylation by adenosine 3',5'-monophosphate (cAMP)-dependent protein kinase (PKA). Mutant RyR2 channels, which had normal function in planar lipid bilayers under basal conditions, were more sensitive to activation by PKA phosphorylation—exhibiting increased activity (open probability) and prolonged open states, as compared with wild-type channels. In addition, PKA-phosphorylated mutant RyR2 channels were resistant to inhibition by $Mg^{2+}$, a physiological inhibitor of the channel, and showed reduced binding to FKBP12.6 (aka calstabin2, which stabilizes the channel in the closed state). These findings indicate that, during exercise, when the RyR2 are PKA-phosphorylated, the mutant CPVT channels are more likely to open in the relaxation phase of the cardiac cycle (diastole), increasing the likelihood of arrhythmias triggered by SR $Ca^{2+}$ leak.

Additionally, co-pending U.S. patent application Ser. No. 09/288,606 discusses a method for regulating contraction of a subject's heart by administering a compound that regulates PKA phosphorylation of an RyR2 receptor and specifically decreases PKA phosphorylation. Co-pending U.S. patent application Ser. No. 10/608,723 also discusses a method for treating and prophylaxis for atrial tachyarrhythmia and exercise and stress-induced arrhythmias by administration of an agent which inhibits PKA phosphorylation of RyR2.

SUMMARY OF THE INVENTION

In view of the foregoing, there is a need to identify new agents effective for treating or preventing disorders and diseases associated with the RyR receptors that regulate calcium channel functioning in cells, including skeletal muscular disorders and diseases and especially cardiac disorders and diseases. More particularly, a need remains to identify new compounds that can be used to treat RyR associated disorders by, for example, repairing the leak in RyR channels, and enhancing binding of FKBP proteins (calstabin1 and calstabin2) to PKA-phosphorylated RyR, and to mutant RyR that otherwise have reduced affinity for, or do not bind to, FKBP12 and FKBP12.6. Embodiments of the invention solve some or all of these needs.

Accordingly, the present invention generally provides compounds that may be classified as 1,4-benzothiazepines and sometimes are referred to herein as "RyCals."

The present invention further provides compounds of Formula I:

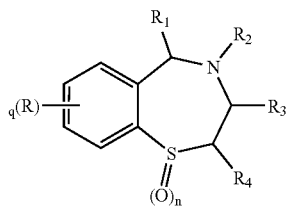

wherein,
n is 0, 1, or 2;
q is 0, 1, 2, 3, or 4;
each R is independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, —O-acyl, alkyl, alkoxyl, alkylamino, alkylarylamino, alkylthio, cycloalkyl, alkylaryl, aryl, heteroaryl, heterocyclyl, heterocyclylalkyl, alkenyl, alkynyl, (hetero-)aryl, (hetero-)arylthio, and (hetero-)arylamino; wherein each acyl, —O-acyl, alkyl, alkoxyl, alkylamino, alkylarylamino, alkylthio, cycloalkyl, alkylaryl, aryl, heteroaryl, heterocyclyl, heterocyclylalkyl, alkenyl, alkynyl, (hetero-)aryl, (hetero-)arylthio, and (hetero-)arylamino may be optionally substituted;
$R_1$ is selected from the group consisting of H, oxo, alkyl, alkenyl, aryl, alkylaryl, cycloalkyl, heteroaryl, and heterocyclyl; wherein each alkyl, alkenyl, aryl, alkylaryl, cycloalkyl, heteroaryl, and heterocyclyl may be optionally substituted;
$R_2$ is selected from the group consisting of H, —C(=O)R$_5$, —C(=S)R$_6$, —SO$_2$R$_7$, —P(=O)R$_8$R$_9$, —(CH$_2$)$_m$—R$_{10}$, alkyl, aryl, alkylaryl, heteroaryl, cycloalkyl, cycloalkylalkyl, and heterocyclyl; wherein each alkyl, aryl, alkylaryl, heteroaryl, cycloalkyl, cycloalkylalkyl, and heterocyclyl may be optionally substituted;
$R_3$ is selected from the group consisting of H , —CO$_2$Y, —C(=O)NHY, acyl, —O-acyl, alkyl, alkenyl, aryl, alkylaryl, cycloalkyl, heteroaryl, and heterocyclyl; wherein each acyl, alkyl, alkenyl, aryl, alkylaryl, cycloalkyl, heteroaryl, and heterocyclyl may be optionally substituted; and wherein Y is selected from the group consisting of H, alkyl, aryl, alkylaryl, cycloalkyl, heteroaryl, and heterocyclyl, and wherein each alkyl, aryl, alkylaryl, cycloalkyl, heteroaryl, and heterocyclyl may be optionally substituted;
R4 is selected from the group consisting of H, alkyl, alkenyl, aryl, alkylaryl, cycloalkyl, heteroaryl, and heterocyclyl; wherein each alkyl, alkenyl, aryl, alkylaryl, cycloalkyl, heteroaryl, and heterocyclyl may be optionally substituted;
$R_5$ is selected from the group consisting of —NR$_{15}$R$_{16}$, —(CH$_2$)$_q$NR$_{15}$R$_{16}$, —NHNR$_{15}$R$_{16}$, —NHOH, —OR$_{15}$, —C(=O)NHNR$_{15}$R$_{16}$, —CO$_2$R$_{15}$, —C(=O)NR$_{15}$R$_{16}$, —CH$_2$X, acyl, alkyl, alkenyl, aryl, alkylaryl, cycloalkyl, cycloalkylalkyl, heteroaryl, heterocyclyl, and heterocyclylalkyl; wherein each acyl, alkyl, alkenyl, aryl, alkylaryl, cycloalkyl, cycloalkylalkyl, heteroaryl, heterocyclyl, and heterocyclylalkyl may be optionally substituted, and wherein q is 1, 2, 3, 4, 5, or 6;
$R_6$ is selected from the group consisting of —OR$_{15}$, —NHNR$_{15}$R$_{16}$, —NHOH, —NR$_{15}$R$_{16}$, —CH$_2$X, acyl, alkenyl, alkyl, aryl, alkylaryl, cycloalkyl, cycloalkylalkyl, heteroaryl, heterocyclyl, and heterocyclylalkyl; wherein each acyl, alkenyl, alkyl, aryl, alkylaryl, cycloalkyl, cycloalkylalkyl, heteroaryl, heterocyclyl, and heterocyclylalkyl may be optionally substituted;
$R_7$ is selected from the group consisting of —OR$_{15}$, —NR$_{15}$R$_{16}$, —NHNR$_{15}$R$_{16}$, —NHOH, —CH$_2$X, alkyl, alkenyl, alkynyl, aryl, alkylaryl, cycloalkyl, cycloalkylalkyl, heteroaryl, heterocyclyl, and heterocyclylalkyl; wherein each alkyl, alkenyl, alkynyl, aryl, alkylaryl, cycloalkyl, cycloalkylalkyl, heteroaryl, heterocyclyl, and heterocyclylalkyl may be optionally substituted;
$R_8$ and $R_9$ independently are selected from the group consisting of OH, acyl, alkenyl, alkoxyl, alkyl, alkylamino, aryl, alkylaryl, cycloalkyl, cycloalkylalkyl, heteroaryl, heterocyclyl, and heterocyclylalkyl; wherein each acyl, alkenyl, alkoxyl, alkyl, alkylamino, aryl, alkylaryl, cycloalkyl, cycloalkylalkyl, heteroaryl, heterocyclyl, and heterocyclylalkyl may be optionally substituted;
$R_{10}$ is selected from the group consisting of —NR$_{15}$R$_{16}$, OH, —SO$_2$R$_{11}$, —NHSO$_2$R$_{11}$, C(=O)(R$_{12}$), NHC=O(R$_{12}$), —OC=O(R$_{12}$), and —P(=O)R$_{13}$R$_{14}$;
$R_{11}$, $R_{12}$, $R_{13}$, and $R_{14}$ independently are selected from the group consisting of H, OH, NH$_2$, —NHNH$_2$, —NHOH, acyl, alkenyl, alkoxyl, alkyl, alkylamino, aryl, alkylaryl, cycloalkyl, cycloalkylalkyl, heteroaryl, heterocyclyl, and heterocyclylalkyl; wherein each acyl, alkenyl, alkoxyl, alkyl, alkylamino, aryl, alkylaryl, cycloalkyl, cycloalkylalkyl, heteroaryl, heterocyclyl, and heterocyclylalkyl may be optionally substituted;
X is selected from the group consisting of halogen, —CN, —CO$_2$R$_{15}$, —C(=O)NR$_{15}$R$_{16}$, —NR$_{15}$R$_{16}$, —OR$_{15}$, —SO$_2$R$_7$, and —P(=O)R$_8$R$_9$; and
$R_{15}$ and $R_{16}$ independently are selected from the group consisting of H, acyl, alkenyl, alkoxyl, OH, NH$_2$, alkyl, alkylamino, aryl, alkylaryl, cycloalkyl, cycloalkylalkyl, heteroaryl, heterocyclyl, and heterocyclylalkyl; wherein each acyl, alkenyl, alkoxyl, alkyl, alkylamino, aryl, alkylaryl, cycloalkyl, cycloalkylalkyl, heteroaryl, heterocyclyl, and heterocyclylalkyl may be optionally substituted; and optionally $R_{15}$ and $R_{16}$ together with the N to which they are bonded may form a heterocycle which may be substituted;
the nitrogen in the benzothiazepine ring may optionally be a quaternary nitrogen; and
enantiomers, diastereomers, tautomers, pharmaceutically acceptable salts, hydrates, solvates, complexes, and prodrugs thereof;

provided that when q is 0 and n is 0, then $R_2$ is not H, Et, —C(═O)$NH_2$, (═O)NHPh, —C(═S)NH-nButyl, —C(═O)NHC(═O)$CH_2$Cl, —C(═O)H, —C(═O)Me, —C(═O)Et, —C(═O)CH═$CH_2$, —S(═O)$_2$Me, or —S(═O)$_2$Et;

further provided that when q is 0 and n is 1 or 2, then $R_2$ is not —C(═O)Me, —C(═O)Et, —S(═O)$_2$Me, or —S(═O)$_2$Et;

further provided that when q is 1, and R is Me, Cl, or F at the 6 position of the benzothiazepene ring, then $R_2$ is not H, Me, —C(═O)H, —C(═O)Me, —C(═O)Et, —C(═O)Ph, —S(═O)$_2$Me, or —S(═O)$_2$Et; and further provided that when q is 1, n is 0, and R is $OCT_3$, OH, $C_1$-$C_3$ alkoxyl at the 7 position of the benzothiazepene ring, then $R_2$ is not H, —C(═O)CH═$CH_2$, or

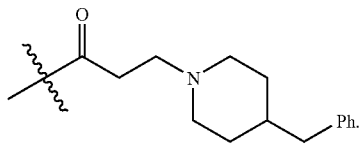

In one embodiment, the present invention provides compounds of Formula I, as described above, with the proviso that the compound is not S24 or S68.

In one embodiment, the present invention provides compounds of Formula I-a:

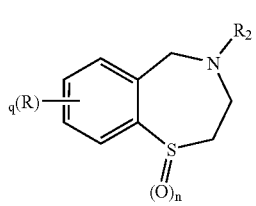

(I-a)

wherein:

n is 0, 1, or 2;

q is 0, 1, 2, 3, or 4;

each R is independently selected from the group consisting of H, halogen, —OH, —$NH_2$, —$NO_2$, —CN, —$CF_3$, —$OCF_3$, —$N_3$, —$SO_3$H, —S(═O)$_2$alkyl, —S(═O)alkyl, —OS(═O)$_2$$CF_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; wherein each acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino may be substituted or unsubstituted;

$R_2$ is selected from the group consisting of H, —C═O($R_5$), —C═S($R_6$), —$SO_2R_7$, —P(═O)$R_8R_9$, —(CH$_2$)$_m$—$R_{10}$, alkyl, aryl, heteroaryl, cycloalkyl, cycloalkylalkyl, and heterocyclyl; wherein each alkyl, aryl, heteroaryl, cycloalkyl, cycloalkylalkyl, and heterocyclyl may be substituted or unsubstituted;

$R_5$ is selected from the group consisting of —$NR_{15}R_{16}$, —$NHNR_{15}R_{16}$, —NHOH, —$OR_{15}$, —C(═O)$NHNR_{15}R_{16}$, —$CO_2R_{15}$, —C(═O)$NR_{15}R_{16}$, —$CH_2$X, acyl, alkyl, alkenyl, alkynyl, aryl, cycloalkyl, cycloalkylalkyl, heterocyclyl, and heterocyclylalkyl; wherein each acyl, alkyl, alkenyl, alkynyl, aryl, cycloalkyl, cycloalkylalkyl, heterocyclyl, and heterocyclylalkyl may be substituted or unsubstituted;

$R_6$ is selected from the group consisting of —$OR_{15}$, —$NHNR_{15}R_{16}$, —NHOH, —$NR_{15}R_{16}$, —$CH_2$X, acyl, alkenyl, alkyl, aryl, cycloalkyl, cycloalkylalkyl, heterocyclyl, and heterocyclylalkyl; wherein each acyl, alkenyl, alkyl, aryl, cycloalkyl, cycloalkylalkyl, heterocyclyl, and heterocyclylalkyl may be substituted or unsubstituted;

$R_7$ is selected from the group consisting of H, —$OR_{15}$, —$NR_{15}R_{16}$, —$NHNR_{15}R_{16}$, —NHOH, —$CH_2$X, alkyl, akenyl, alkynyl, aryl, cycloalkyl, cycloalkylalkyl, heterocyclyl, and heterocyclylalkyl; wherein each alkyl, akenyl, alkynyl, aryl, cycloalkyl, cycloalkylalkyl, heterocyclyl, and heterocyclylalkyl may be substituted or unsubstituted;

$R_8$ and $R_9$ independently are selected from the group consisting of —OH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted;

$R_{10}$ is selected from the group consisting of —$NR_{15}R_{16}$, OH, —$SO_2R_{11}$, —$NHSO_2R_{11}$, —C(═O)$R_{12}$, —NH(C═O)$R_{12}$, —O(C═O)$R_{12}$, and —P(═O)$R_{13}R_{14}$;

m is 0, 1, 2, 3, or 4;

$R_{11}$, $R_{12}$, $R_{13}$, and $R_{14}$ independently are selected from the group consisting of H, OH, $NH_2$, —$NHNH_2$, —NHOH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted;

X is selected from the group consisting of halogen, —CN, —$CO_2R_{15}$, —C(═O)$NR_{15}R_{16}$, —$NR_{15}R_{16}$, —$OR_{15}$, —$SO_2R_7$, and —P(═O)$R_8R_9$; and $R_{15}$ and $R_{16}$ independently are selected from the group consisting of H, acyl, alkenyl, alkoxyl, OH, $NH_2$, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and optionally $R_{15}$ and $R_{16}$ together with the N to which they are bonded may form a heterocycle which may be substituted or unsubstituted;

the nitrogen in the benzothiazepine ring may be optionally a quaternary nitrogen; and enantiomers, diastereomers, tautomers, pharmaceutically acceptable salts, hydrates, solvates, complexes, and prodrugs thereof;

provided that when q is 0 and n is 0, then $R_2$ is not H, Et, —C(═O)$NH_2$, (═O)NHPh, —C(═S)NH-nButyl, —C(═O)NHC(═O)$CH_2$Cl, —C(═O)H, —C(═O)Me, —C(═O)Et, —C(═O)CH═$CH_2$, —S(═O)$_2$Me, or —S(═O)$_2$Et;

further provided that when q is 0 and n is 1 or 2, then $R_2$ is not —C(═O)Me, —C(═O)Et, —S(═O)$_2$Me, or —S(═O)$_2$Et;

further provided that when q is 1, and R is Me, Cl, or F at the 6 position of the benzothiazepene ring, then $R_2$ is not H, Me, —C(═O)H, —C(═O)Me, —C(═O)Et, —C(═O)Ph, —S(═O)$_2$Me, or —S(═O)$_2$Et; and further provided that when q is 1, n is 0, and R is $OCT_3$, OH, $C_1$-$C_3$ alkoxyl at the 7 position of the benzothiazepene ring, then $R_2$ is not H, —C(═O)CH═$CH_2$, or

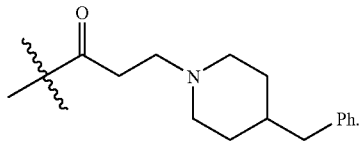

In certain embodiments, the present invention provides compounds of formula I-a, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1, or 2.

In other embodiments, the present invention provides compounds of formula I-a, wherein R$_2$ is selected from the group consisting of —C=O(R$_5$), —C=S(R$_6$), —SO$_2$R$_7$, —P(=O)R$_8$R$_9$, and —(CH$_2$)$_m$—R$_{10}$.

In yet another embodiment, the present invention provides compounds of formula I-b:

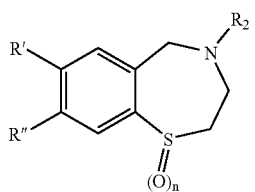

(I-b)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

R$_2$ and n are as defined in compounds of formula I-a above;

and enantiomers, diastereomers, tautomers, pharmaceutically acceptable salts, hydrates, solvates, complexes and pro-drugs thereof.

In certain embodiments, the present invention provides compounds of formula I-b, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-b, wherein R$_2$ is selected from the group consisting of —C=O(R$_5$), —C=S(R$_6$), —SO$_2$R$_7$, —P(=O)R$_8$R$_9$, and —(CH$_2$)$_m$—R$_{10}$.

In yet another embodiment, the present invention provides compounds formula of I-c:

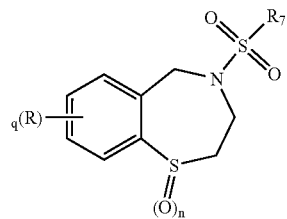

(I-c)

wherein each R, R$_7$, q, and n is as defined in compounds of formula I-a above; and enantiomers, diastereomers, tautomers, pharmaceutically acceptable salts, hydrates, solvates, complexes and pro-drugs thereof.

In certain embodiments, the present invention provides compounds of formula I-c, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1, or 2.

In other embodiments, the present invention provides compounds of formula I-c, wherein R$_7$ is selected from the group consisting of —OH, —NR$_{15}$R$_{16}$, alkyl, alkenyl, aryl, cycloalkyl, cycloalkylalkyl, heterocyclyl, and heterocyclylalkyl; wherein each alkyl, akenyl, aryl, cycloalkyl, cycloalkylalkyl, heterocyclyl, and heterocyclylalkyl may be substituted or unsubstituted.

In a further embodiment, the present invention provides compounds of formula of I-d:

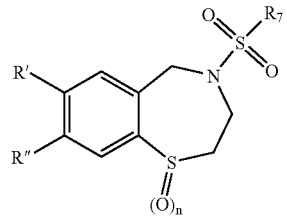

(I-d)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

R$_7$ and n are as defined in compounds of formula I-a above;
and enantiomers, diastereomers, tautomers, pharmaceutically acceptable salts, hydrates, solvates, complexes and pro-drugs thereof.

In certain embodiments, the present invention provides compounds of formula I-d, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-d, wherein $R_7$ is selected from the group consisting of —OH, —$NR_{15}R_{16}$, alkyl, alkenyl, aryl, cycloalkyl, cycloalkylalkyl, heterocyclyl, and heterocyclylalkyl; wherein each alkyl, akenyl, aryl, cycloalkyl, cycloalkylalkyl, heterocyclyl, and heterocyclylalkyl may be substituted or unsubstituted.

In one embodiment, the present invention provides compounds of formula of I-e:

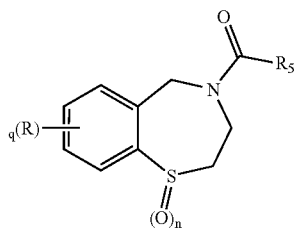

(I-e)

wherein each R, $R_5$, q and n is as defined compounds of formula I-a above; and enantiomers, diastereomers, tautomers, pharmaceutically acceptable salts, hydrates, solvates, complexes and pro-drugs thereof.

In certain embodiments, the present invention provides compounds of formula I-e, wherein each R is independently selected from the group consisting of H, halogen, —OH, OMe, —$NH_2$, —$NO_2$, —CN, —$CF_3$, —$OCF_3$, —$N_3$, —$S(=O)_2C_1$-$C_4$alkyl, —$S(=O)C_1$-$C_4$alkyl, —S—$C_1$-$C_4$alkyl, —$OS(=O)_2CF_3$, Ph, —$NHCH_2$Ph, —C(=O)Me, —OC(=O)Me, morpholinyl and propenyl; and n is 0, 1, or 2.

In other embodiments, the present invention provides compounds of formula I-e, wherein $R_5$ is selected from the group consisting of —$NR_{15}R_{16}$, —NHOH, —$OR_{15}$, —$CH_2X$, alkyl, alkenyl, aryl, cycloalkyl, cycloalkylalkyl, heterocyclyl, and heterocyclylalkyl; wherein each acyl, alkyl, alkenyl, aryl, cycloalkyl, cycloalkylalkyl, heterocyclyl, and heterocyclylalkyl may be substituted or unsubstituted.

In some embodiments, the present invention provides compounds of formula I-e, wherein $R_5$ is an alkyl substituted by at least one labeling group, such as a fluorescent, a bioluminescent, a chemiluminescent, a colorimetric and a radioactive labeling group. A fluorescent labeling group can be selected from bodipy, dansyl, fluorescein, rhodamine, Texas red, cyanine dyes, pyrene, coumarins, Cascade Blue™, Pacific Blue, Marina Blue, Oregon Green, 4',6-Diamidino-2-phenylindole (DAPI), indopyra dyes, lucifer yellow, propidium iodide, porphyrins, arginine, and variants and derivatives thereof.

In another embodiment, the present invention provides compounds of formula of I-f:

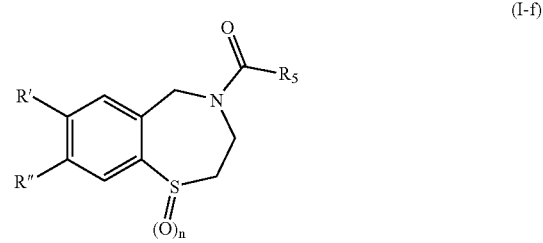

(I-f)

wherein R' and R" are independently selected from the group consisting of H, halogen, —OH, —$NH_2$, —$NO_2$, —CN, —$CF_3$, —$OCF_3$, —$N_3$, —$SO_3H$, —$S(=O)_2$alkyl, —$S(=O)$alkyl, —$OS(=O)_2CF_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_5$ and n are as defined in compounds of formula I-a above;

and enantiomers, diastereomers, tautomers, pharmaceutically acceptable salts, hydrates, solvates, complexes and pro-drugs thereof.

In certain embodiments, the present invention provides compounds of formula I-f, wherein R' and R" are independently selected from the group consisting of H, halogen, —OH, OMe, —$NH_2$, —$NO_2$, —CN, —$CF_3$, —$OCF_3$, —$N_3$, —$S(=O)_2C_1$-$C_4$alkyl, —$S(=O)C_1$-$C_4$alkyl, —S—$C_1$-$C_4$alkyl, —$OS(=O)_2CF_3$, Ph, —$NHCH_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-f, wherein $R_5$ is selected from the group consisting of —$NR_{15}R_{16}$, —NHOH, —$OR_{15}$, —$CH_2X$, alkyl, alkenyl, aryl, cycloalkyl, cycloalkylalkyl, heterocyclyl, and heterocyclylalkyl; wherein each acyl, alkyl, alkenyl, aryl, cycloalkyl, cycloalkylalkyl, heterocyclyl, and heterocyclylalkyl may be substituted or unsubstituted.

In yet another embodiment, the present invention provides compounds of formula of I-g:

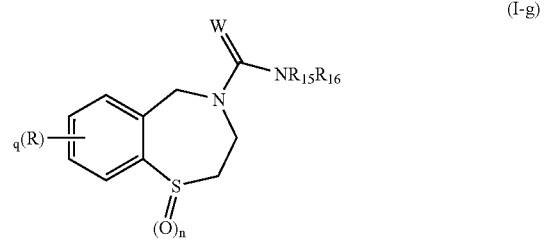

(I-g)

wherein W is S or O; each R, $R_{15}$, $R_{16}$, q, and n is as defined in compounds of formula I-a above; and enantiomers, diastereomers, tautomers, pharmaceutically acceptable salts, hydrates, solvates, complexes and pro-drugs thereof.

In certain embodiments, the present invention provides compounds of formula I-g, wherein each R is independently selected from the group consisting of H, halogen, —OH, OMe, —$NH_2$, —$NO_2$, —CN, —$CF_3$, —$OCF_3$, —$N_3$, —$S(=O)_2C_1$-$C_4$alkyl, —$S(=O)C_1$-$C_4$alkyl, —S—$C_1$-

$C_4$alkyl, $-OS(=O)_2CF_3$, Ph, $-NHCH_2Ph$, $-C(=O)Me$, $-OC(=O)Me$, morpholinyl and propenyl; and n is 0, 1, or 2.

In other embodiments, the present invention provides compounds of formula I-g, wherein $R_{15}$ and $R_{16}$ independently are selected from the group consisting of H, OH, $NH_2$, alkyl, alkylamino, aryl, cycloalkyl, cycloalkylalkyl, heterocyclyl, and heterocyclylalkyl; wherein each alkyl, alkylamino, aryl, cycloalkyl, cycloalkylalkyl, heterocyclyl, and heterocyclylalkyl may be substituted; and optionally $R_{15}$ and $R_{16}$ together with the N to which they are bonded may form a heterocycle which may be substituted.

In some embodiments, the present invention provides compounds of formula I-g, wherein W is O or S.

In yet another embodiment, the present invention provides compounds of formula of I-h:

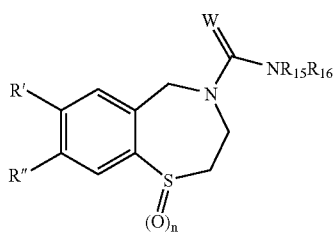

(I-h)

wherein W is S or O;
wherein R' and R" are independently selected from the group consisting of H, halogen, $-OH$, $-NH_2$, $-NO_2$, $-CN$, $-CF_3$, $-OCF_3$, $-N_3$, $-SO_3H$, $-S(=O)_2$alkyl, $-S(=O)$alkyl, $-OS(=O)_2CF_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;
$R_{15}$, $R_{16}$ and n are as defined in compounds of formula I-a above;

and enantiomers, diastereomers, tautomers, pharmaceutically acceptable salts, hydrates, solvates, complexes and pro-drugs thereof.

In certain embodiments, the present invention provides compounds of formula I-h, wherein R' and R" are independently-selected from the group consisting of H, halogen, $-OH$, OMe, $-NH_2$, $-NO_2$, $-CN$, $-CF_3$, $-OCF_3$, $-N_3$, $-S(=O)_2C_1$-$C_4$alkyl, $-S(=O)C_1$-$C_4$alkyl, $-S-C_1$-$C_4$alkyl, $-OS(=O)_2CF_3$, Ph, $-NHCH_2Ph$, $-C(=O)Me$, $-OC(=O)Me$, morpholinyl and propenyl; and n is 0, 1 or 3. In some cases, R' is H or OMe, and R" is H.

In other embodiments, the present invention provides compounds of formula I-h, wherein $R_{15}$ and $R_{16}$ independently are selected from the group consisting of H, OH, $NH_2$, alkyl, alkylamino, aryl, cycloalkyl, cycloalkylalkyl, heterocyclyl, and heterocyclylalkyl; wherein each alkyl, alkylamino, aryl, cycloalkyl, cycloalkylalkyl, heterocyclyl, and heterocyclylalkyl may be substituted; and optionally $R_{15}$ and $R_{16}$ together with the N to which they are bonded may form a heterocycle which may be substituted.

In some embodiments, the present invention provides compounds of formula I-g, wherein W is O or S.

In a further embodiment, the present invention provides compounds of formula of I-i:

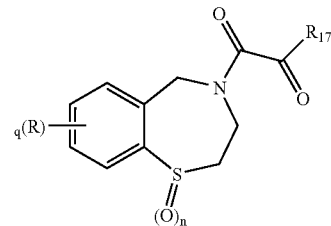

(I-i)

wherein $R_{17}$ is selected from the group consisting of $-NR_{15}R_{16}$, $-NHNR_{15}R_{16}$, $-NHOH$, $-OR_{15}$, $-CH_2X$, alkenyl, aryl, cycloalkyl, cycloalkylalkyl, heterocyclyl, and heterocyclylalkyl;
wherein each alkenyl, aryl, cycloalkyl, cycloalkylalkyl, heterocyclyl, and heterocyclylalkyl may be substituted or unsubstituted;

each R, q, and n is as defined in compounds of formula I-a above; and enantiomers, diastereomers, tautomers, pharmaceutically acceptable salts, hydrates, solvates, complexes and pro-drugs thereof.

In certain embodiments, the present invention provides compounds of formula I-i, wherein each R is independently selected from the group consisting of H, halogen, $-OH$, OMe, $-NH_2$, $-NO_2$, $-CN$, $-CF_3$, $-OCF_3$, $-N_3$, $-S(=O)_2C_1$-$C_4$alkyl, $-S(=O)C_1$-$C_4$alkyl, $-S-C_1$-$C_4$alkyl, $-OS(=O)_2CF_3$, Ph, $-NHCH_2Ph$, $-C(=O)Me$, $-OC(=O)Me$, morpholinyl and propenyl; and n is 0, 1, or 2.

In other embodiments, the present invention provides compounds of formula I-i, wherein $R_{17}$ is $-NR_{15}R_{16}$, and $-OR_{15}$. In certain other embodiments, $R_{17}$ is $-OH$, $-OMe$, $-NEt$, $-NHEt$, $-NHPh$, $-NH_2$, or $-NHCH_2$pyridyl.

In one embodiment, the present invention provides compounds of formula of I-j:

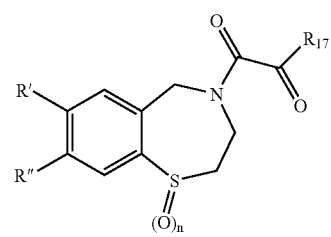

(I-j)

wherein R' and R" are independently selected from the group consisting of H, halogen, $-OH$, $-NH_2$, $-NO_2$, $-CN$, $-CF_3$, $-OCF_3$, $-N_3$, $-SO_3H$, $-S(=O)_2$alkyl, $-S(=O)$alkyl, $-OS(=O)_2CF_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;
$R_{17}$ is selected from the group consisting of $-NR_{15}R_{16}$, $-NHNR_{15}R_{16}$, $-NHOH$, $-OR_{15}$, $-CH_2X$, alkenyl, aryl, cycloalkyl, cycloalkylalkyl, heterocyclyl, and heterocyclylalkyl; wherein each alkenyl, aryl, cycloalkyl, cycloalkylalkyl, heterocyclyl, and heterocyclylalkyl may be substituted or unsubstituted;

n is as defined in compounds of formula I-a; and enantiomers, diastereomers, tautomers, pharmaceutically acceptable salts, hydrates, solvates, complexes and pro-drugs thereof.

In certain embodiments, the present invention provides compounds of formula I-j, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-j, wherein $R_{17}$ is —NR$_{15}$R$_{16}$ or —OR$_{15}$. In certain other embodiments, $R_{17}$ is —OH, —OMe, —NEt, —NHEt, —NHPh, —NH$_2$, or —NHCH$_2$pyridyl.

In another embodiment, the present invention provides compounds of formula I-k:

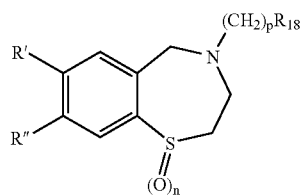

(I-k)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_{18}$ is selected from the group consisting of —NR$_{15}$R$_{16}$, —C(=O)NR$_{15}$R$_{16}$, —(C=O)OR$_{15}$, —OR$_{15}$, alkyl, aryl, cycloalkyl, heterocyclyl, and at one labeling group; wherein each alkyl, aryl, cycloalkyl, and heterocyclyl may be substituted or unsubstituted;

wherein p is 1, 2, 3, 4, 5, 6, 7, 8 9, or 10;

and n is 0, 1, or 2;

and enantiomers, diastereomers, tautomers, pharmaceutically acceptable salts, hydrates, solvates, complexes and pro-drugs thereof.

In certain embodiments, the present invention provides compounds of formula I-k, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-k, wherein $R_{18}$ is selected from the group consisting of —NR$_{15}$R$_{16}$, —(C=O)OR$_{15}$, —OR$_{15}$, alkyl, aryl, and at one labeling group; and wherein each alkyl and aryl may be substituted or unsubstituted. In some cases, m is 1, and $R^{18}$ is Ph, C(=O)OMe, C(=O)OH, aminoalkyl, NH$_2$, NHOH, or NHCbz. In other cases, m is 0, and $R_{18}$ is C$_1$-C$_4$ alkyl, such as Me, Et, propyl, and butyl. In yet other cases, m is 2, and $R_{18}$ is pyrrolidine, piperidine, piperazine, or morpholine. In some embodiments, m is 3, 4, 5, 5, 7, or 8, and $R_{18}$ is a fluorescent labeling group selected from bodipy, dansyl, fluorescein, rhodamine, Texas red, cyanine dyes, pyrene, coumarins, Cascade Blue™, Pacific Blue, Marina Blue, Oregon Green, 4',6-Diamidino-2-phenylindole (DAPI), indopyra dyes, lucifer yellow, propidium iodide, porphyrins, arginine, and variants and derivatives thereof.

In yet another embodiment, the present invention provides compounds of formula of I-l:

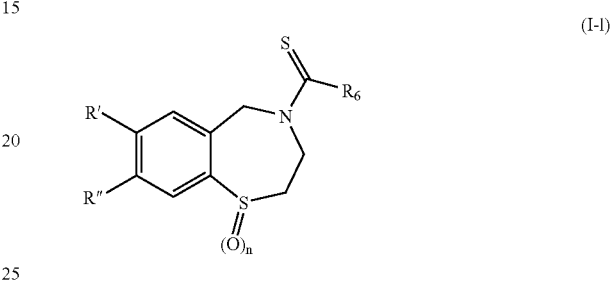

(I-l)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_6$ and n are as defined in compounds of formula I-a;

and enantiomers, diastereomers, tautomers, pharmaceutically acceptable salts, hydrates, solvates, complexes and pro-drugs thereof.

In certain embodiments, the present invention provides compounds of formula I-l, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-l, wherein $R_6$ is selected from the group consisting of —NR$_{15}$R$_{16}$, —NHNR$_{15}$R$_{16}$, —OR$_{15}$, —NHOH, —CH$_2$X, acyl, alkenyl, alkyl, aryl, cycloalkyl, cycloalkylalkyl, heterocyclyl, and heterocyclylalkyl; wherein each acyl, alkenyl, alkyl, aryl, cycloalkyl, cycloalkylalkyl, heterocyclyl, and heterocyclylalkyl may be substituted or unsubstituted. In some cases, $R_6$ is —NR$_{15}$R$_{16}$ such as —NHPh, pyrrolidine, piperidine, piperazine, morpholine, and the like. In some other cases, $R_6$ is alkoxyl, such as —O-tBu.

In a further embodiment, the present invention provides compounds of formula I-m:

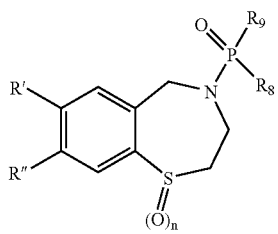

(I-m)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O) alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

R$_8$, R$_9$ and n are as defined in compounds of formula I-a above; and enantiomers, diastereomers, tautomers, pharmaceutically acceptable salts, hydrates, solvates, complexes and pro-drugs thereof.

In certain embodiments, the present invention provides compounds of formula I-m, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-m, wherein R$_8$ and R$_9$ are independently alkyl, aryl, —OH, alkoxyl, or alkylamino. In some cases, R8 is C$_1$-C$_4$ alkyl such as Me, Et, propyl and butyl; and R$_9$ is aryl such as phenyl.

In one embodiment, the compound is selected from the group consisting of S1, S2, S3, S4, S5, S6, S7, S9, S11, S12, S13, S14, S19, S20, S22, S23, S25, S26, S36, S37, S38, S40, S43, S44, S45, S46, S47, S48, S49, S50, S51, S52, S53, S54, S55, S56, S57, S58, S59, S60, S61, S62, S63, S64, S66, S67, S68, S69, S70, S71, S72, S73, S74, S75, S76, S77, S78, S79, S80, S81, S82, S83, S84, S85, S86, S87, S88, S89, S90, S91, S92, S93, S94, S95, S96, S97, S98, S99, S100, S101, S102, S103, S104, S105, S107, S108, S109, S110, S111, S112, S113, S114, S115, S116, S117, S118, S119, S120, S121, S122, and S123.

The compounds of the invention may optionally comprise a labeling group, such as a fluorescent, bioluminescent, chemiluminescent, colorimetric or radioactive labeling group. Suitable fluorescent labeling groups include, but are not limited to, bodipy, dansyl, fluorescein, rhodamine, Texas red, cyanine dyes, pyrene, coumarins, Cascade Blue™, Pacific Blue, Marina Blue, Oregon Green, 4',6-Diamidino-2-phenylindole (DAPI), indopyra dyes, lucifer yellow, propidium iodide, porphyrins, and variants and derivatives thereof. One of skill in the art can readily select a suitable marker or labeling group, and conjugate such a labeling group to any of the compounds of the invention, without undue experimentation.

The present invention also provides methods for the synthesis of compounds of Formula I, I-a, I-b, I-c, I-d, I-e, I-f, I-g, I-h, I-i, I-j, I-k, I-l and I-m, and salts, hydrates, solvates, complexes and pro-drugs thereof.

The present invention further provides a method of treating or preventing various disorders and diseases in a subject that are associated with RyR receptors, such as muscular and cardiac disorders, comprising administering to the subject an amount of a compound effective to prevent or treat a disorder or disease associated with the RyR receptors, wherein the compound is of Formula I, I-a, I-b, I-c, I-d, I-e, I-f, I-g, I-h, I-i, I-j, I-k, I-l or I-m, or salts, hydrates, solvates, complexes and pro-drugs thereof.

Also provided is a method of preventing or treating a leak in a RyR2 receptor in a subject, including administering to the subject an amount of a compound effective to prevent or treat a leak in the RyR2 receptor, wherein the compound of Formula I, I-a, I-b, I-c, I-d, I-e, I-f, I-g, I-h, I-i, I-j, I-k, I-l or I-m, or salts, hydrates, solvates, complexes and pro-drugs thereof. The subject is, for example, an in vitro system (e.g., cultured cells or tissues) or in vivo system (e.g., animal or human).

In addition, the present invention provides a method of modulating the binding of RyR and FKBP in a subject, including administering to the subject an amount of a compound effective to modulate the level of RyR-bound FKBP, wherein the compound is of Formula I, I-a, I-b, I-c, I-d, I-e, I-f, I-g, I-h, I-i, I-j, I-k, I-l or I-m, or salts, hydrates, solvates, complexes and pro-drugs thereof. The subject is, for example, an in vitro system (e.g., cultured cells or tissues) or in vivo system (e.g., animal or human).

The present invention also provides articles of manufacture for treating and preventing disorders and diseases associated with the RyR receptors, such as muscular and cardiac disorders, in a subject. The articles of manufacture comprise a pharmaceutical composition of one or more of the compounds of Formula I, I-a, I-b, I-c, I-d, I-e, I-f, I-g, I-h, I-i, I-j, I-k, I-l or I-m, or salts, hydrates, solvates, complexes and pro-drugs thereof. The articles of manufacture are packaged with indications for various disorders that the pharmaceutical compositions are capable of treating and/or preventing.

Other features and advantages of the present invention will become apparent from the following detailed description. It should be understood, however, that the detailed description and the specific examples while indicating various embodiments of the invention are given by way of illustration only, since various changes and modifications within the spirit and scope of the invention will become apparent to those skilled in the art from this detailed description.

DETAILED DESCRIPTION OF THE INVENTION

Figure 1:
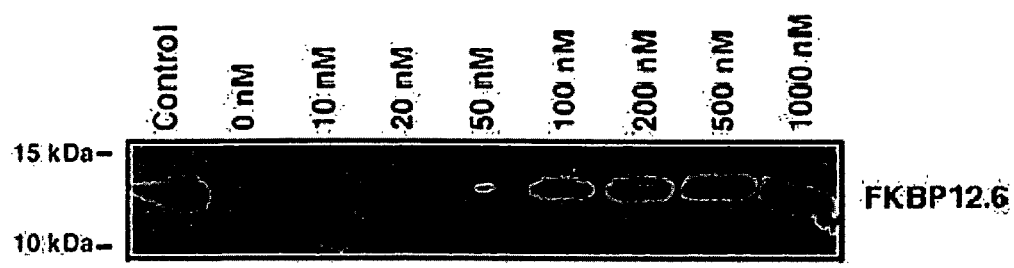
FIG. 1, embodiments A, B, C, and D are, respectively, (A) immunoblots of PKA phosphorylated RyR2 in the presence of FKBP12.6 and increasing JTV-519 concentrations; (B) immunoblots of PKA phosphorylated RyR2 in the presence of 0.5 nM S36; (C) a graph of current through plasma membrane, voltage dependent L-type Ca$^{2+}$ channels which are completely blocked by nifedipine but not by S36 in isolated mouse cardiomyocytes; and (D) a graph of the voltage-dependence of L-type Ca$^{2+}$ current in channels in the presence of JTV-519 and S36.
Figure 1:
Figure 1:
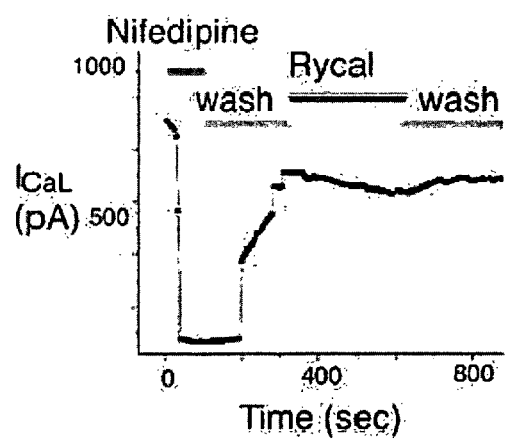
Figure 1:
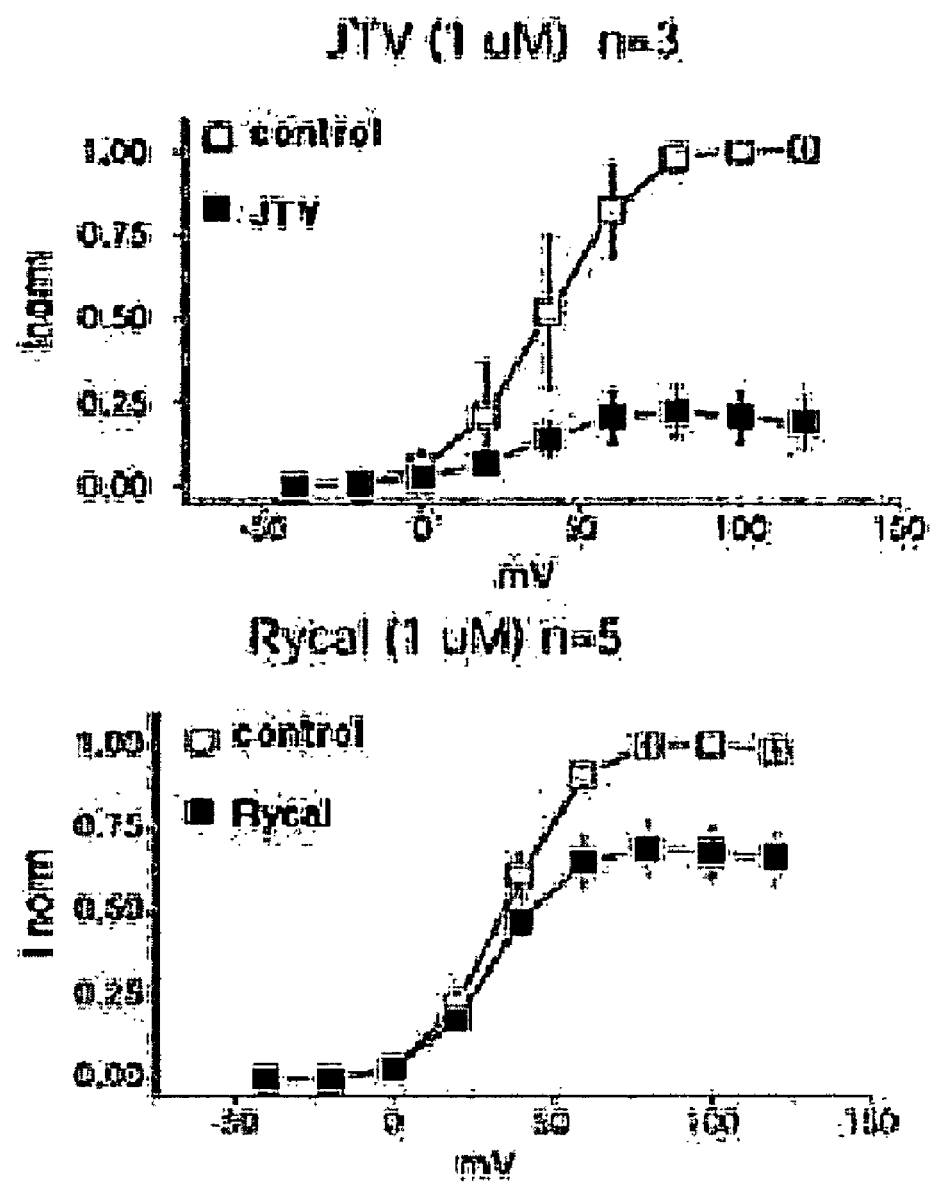

As used herein and in the appended claims, the singular forms "a," "an," and "the" include plural references unless the content clearly dictates otherwise. Thus, for example, reference to "an agent" includes a plurality of such agents and equivalents thereof known to those skilled in the art, and reference to "the FKBP12.6 polypeptide" is a reference to one or more FKBP12.6 polypeptides (also known as calstabin2) and equivalents thereof known to those skilled in the art, and so forth. All publications, patent applications, patents, and other references mentioned herein are incorporated by reference in their entirety.

The following are definitions of terms used in the present specification. The initial definition provided for a group or term herein applies to that group or term throughout the present specification individually or as part of another group, unless otherwise indicated.

As used herein, the term "RyCal compounds" refers to compounds of the general Formula I, I-a, I-b, I-c, I-d, I-e, I-f, I-g, I-h, I-i, I-j, I-k, I-l, I-m or II as provided by the invention, and herein referred to as "compound(s) of the invention".

The compounds of the invention are referred using a numerical naming system, with compound numbers 1 to 123 provided herein. These numbered compounds are referred to using either the prefix "S" or the prefix "ARM." Thus, the first numbered compound is referred to either as "S1" or "ARM001", the second numbered compound is referred to as either "S2" or "ARM002", the third numbered compound is referred to as either "S3" or "ARM003", and so on. The "S" and the "ARM" nomenclature systems are used interchangeably throughout the specification, the drawings, and the claims.

The term "alkyl" as used herein refers to a linear or branched, saturated hydrocarbon having from 1 to 6 carbon atoms. Representative alkyl groups include, but are not limited to, methyl, ethyl, propyl, isopropyl, butyl, sec-butyl, tert-butyl, pentyl, isopentyl, neopentyl, hexyl, isohexyl, and neohexyl. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl.

The term "alkenyl" as used herein refers to a linear or branched hydrocarbon having from 2 to 6 carbon atoms and having at least one carbon-carbon double bond. In one embodiment, the alkenyl has one or two double bonds. The alkenyl moiety may exist in the E or Z conformation and the compounds of the present invention include both conformations.

The term "alkynyl" as used herein refers to a linear or branched hydrocarbon having from 2 to 6 carbon atoms and having at least one carbon-carbon triple bond.

The term "aryl" as used herein refers to an aromatic group containing 1 to 3 aromatic rings, either fused or linked.

The term "cyclic group" as used herein includes a cycloalkyl group and a heterocyclic group.

The term "cycloalkyl group" as used herein refers to a three- to seven-membered saturated or partially unsaturated carbon ring. Any suitable ring position of the cycloalkyl group may be covalently linked to the defined chemical structure. Exemplary cycloalkyl groups include cyclopropyl, cyclobutyl, cyclopentyl, cyclohexyl, and cycloheptyl.

The term "halogen" as used herein refers to fluorine, chlorine, bromine, and iodine.

The term "heterocyclic group" or "heterocyclic" or "heterocyclyl" or "heterocyclo" as used herein refers to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1,2,3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached to the remainder of the molecule at any heteroatom or carbon atom of the ring or ring system. Exemplary heterocyclic groups include, but are not limited to, azepanyl, azetidinyl, aziridinyl, dioxolanyl, furanyl, furazanyl, homo piperazinyl, imidazolidinyl, imidazolinyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, and triazolyl. Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxoquinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

The term "phenyl" as used herein refers to a substituted or unsubstituted phenyl group.

The aforementioned terms "alkyl," "alkenyl," "alkynyl," "aryl," "phenyl," "cyclic group," "cycloalkyl," "heterocyclyl," "heterocyclo," and "heterocycle" may further be optionally substituted with one or more substituents. Exemplary substituents include but are not limited to one or more of the following groups: hydrogen, halogen, $CF_3$, $OCF_3$, cyano, nitro, $N_3$, oxo, cycloalkyl, alkenyl, alkynyl, heterocycle, aryl, alkylaryl, heteroaryl, $OR_a$, $SR_a$, $S(=O)R_e$, $S(=O)_2R_e$, $P(=O)_2R_e$, $S(=O)_2OR_a$, $P(=O)_2OR_a$, $NR_bR_c$, $NR_bS(=O)_2R_e$, $NR_bP(=O)_2R_e$, $S(=O)2NR_bR_c$, $P(=O)2NR_bR_c$, $C(=O)OR_a$, $C(=O)R_a$, $C(=O)NR_bR_c$, $OC(=O)R_a$, $OC(=O)NR_bR_c$, $NR_bC(=O)OR_a$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, alkynyl, alkylaryl, heteroaryl, heterocycle, or aryl; $R_b$, $R_c$ and $R_d$ are independently hydrogen, alkyl, cycloalkyl, alkylaryl, heteroaryl, heterocycle, aryl, or said $R_b$ and $R_c$ together with the N to which they are bonded optionally form a heterocycle; and $R_e$ is alkyl, cycloalkyl, alkenyl, cycloalkenyl, alkynyl, alkylaryl, heteroaryl, heterocycle, or aryl. In the aforementioned exemplary substituents, groups such as alkyl, cycloalkyl, alkenyl, alkynyl, cycloalkenyl, alkylaryl, heteroaryl, heterocycle and aryl can themselves be optionally substituted.

Exemplary substituents may further optionally include at least one labeling group, such as a fluorescent, a bioluminescent, a chemiluminescent, a colorimetric and a radioactive labeling group. A fluorescent labeling group can be selected from bodipy, dansyl, fluorescein, rhodamine, Texas red, cyanine dyes, pyrene, coumarins, Cascade Blue™, Pacific Blue, Marina Blue, Oregon Green, 4',6-Diamidino-2-phenylindole (DAPI), indopyra dyes, lucifer yellow, propidium iodide, porphyrins, arginine, and variants and derivatives thereof. For example, ARM118 of the present invention contains a labeling group BODIPY, which is a family of fluorophores based on the 4,4-difluoro-4-bora-3a,4a-diaza-s-indacene moiety.

For further information on fluorescent label moieties and fluorescence techniques, see, e.g., *Handbook of Fluorescent Probes and Research Chemicals*, by Richard P. Haughland, Sixth Edition, Molecular Probes, (1996), which is hereby incorporated by reference in its entirety. One of skill in the art can readily select a suitable labeling group, and conjugate such a labeling group to any of the compounds of the invention, without undue experimentation.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methylmorpholine-N-oxide, pyridine-N-oxide), and the positively charged nitrogen in an N-amino-ammonium group (e.g., N-aminopyridinium).

Throughout the specification, unless otherwise noted, the nitrogen in the benzothiazepine ring of compounds of the present invention may optionally be a quaternary nitrogen. Non-limiting examples include ARM-113 and ARM-119.

Compounds of the present invention may exist in their tautomeric form (for example, as an amide or imino ether). All such tautomeric forms are contemplated herein as part of the present invention.

The term "prodrug" as employed herein denotes a compound that, upon administration to a subject, undergoes chemical conversion by metabolic or chemical processes to yield compounds of the present invention.

All stereoisomers of the compounds of the present invention (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 99% of the compound ("substantially pure" compound), which is then used or formulated as described herein. Such "substantially pure" compounds of the present invention are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

The present invention provides compounds that are capable of treating and preventing disorders and diseases associated with the RyR receptors that regulate calcium channel functioning in cells. More particularly, the present invention provides compounds that are capable of treating or preventing a leak in RyR channels. "Disorders and diseases associated with the RyR receptors" means disorders and diseases that can be treated and/or prevented by modulating the RyR receptors that regulate calcium channel functioning in cells. "Disorders and diseases associated with the RyR receptors" include, without limitation, cardiac disorders and diseases, skeletal muscular disorders and diseases, cognitive disorders and diseases, malignant hyperthermia, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's Disease, forms of memory loss, and age-dependent memory loss.

Compounds

In one embodiment, the present invention provides compounds of Formula I:

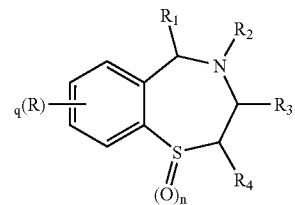

wherein, n is 0, 1, or 2;

q is 0, 1, 2, 3, or 4;

each R is independently selected from the group consisting of H, halogen, —OH, —NH$_2$, —NO$_2$, —CN, —CF$_3$, —OCF$_3$, —N$_3$, —SO$_3$H, —S(═O)$_2$alkyl, —S(═O)alkyl, —OS(═O)$_2$CF$_3$, acyl, —O-acyl, alkyl, alkoxyl, alkylamino, alkylarylamino, alkylthio, cycloalkyl, alkylaryl, aryl, heteroaryl, heterocyclyl, heterocyclylalkyl, alkenyl, alkynyl, (hetero-)aryl, (hetero-)arylthio, and (hetero-)arylamino; wherein each acyl, —O-acyl, alkyl, alkoxyl, alkylamino, alkylarylamino, alkylthio, cycloalkyl, alkylaryl, aryl, heteroaryl, heterocyclyl, heterocyclylalkyl, alkenyl, alkynyl, (hetero-)aryl, (hetero-)arylthio, and (hetero-)arylamino may be optionally substituted;

R$_1$ is selected from the group consisting of H, oxo, alkyl, alkenyl, aryl, alkylaryl, cycloalkyl, heteroaryl, and heterocyclyl; wherein each alkyl, alkenyl, aryl, alkylaryl, cycloalkyl, heteroaryl, and heterocyclyl may be optionally substituted;

$R_2$ is selected from the group consisting of H, —C(=O)$R_5$, —C(=S)$R_6$, —SO$_2$$R_7$, —P(=O)$R_8$$R_9$, —(CH$_2$)$_m$—$R_{10}$, alkyl, aryl, alkylaryl, heteroaryl, cycloalkyl, cycloalkylalkyl, and heterocyclyl; wherein each alkyl, aryl, alkylaryl, heteroaryl, cycloalkyl, cycloalkylalkyl, and heterocyclyl may be optionally substituted;

$R_3$ is selected from the group consisting of H, —CO$_2$Y, —C(=O)NHY, acyl, —O-acyl, alkyl, alkenyl, aryl, alkylaryl, cycloalkyl, heteroaryl, and heterocyclyl; wherein each acyl, alkyl, alkenyl, aryl, alkylaryl, cycloalkyl, heteroaryl, and heterocyclyl may be optionally substituted; and wherein Y is selected from the group consisting of H, alkyl, aryl, alkylaryl, cycloalkyl, heteroaryl, and heterocyclyl, and wherein each alkyl, aryl, alkylaryl, cycloalkyl, heteroaryl, and heterocyclyl may be optionally substituted;

R4 is selected from the group consisting of H, alkyl, alkenyl, aryl, alkylaryl, cycloalkyl, heteroaryl, and heterocyclyl; wherein each alkyl, alkenyl, aryl, alkylaryl, cycloalkyl, heteroaryl, and heterocyclyl may be optionally substituted;

$R_5$ is selected from the group consisting of —NR$_{15}$$R_6$, —(CH$_2$)$_q$NR$_{15}$R$_{16}$, —NHNR$_{15}$R$_{16}$, —NHOH, —OR$_{15}$, —C(=O)NHNR$_{15}$R$_{16}$, —CO$_2$R$_{15}$, —C(=O)NR$_{15}$R$_{16}$, —CH$_2$X, acyl, alkyl, alkenyl, aryl, alkylaryl, cycloalkyl, cycloalkylalkyl, heteroaryl, heterocyclyl, and heterocyclylalkyl; wherein each acyl, alkyl, alkenyl, aryl, alkylaryl, cycloalkyl, cycloalkylalkyl, heteroaryl, heterocyclyl, and heterocyclylalkyl may be optionally substituted, and wherein q is 1, 2, 3, 4, 5, or 6;

$R_6$ is selected from the group consisting of —OR$_{15}$, —NHNR$_{15}$R$_{16}$, —NHOH, —NR$_{15}$R$_{16}$, —CH$_2$X, acyl, alkenyl, alkyl, aryl, alkylaryl, cycloalkyl, cycloalkylalkyl, heteroaryl, heterocyclyl, and heterocyclylalkyl; wherein each acyl, alkenyl, alkyl, aryl, alkylaryl, cycloalkyl, cycloalkylalkyl, heteroaryl, heterocyclyl, and heterocyclylalkyl may be optionally substituted;

$R_7$ is selected from the group consisting of —OR$_{15}$, —NR$_{15}$R$_{16}$, —NHNR$_{15}$R$_{16}$, —NHOH, —CH$_2$X, alkyl, alkenyl, alkynyl, aryl, alkylaryl, cycloalkyl, cycloalkylalkyl, heteroaryl, heterocyclyl, and heterocyclylalkyl; wherein each alkyl, alkenyl, alkynyl, aryl, alkylaryl, cycloalkyl, cycloalkylalkyl, heteroaryl, heterocyclyl, and heterocyclylalkyl may be optionally substituted;

$R_8$ and $R_9$ independently are selected from the group consisting of OH, acyl, alkenyl, alkoxyl, alkyl, alkylamino, aryl, alkylaryl, cycloalkyl, cycloalkylalkyl, heteroaryl, heterocyclyl, and heterocyclylalkyl; wherein each acyl, alkenyl, alkoxyl, alkyl, alkylamino, aryl, alkylaryl, cycloalkyl, cycloalkylalkyl, heteroaryl, heterocyclyl, and heterocyclylalkyl may be optionally substituted;

$R_{10}$ is selected from the group consisting of —NR$_{15}$R$_{16}$, OH, —SO$_2$R$_{11}$, —NHSO$_2$R$_{11}$, C(=O)(R$_{12}$), NHC=O(R$_{12}$), —OC=O(R$_{12}$), and —P(=O)R$_{13}$R$_{14}$;

$R_{11}$, $R_{12}$, $R_{13}$, and $R_{14}$ independently are selected from the group consisting of H, OH, NH$_2$, —NHNH$_2$, —NHOH, acyl, alkenyl, alkoxyl, alkyl, alkylamino, aryl, alkylaryl, cycloalkyl, cycloalkylalkyl, heteroaryl, heterocyclyl, and heterocyclylalkyl; wherein each acyl, alkenyl, alkoxyl, alkyl, alkylamino, aryl, alkylaryl, cycloalkyl, cycloalkylalkyl, heteroaryl, heterocyclyl, and heterocyclylalkyl may be optionally substituted;

X is selected from the group consisting of halogen, —CN, —CO$_2$R$_{15}$, —C(=O)NR$_{15}$R$_{16}$, —NR$_{15}$R$_{16}$, —OR$_{15}$, —SO$_2$R$_7$, and —P(=O)R$_8$R$_9$; and $R_{15}$ and $R_{16}$ independently are selected from the group consisting of H, acyl, alkenyl, alkoxyl, OH, NH$_2$, alkyl, alkylamino, aryl, alkylaryl, cycloalkyl, cycloalkylalkyl, heteroaryl, heterocyclyl, and heterocyclylalkyl; wherein each acyl, alkenyl, alkoxyl, alkyl, alkylamino, aryl, alkylaryl, cycloalkyl, cycloalkylalkyl, heteroaryl, heterocyclyl, and heterocyclylalkyl may be optionally substituted; and optionally $R_{15}$ and $R_{16}$ together with the N to which they are bonded may form a heterocycle which may be substituted;

the nitrogen in the benzothiazepine ring may optionally be a quaternary nitrogen; and enantiomers, diastereomers, tautomers, pharmaceutically acceptable salts, hydrates, solvates, complexes, and prodrugs thereof;

provided that when q is 0 and n is 0, then $R_2$ is not H, Et, —C(=O)NH$_2$, (=O)NHPh, —C(=S)NH-nButyl, —C(=O)NHC(=O)CH$_2$Cl, —C(=O)H, —C(=O)Me, —C(=O)Et, —C(=O)CH=CH$_2$, —S(=O)$_2$Me, or —S(=O)$_2$Et;

further provided that when q is 0 and n is 1 or 2, then $R_2$ is not —C(=O)Me, —C(=O)Et, —S(=O)$_2$Me, or —S(=O)$_2$Et;

further provided that when q is 1, and R is Me, Cl, or F at the 6 position of the benzothiazepene ring, then $R_2$ is not H, Me, —C(=O)H, —C(=O)Me, —C(=O)Et, —C(=O)Ph, —S(=O)$_2$Me, or —S(=O)$_2$Et; and further provided that when q is 1, n is 0, and R is OCT$_3$, OH, $C_1$-$C_3$ alkoxyl at the 7 position of the benzothiazepene ring, then $R_2$ is not H, —C(=O)CH=CH$_2$, or

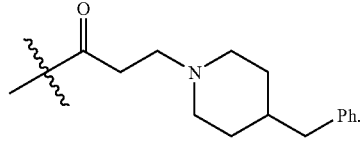

In one embodiment, the present invention provides compounds of Formula I, as described above, with the proviso that said compound is not S24 or S68.

In one embodiment, the present invention provides compounds of Formula I-a:

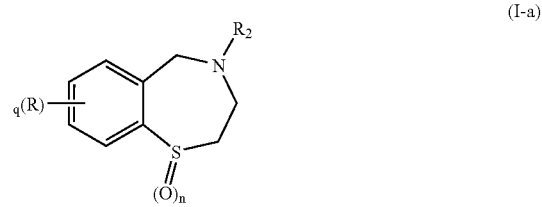

wherein:

n is 0, 1, or 2;

q is 0, 1, 2, 3, or 4;

each R is independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; wherein each acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino may be substituted or unsubstituted;

$R_2$ is selected from the group consisting of H, —C=O($R_5$), —C=S($R_6$), —SO$_2R_7$, —P(=O)$R_8R_9$, —(CH$_2$)$_m$—$R_{10}$, alkyl, aryl, heteroaryl, cycloalkyl, cycloalkylalkyl, and heterocyclyl; wherein each alkyl, aryl, heteroaryl, cycloalkyl, cycloalkylalkyl, and heterocyclyl may be substituted or unsubstituted;

$R_5$ is selected from the group consisting of —NR$_{15}R_{16}$, —NHNR$_{15}R_{16}$, —NHOH, —OR$_{15}$, —C(=O)NHNR$_{15}R_{16}$, —CO$_2R_{15}$, —C(=O)NR$_{15}R_{16}$, —CH$_2$X, acyl, alkyl, alkenyl, alkynyl, aryl, cycloalkyl, cycloalkylalkyl, heterocyclyl, and heterocyclylalkyl; wherein each acyl, alkyl, alkenyl, alkynyl, aryl, cycloalkyl, cycloalkylalkyl, heterocyclyl, and heterocyclylalkyl may be substituted or unsubstituted;

$R_6$ is selected from the group consisting of —OR$_{15}$, —NHNR$_{15}R_{16}$, —NHOH, —NR$_{15}R_{16}$, —CH$_2$X, acyl, alkenyl, alkyl, aryl, cycloalkyl, cycloalkylalkyl, heterocyclyl, and heterocyclylalkyl; wherein each acyl, alkenyl, alkyl, aryl, cycloalkyl, cycloalkylalkyl, heterocyclyl, and heterocyclylalkyl may be substituted or unsubstituted;

$R_7$ is selected from the group consisting of H, —OR$_{15}$, —NR$_{15}R_{16}$, —NHNR$_{15}R_{16}$, —NHOH, —CH$_2$X, alkyl, akenyl, alkynyl, aryl, cycloalkyl, cycloalkylalkyl, heterocyclyl, and heterocyclylalkyl; wherein each alkyl, akenyl, alkynyl, aryl, cycloalkyl, cycloalkylalkyl, heterocyclyl, and heterocyclylalkyl may be substituted or unsubstituted;

$R_8$ and $R_9$ independently are selected from the group consisting of —OH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted;

$R_{10}$ is selected from the group consisting of —NR$_{15}R_{16}$, OH, —SO$_2R_{11}$, —NHSO$_2R_{11}$, —C(=O)R$_{12}$, —NH(C=O)R$_{12}$, —O(C=O)R$_{12}$, and —P(=O)R$_{13}R_{14}$;

m is 0, 1, 2, 3, or 4;

$R_{11}$, $R_{12}$, $R_{13}$, and $R_{14}$ independently are selected from the group consisting of H, OH, NH$_2$, —NHNH$_2$, —NHOH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted;

X is selected from the group consisting of halogen, —CN, —CO$_2R_{15}$, —C(=O)NR$_{15}R_{16}$, —NR$_{15}R_{16}$, —OR$_{15}$, —SO$_2R_7$, and —P(=O)R$_8R_9$; and $R_{15}$ and $R_{16}$ independently are selected from the group consisting of H, acyl, alkenyl, alkoxyl, OH, NH$_2$, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and optionally $R_{15}$ and $R_{16}$ together with the N to which they are bonded may form a heterocycle which may be substituted or unsubstituted;

the nitrogen in the benzothiazepine ring may be optionally a quaternary nitrogen; and enantiomers, diastereomers, tautomers, pharmaceutically acceptable salts, hydrates, solvates, complexes, and prodrugs thereof;

provided that when q is 0 and n is 0, then $R_2$ is not H, Et, —C(=O)NH$_2$, (=O)NHPh, —C(=S)NH-nButyl, —C(=O)NHC(=O)CH$_2$Cl, —C(=O)H, —C(=O)Me, —C(=O)Et, —C(=O)CH=CH$_2$, —S(=O)$_2$Me, or —S(=O)$_2$Et;

further provided that when q is 0 and n is 1 or 2, then $R_2$ is not —C(=O)Me, —C(=O)Et, —S(=O)$_2$Me, or —S(=O)$_2$Et;

further provided that when q is 1, and R is Me, Cl, or F at the 6 position of the benzothiazepene ring, then $R_2$ is not H, Me, —C(=O)H, —C(=O)Me, —C(=O)Et, —C(=O)Ph, —S(=O)$_2$Me, or —S(=O)$_2$Et; and further provided that when q is 1, n is 0, and R is OCT$_3$, OH, $C_1$-$C_3$ alkoxyl at the 7 position of the benzothiazepene ring, then $R_2$ is not H, —C(=O)CH=CH$_2$, or

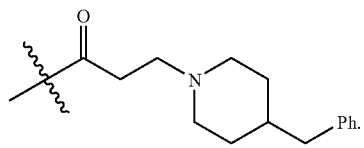

In certain embodiments, the present invention provides compounds of formula I-a, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1, or 2.

In other embodiments, the present invention provides compounds of formula I-a, wherein $R_2$ is selected from the group consisting of —C=O($R_5$), —C=S($R_6$), —SO$_2R_7$, —P(=O)$R_8R_9$, and —(CH$_2$)$_m$—$R_{10}$.

In yet another embodiment, the present invention provides compounds of formula I-b:

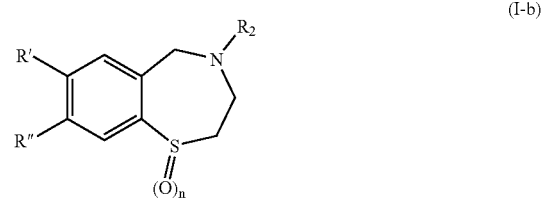

(I-b)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_2$ and n are as defined in compounds of formula I-a above;

and enantiomers, diastereomers, tautomers, pharmaceutically acceptable salts, hydrates, solvates, complexes and prodrugs thereof.

In certain embodiments, the present invention provides compounds of formula I-b, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-b, wherein $R_2$ is selected from the group consisting of —C=O($R_5$), —C=S($R_6$), —SO$_2R_7$, —P(=O)$R_8R_9$, and —(CH$_2)_m$—$R_{10}$.

In yet another embodiment, the present invention provides compounds formula of I-c:

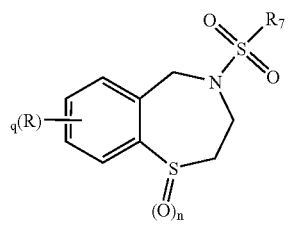

(I-c)

wherein each R, $R_7$, q, and n is as defined in compounds of formula I-a above; and enantiomers, diastereomers, tautomers, pharmaceutically acceptable salts, hydrates, solvates, complexes and pro-drugs thereof.

In certain embodiments, the present invention provides compounds of formula I-c, wherein each R is independently selected from the group consisting of H, halogen, —OH, OMe, —NH$_2$, —NO$_2$, —CN, —CF$_3$, —OCF$_3$, —N$_3$, —S(=O)$_2C_1$-$C_4$alkyl, —S(=O)$C_1$-$C_4$alkyl, —S—$C_1$-$C_4$alkyl, —OS(=O)$_2$CF$_3$, Ph, —NHCH$_2$Ph, —C(=O)Me, —OC(=O)Me, morpholinyl and propenyl; and n is 0, 1, or 2.

In other embodiments, the present invention provides compounds of formula I-c, wherein $R_7$ is selected from the group consisting of —OH, —NR$_{15}R_{16}$, alkyl, alkenyl, aryl, cycloalkyl, cycloalkylalkyl, heterocyclyl, and heterocyclylalkyl; wherein each alkyl, akenyl, aryl, cycloalkyl, cycloalkylalkyl, heterocyclyl, and heterocyclylalkyl may be substituted or unsubstituted.

In a further embodiment, the present invention provides compounds of formula of I-d:

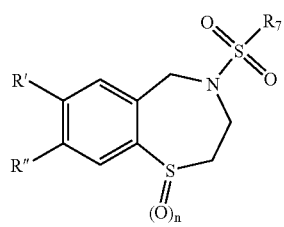

(I-d)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O) alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_7$ and n are as defined in compounds of formula I-a above; and enantiomers, diastereomers, tautomers, pharmaceutically acceptable salts, hydrates, solvates, complexes and pro-drugs thereof.

In certain embodiments, the present invention provides compounds of formula I-d, wherein R' and R" are independently selected from the group consisting of H, halogen, —OH, OMe, —NH$_2$, —NO$_2$, —CN, —CF$_3$, —OCF$_3$, —N$_3$, —S(=O)$_2C_1$-$C_4$alkyl, —S(=O)$C_1$-$C_4$alkyl, —S—$C_1$-$C_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-d, wherein $R_7$ is selected from the group consisting of —OH, —NR$_{15}R_{16}$, alkyl, alkenyl, aryl, cycloalkyl, cycloalkylalkyl, heterocyclyl, and heterocyclylalkyl; wherein each alkyl, akenyl, aryl, cycloalkyl, cycloalkylalkyl, heterocyclyl, and heterocyclylalkyl may be substituted or unsubstituted.

In one embodiment, the present invention provides compounds of formula of I-e:

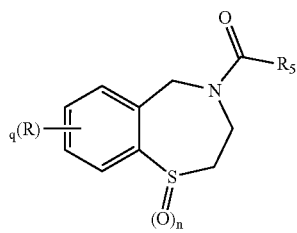

(I-e)

wherein each R, $R_5$, q and n is as defined compounds of formula I-a above; and enantiomers, diastereomers, tautomers, pharmaceutically acceptable salts, hydrates, solvates, complexes and pro-drugs thereof.

In certain embodiments, the present invention provides compounds of formula I-e, wherein each R is independently selected from the group consisting of H, halogen, —OH, OMe, —NH$_2$, —NO$_2$, —CN, —CF$_3$, —OCF$_3$, —N$_3$, —S(=O)$_2C_1$-$C_4$alkyl, —S(=O)$C_1$-$C_4$alkyl, —S—$C_1$-$C_4$alkyl, —OS(=O)$_2$CF$_3$, Ph, —NHCH$_2$Ph, —C(=O)Me, —OC(=O)Me, morpholinyl and propenyl; and n is 0, 1, or 2.

In other embodiments, the present invention provides compounds of formula I-e, wherein $R_5$ is selected from the group consisting of —NR$_{15}R_{16}$, —NHOH, —OR$_{15}$, —CH$_2$X, alkyl, alkenyl, aryl, cycloalkyl, cycloalkylalkyl, heterocyclyl, and heterocyclylalkyl; wherein each acyl, alkyl, alkenyl, aryl, cycloalkyl, cycloalkylalkyl, heterocyclyl, and heterocyclylalkyl may be substituted or unsubstituted.

In some embodiments, the present invention provides compounds of formula I-e, wherein $R_5$ is an alkyl substituted by at least one labeling group, such as a fluorescent, a bioluminescent, a chemiluminescent, a colorimetric and a radioactive labeling group. A fluorescent labeling group can be selected from bodipy, dansyl, fluorescein, rhodamine, Texas red, cyanine dyes, pyrene, coumarins, Cascade Blue™, Pacific Blue, Marina Blue, Oregon Green, 4',6Diamidino-2-phenylindole (DAPI), indopyra dyes, lucifer yellow, propidium iodide, porphyrins, arginine, and variants and derivatives thereof.

In another embodiment, the present invention provides compounds of formula of I-f:

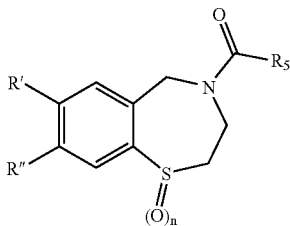

(I-f)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

R$_5$ and n are as defined in compounds of formula I-a above;

and enantiomers, diastereomers, tautomers, pharmaceutically acceptable salts, hydrates, solvates, complexes and pro-drugs thereof.

In certain embodiments, the present invention provides compounds of formula I-f, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-f, wherein R$_5$ is selected from the group consisting of —NR$_{15}$R$_{16}$, —NHOH, —OR$_{15}$, —CH$_2$X, alkyl, alkenyl, aryl, cycloalkyl, cycloalkylalkyl, heterocyclyl, and heterocyclylalkyl; wherein each acyl, alkyl, alkenyl, aryl, cycloalkyl, cycloalkylalkyl, heterocyclyl, and heterocyclylalkyl may be substituted or unsubstituted.

In yet another embodiment, the present invention provides compounds of formula I-g:

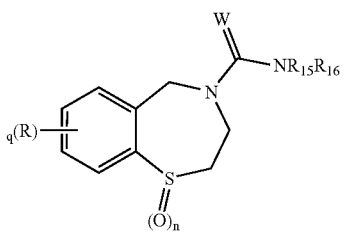

(I-g)

wherein W is S or O; each R, R$_{15}$, R$_{16}$, q, and n is as defined in compounds of formula I-a above; and enantiomers, diastereomers, tautomers, pharmaceutically acceptable salts, hydrates, solvates, complexes and pro-drugs thereof.

In certain embodiments, the present invention provides compounds of formula I-g, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1, or 2.

In other embodiments, the present invention provides compounds of formula I-g, wherein R$_{15}$ and R$_{16}$ independently are selected from the group consisting of H, OH, NH$_2$, alkyl, alkylamino, aryl, cycloalkyl, cycloalkylalkyl, heterocyclyl, and heterocyclylalkyl; wherein each alkyl, alkylamino, aryl, cycloalkyl, cycloalkylalkyl, heterocyclyl, and heterocyclylalkyl may be substituted; and optionally R$_{15}$ and R$_{16}$ together with the N to which they are bonded may form a heterocycle which may be substituted.

In some embodiments, the present invention provides compounds of formula I-g, wherein W is O or S.

In yet another embodiment, the present invention provides compounds of formula of I-h:

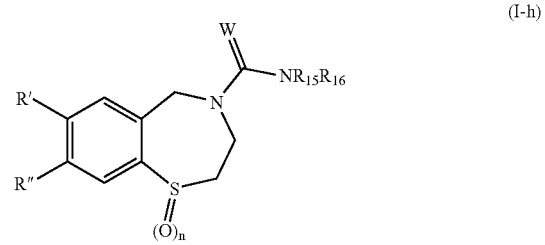

(I-h)

wherein W is S or O;

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

R$_{15}$, R$_{16}$ and n are as defined in compounds of formula I-a above;

and enantiomers, diastereomers, tautomers, pharmaceutically acceptable salts, hydrates, solvates, complexes and pro-drugs thereof.

In certain embodiments, the present invention provides compounds of formula I-h, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-h, wherein R$_{15}$ and R$_{16}$ independently are selected from the group consisting of H, OH, NH$_2$, alkyl, alkylamino, aryl, cycloalkyl, cycloalkylalkyl, heterocyclyl, and heterocyclylalkyl; wherein each alkyl, alkylamino, aryl, cycloalkyl, cycloalkylalkyl, heterocyclyl, and heterocyclylalkyl may be substituted; and optionally R$_{15}$ and R$_{16}$ together with the N to which they are bonded may form a heterocycle which may be substituted.

In some embodiments, the present invention provides compounds of formula I-g, wherein W is O or S.

In a further embodiment, the present invention provides compounds of formula of I-i:

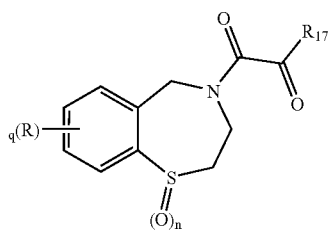

(I-i)

wherein $R_{17}$ is selected from the group consisting of —$NR_{15}R_{16}$, —$NHNR_{15}R_{16}$, —NHOH, —$OR_{15}$, —$CH_2X$, alkenyl, aryl, cycloalkyl, cycloalkylalkyl, heterocyclyl, and heterocyclylalkyl;

wherein each alkenyl, aryl, cycloalkyl, cycloalkylalkyl, heterocyclyl, and heterocyclylalkyl may be substituted or unsubstituted;

each R, q, and n is as defined in compounds of formula I-a above; and enantiomers, diastereomers, tautomers, pharmaceutically acceptable salts, hydrates, solvates, complexes and pro-drugs thereof.

In certain embodiments, the present invention provides compounds of formula I-i, wherein each R is independently selected from the group consisting of H, halogen, —OH, OMe, —$NH_2$, —$NO_2$, —CN, —$CF_3$, —$OCF_3$, —$N_3$, —$S(=O)_2C_1$-$C_4$alkyl, —$S(=O)C_1$-$C_4$alkyl, —S—$C_1$-$C_4$alkyl, —$OS(=O)_2CF_3$, Ph, —$NHCH_2$Ph, —$C(=O)$Me, —$OC(=O)$Me, morpholinyl and propenyl; and n is 0, 1, or 2.

In other embodiments, the present invention provides compounds of formula I-i, wherein $R_{17}$ is —$NR_{15}R_{16}$, and —$OR_{15}$. In certain other embodiments, $R_{17}$ is —OH, —OMe, —NEt, —NHEt, —NHPh, —$NH_2$, or —$NHCH_2$pyridyl.

In one embodiment, the present invention provides compounds of formula of I-j:

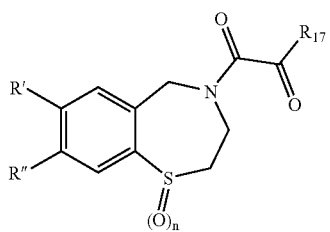

(I-j)

wherein R' and R" are independently selected from the group consisting of H, halogen, —OH, —$NH_2$, —$NO_2$, —CN, —$CF_3$, —$OCF_3$, —$N_3$, —$SO_3H$, —$S(=O)_2$alkyl, —$S(=O)$alkyl, —$OS(=O)_2CF_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_{17}$ is selected from the group consisting of —$NR_{15}R_{16}$, —$NHNR_{15}R_{16}$, —NHOH, —$OR_{15}$, —$CH_2X$, alkenyl, aryl, cycloalkyl, cycloalkylalkyl, heterocyclyl, and heterocyclylalkyl; wherein each alkenyl, aryl, cycloalkyl, cycloalkylalkyl, heterocyclyl, and heterocyclylalkyl may be substituted or unsubstituted;

n is as defined in compounds of formula I-a; and enantiomers, diastereomers, tautomers, pharmaceutically acceptable salts, hydrates, solvates, complexes and pro-drugs thereof.

In certain embodiments, the present invention provides compounds of formula I-j, wherein R' and R" are independently selected from the group consisting of H, halogen, —OH, OMe, —$NH_2$, —$NO_2$, —CN, —$CF_3$, —$OCF_3$, —$N_3$, —$S(=O)_2C_1$-$C_4$alkyl, —$S(=O)C_1$-$C_4$alkyl, —S—$C_1$-$C_4$alkyl, —$OS(=O)_2CF_3$, Ph, —$NHCH_2$Ph, —$C(=O)$Me, —$OC(=O)$Me, morpholinyl and propenyl; and n is 0, 1 or 3. In some cases, R' is H or OMe, and R" is H.

In other embodiments, the present invention provides compounds of formula I-j, wherein $R_{17}$ is —$NR_{15}R_{16}$ or —$OR_{15}$. In certain other embodiments, $R_{17}$ is —OH, —OMe, —NEt, —NHEt, —NHPh, —$NH_2$, or —$NHCH_2$pyridyl.

In another embodiment, the present invention provides compounds of formula I-k:

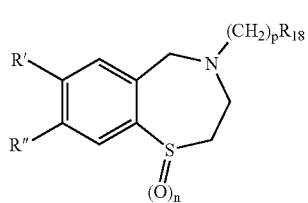

(I-k)

wherein R' and R" are independently selected from the group consisting of H, halogen, —OH, —$NH_2$, —$NO_2$, —CN, —$CF_3$, —$OCF_3$, —$N_3$, —$SO_3H$, —$S(=O)_2$alkyl, —$S(=O)$alkyl, —$OS(=O)_2CF_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_{18}$ is selected from the group consisting of —$NR_{15}R_{16}$, —$C(=O)NR_{15}R_{16}$, -$(C=O)OR_{15}$, —$OR_{15}$, alkyl, aryl, cycloalkyl, heterocyclyl, and at one labeling group; wherein each alkyl, aryl, cycloalkyl, and heterocyclyl may be substituted or unsubstituted;

wherein p is 1, 2, 3, 4, 5, 6, 7, 8 9, or 10;

and n is 0, 1, or 2;

and enantiomers, diastereomers, tautomers, pharmaceutically acceptable salts, hydrates, solvates, complexes and pro-drugs thereof.

In certain embodiments, the present invention provides compounds of formula I-k, wherein R' and R" are independently selected from the group consisting of H, halogen, —OH, OMe, —$NH_2$, —$NO_2$, —CN, —$CF_3$, —$OCF_3$, —$N_3$, —$S(=O)_2C_1$-$C_4$alkyl, —$S(=O)C_1$-$C_4$alkyl, —S—$C_1$-$C_4$alkyl, —$OS(=O)_2CF_3$, Ph, —$NHCH_2$Ph, —$C(=O)$Me, —$OC(=O)$Me, morpholinyl and propenyl; and n is 0, 1 or 3. In some cases, R' is H or OMe, and R" is H.

In other embodiments, the present invention provides compounds of formula I-k, wherein $R_{18}$ is selected from the group consisting of —$NR_{15}R_{16}$, -$(C=O)OR_{15}$, —$OR_{15}$, alkyl, aryl, and at one labeling group; and wherein each alkyl and aryl may be substituted or unsubstituted. In some cases, m is 1, and $R_{18}$ is Ph, $C(=O)$OMe, $C(=O)$OH, aminoalkyl, $NH_2$, NHOH, or NHCbz. In other cases, m is 0, and $R_{18}$ is $C_1$-$C_4$ alkyl, such as Me, Et, propyl, and butyl. In yet other cases, m is 2, and $R_{18}$ is pyrrolidine, piperidine, piperazine, or morpholine. In some embodiments, m is 3, 4, 5, 5, 7, or 8, and $R_{18}$ is a fluorescent labeling group selected from bodipy, dansyl, fluorescein, rhodamine, Texas red, cyanine dyes, pyrene, coumarins, Cascade Blue™, Pacific Blue, Marina Blue, Oregon Green, 4',6-Diamidino-2-phenylindole (DAPI), indopyra dyes, lucifer yellow, propidium iodide, porphyrins, arginine, and variants and derivatives thereof.

In yet another embodiment, the present invention provides compounds of formula of I-l:

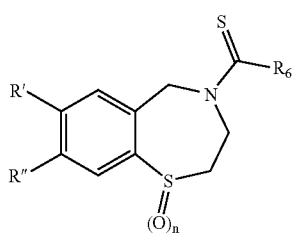
(I-l)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_6$ and n are as defined in compounds of formula I-a;

and enantiomers, diastereomers, tautomers, pharmaceutically acceptable salts, hydrates, solvates, complexes and pro-drugs thereof.

In certain embodiments, the present invention provides compounds of formula I-l, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-l, wherein $R_6$ is selected from the group consisting of —NR$_{15}$R$_{16}$, —NHNR$_{15}$R$_{16}$, —OR$_{15}$, —NHOH, —CH$_2$X, acyl, alkenyl, alkyl, aryl, cycloalkyl, cycloalkylalkyl, heterocyclyl, and heterocyclylalkyl; wherein each acyl, alkenyl, alkyl, aryl, cycloalkyl, cycloalkylalkyl, heterocyclyl, and heterocyclylalkyl may be substituted or unsubstituted. In some cases, $R_6$ is —NR$_{15}$R$_{16}$ such as —NHPh, pyrrolidine, piperidine, piperazine, morpholine, and the like. In some other cases, $R_6$ is alkoxyl, such as —O-tBu.

In a further embodiment, the present invention provides compounds of formula I-m:

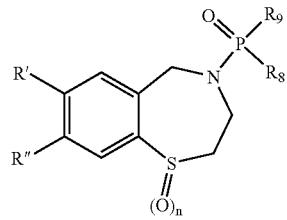
(I-m)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_8$, $R_9$ and n are as defined in compounds of formula I-a above; and enantiomers, diastereomers, tautomers, pharmaceutically acceptable salts, hydrates, solvates, complexes and pro-drugs thereof.

In certain embodiments, the present invention provides compounds of formula I-m, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 3. In some cases, R' is H or OMe, and R" is H.

In other embodiments, the present invention provides compounds of formula I-m, wherein $R_8$ and $R_9$ are independently alkyl, aryl, —OH, alkoxyl, or alkylamino. In some cases, $R_8$ is C$_1$-C$_4$ alkyl such as Me, Et, propyl and butyl; and $R_9$ is aryl such as phenyl.

The compounds of Formula I, I-a, I-b, I-c, I-d, I-e, I-f, I-g, I-h, I-i, I-j, I-k, I-l and I-m treat and prevent disorders and diseases associated with the RyR receptors.

Examples of such compounds include, without limitation, S1, S2, S3, S4, S5, S6, S7, S9, S11, S12, S13, S14, S19, S20, S22, S23, S25, S26, S36, S37, S38, S40, S43, S44, S45, S46, S47, S48, S49, S50, S51, S52, S53, S54, S55, S56, S57, S58, S59, S60, S61, S62, S63, S64, S66, S67, S68, S69, S70, S71, S72, S73, S74, S75, S76, S77, S78, S79, S80, S81, S82, S83, S84, S85, S86, S87, S88, S89, S90, S91, S92, S93, S94, S95, S96, S97, S98, S99, S100, S101, S102, S103, S104, S105, S107, S108, S109, S110, S111, S112, S113, S114, S115, S116, S117, S118, S119, S120, S121, S122, and S123. These compounds have the following structures:

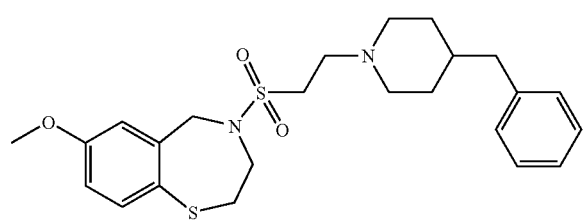
S1

-continued
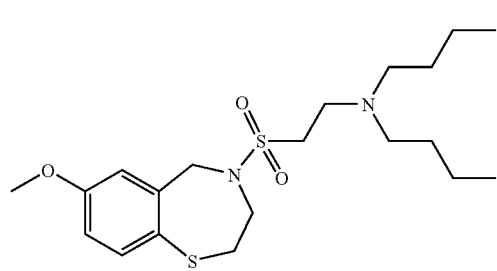
S2
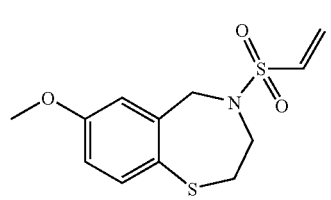
S3
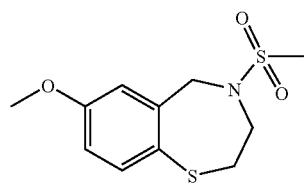
S4
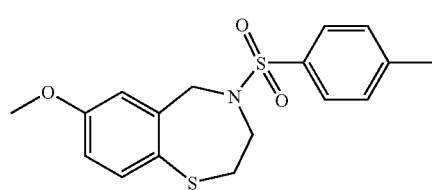
S5
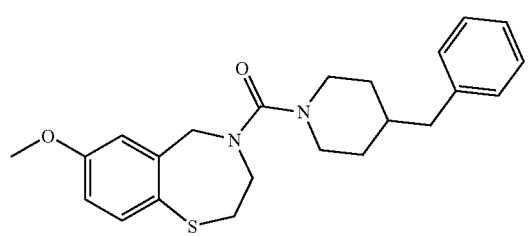
S6
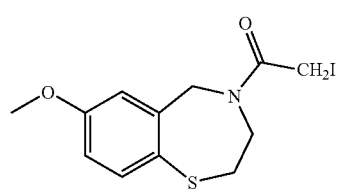
S7
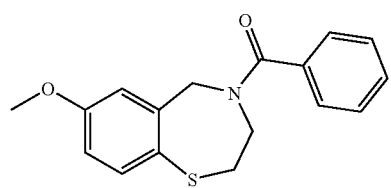
S9
-continued
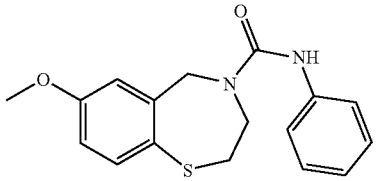
S11
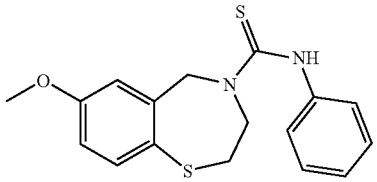
S12
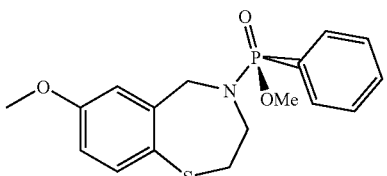
S13
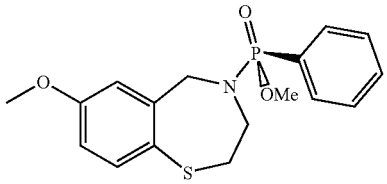
S14
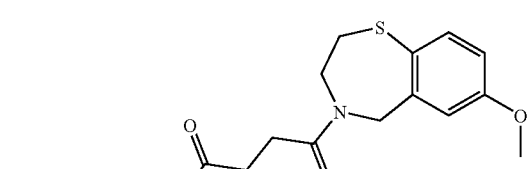
S19
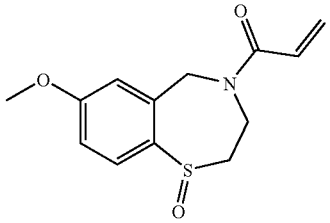
S20
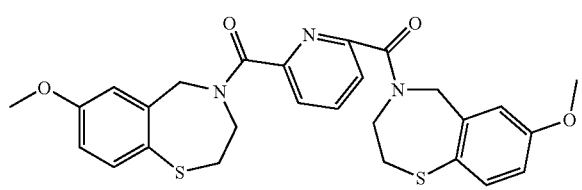
S22

-continued
S23
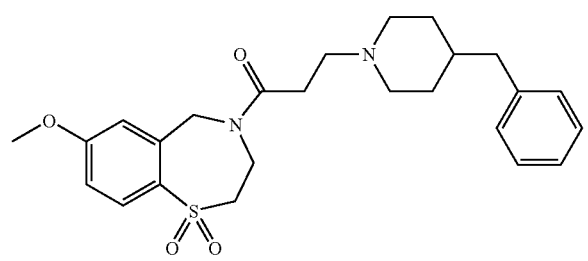
S25
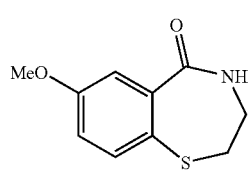
S26
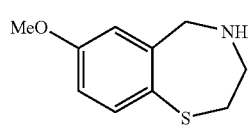
S36
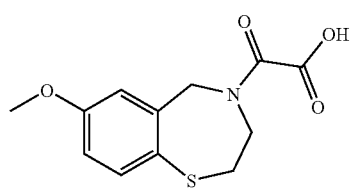
S37
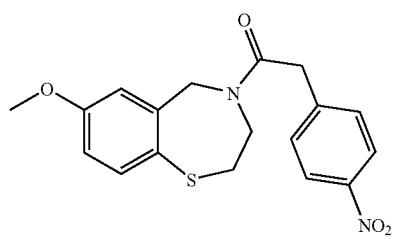
S38
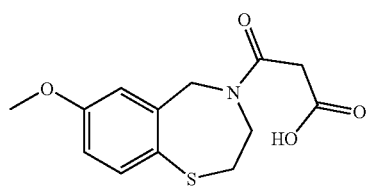
S40
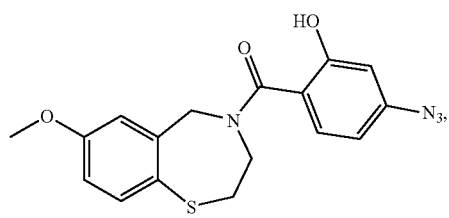
S43
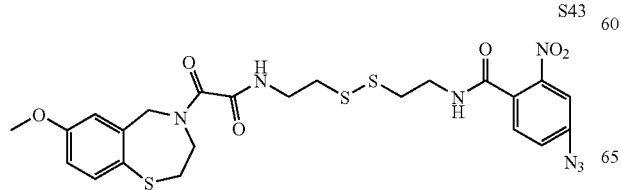
-continued
S44
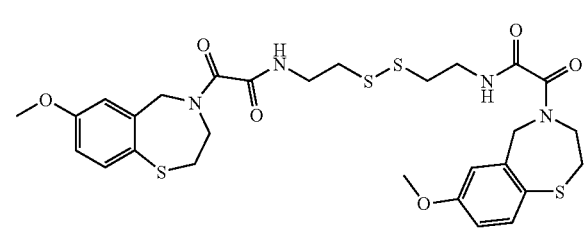
S45
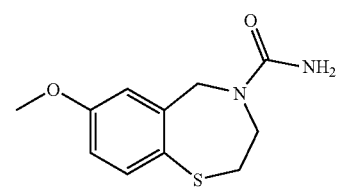
S46
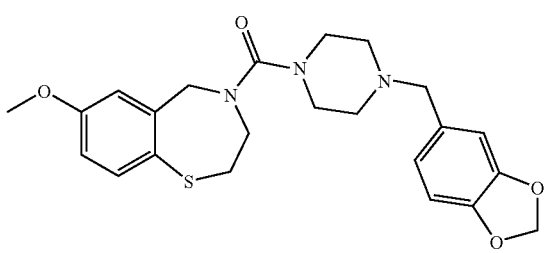
S47
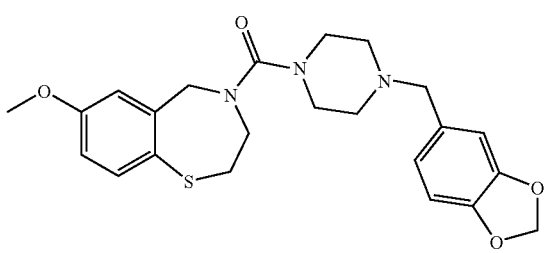
S48
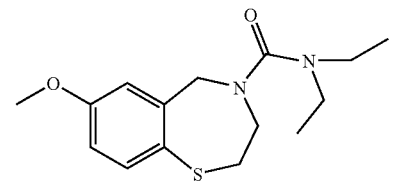
S49
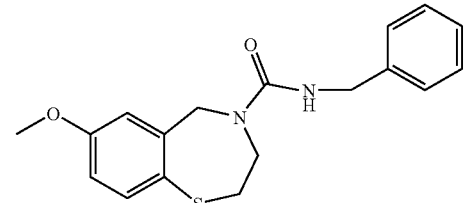
S50
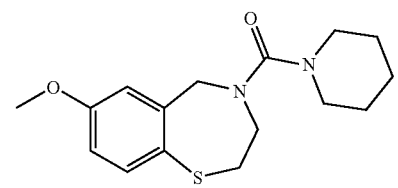

S51 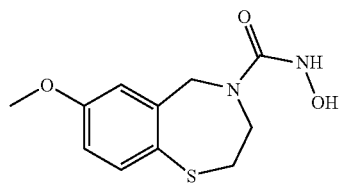
S52 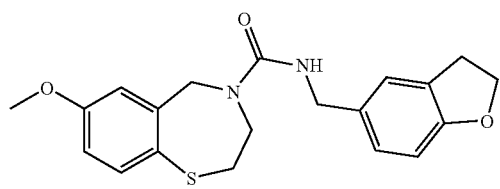
S53 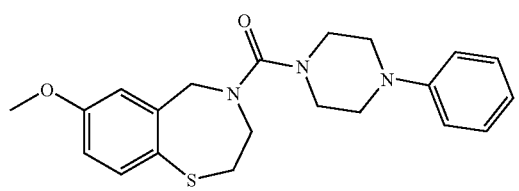
S54 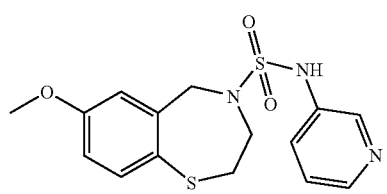
S55 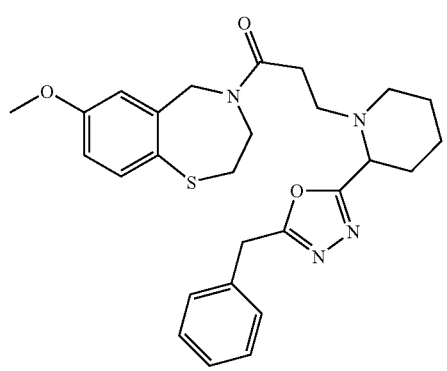
S56 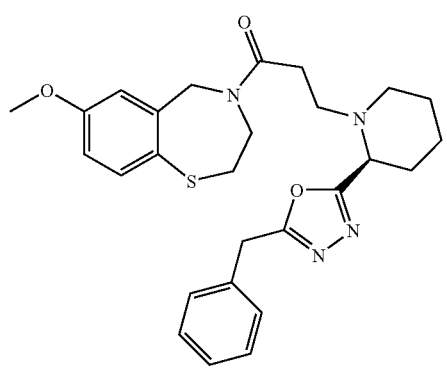
S57 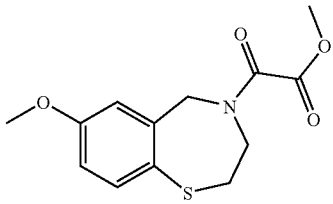
S58 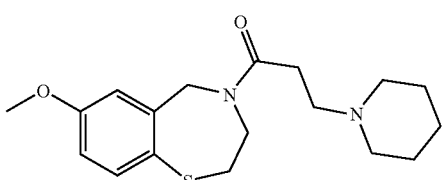
S59 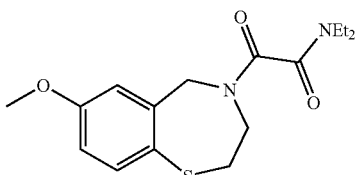
S60 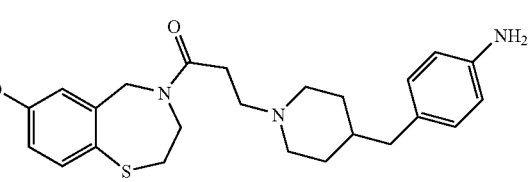
S61 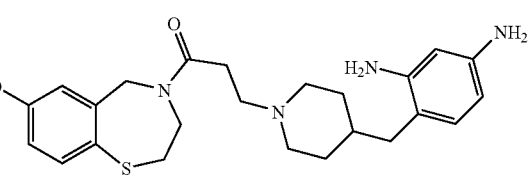
S62 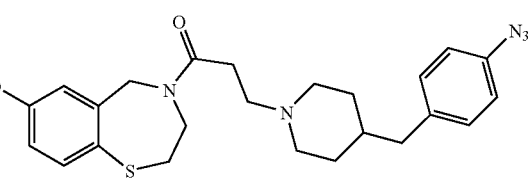
S63 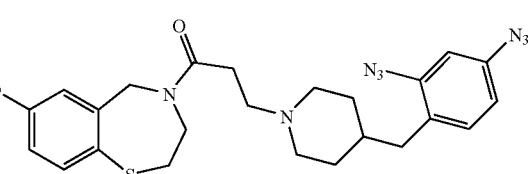
S64 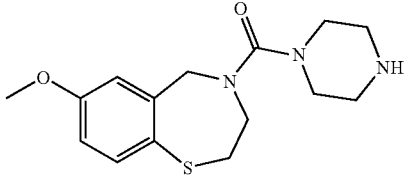

-continued

-continued

S98 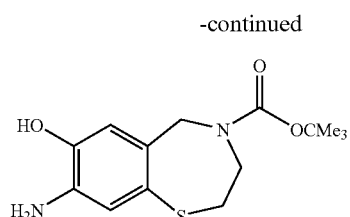
S99 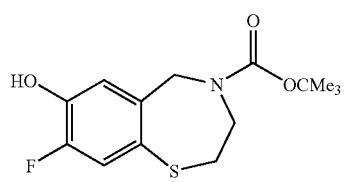
S100 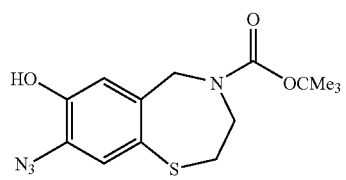
S101 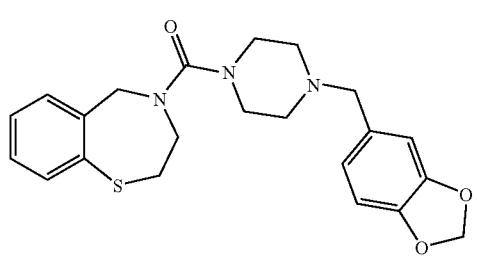
S102 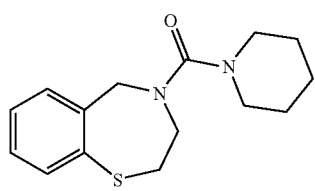
S103 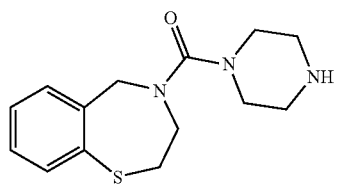
S104 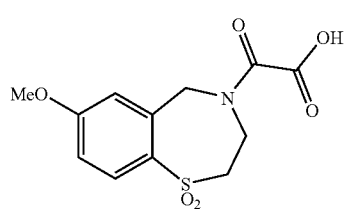
S105 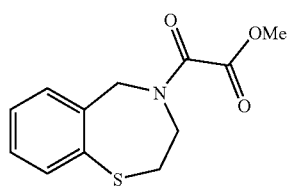
S107 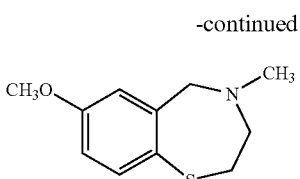
S108 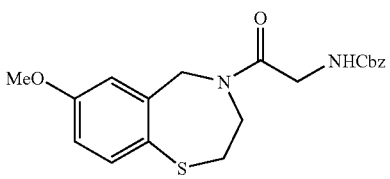
S109 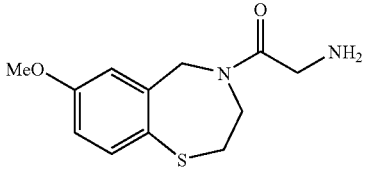
S110 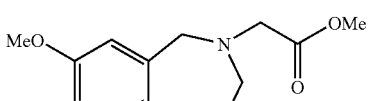
S111 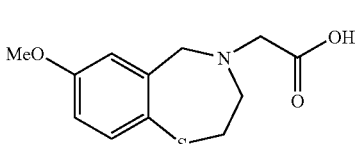
S112 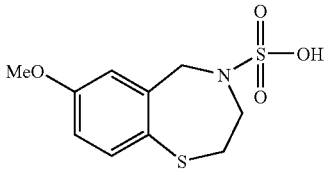
S113 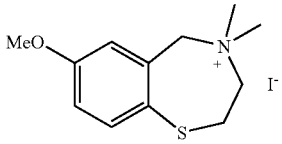
S114 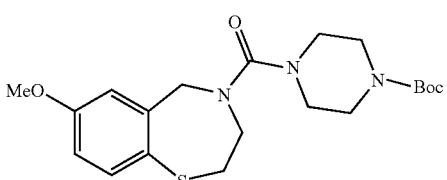
S115 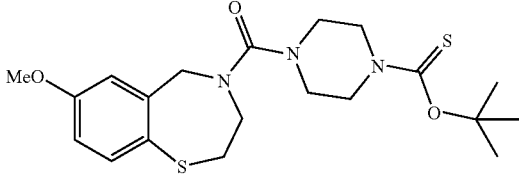

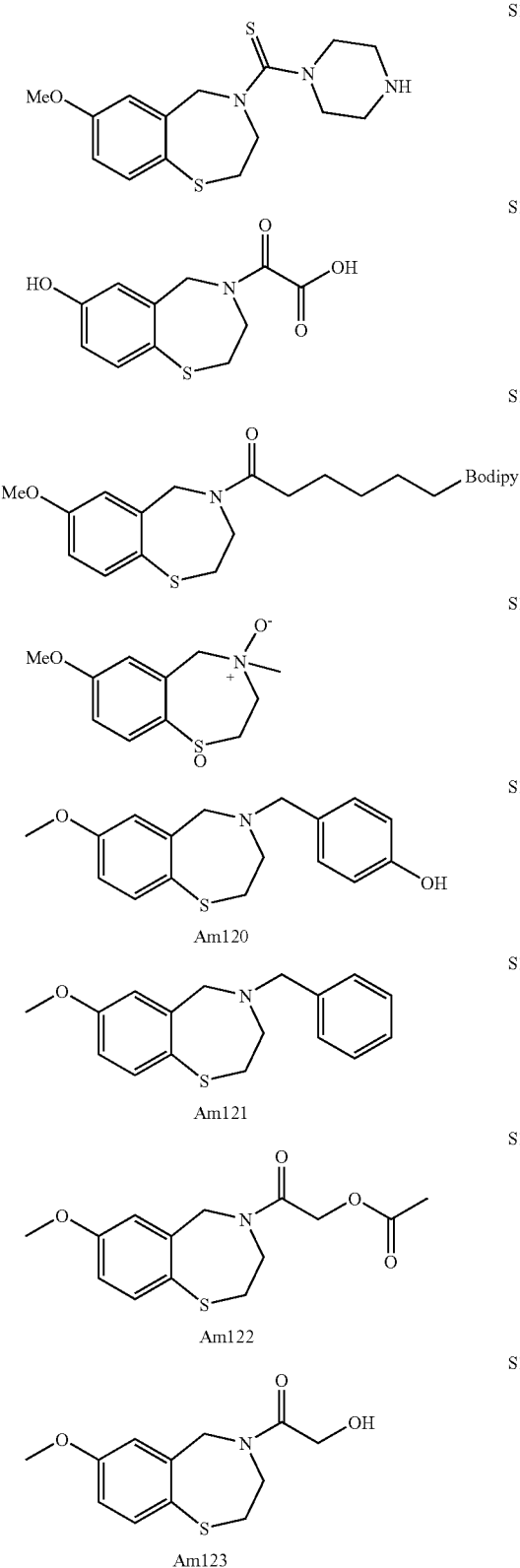

Am120

Am121

Am122

Am123

In one embodiment of the present invention, for compounds of Formula I, if $R_2$ is C=O($R_5$) or $SO_2R_7$, then R is at positions 2, 3, or 5 on the benzene ring.

In another embodiment of the invention, for compounds of Formula I, if $R_2$ is C=O($R_5$) or $S_2R_7$, then each R is independently selected from the group consisting of H, halogen, —OH, —NH$_2$, —NO$_2$, —CN, —N$_3$, —SO$_3$H, acyl, alkyl, alkylamino, cycloalkyl, heterocyclyl, heterocyclylalkyl, alkenyl, (hetero-)aryl, (hetero-)arylthio, and (hetero-)arylamino; wherein each acyl, alkyl, alkoxyl, alkylamino, cycloalkyl, heterocyclyl, heterocyclylalkyl, alkenyl, (hetero-)aryl, (hetero-)arylthio, and (hetero-)arylamino may be substituted with one or more radicals independently selected from the group consisting of halogen, N, O, —S—, —CN, —N$_3$, —SH, nitro, oxo, acyl, alkyl, alkoxyl, alkylamino, alkenyl, aryl, (hetero-)cycloalkyl, and (hetero-)cyclyl.

In another embodiment of the invention, for compounds of Formula I, if $R_2$ is C=O($R_5$) or $SO_2R_7$, then there are at least two R groups attached to the benzene ring. Furthermore, there are at least two R groups attached to the benzene ring, and both R groups are attached at positions 2, 3, or 5 on the benzene ring. Still furthermore, each R is independently selected from the group consisting of H, halogen, —OH, —NH$_2$, —NO$_2$, —CN, —N$_3$, —SO$_3$H, acyl, alkyl, alkylamino, cycloalkyl, heterocyclyl, heterocyclylalkyl, alkenyl, (hetero-)aryl, (hetero-)arylthio, and (hetero-)arylamino; wherein each acyl, alkyl, alkoxyl, alkylamino, cycloalkyl, heterocyclyl, heterocyclylalkyl, alkenyl, (hetero-)aryl, (hetero-)arylthio, and (hetero-)arylamino may be substituted with one or more radicals independently selected from the group consisting of halogen, N, O, —S—, —CN, —N$_3$, —SH, nitro, oxo, acyl, alkyl, alkoxyl, alkylamino, alkenyl, aryl, (hetero-)cycloalkyl, and (hetero-)cyclyl.

In another embodiment of the invention, for compounds of Formula I, if $R_2$ is C=O($R_5$), then $R_5$ is selected from the group consisting of —NR$_{16}$, NHNHR$_{16}$, NHOH, —OR$_{15}$, CONH$_2$NHR$_{16}$, CONR$_{16}$, CH$_2$X, acyl, aryl, cycloalkyl, cycloalkylalkyl, heterocyclyl, and heterocyclylalkyl; wherein each acyl, aryl, cycloalkyl, cycloalkylalkyl, heterocyclyl, and heterocyclylalkyl may be substituted with one or more radicals independently selected from the group consisting of halogen, N, O, —S—, —CN, —N$_3$, nitro, oxo, acyl, alkyl, alkoxyl, alkylamino, alkenyl, aryl, (hetero-)cycloalkyl, and (hetero-)cyclyl.

In another embodiment, the present invention provides compounds of Formula II:

In another embodiment, the present invention provides compounds of Formula II:

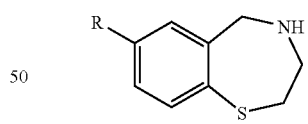

wherein R=OR''', SR''', NR''', alkyl, or halide and R'''=alkyl, aryl, or H, and wherein R can be at position 6, 7, 8, or 9. Formula II is discussed also in co-pending application Ser. No. 10/680,988, the disclosure of which is incorporated herein in its entirety by reference.

Routes of Activity

The compounds of the invention, such as the compounds of Formula I, I-a, I-b, I-c, I-d, I-e, I-f, I-g, I-h, I-i, I-j, I-k, I-l and I-m, reduce the open probability of RyR by increasing the affinity of FKBP12 (calstabin1) and FKBP12.6 (calstabin2) for, respectively PKA-phosphorylated RyR1 and PKA-phosphorylated RyR2. Moreover, the compounds of the invention normalize gating of mutant RyR channels, including CPVT-associated mutant RyR2 channels, by increasing FKBP12 (calstabin1) and FKBP12.6 (calstabin2) binding affinity. Therefore, the compounds of the invention revent disorders and conditions involving modulation of the RyR receptors, particularly the RyR1 and RyR2 receptors. Examples of such disorders and conditions include, without limitation, cardiac disorders and diseases, skeletal muscular disorders and diseases, cognitive disorders and diseases, malignant hyperthermia, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's Disease, forms of memory loss, and age-dependent memory loss. The compounds of the invention treat these disorders and conditions by increasing FKBP12 (calstabin1)-RyR1 binding affinity and increasing FKBP12.6 (calstabin2)-RyR2 binding affinity.

In accordance with the foregoing, the present invention provides a method for limiting or preventing a decrease in the level of RyR-bound FKBP (calstabin) in cells of a subject. As used herein, "RyR" includes RyR1, RyR2, and RyR3. Additionally, FKBP includes both FKBP12 (calstabin1) and FKBP12.6 (calstabin2). "RyR-bound FKBP" therefore refers to RyR1-bound FKBP12 (calstabin1), RyR2-bound FKBP12.6 (calstabin2), and RyR3-bound FKBP12 (calstabin1).

As used herein, "RyR" also includes a "RyR protein" and a "RyR analogue." A "RyR analogue" is a functional variant of the RyR protein, having RyR biological activity, that has 60% or greater amino-acid-sequence homology with the RyR protein. The RyR of the present invention are unphosphorylated, phosphorylated (e.g., by PKA), or hyperphosphorylated (e.g., by PKA). As further used herein, the term "RyR biological activity" refers to the activity of a protein or peptide that demonstrates an ability to associate physically with, or bind with, FKBP12 (calstabin1) in the case of RyR1 and RyR3, and FKBP12.6 (calstabin2) in the case of RyR2 (i.e., binding of approximately two fold or, approximately five fold, above the background binding of a negative control), under the conditions of the assays described herein.

As used herein, "FKBP" includes both an "FKBP protein" and an "FKBP analogue," whether it be FKBP12 (calstabin1) or FKBP12.6 (calstabin2). Unless otherwise indicated herein, "protein" shall include a protein, protein domain, polypeptide, or peptide, and any fragment thereof. An "FKBP analogue" is a functional variant of the FKBP protein, having FKBP biological activity, that has 60% or greater amino-acid-sequence homology with the FKBP protein, whether it be FKBP12 (calstabin1) or FKBP12.6 (calstabin2). As further used herein, the term "FKBP biological activity" refers to the activity of a protein or peptide that demonstrates an ability to associate physically with, or bind with, unphosphorylated or non-hyperphosphorylated RyR2 (i.e., binding of approximately two fold, or approximately five fold, above the background binding of a negative control), under the conditions of the assays described herein.

FKBP binds to the RyR channel, one molecule per RyR subunit. Accordingly, as used herein, the term "RyR-bound FKBP" includes a molecule of an FKBP12 (calstabin1) protein that is bound to an RyR1 protein subunit or a tetramer of FKBP12 that is in association with a tetramer of RyR1, a molecule of FKBP12.6 (calstabin2) protein that is bound to an RyR2 protein subunit or a tetramer of FKBP12.6 that is in association with a tetramer of RyR2, and a molecule of an FKBP12 (calstabin1) protein that is bound to an RyR3 protein subunit or a tetramer of FKBP12 that is in association with a tetramer of RyR3. Therefore, "RyR-bound FKBP" refers to "RyR1-bound FKBP12," "RyR2-bound FKBP12.6," and "RyR3-bound FKBP12."

In accordance with the method of the present invention, a "decrease" or "disorder" in the level of RyR-bound FKBP in cells of a subject refers to a detectable decrease, diminution or reduction in the level of RyR-bound FKBP in cells of the subject. Such a decrease is limited or prevented in cells of a subject when the decrease is in any way halted, hindered, impeded, obstructed or reduced by the administration of compounds of the invention, such that the level of RyR-bound FKBP in cells of the subject is higher than it would otherwise be in the absence of the administered compound.

The level of RyR-bound FKBP in a subject is detected by standard assays and techniques, including those readily determined from the known art (e.g., immunological techniques, hybridization analysis, immunoprecipitation, Western-blot analysis, fluorescence imaging techniques and/or radiation detection, etc.), as well as any assays and detection methods disclosed herein. For example, protein is isolated and purified from cells of a subject using standard methods known in the art, including, without limitation, extraction from the cells (e.g., with a detergent that solubilizes the protein) where necessary, followed by affinity purification on a column, chromatography (e.g., FTLC and HPLC), immunoprecipitation (with an antibody), and precipitation (e.g., with isopropanol and a reagent such as Trizol). Isolation and purification of the protein is followed by electrophoresis (e.g., on an SDS-polyacrylamide gel). A decrease in the level of RyR-bound FKBP in a subject, or the limiting or prevention thereof, is determined by comparing the amount of RyR-bound FKBP detected prior to the administration of JTV-519 or a compound of Formula I, I-a, I-b, I-c, I-d, I-e, I-f, I-g, I-h, I-i, I-j, I-k, I-l or I-m, (in accordance with methods described below) with the amount detected a suitable time after administration of the compound.

A decrease in the level of RyR-bound FKBP in cells of a subject is limited or prevented, for example, by inhibiting dissociation of FKBP and RyR in cells of the subject; by increasing binding between FKBP and RyR in cells of the subject; or by stabilizing the RyR-FKBP complex in cells of a subject. As used herein, the term "inhibiting dissociation" includes blocking, decreasing, inhibiting, limiting or preventing the physical dissociation or separation of an FKBP subunit from an RyR molecule in cells of the subject, and blocking, decreasing, inhibiting, limiting or preventing the physical dissociation or separation of an RyR molecule from an FKBP subunit in cells of the subject. As further used herein, the term "increasing binding" includes enhancing, increasing, or improving the ability of phosphorylated RyR to associate physically with FKBP (e.g., binding of approximately two fold or, approximately five fold, above the background binding of a negative control) in cells of the subject and enhancing, increasing or improving the ability of FKBP to associate physically with phosphorylated RyR (e.g., binding of approximately two fold, or, approximately five fold, above the background binding of a negative control) in cells of the subject. Additionally, a decrease in the level of RyR-bound FKBP in cells of a subject is limited or prevented by directly decreasing the level of phosphorylated RyR in cells of the subject or by indirectly decreasing the level of phosphorylated RyR in the cells (e.g., by targeting an enzyme (such as PKA) or another endogenous molecule that regulates or modulates the functions or levels of phosphorylated RyR in the cells). In one embodiment, the level of phosphorylated RyR in the cells is decreased by at least 10% in the method of the present invention. In another embodiment, the level of phosphorylated RyR is decreased by at least 20%.

The subject of the present invention are in vitro and in vivo systems, including, without limitation, isolated or cultured cells or tissues, non-cell in vitro assay systems and an animal (e.g., an amphibian, a bird, a fish, a mammal, a marsupial, a human, a domestic animal (such as a cat, dog, monkey, mouse or rat) or a commercial animal (such as a cow or pig)).

The cells of a subject include striated muscle cells. A striated muscle is a muscle in which the repeating units (sarcomeres) of the contractile myofibrils are arranged in registry throughout the cell, resulting in transverse or oblique striations that are observed at the level of a light microscope. Examples of striated muscle cells include, without limitation, voluntary (skeletal) muscle cells and cardiac muscle cells. In one embodiment, the cell used in the method of the present invention is a human cardiac muscle cell. As used herein, the term "cardiac muscle cell" includes cardiac muscle fibers, such as those found in the myocardium of the heart. Cardiac muscle fibers are composed of chains of contiguous heart-muscle cells, or cardiomyocytes, joined end to end at intercalated disks. These disks possess two kinds of cell junctions: expanded desmosomes extending along their transverse portions, and gap junctions, the largest of which lie along their longitudinal portions.

A decrease in the level of RyR-bound FKBP is limited or prevented in cells of a subject by administering the compounds of the invention to the subject; this would also permit contact between cells of the subject and the compounds of the invention. The compounds of the invention are modulators of calcium-ion channels. In addition to regulating $Ca^{2+}$ levels in myocardial cells, the compounds of the invention modulate the $Na^+$ current and the inward-rectifier $K^+$ current in cells, such as guinea pig ventricular cells, and inhibits the delayed-rectifier $K^+$ current in cells, such as guinea pig atrial cells.

Pharmaceutical Composition

The compounds of the invention are formulated into pharmaceutical compositions for administration to human subjects in a biologically compatible form suitable for administration in vivo. According to another aspect, the present invention provides a pharmaceutical composition comprising compounds of Formula I, I-a, I-b, I-c, I-d, I-e, I-f, I-g, I-h, I-i, I-j, I-k, I-l or I-m, in admixture with a pharmaceutically acceptable diluent and/or carrier. The pharmaceutically-acceptable carrier must be "acceptable" in the sense of being compatible with the other ingredients of the composition and not deleterious to the recipient thereof. The pharmaceutically-acceptable carrier employed herein is selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. If necessary, pharmaceutical additives, such as antioxidants, aromatics, colorants, flavor-improving agents, preservatives, and sweeteners, are also added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others.

The pharmaceutical formulations of the present invention are prepared by methods well-known in the pharmaceutical arts. For example, the compounds of Formula I, I-a, I-b, I-c, I-d, I-e, I-f, I-g, I-h, I-i, I-j, I-k, I-l or I-m, are brought into association with a carrier and/or diluent, as a suspension or solution. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

The compounds of Formula I, I-a, I-b, I-c, I-d, I-e, I-f, I-g, I-h, I-i, I-j, I-k, I-l or I-m, are administered to a subject by contacting target cells (e.g., cardiac muscle cells) in vivo in the subject with the compounds. The compounds are contacted with (e.g., introduced into) cells of the subject using known techniques utilized for the introduction and administration of proteins, nucleic acids and other drugs. Examples of methods for contacting the cells with (i.e., treating the cells with) the compounds of the invention include, without limitation, absorption, electroporation, immersion, injection, introduction, liposome delivery, transfection, transfusion, vectors and other drug-delivery vehicles and methods. When the target cells are localized to a particular portion of a subject, it is desirable to introduce the compounds of the invention directly to the cells, by injection or by some other means (e.g., by introducing the compounds into the blood or another body fluid). The target cells are contained in tissue of a subject and are detected by standard detection methods readily determined from the known art, examples of which include, without limitation, immunological techniques (e.g., immunohistochemical staining), fluorescence imaging techniques, and microscopic techniques.

Additionally, the compounds of the present invention are administered to a human or animal subject by known procedures including, without limitation, oral administration, sublingual or buccal administration, parenteral administration, transdermal administration, via inhalation or intranasally, vaginally, rectally, and intramuscularly. The compounds of the invention are administered parenterally, by epifascial, intracapsular, intracranial, intracutaneous, intrathecal, intramuscular, intraorbital, intraperitoneal, intraspinal, intrasternal, intravascular, intravenous, parenchymatous, subcutaneous or sublingual injection, or by way of catheter. In one embodiment, the agent is administered to the subject by way of delivery to the subject's muscles including, but not limited to, the subject's cardiac muscles. In an embodiment, the agent is administered to the subject by way of targeted delivery to cardiac muscle cells via a catheter inserted into the subject's heart.

For oral administration, a formulation of the compounds of the invention may be presented as capsules, tablets, powders, granules, or as a suspension or solution. The formulation has conventional additives, such as lactose, mannitol, cornstarch or potato starch. The formulation also is presented with binders, such as crystalline cellulose, cellulose derivatives, acacia, cornstarch or gelatins. Additionally, the formulation is presented with disintegrators, such as cornstarch, potato starch or sodium carboxymethylcellulose. The formulation also is presented with dibasic calcium phosphate anhydrous or sodium starch glycolate. Finally, the formulation is presented with lubricants, such as talc or magnesium stearate.

For parenteral administration (i.e., administration by injection through a route other than the alimentary canal), the compounds of the invention are combined with a sterile aqueous solution that is isotonic with the blood of the subject. Such a formulation is prepared by dissolving a solid active ingredient in water containing physiologically-compatible substances, such as sodium chloride, glycine and the like, and having a buffered pH compatible with physiological conditions, so as to produce an aqueous solution, then rendering said solution sterile. The formulation is presented in unit or multi-dose containers, such as sealed ampoules or vials. The formulation is delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual or by way of catheter into the subject's heart.

For transdermal administration, the compounds of the invention are combined with skin penetration enhancers, such as propylene glycol, polyethylene glycol, isopropanol, ethanol, oleic acid, N-methylpyrrolidone and the like, which increase the permeability of the skin to the compounds of the invention and permit the compounds to penetrate through the skin and into the bloodstream. The compound/enhancer compositions also may be further combined with a polymeric substance, such as ethylcellulose, hydroxypropyl cellulose, ethylene/vinylacetate, polyvinyl pyrrolidone, and the like, to provide the composition in gel form, which are dissolved in a solvent, such as methylene chloride, evaporated to the desired viscosity and then applied to backing material to provide a patch.

In some embodiments, the composition is in unit dose form such as a tablet, capsule or single-dose vial. Suitable unit doses, i.e., therapeutically effective amounts, can be determined during clinical trials designed appropriately for each of the conditions for which administration of a chosen compound is indicated and will, of course, vary depending on the desired clinical endpoint. The present invention also provides articles of manufacture for treating and preventing disorders, such as cardiac disorders, in a subject. The articles of manufacture comprise a pharmaceutical composition of one or more of the compounds of Formula I, I-a, I-b, I-c, I-d, I-e, I-f, I-g, I-h, I-i, I-j, I-k, I-l or I-m, as described herein. The articles of manufacture are packaged with indications for various disorders that the pharmaceutical compositions are capable of treating and/or preventing. For example, the articles of manufacture comprise a unit dose of a compound disclosed herein that is capable of treating or preventing a muscular disorder, and an indication that the unit dose is capable of treating or preventing a certain disorder, for example an arrhythmia.

In accordance with a method of the present invention, the compounds of Formula I, I-a, I-b, I-c, I-d, I-e, I-f, I-g, I-h, I-i, I-j, I-k, I-l or I-m, are administered to the subject (or are contacted with cells of the subject) in an amount effective to limit or prevent a decrease in the level of RyR-bound FKBP in the subject, particularly in cells of the subject. This amount is readily determined by the skilled artisan, based upon known procedures, including analysis of titration curves established in vivo and methods and assays disclosed herein. In one embodiment, a suitable amount of the compounds of the invention effective to limit or prevent a decrease in the level of RyR-bound FKBP in the subject ranges from about 0.01 mg/kg/day to about 20 mg/kg/day, and/or is an amount sufficient to achieve plasma levels ranging from about 300 ng/ml to about 1000 ng/ml. In an embodiment, the amount of compounds from the invention ranges from about 10 mg/kg/day to about 20 mg/kg/day. In another embodiment, from about 0.01 mg/kg/day to about 10 mg/kg/day is administered. In another embodiment, from about 0.01 mg/kg/day to about 5 mg/kg/day is administered. In another embodiment, from about 0.05 mg/kg/day to about 5 mg/kg/day is administered. In another, preferred embodiment, from about 0.05 mg/kg/day to about 1 mg/kg/day is administered.

Uses

The present invention provides a new range of therapeutic treatments for patients with various disorders involving modulation of the RyR receptors, particularly skeletal muscular disorders (RyR1), cardiac (RyR2) disorders, and cognitive (RyR3) disorders.

In one embodiment of the present invention, the subject has not yet developed a disorder, such as cardiac disorders (e.g., exercise-induced cardiac arrhythmia). In another embodiment of the present invention, the subject is in need of treatment for a disorder, including a cardiac disorder.

Various disorders that the compounds of the invention treat or prevent include, but are not limited to, cardiac disorders and diseases, skeletal muscular disorders and diseases, cognitive disorders and diseases, malignant hyperthermia, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's Disease, forms of memory loss, and age-dependent memory loss. One skilled in the art will recognize still other diseases, including but not limited to muscular and cardiac disorders, that the compounds of the invention can be useful to treat, in accordance with the information provided herein.

The amount of compounds of the invention effective to limit or prevent a decrease in the level of RyR2-bound FKBP12.6 in the subject is an amount effective to prevent exercise-induced cardiac arrhythmia in the subject. Cardiac arrhythmia is a disturbance of the electrical activity of the heart that manifests as an abnormality in heart rate or heart rhythm. As used herein, an amount of compounds of the invention "effective to prevent exercise-induced cardiac arrhythmia" includes an amount of compounds of Formula I, I-a, I-b, I-c, I-d, I-e, I-f, I-g, I-h, I-i, I-j, I-k, I-l and I-m, effective to prevent the development of the clinical impairment or symptoms of the exercise-induced cardiac arrhythmia (e.g., palpitations, fainting, ventricular fibrillation, ventricular tachycardia and sudden cardiac death). The amount of the compounds effective to prevent exercise-induced cardiac arrhythmia in a subject will vary depending upon the particular factors of each case, including the type of exercise-induced cardiac arrhythmia, the subject's weight, the severity of the subject's condition, and the mode of administration of the compounds. This amount is readily determined by the skilled artisan, based upon known procedures, including clinical trials, and methods disclosed herein. In one embodiment, the amount of the compounds of the invention effective to prevent the exercise-induced cardiac arrhythmia is an amount effective to prevent exercise-induced sudden cardiac death in the subject. In another embodiment, the compounds of the invention prevent exercise-induced cardiac arrhythmia and exercise-induced sudden cardiac death in the subject.

Because of its ability to stabilize RyR-bound FKBP and maintain and restore balance in the context of dynamic PKA phosphorylation and dephosphorylation of RyR, the compounds of the invention are also useful in treating a subject who has already experienced clinical symptoms of these various disorders. For example, if the symptoms of the disorder are observed in the subject early enough, the compounds of Formula I, I-a, I-b, I-c, I-d, I-e, I-f, I-g, I-h, I-i, I-j, I-k, I-l and I-m, are effective in limiting or preventing a further decrease in the level of RyR-bound FKBP in the subject.

Additionally, the subject of the present invention is a candidate for exercise-induced cardiac disorders, such as exercise-induced cardiac arrhythmia. Exercise-induced cardiac arrhythmia is a heart condition (e.g., a ventricular fibrillation or ventricular tachycardia, including any that leads to sudden cardiac death) that develops during/after a subject has undergone physical exercise. A "candidate" for an exercise-induced cardiac disorder is a subject who is known to be, or is believed to be, or is suspected of being, at risk for developing a cardiac disorder during/after physical exercise. Examples of candidates for exercise-induced cardiac arrhythmia include, without limitation, an animal/person known to have catecholaminergic polymorphic ventricular tachycardia (CPVT); an animal/person suspected of having CPVT; and an animal/person who is known to be, or is believed to be, or is suspected of being at risk for developing cardiac arrhythmia during/after physical exercise, and who is about to exercise, is currently exercising or has just completed exercise. As discussed above, CPVT is an inherited disorder in individuals with structurally-normal hearts. It is characterized by stress-induced ventricular tachycardia—a lethal arrhythmia that causes sudden cardiac death. In subjects with CPVT, physical exertion and/or stress induce bidirectional and/or polymorphic ventricular tachycardias that lead to sudden cardiac death (SCD) in the absence of detectable structural heart disease. Individuals with CPVT have ventricular arrhythmias when subjected to exercise, but do not develop arrhythmias at rest.

Accordingly, in still another embodiment of the present invention, the subject has been exercising, or is currently exercising, and has developed an exercise-induced disorder. In this case, the amount of the compounds of the invention effective to limit or prevent a decrease in the level of RyR-bound FKBP in the subject is an amount of compound effective to treat the exercise-induced disorder in the subject. As used herein, an amount of compounds of the invention "effective to treat an exercise-induced disorder" includes an amount of a compound of Formula I, I-a, I-b, I-c, I-d, I-e, I-f, I-g, I-h, I-i, I-j, I-k, I-l or I-m, effective to alleviate or ameliorate the clinical impairment or symptoms of the exercise-induced disorder (e.g., in the case of cardiac arrhythmia, palpitations, fainting, ventricular fibrillation, ventricular tachycardia, and sudden cardiac death). The amount of the compounds of the invention effective to treat an exercise-induced disorder in a subject will vary depending upon the particular factors of each case, including the type of exercise-induced disorder, the subject's weight, the severity of the subject's condition, and the mode of administration of the compounds. This amount is readily determined by the skilled artisan, based upon known procedures, including clinical trials, and methods disclosed herein. In one embodiment, the compounds of Formula I, I-a, I-b, I-c, I-d, I-e, I-f, I-g, I-h, I-i, I-j, I-k, I-l and I-m, treat exercise-induced disorders in the subject.

The present invention further provides a method for treating exercise-induced disorders in a subject. The method comprises administering the compounds of Formula I, I-a, I-b, I-c, I-d, I-e, I-f, I-g, I-h, I-i, I-j, I-k, I-l or I-m, to the subject in an amount effective to treat the exercise-induced disorder in the subject. A suitable amount of the compounds effective to treat, for example, exercise-induced cardiac arrhythmia in the subject ranges from about 5 mg/kg/day to about 20 mg/kg/day, and/or is an amount sufficient to achieve plasma levels ranging from about 300 ng/ml to about 1000 ng/ml. The present invention also provides a method for preventing an exercise-induced disorder in a subject. The method comprises administering the compounds of the invention to the subject in an amount effective to prevent the exercise-induced disorder in the subject. A suitable amount of the compounds of the invention effective to prevent the exercise-induced disorder in the subject ranges from about 5 mg/kg/day to about 20 mg/kg/day, and/or is an amount sufficient to achieve plasma levels ranging from about 300 ng/ml to about 1000 ng/ml. Additionally, the present invention provides a method for preventing exercise-induced disorders in a subject. The method comprises administering the compounds of the invention to the subject in an amount effective to prevent an exercise-induced disorder in the subject. A suitable amount of the compounds of the invention effective to prevent an exercise-induced disorder in the subject ranges from about 5 mg/kg/day to about 20 mg/kg/day, and/or is an amount sufficient to achieve plasma levels ranging from about 300 ng/ml to about 1000 ng/ml.

Additionally, the compounds prevent irregular heartbeat disorders in subjects with heterozygous defects in the FKBP12.6 gene.

The compounds of Formula I, I-a, I-b, I-c, I-d, I-e, I-f, I-g, I-h, I-i, I-j, I-k, I-l and I-m, can be used alone, in combination with each other, or in combination with other agents that have cardiovascular activity including, but not limited to, diuretics, anticoagulants, antiplatelet agents, antiarrhythmics, inotropic agents, chronotropic agents, α and β blockers, angiotensin inhibitors and vasodilators. Further, such combinations of the compounds of the present invention and other cardiovascular agents are administered separately or in conjunction. In addition, the administration of one element of the combination is prior to, concurrent to or subsequent to the administration of other agent(s).

In various embodiments of the above-described methods, the exercise-induced cardiac arrhythmia in the subject is associated with VT. In some embodiments, the VT is CPVT. In other embodiments of these methods, the subject is a candidate for exercise-induced cardiac arrhythmia, including candidates for exercise-induced sudden cardiac death.

In view of the foregoing methods, the present invention also provides use of the compounds of the invention in a method for limiting or preventing a decrease in the level of RyR-bound FKBP in a subject who is a candidate for a disorder. The present invention also provides use of the compounds of the invention in a method for treating or preventing a muscular disorder in a subject. Furthermore, the present invention provides use of the compounds of the invention in a method for preventing treating or preventing exercise-induced muscular disorders in a subject.

Accordingly, the present invention further provides a method for assaying the effects of the compounds of the invention in preventing disorders and diseases associated with the RyR receptors. The method comprises the steps of: (a) obtaining or generating a culture of cells containing RyR; (b) contacting the cells with one or more of the compounds of the invention; (c) exposing the cells to one or more conditions known to increase phosphorylation of RyR in cells; and (d) determining if the one or more compounds of the invention limits or prevents a decrease in the level of RyR-bound FKBP in the cells. As used herein, a cell "containing RyR" is a cell in which RyR, including RyR1, RyR2, and RyR3, or a derivative or homologue thereof, is naturally expressed or naturally occurs. Conditions known to increase phosphorylation of RyR in cells include, without limitation, PKA.

In the method of the present invention, cells are contacted with one or more of the compounds of the invention by any of the standard methods of effecting contact between drugs/agents and cells, including any modes of introduction and administration described herein. The level of RyR-bound FKBP in the cell is measured or detected by known procedures, including any of the methods, molecular procedures and assays known to one of skill in the art or described herein. In one embodiment of the present invention, the one or more compounds of the invention limits or prevents a decrease in the level of RyR-bound FKBP in the cells.

RyR, including RyR1, RyR2, and RyR3, has been implicated in a number of biological events in cells. For example, it has been shown that RyR2 channels play an important role in EC coupling and contractility in cardiac muscle cells. Therefore, it is clear that preventive drugs designed to limit or prevent a decrease in the level of RyR-bound FKBP in cells, particularly RyR2-bound FKPB12.6 in cardiac muscle cells, are useful in the regulation of a number of RyR-associated biological events, including EC coupling and contractility. Thus, the one or more compounds of the invention are evaluated for effect on EC coupling and contractility in cells, particularly cardiac muscle cells, and therefore, usefulness for preventing exercise-induced sudden cardiac death.

Accordingly, the method of the present invention further comprises the steps of contacting one or more compounds of the invention with a culture of cells containing RyR; and determining if the one or more compounds has an effect on an RyR-associated biological event in the cells. As used herein, a "RyR-associated biological event" includes a biochemical or physiological process in which RyR levels or activity have been implicated. As disclosed herein, examples of RyR-associated biological events include, without limitation, EC coupling and contractility in cardiac muscle cells. According to this method of the present invention, the one or more compounds are contacted with one or more cells (such as cardiac muscle cells) in vitro. For example, a culture of the cells is incubated with a preparation containing the one or more compounds of Formula I, I-a, I-b, I-c, I-d, I-e, I-f, I-g, I-h, I-i, I-j, I-k, I-l or I-m. The compounds' effect on a RyR-associated biological event then is assessed by any biological assays or methods known in the art, including immunoblotting, single-channel recordings and any others disclosed herein.

The present invention is further directed to one or more compounds of Formula I, I-a, I-b, I-c, I-d, I-e, I-f, I-g, I-h, I-i, I-j, I-k, I-l or I-m, identified by the above-described identification method, as well as a pharmaceutical composition comprising the compound and a pharmaceutically acceptable carrier and/or diluent. The compounds are useful for preventing exercise-induced sudden cardiac death in a subject, and for treating or preventing other RyR-associated conditions. As used herein, a "RyR-associated condition" is a condition, disease, or disorder in which RyR level or activity has been implicated, and includes an RyR-associated biological event.

The RyR-associated condition is treated or prevented in the subject by administering to the subject an amount of the compound effective to treat or prevent the RyR-associated condition in the subject. This amount is readily determined by one skilled in the art. In one embodiment, the present invention provides a method for preventing exercise-induced sudden cardiac death in a subject, by administering the one or more compounds of the invention to the subject in an amount effective to prevent the exercise-induced sudden cardiac death in the subject.

The present invention also provides an in vivo method for assaying the effectiveness of the compounds of the invention in preventing disorders and diseases associated with the RyR receptors. The method comprises the steps of: (a) obtaining or generating an animal containing RyR; (b) administering one or more of the compounds of the invention to the animal; (c) exposing the animal to one or more conditions known to increase phosphorylation of RyR in cells; and (d) determining the extent the compound limits or prevents a decrease in the level of RyR-bound FKBP in the animal. The method further comprises the steps of: (e) administering one or more of the compounds of the invention to an animal containing RyR; and (f) determining the extent of the effect of the compound on a RyR-associated biological event in the animal. Also provided is a pharmaceutical composition comprising this compound; and a method for preventing exercise-induced sudden cardiac death in a subject, by administering this compound to the subject in an amount effective to prevent the exercise-induced sudden cardiac death in the subject.

It has been demonstrated that compounds which block PKA activation would be expected to reduce the activation of the RyR channel, resulting in less release of calcium into the cell. Compounds that bind to the RyR channel at the FKBP binding site, but do not come off the channel when the channel is phosphorylated by PKA, would also be expected to decrease the activity of the channel in response to PKA activation or other triggers that activate the RyR channel. Such compounds would also result in less calcium release into the cell.

By way of example, the diagnostic assays screen for the release of calcium into cells via the RyR channel, using calcium-sensitive fluorescent dyes (e.g., Fluo-3, Fura-2, and the like). Cells are loaded with the fluorescent dye of choice, then stimulated with RyR activators to determine the reduction of the calcium-dependent fluorescent signal (Brillantes, et al., Stabilization of calcium release channel (ryanodine receptor) function by FK506-binding protein. *Cell,* 77:513-23, 1994; Gillo, et al., Calcium entry during induced differentiation in murine erythroleukemia cells. *Blood,* 81:783-92, 1993; Jayaraman, et al., Regulation of the inositol 1,4,5-trisphosphate receptor by tyrosine phosphorylation. *Science,* 272:1492-94, 1996). Calcium-dependent fluorescent signals are monitored with a photomultiplier tube, and analyzed with appropriate software. This assay can easily be automated to screen the compounds of the invention using multiwell dishes.

To demonstrate that the compounds of inhibit the PKA-dependent activation of RyR-mediated intracellular calcium release, an assay involves the expression of recombinant RyR channels in a heterologous expression system, such as Sf9, HEK293, or CHO cells. RyR could also be co-expressed with beta-adrenergic receptors. This would permit assessment of the effect of compounds of the invention on RyR activation, in response to addition of beta-adrenergic receptor agonists.

The level of PKA phosphorylation of RyR2 which correlates with the degree of heart failure also is assayed and then used to determine the efficacy of the one or more compounds of the invention to block the PKA phosphorylation of the RyR2 channel. Such an assay is based on the use of antibodies that are specific for the RyR2 protein. For example, the RyR2-channel protein is immunoprecipitated and then back-phosphorylated with PKA and [gamma $^{32}$P]-ATP. The amount of radioactive [$^{32}$P] label that is transferred to the RyR2 protein then is measured using a phosphorimager (Marx, et al., PKA phosphorylation dissociates FKBP12.6 from the calcium release channel (ryanodine receptor): defective regulation in failing hearts. *Cell,* 101:365-76, 2000).

Another assay of the compounds of the invention involves use of a phosphoepitope-specific antibody that detects RyR1 that is PKA phosphorylated on Ser 2843 or RyR2 that is PKA phosphorylated on Ser 2809. Immunoblotting with such an antibody can be used to assess efficacy of these compounds for therapy for heart failure and cardiac arrhythmias. Additionally, RyR2 S2809A and RyR2 S2809D knock-in mice are used to assess efficacy of therapy for heart failure and cardiac arrhythmias. Such mice further provide evidence that PKA hyperphosphorylation of RyR2 is a contributing factor in heart failure and cardiac arrhythmias by showing that the RyR2 S2809A mutation inhibits heart failure and arrhythmias, and that the RyR2 S2809D mutation worsens heart failure and arrhythmias.

Therefore, in a specific embodiment, the present invention provides a method of treating heart failure, atrial fibrillation or exercise-induced cardiac arrhythmia, comprising administering to an animal in need thereof, a therapeutically effective amount of a compound selected from the compounds of Formula I, I-a, I-b, I-c, I-d, I-e, I-f, I-g, I-h, I-i, I-j, I-k, I-l and I-m.

Intracellular $Ca^{2+}$ leak is proposed as a principal mediator of depressed muscle performance and dystrophic muscle remodeling. Muscular dystrophies are heterogeneous hereditary diseases characterized by weakness and progressive muscle wasting. Of all forms of muscular dystrophies involving the dystrophin-associated protein complex (referred to as dystrophinopathies), Duchenne muscular dystrophy (DMD) is one of the most frequent genetic diseases (X-linked; 1 in 3,500 boys) with death usually occurring before age 30 by respiratory and/or cardiac failure in high numbers of patients. Becker muscular dystrophy (BMD) represents a milder form of the disease associated with a reduction in the amount or expression of a truncated form of the dystrophin protein whereas Duchenne patients have been characterized by complete absence or very low levels of dystrophin. Duchenne and Becker's muscular dystrophy (DMD/BMD) are caused by mutations in the gene encoding the 427-kDa cytoskeletal protein dystrophin. However, with increasing age in BMD cardiac symptoms are more common than in DMD patients and do not correlate with skeletal muscle symptoms. Since genetic screening will not eliminative DMD due to a high incidence of sporadic cases, an effective therapy is highly desirable. DMD/BMD have been consistently associated with disturbed intracellular calcium metabolism. Because alterations of intracellular $Ca^{2+}$ concentrations in DMD myofibers are believed to represent a central pathogenic mechanism, development of a therapeutic intervention that prevents intracellular $Ca^{2+}$ abnormalities as a cause of skeletal muscle degeneration is highly desirable.

It is well established that lack of dystrophin expression is the primary genetic defect in DMD and BMD. However, the key mechanism leading to progressive muscle damage is largely unknown. It has been suggested that elevations of intracellular $Ca^{2+}$ concentrations ($[Ca^{2+}]_i$) under resting conditions directly contributed to toxic muscle cell (myofiber) damage and concurrent activation of $Ca^{2+}$-dependent proteases. Since calpain activity is increased in necrotic muscle fibers of mdx mice and calpain dysfunction contributes to limb-girdle muscular dystrophy, preventing activation of calcium-dependent proteases by inhibiting intracellular $Ca^{2+}$ elevations represents a strategy to prevent muscle wasting in DMD. Significant differences in $[Ca^{2+}]_i$ between normal and dystrophic muscles have been reported in myotubes and animal models including the dystrophin-deficient mdx mouse. Intracellular $Ca^{2+}$ elevations are prevented by administration of a pharmaceutical composition comprising a compound of Formula I, I-a, I-b, I-c, I-d, I-e, I-f, I-g, I-h, I-i, I-j, I-k, I-l or I-m.

The present invention also provides a method of diagnosis of a disease or disorder in a subject, said method comprising: obtaining a cell or tissue sample from the subject; obtaining DNA from the cell or tissue; comparing the DNA from the cell or tissue with a control DNA encoding RyR to determine whether a mutation is present in the DNA from the cell or tissue, the presence of a mutation indicating a disease or disorder. In one embodiment, the mutation is a RyR2 mutation on chromosome 1q42-q43. In another embodiment, the mutation is one or more CPTV mutations. In another embodiment, the mutation may be a mutation that is present in the DNA encoding RyR2 of a SIDS subject. The diagnostic method is used to detect the presence of a disease or disorder in an adult, a child or a fetus. The disease and disorders include, but are not limited to, cardiac disorders and diseases, skeletal muscular disorders and diseases, cognitive disorders and diseases, malignant hyperthermia, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's Disease, forms of memory loss, and age-dependent memory loss.

The present invention further provides a method of diagnosis of disorders and diseases in a subject, said method comprising: obtaining cells or tissue sample from the subject; incubating the cells or tissue sample with the compound of the invention under conditions which increase phosphorylation of RyR in cells; determining (a) whether RyR bound to calstabin (i.e. RyR1 bound to calstabin1, RyR2 bound to calstabin2, or RyR3 bound to calstabin1) is increased in the cells or tissue compared to RyR bound to calstabin in control cells or tissues said control cells or tissues lacking mutant RyR calcium channels, or (b) whether a decrease in release of calcium occurs in RyR channels compared to a lack of decrease in release of calcium in the control cells; an increase in RyR-bound calstabin in (a) indicating a disorder or disease in the subject or a decrease in release of calcium in RyR channels in (b) compared to the control cells indicating a cardiac disease or disorder in the subject. The diagnostic method is used to detect the presence of a disease or disorder in an adult, a child or a fetus. The disease and disorders include, but are not limited to, cardiac disorders and diseases, skeletal muscular disorders and diseases, cognitive disorders and diseases, malignant hyperthermia, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's Disease, forms of memory loss, and age-dependent memory loss.

The present invention further provides a method of diagnosis of a cardiac disorder or disease in a subject, said method comprising: obtaining cardiac cells or tissue sample from the subject; incubating the cardiac cells or tissue sample with the compound of Formula I, I-a, I-b, I-c, I-d, I-e, I-f, I-g, I-h, I-i, I-j, I-k, I-l or I-m, under conditions which increase phosphorylation of RyR2 in cells; determining (a) whether RyR2 bound to calstabin2 is increased in the cells or tissue compared to RyR2 bound to calstabin2 in control cells or tissues said control cells or tissues lacking mutant RyR2 calcium channels, or (b) whether a decrease in release of calcium occurs in RyR2 channels compared to a lack of decrease in release of calcium in the control cells; an increase in RyR2-bound calstabin2 in (a) indicating a disorder or disease in the subject or a decrease in release of calcium in RyR2 channels in (b) compared to the control cells indicating a cardiac disease or disorder in the subject. The provided method is used to diagnose CPTV. The provided method also is used to diagnose sudden infant death syndrome (SIDS). The provided method additionally is used to diagnose cardiac irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof.

In addition to the above-mentioned therapeutic uses, the compounds of the invention are also useful in diagnostic assays, screening assays and as research tools.

Methods of Synthesis

The present invention, provides, in a further aspect, processes for the preparation of a compound of Formula I, I-a, I-b, I-c, I-d, I-e, I-f, I-g, I-h, I-i, I-j, I-k, I-l or I-m, and salts, solvates, hydrates, complexes, and pro-drugs thereof, and pharmaceutically acceptable salts of such pro-drugs. More particularly, the present invention provides processes for the preparation of compounds selected from the group consisting of S1, S2, S3, S4, S5, S6, S7, S9, S11, S12, S13, S14, S19, S20, S22, S23, S26, S36, S37, S38, S40, S43, S44, S45, S46, S47, S48, S49, S50, S51, S52, S53, S54, S55, S56, S57, S58, S59, S60, S61, S62, S63, S64, S66, S67, S69, S70, S71, S72, S73, S74, S75, S76, S77, S78, S79, S80, S81, S82, S83, S84, S85, S86, S87, S88, S89, S90, S91, S92, S93, S94, S95, S96, S97, S98, S99, S100, S101, S102, S103, S104, S105, S107, S108, S109, S110, S111, S112, S113, S114, S115, S116, S117, S118, S119, S120, S121, S122, and S123, and salts, solvates, hydrates, complexes, and pro-drugs thereof, and pharmaceutically acceptable salts of such pro-drugs. The various synthetic routes to the compounds are described herein.

Some of the following syntheses utilize solvents. In one embodiment, the solvent is an organic solvent. In another embodiment, the organic solvent is methylene chloride ($CH_2Cl_2$), chloroform ($CCl_4$), formaldehyde ($CH_2O$) or methanol ($CH_3OH$). Some of the following syntheses also utilize a base catalyst. In one embodiment, the base catalyst is an amine compound. In another embodiment, the base catalyst is an alkylamine such as triethylamine (TEA). In still another embodiment, the base catalyst is pyridine. Some of the following syntheses also utilize basic solutions. In one embodiment, the basic solution is sodium bicarbonate or calcium carbonate. In another embodiment, the basic solution is saturated sodium bicarbonate or saturated calcium carbonate. Some of the following syntheses use acidic solutions. In one embodiment, the acidic solution is a sulfuric acid solution, a hydrochloric acid solution, or a nitric acid solution. In one embodiment, the solution is 1N HCl. One of skill in the art will appreciate still other solvents, organic solvents, base catalysts, basic solutions, and acidic solutions that are used in the embodiments, according to the description herein. The solvents, organic solvents, reactants, catalysts, wash solutions, and so forth are added at appropriate temperatures (e.g. room temperature or about 20° C.-25° C., 0° C., etc.).

Some of the following syntheses utilize the compound S68 as a starting material. S68 is available commercially from MicroChemistry Ltd. (Moscow, Russia). See also WO01/55118 for the preparation of S68.

Several of the following syntheses use S26 as a starting material. S26 is synthesized as an intermediate in the synthesis of S3, S4, S5, and S54, as illustrated in scheme 1 in example 4. Methods for synthesizing S26 are also described in U.S. patent application Ser. No. 10/680,988.

Some of the following syntheses requiring purification of the reaction mixture to yield a final product. Purification of the reaction mixture involves one or more processes such as removal of any solvent, crystallization of the product, chromatographic separation of the product (including HPLC, silica gel chromatography, column chromatography, and so forth), washing with basic solution, washing with acidic solution, re-dissolving the product in another solvent, and so forth. One of skill in the art will appreciate still other processes that are used in the embodiments, according to the description herein.

The reactions are carried out as long as needed (e.g., one hour, several hours, overnight, 24 hours, etc.) to obtain the desired or optimal yields of the desired compounds. Often, the reaction mixtures are stirred. The reactions are carried out at appropriate temperatures (e.g. room temperature or about 20° C.-25° C., 0° C., 100° C., etc.).

Synthon S26 is prepared according to methods described in U.S. patent application Ser. No. 10/680,988.

S3, S4, S5, and S54 are prepared from S26. S26 is reacted with $RSO_2Cl$, wherein R is $CH_2=CH-$ (S3), Me- (S4), p-Me-$C_6H_4-$ (S5), or NH-2-Py (S54), to form a product. The product is purified, for example by column chromatography, to yield S3, S4, S5, or S54. In one embodiment, the reaction occurs in a solvent, such as an organic solvent like $CH_2Cl_2$, so that a reaction mixture is formed, and the solvent is removed from the reaction mixture before or during purification of the product. If necessary, a base catalyst, such as triethylamine, is used in the synthesis. Also, basic (e.g., saturated sodium bicarbonate) and acidic washes (e.g., 1N HCl) are used if needed to purifying the reaction mixture and/or product, and are accompanied by drying, for example over sodium sulfate, if needed. Column chromatography, for example, is used to purifying the residue to isolate the desired product.

S1 and S2 are prepared from S3 by reaction with $HNR_1R_2$, where R is

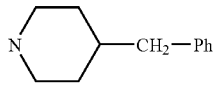

(S1) or $NBu_2$ (S2). The product is purified, for example by column chromatography, to yield S1 or S2. In one embodiment, the reaction occurs in a solvent, such as an organic solvent like $CH_2Cl_2$, so that a reaction mixture is formed, and the solvent is removed from the reaction mixture before or during purification of the product. Column chromatography, for example, is used to purifying the residue to isolate the desired product.

S7, S9, S27 and S40 are prepared from S26 by reaction with an alcohol of formula RCOX, where X is Cl or NHS and R is $ICH_2$— (S7), Ph- (S9), $CH_2$=CH— (S27), or $4-N_3-2-OH-C_6H_5$ (S40). In one embodiment, the reaction occurs in a solvent, such as an organic solvent like $CH_2Cl_2$, so that a reaction mixture is formed, and the solvent is removed from the reaction mixture before or during purification of the product. If necessary, a base catalyst, such as triethylamine, is used in the synthesis. Also, basic (e.g., saturated sodium bicarbonate) and acidic washes (e.g., 1N HCl) are used if needed to purifying the reaction mixture and/or product, and are accompanied by drying, if needed. In another embodiment, S40 is formed by reaction with an alcohol of formula RCOX, where R is $4-N_3-2-OH-C_6H_5$ and X is NHS. Column chromatography, for example, is used to purifying the residue to isolate the desired product.

S11 and S12 are prepared from S26 by reaction with a compound of formula $C_6H_4$—NCX, wherein X is O (S11) or S (S12). In one embodiment, the reaction occurs in a solvent, such as an organic solvent like $CH_2Cl_2$, so that a reaction mixture is formed, and the solvent is removed from the reaction mixture before or during purification of the product. If necessary, a base catalyst, such as triethylamine or pyridine, is used in the synthesis. In another embodiment, a base catalyst such as pyridine is used as the solvent in which the reaction takes place, and additional solvent, such as ethyle acetate or another appropriate organic solvent, is added after the reaction occurs. Also, basic (e.g., saturated sodium bicarbonate) and acidic washes (e.g., 1N HCl) are used if needed to purifying the reaction mixture and/or product, and are accompanied by drying, if needed. Column chromatography, for example, is used to purifying the residue to isolate the desired product.

The isomers S13 and S14 are prepared from S26 by reaction with phenyl methoxyphosphonyl chloride (Ph(MeO)P (O)Cl). In one embodiment, the reaction occurs in a solvent, such as an organic solvent, such as methylene chloride. If necessary, a base catalyst such as triethylamine may be used, for example, by adding it to a reaction mixture formed by mixing the reactants in a solvent. Also, the reaction mixture is washed with basic solution, for example saturated sodium bicarbonate, if necessary. The isomers are separated and purified, for example, using silica gel chromatography.

S19 and 22 are prepared from S26 by reaction with a compound of formula ClOC—X—COCl, where X is $CH_2$—$CH_2$ (SI19) or

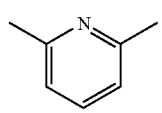

(S22)

In one embodiment, the reaction occurs in the presence of a solvent, such as an organic solvent, such as methylene chloride. If necessary, a base catalyst such as triethylamine is added to the reaction mixture formed by mixing the reactants in a solvent. Also, base (e.g., saturated sodium bicarbonate), acid (e.g., 1N HCl), and water washes are used to remove unwanted compounds from the reaction mixture, if needed.

S20 and S23 are prepared from an intermediate compound of formula

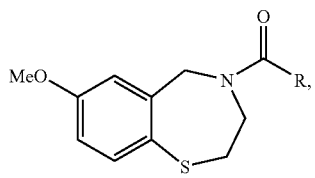

where R is $CH_2$=CH— (S20) or

(S23)

The intermediate compound is treated with $H_2O_2$. If necessary, sodium thiosulfate also is used to treat the intermediate. In one embodiment, the reaction occurs in the presence of a solvent, such as an organic solvent, such as methanol ($CH_3OH$), forming a reaction mixture. The solvent is removed from the reaction mixture after the reaction takes place and, if desired, the residue is redissolved in another solvent, such as another organic solvent, such as ethyl acetate. The reaction mixture is washed with basic solution (e.g., saturated sodium carbonate) if desired to remove unwanted compounds from the reaction mixture. The reaction mixture is dried (e.g., using sodium sulfate) if it is washed with basic solution. The final residue is purified, for example by column chromatography, to obtain the final product.

S57 is prepared from S26 and methyl chlorooxoacetate. In an embodiment, the reaction occurs in the presence of a solvent, such as an organic solvent, such as methylene chloride. A base catalyst such as pyridine is used as necessary to facilitate or hasten the reaction. The reaction mixture formed by mixing the reactants and a solvent is washed with basic solution (e.g., saturated sodium bicarbonate), acidic solution (e.g. HCl), and water. Purification such as silic gel chromatography yields S57.

S36 is prepared from S57 by reaction with sodium hydroxide. In one embodiment, the reaction takes place in a solvent, such as an organic solvent, such as methanol. The solvent is removed from the reaction mixture formed by mixing the reactants and the solvent, thereby forming a residue. The residue is dissolved in water and washed with another organic solvent, such as ether, to remove unwanted hydrophobic compounds. The aqueous phase from the basic washes is acidified and the product is extracted therefrom using an organic solvent, such as methylene chloride. Further purification is used if necessary.

S38 is prepared in a manner similar to S36, except a compound of formula

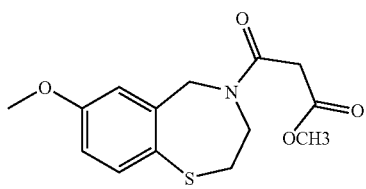

is used as the starting material in the synthesis.

S44 is prepared by treating S36 with thionyl chloride to form crude S36-Cl. Excess thionyl chloride, if any, is removed from the reaction mixture. The crude S36-Cl then is dissolved in a solvent, such as an organic solvent like methylene chloride, and reacted with mono-protected (e.g., mono-Boc protected) cystamine. A base catalyst such as pyridine is used if desired, and the reaction mixture is quenched with a basic solution (e.g., saturated sodium bicarbonate). The reaction mixture formed by mixing the cystamine and S36-Cl reactants is purified. The protecting groups (e.g., Boc) are removed using an appropriate acid or base wash (e.g., trifluoroacetic acid in an organic solvent in the case of the Boc protecting group). The final product then is purified, for example, using chromatography techniques.

S57 and S59 are prepared from S36-Cl, which is reacted with methanol (S57) or ethylamine (S59).

S43 and S45 are prepared from S36-cystamine, which is prepared as disclosed herein. S-36 cystamine is reacted with an NHS activated ester of an appropriate azido compound to yield S43 and S45. The reaction takes place in a solvent, such as an organic solvent.

S37 is prepared from S26 by reaction with 4-nitrophenyl chloroformate (NO$_2$C$_6$H$_5$OCOCl). The reaction takes place in a solvent and, if desired, a base catalyst such as triethylamine may be used. The reaction mixture formed by mixing the reactants and a solvent is washed with water to remove unwanted hydrophilic compounds. The solvent is removed from the reaction mixture to form a residue, which is purified (e.g., using chromatography techniques) to yield S37.

S6, S46-53, S64, S66, and S67 are prepared from S37 by reaction with an amine of formula RNH$_2$, wherein NR is NH$_2$ (S46), NEt$_2$ (S48), NHCH$_2$Ph (S49), NHOH (S51),

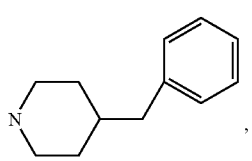
(S6)

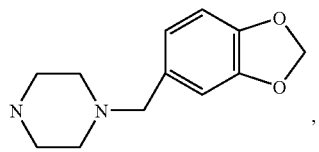
(S47)

(S50)

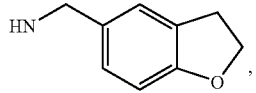
(S52)

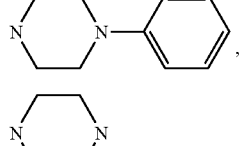
(S53)

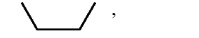
(S64)

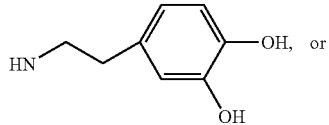
(S66)

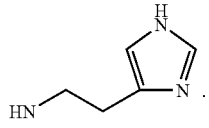
(S67)

The reaction takes place in the presence of a solvent, such as an organic solvent, such as DMF. In one embodiment, only one equivalent of amine is used in the reaction. Purification is accomplished, for example, by SiO$_2$ column chromatography.

S6, S46-53, S64, S66, and S67 also are prepared from S26, via the S26-phosgene intermediate. The S26-phosgene intermediate is formed by reacting S26 with triphosgene. Thereafter, the S26-phosgene is reacted with an amine of formula RNH$_2$, where NR is NH$_2$ (S46), NEt$_2$ (S48), NHCH$_2$Ph (S49), NHOH (S51),

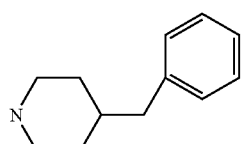
(S6)

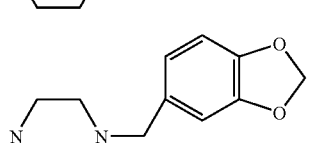
(S47)

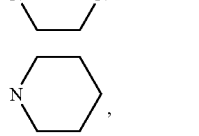
(S50)

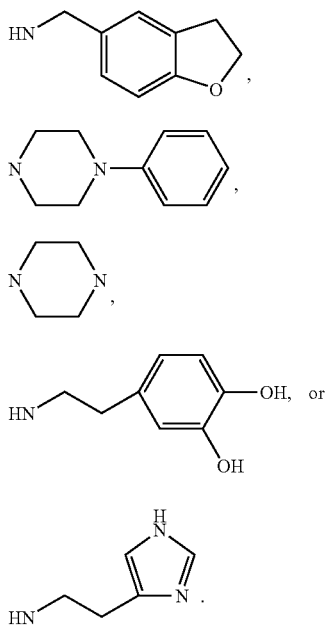

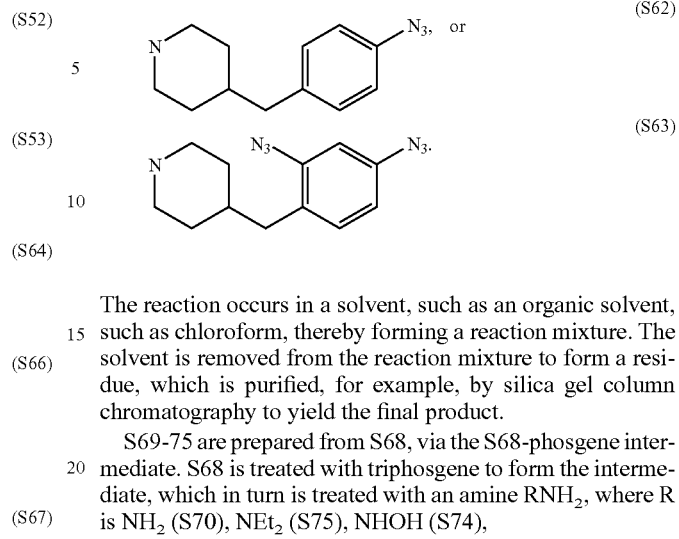

The reaction occurs in a solvent, such as an organic solvent, such as chloroform, thereby forming a reaction mixture. The solvent is removed from the reaction mixture to form a residue, which is purified, for example, by silica gel column chromatography to yield the final product.

S69-75 are prepared from S68, via the S68-phosgene intermediate. S68 is treated with triphosgene to form the intermediate, which in turn is treated with an amine RNH$_2$, where R is NH$_2$ (S70), NEt$_2$ (S75), NHOH (S74),

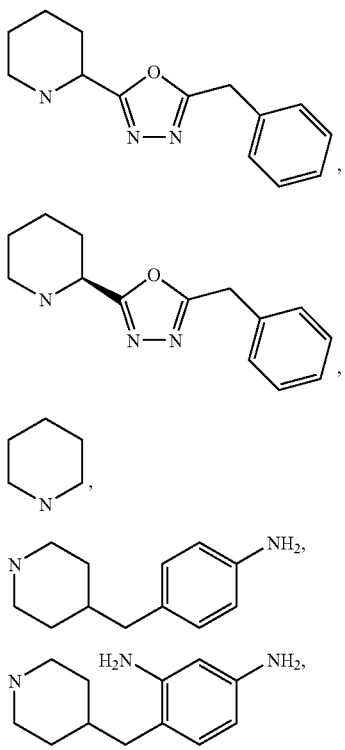

The reaction takes place in the presence of a solvent, such as an organic solvent. In one embodiment, only one equivalent of amine is used in the reaction. Purification is accomplished, for example, by SiO$_2$ column chromatography.

S55, S56, S58, and S60-63 are prepared from S27 by reaction with HNR$_1$R$_2$, where NR$_1$R$_2$ is The reaction occurs in a solvent, such as an organic solvent, such as chloroform, thereby forming a reaction mixture. The solvent is removed from the reaction mixture to form a residue, which is purified, for example, by silica gel column chromatography to yield the final product.

S76 is prepared from S68 by reaction with methyl chlorooxoacetate. In an embodiment, the reaction occurs in the presence of a solvent, such as an organic solvent, such as methylene chloride. A base catalyst such as pyridine is used as necessary to facilitate or hasten the reaction. The reaction mixture formed by mixing the reactants and a solvent is washed with basic solution (e.g., saturated sodium bicarbonate), acidic solution (e.g. HCl), and water. Purification such as silic gel chromatography yields S76.

S77 is prepared from S76 by reaction with sodium hydroxide. In one embodiment, the reaction takes place in a solvent, such as an organic solvent, such as methanol. The solvent is removed from the reaction mixture formed by mixing the reactants and the solvent, thereby forming a residue. The residue is dissolved in water and washed with another organic solvent, such as ether, to remove unwanted hydrophobic compounds. The aqueous phase from the basic washes is acidified and the product is extracted therefrom using an organic solvent, such as methylene chloride. Further purification is used if necessary.

S78-S81 are prepared by treating S77 with thionyl chloride to form crude S77-Cl. Excess thionyl chloride, if any, is removed from the reaction mixture. The crude S77—Cl then is dissolved in a solvent, such as an organic solvent like methylene chloride, and reacted with HX, where X is NHEt (S78), NHPh (S79), $NH_2$ (S80), and $NHCH_2$-pyridine (S81). The solvent is removed, and the residue is purified.

S82 is prepared from S68. S68 is reacted with $CH_2CHSO_2Cl$ in a manner analogous to the production of S3. The product then is treated with $HNR_1R_2$ in a manner analogous to the production of $S_1$ and S2, except that $NR_1R_2$ is

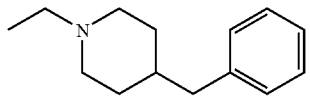

S83 is prepared from S68. S68 is reacted with RCOCl, wherein R is

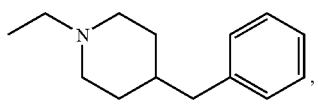

in a manner analogous to the production of S7, S9, and S40. S84 is prepared from S68 by reaction with benzyl bromide. In an embodiment, the reaction takes place in a solvent, such as an organic solvent like methylene chloride. A base catalyst such as triethylamine is added as necessary to catalyze the reaction. The reaction mixture formed by mixing the reactants and the solvent is purified to yield S84.

S85 is prepared from S26. S26 is reacted with di-tert-butyl dicarbonate in a solvent, for example an organic solvent like methylene chloride. A base catalyst such as triethylamine also is used, if necessary. The reaction mixture formed by mixing the reactants and the solvent is washed with saturated sodium bicarbonate solution and the aqueous layer is extracted with an organic solvent. The combined organic layers are dried and concentrated provide S85.

S86 is prepared from S85 in a solvent, for example an organic solvent. S85 is treated with $BBr_3$ to form a reaction mixture. If necessary, a base catalyst, such as triethylamine, is used in the reaction. The reaction is quenched (e.g., in the case of triethylamine, with methanol) and concentrated. Purification, for example by column chromatography, yields S86.

S87 is prepared by reacting S86 with trifluoromethylsulfonyl anhydride. The reaction is carried out in a solvent, such as an organic solvent. A base catalyst such as triethylamine is added if necessary. In the case of triethylamine, the reaction mixture formed by mixing the reactants and the solvent is quenched with water, after which the aqueous layer is extracted with an appropriate organic solvent. If desired, the organic layers are dried (e.g., using magnesium sulfate), and the organic layers are concentrated. Purification of the concentrated organic layers yields S87.

S88 is prepared from S87 by reaction of morpholine, tris (dibenzylideneacetone)dipalladium(0), 2-(di-tert-butylphosphino)-biphenyl, and potassium phosphate. The reaction mixture is diluted with a solvent, such as methylene chloride or another appropriate organic solvent, and washed with water. The aqueous layer, formed by washing with water, is extracted with an organic solvent, such as methylene chloride. The organic layers then are dried (e.g., over magnesium sulfate) and concentrated. The residue is purified, for example by silica gel flash chromatography, to yield S88.

S89 is prepared from S87 by reaction with benzenethiol and i-$Pr_2NEt$ in a solvent, such as $CH_3CN$ or another appropriate organic solvent. After reaction, an organic solvent such as ethyl acetate is added to the reaction mixture. If necessary, the reaction mixture is washed with one or more of acidic (e.g., HCl), basic (e.g. NaOH), and water solutions. After drying (e.g. with $Na_2SO_4$), the solution is concentrated. Purification, for example by chromatography, yields S89. In an alternative, refluxing S87 with benezethiol in an appropriate solvent such as dioxane with a catalyst such as i-$Pr_2NEt/Pd_2$ $(dba)_3$/xantphos yields S89.

S90 is prepared from S87 reacted with a base, phenylboronic acid, and a catalyst. In an embodiment, the base is $K_2CO_3$ and the catalyst is $(Pd(Ph_3P)_4)$. In one embodiment, the reaction occurs in a solvent, such as an organic solvent, such as dioxane. The reaction mixture formed by mixing the reactants and the solvent is diluted with a solvent (e.g. methylene chloride), and washed with water to remove unwanted hydrophilic compounds. Concentration and purification of the residue yields S90.

S92 is prepared from S87 reacted with zinc cyanide. In an embodiment, the reaction occurs in a solvent, such as an organic solvent like DMF. A catalyst such as $Pd(Ph_3P)_4$ also is used to facilitate and hasten the reaction. The reaction mixture formed by mixing the reactants and the solvent, if necessary, is diluted with water and an acidic solution and extracted with an organic solvent. The organic extracts then are washed using a salt solution, dred, filtered, and concentrated. Purification of the residue proceeds, for example, by silica gel column chromatography.

S94 is prepared for S86 by reaction with acetic anhydride. In an embodiment, the reaction takes place in a solvent, such as an organic solvent like methylene chloride. Triethylamine or another base catalyst is added as necessary. Washing with water, followed by drying (e.g., using sodium sulfate), is used as desired. Purification of the residue yields S94.

S95 is prepared from S94 by reaction with anhydrous $AlCl_3$, in a solvent if desired. The solvent is an organic solvent like benzene. The reaction mixture is refluxed and cooled on ice. Extraction with an organic solvent, concentration, and purification of the residue yields S95.

S96 is prepared from S86 by iodination. For example, S86 is added to a solvent, such as an organic solvent like methanol, with excess NaI and Chloramine-T. The reaction mixture is quenched with $Na_2S_2O_3$ solution. Concentration and purification of the residue yields S96 as a mixture of mono-iodinated and di-iodinated products.

S97 is prepared from S86 by reaction with a nitric acid. S86 is protected (e.g., using the Boc protecting groups) and added to concentrated sulfuric acid. Nitric acid is added to the reaction mixture. The reaction mixture is cooled and neutralized (e.g., using $Na_2CO_3$) to quench the reaction. Organic extraction and subsequent concentration is used to isolate the product. Purification yields S97.

S98 is prepared by hydrogenation of S97. For example, S97 is added to a solution, such as an organic solution like methanol. $H_2$ gas is bubbled through the solution and Pd/C catalyst or another applicable catalyst is added. Filtration to remove the catalyst and purification yields S97.

S100 is prepared from S98. S98 is dissolved in acid solution, such as aqueous HCl. To this a solution of sodium nitrite, and then $NaN_3$ in water, are added. The reaction mixture is extracted using an organic solvent. If needed, the extract is washed with a basic solution (e.g., saturated sodium bicarbonate) and water. Organic layers from the washing are dried using, for example, anhydrous sodium sulfate, and concentrated to form a residue. The residue is purified to yield S100. To prepare S99, $NaN_3$ is substituted with $NaBF_4$ in a similar manner.

S101, S102, and S103 may each be prepared from S68.

S101 may be prepared from S68 as follows. Triphosgene is reacted with S68 in the presence of a solvent (such as the organic solvent dichloromethane, $CH_2Cl_2$) to generate S68-phosgene. Optionally, a base is also present or added to scavenge acid generated during the reaction. Any suitable base may be used. For example, organic bases such as organic amines like triethylamine, di-isopropylethylamine or pyridine may be used. Inorganic bases such as as sodium bicarbonate may also be used. Then, without the need for purification, the reaction mixture containing the S68-phosgene is treated with 1-piperonylpiperazine. If necessary, the reaction mixture is washed with one or more of acidic (e.g., HCl), basic (e.g. NaOH), and water solutions. The solvents are removed, for example under reduced pressure. The S101 product can then be purified, for example using $SiO_2$ column chromatography.

S102 may be prepared from S68 using the same scheme as for S101, with the exception that piperidine is used in the place of piperonylpiperazine.

S103 may be prepared from S68 using the same scheme as for SI 01, with the exception that N-Boc 1-piperazine is used in the place of piperonylpiperazine. Also, trifluoroacetic acid (TFA) is added de-protect the Boc group.

S104 may be prepared by reacting S36 with hydrogen peroxide ($H_2O_2$) in the presence of a solvent (such as MeOH). The solvents are removed (for example under reduced pressure), and the S104 product can then be purified, for example by re-crystallization.

S105 may be prepared from S68 as follows. S68 is be reacted with $CH_3O\text{-}C(O)C(O)Cl$ in the presence of a solvent (such as the organic solvent dichloromethane ($CH_2Cl_2$)) and optionally a catalyst (such as pyridine). Preferably, the $CH_3O$—$C(O)C(O)Cl$ should be added dropwise. If necessary, the reaction mixture is washed with one or more of acidic (for example HCl), basic (for example NaOH), and water solutions. The solvents are removed and the product may be further purified, for example by $SiO_2$ column chromatography.

S107 may be prepared from S26 as follows. To a solution of S26 in a solvent (such as MeOH), formaldehyde ($CH_2O$) and sodium cyanoborohydride ($NaBCNH_3$) are added and allowed to react. Preferably, the reaction mixture is maintained at around pH 4-5, for example by addition of a few drops of IN HCl. The solvents are then removed, for example under reduced pressure. If necessary, the residue may be dissolved in ethyl acetate and washed with with one or more of a basic solution (for example NaOH), and water. The solvents may be removed, and the product may be further purified, for example using $SiO_2$ column chromatography.

S108 may be prepared as follows. A mixture of N-benzyloxycarbonyl-glycine (Cbz-Gly,), Diisopropyl-carbodiimide (DIC), and N-hydroxysuccinimide (NHS), are reacted together in a solvent (such as the organic solvent dichloromethane ($CH_2Cl_2$)) for a suitable amount of time. S26 is then added to the mixture and the reaction is allowed to proceed further. If necessary, the reaction mixture is washed with one or more of acidic (for example HCl), basic (for example NaOH), and water solutions. The solvents may then be removed, for example by evaporation. The product may be further purified, for example using $SiO_2$ column chromatography.

S109 may be prepared from S 108, as follows. S108 in a solvent (such as the organic solvent dichloromethane ($CH_2Cl_2$)) is reacted with $HBr/CH_3CO_2H$. After a suitable amount of time, the reaction mixture is evaporated, for example under reduced pressure. The residue is dissolved in a suitable solvent, such as MeOH, and is treated with propylene oxide. The solvent may then be removed, for example under reduced pressure, to provide crude S109. The S100 may be further purified, for example by dissolving in an acidic solution (such as HCl), washing with ethyl acetate, and evaporating.

S110 may be prepared as follows. A mixture of S26, methyl 1-bromoacetate and pyridine are reacted in DMF for a suitable amount of time. To this mixture, ethyl aceate is added, and if necessary, the reaction mixture is washed with a basic solution (for example $NaHCO_3$), or water. The product S110, as an oil, may be purified, for example by $SiO_2$ column chromatography.

S111 may be prepared as follows. A base (such as 1N NaOH) is added to S110 in a solvent (such as MeOH), and the mixture is allowed to react for a suitable amount of time. The solvents are then removed, for example under reduced pressure, and the residue may then be dissolved in an aqueous solution, such as water. The aqueous phase may be washed with ethyl acetate and acidified, for example with 1N HCl, to pH of around 4. The solvents may then be removed, for example under reduced pressure, to produce crude S111. The NaCl may be removed using an alcohol, such as ethanol, to yield pure S111 as a solid.

S112 may be prepared as follows: To a mixture of S26 and pyridine in an solvent (such as the organic solvent dichloromethane ($CH_2Cl_2$)), $SO_2Cl_2$ is added drop-wise at around 0° C. and reacted for a suitable amount of time. The solvents may be removed, for example under reduced pressure. The residue can be dissolved in a suitable basic solution, such as NaOH. The aqueous solution may then be washed with ethyl acetate, and acidified (for example with 1N HCl) to around pH 4. The aqueous phase may be extracted again with ethyl acetate, and the ethyl acetate phase evaporated, for example under reduced pressure, to provide S112, as a powder.

S113 may be prepared as follows. S107 in ethyl acetate is treated with $CH_3I$. The mixture is stirred for a suitable amount of time, and the product S113, as white solid, is collected by filtration.

S114 may be prepared as follows. The compound S26, in a solvent such as the organic solvent $CH_2Cl_2$ is ideally cooled to around 0° C. To this solution, triphosgene, is added. Optionally, a base is also present or added to scavenge acid generated during the reaction. Any suitable base may be used. For example, organic bases such as organic amines like triethylamine, di-isopropylethylamine or pyridine may be used. Inorganic bases such as as sodium bicarbonate may also be used. The reaction is allowed to proceed (ideally around 0° C.) for a suitable amount of time (for example about 1 hour). Without the need for purification, the resulting S26-phosgene in the reaction mixture may then be treated with N-Boc 1-piperazine, again ideally at around 0° C., and the reaction is allowed to proceed (ideally at around 0° C.) for a suitable amount of time (for example about 1 hour). If necessary, the reaction mixture is washed with one or more of acidic (for example HCl), basic (for example NaOH), and water solutions. The solvents are removed and the product may be further purified, for example by $SiO_2$ column chromatography.

S115 may be prepared as follows. A mixture of S114 and Lawesson Reagent in toluene is stirred at around 90° C. for several hours. The mixture is cooled to room temperature and washed with a suitable base, such as saturated $NaHCO_3$. The product S115 may be purified, for example by $SiO_2$ chromatography.

S116 may be prepared as follows. A mixture of S115 and trifluoroacetic acid (TFA) in a suitable solvent solvent (such as the organic solvent dichloromethane ($CH_2Cl_2$)) is stirred at around room temperature for a suitable amount of time (for example, about 2 hours). Evaporation of the solvents, for example under reduced pressure, produces S116.

S117 (S117) may be prepared as follows. A solution of S057 in a suitable solvent (such as the organic solvent dichloromethane ($CH_2Cl_2$)) is cooled to about −78° C. To this, 1M $BBr_3$ a suitable solvent (such as the organic solvent dichloromethane ($CH_2Cl_2$)) is added, and the mixture is stirred (still at about 78° C.) for a suitable amount of time (for example around 3 hours) and then wSed to room temperature. If necessary, the mixture is washed with an acid (such as 1N HCl) and/or $H_2O$. After removal of the solvents, the product S117 may be purified, for example by $SiO_2$ column chromatography.

S118 may be synthesized as follows. S26 in as suitable solvent a suitable solvent (such as the organic solvent dichloromethane ($CH_2Cl_2$)) is treated with BODIPY TMR-X, SE (Molecular Probes Inc.) for a suitable amount of time (for example, around 3 hours). If necessary, the mixture may be washed with an acid (such as 0.01 N HCl) and/or a base (such as $NaHCO_3$). Removal of the solvents, for example under reduced pressure, will yield S118.

S119 may be synthesized as follows. A mixture S107, $H_2O_2$ (for example around 50%), and an alcohol (such as MeOH), is stirred at around room temperature for a suitable amount of time (typically around 2 days). If desired, mass spectrometry may be used to monitor the disappearance of S107 and the formation of the S119 product). The solvents may be removed, for example under reduced pressure, to give S119.

S120 may be synthesized as follows. A mixture S26, benzyl bromide and $Na_2CO_3$ in a solvent (such as DMF), is reacted for a suitable amount of time, preferably overnight. Ethyl acetate is added to the reaction, and then, if necessary, the reaction is washed with a suitable solvent, for example with $H_2O$ (4×10 ml). The organic phase may be concentrated, for example under reduced pressure, and the residue may be purified, for example by column chromatography to give S121.

S121 may be synthesized as for S120, but using 4-OH-benzyl bromide instead of benzyl bromide.

S122 may be synthesized as follows. To a cold solution of compound S26 in a solvent, such as the organic solvent in $CH_2Cl_2$, DIEA is added, and subsequently acetoxyacetyl chloride is added. The reaction is allowed to proceed for a suitable amount of time, and then diluted, (for example with 1.0 M HCl aqueous solution) and extracted (for example using $CH_2Cl_2$). The combined organic layers may, if necessary, be washed (for example with $H_2O$, brine), dried (for example with $Na_2SO_4$), filtered, and dried (for example by evaporation). The product may be further purified, for example by chromatography on a silica gel column, and may be eluted with a gradient increasing in polarity from 0 to 50% of petroleum in ethyl acetate. Relevant fractions may then be combined to give the desired product.

S123 may be synthesized as follows. To a solution of compound S122 in a solvent (such as MeOH) and THF, preferably at room temperature, is added LiOH. The reaction is allowed to proceed for a suitable amount of time at a suitable temperature (ideally around room temperature, and may then be diluted (for example with with 1.0 M HCl aqueous solution) and extracted (for example with $CH_2Cl_2$). The combined organic layers may be washed (for example with $H_2O$, brine), dried (for example with $Na_2SO_4$), filtered and dried (for example by evaporation). The crude product may be purified, for example by chromatography on a silica gel column, eluted, for example with a gradient increasing in polarity from 0 to 70% petroleum in ethyl acetate. Relevant fractions may then be0 combined to give S123.

It should be noted that the compounds used as starting materials for, or generated as intermediates in, the synthesis of the compounds of the invention, may themselves have structures encompassed by the formulae of the invention, and/or may themselves be active agents useful in the methods and compositions of the present invention. Such starting materials and intermediates may be useful for, inter alia, treating or preventing various disorders and diseases associated with RyR receptors such as muscular and cardiac disorders, treating or preventing a leak in a RyR2 receptor in a subject, or modulating the binding of RyR and FKBP in a subject. The present invention encompasses any of the starting materials or intermediates disclosed herein that have structures encompassed by Formula I, I-a, I-b, I-c, I-d, I-e, I-f, I-g, I-h, I-i, I-j, I-k, I-l or I-m, and/or which are useful as active agents in the methods and compositions of the present invention. For example, in one embodiment the compound S68, which is useful as a starting material for the synthesis of compounds S69-S75, may be used for, inter alia, treating or preventing various disorders and diseases associated with RyR receptors, treating or preventing a leak in a RyR2 receptor, or modulating the binding of RyR and FKBP in a subject.

In another embodiment, the compound S26, which is useful in the synthesis of many of the compounds described herein (including S3, S4, S5, S7, S9, S11, S12, S13, S14 and other compounds) may be used for, inter alia, treating or preventing various disorders and diseases associated with RyR receptors, treating or preventing a leak in a RyR2 receptor, or modulating the binding of RyR and FKBP in a subject.

Similarly, in another embodiment, the compound S25 (see U.S. patent application Ser. No. 10/809,089) may also be used for, inter alia, treating or preventing various disorders and diseases associated with RyR receptors, treating or preventing a leak in a RyR2 receptor, or modulating the binding of RyR and FKBP in a subject.

The compounds of the present invention are prepared in different forms, such as salts, hydrates, solvates, complexes, pro-drugs or salts of pro-drugs and the invention includes all variant forms of the compounds.

The term "compound(s) of the invention" as used herein means a compound of Formula I, I-a, I-b, I-c, I-d, I-e, I-f, I-g, I-h, I-i, I-j, I-k, I-l or I-m, and salts, hydrates, prodrugs and solvates thereof.

A "pharmaceutical composition" refers to a mixture of one or more of the compounds described herein, or pharmaceutically acceptable salts, hydrates or pro-drugs thereof, with other chemical components, such as physiologically acceptable carriers and excipients. The purpose of a pharmaceutical composition is to facilitate administration of a compound to an organism.

A "pro-drug" refers to an agent which is converted into the parent drug in vivo. Pro-drugs are often useful because, in some situations, they are easier to administer than the parent drug. They are bioavailable, for instance, by oral administration whereas the parent drug is not. The pro-drug also has improved solubility in pharmaceutical compositions over the parent drug. For example, the compound carries protective groups which are split off by hydrolysis in body fluids, e.g., in the bloodstream, thus releasing active compound or is oxidized or reduced in body fluids to release the compound.

A compound of the present invention also can be formulated as a pharmaceutically acceptable salt, e.g., acid addition salt, and complexes thereof. The preparation of such salts can facilitate the pharmacological use by altering the physical characteristics of the agent without preventing its physiological effect. Examples of useful alterations in physical properties include, but are not limited to, lowering the melting point to facilitate transmucosal administration and increasing the solubility to facilitate administering higher concentrations of the drug.

The term "pharmaceutically acceptable salt" means an acid addition salt which is suitable for or compatible with the treatment of a patient or a subject such as a human patient or an animal such as a dog.

The term "pharmaceutically acceptable acid addition salt" as used herein means any non-toxic organic or inorganic salt of any base compounds represented by Formula I, I-a, I-b, I-c, I-d, I-e, I-f, I-g, I-h, I-i, I-j, I-k, I-l or I-m, or any of their intermediates. Illustrative inorganic acids which form suitable acid addition salts include hydrochloric, hydrobromic, sulfuric and phosphoric acids, as well as metal salts such as sodium monohydrogen orthophosphate and potassium hydrogen sulfate. Illustrative organic acids that form suitable acid addition salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either mono or di-acid salts can be formed, and such salts exist in either a hydrated, solvated or substantially anhydrous form. In general, the acid addition salts of compounds of Formula I, I-a, I-b, I-c, I-d, I-e, I-f, I-g, I-h, I-i, I-j, I-k, I-l and I-m, are more soluble in water and various hydrophilic organic solvents, and generally demonstrate higher melting points in comparison to their free base forms. The selection of an appropriate salt will be known to one skilled in the art. Other non-pharmaceutically acceptable salts, e.g., oxalates, are used, for example, in the isolation of compounds of the invention for laboratory use or for subsequent conversion to a pharmaceutically acceptable acid addition salt.

The compounds of the present invention form hydrates or solvates, which are included in the scope of the claims. When the compounds of the present invention exist as regioisomers, configurational isomers, conformers or diasteroisomeric forms all such forms and various mixtures thereof are included in the scope of Formula I, I-a, I-b, I-c, I-d, I-e, I-f, I-g, I-h, I-i, I-j, I-k, I-l and I-m. It is possible to isolate individual isomers using known separation and purification methods, if desired. For example, when a compound of the present invention is a racemate, the racemate can be separated into the (S)-compound and (R)-compound by optical resolution. Individual optical isomers and mixtures thereof are included in the scope of Formula I, Ia, I-b, I-c, I-d, I-e, I-f, I-g, I-h, I-i, I-j, I-k, I-l and I-m.

The term "solvate" as used herein means a compound of Formula I, I-a, I-b, I-c, I-d, I-e, I-f, I-g, I-h, I-i, I-j, I-k, I-l or I-m, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

The term an "effective amount," "sufficient amount" or "therapeutically effective amount" of an agent as used herein is that amount sufficient to effect beneficial or desired results, including clinical results and, as such, an "effective amount" depends upon the context in which it is being applied. The response is preventative and/or therapeutic. The term "effective amount" also includes that amount of the compound of Formula I, I-a, I-b, I-c, I-d, I-e, I-f, I-g, I-h, I-i, I-j, I-k, I-l or I-m, which is "therapeutically effective" and which avoids or substantially attenuates undesirable side effects.

As used herein and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The terms "animal," "subject" and "patient" as used herein include all members of the animal kingdom including, but not limited to, mammals, animals (e.g., cats, dogs, horses, etc.) and humans.

The present invention further provides a composition, comprising radio labeled compounds of Formula I, I-a, I-b, I-c, I-d, I-e, I-f, I-g, I-h, I-i, I-j, I-k, I-l and I-m. Labeling of the compounds is accomplished using one of a variety of different radioactive labels known in the art. The radioactive label of the present invention is, for example, a radioisotope. The radioisotope is any isotope that emits detectable radiation including, without limitation, $^{35}S$, $^{125}I$, $^{3}H$, or $^{14}C$. Radioactivity emitted by the radioisotope can be detected by techniques well known in the art. For example, gamma emission from the radioisotope is detected using gamma imaging techniques, particularly scintigraphic imaging.

By way of example, radio-labeled compounds of the invention are prepared as follows. A compound of the invention may be demethylated at the phenyl ring using $BBr_3$. The resulting phenol compound then is re-methylated with a radio-labeled methylating agent (such as $^{3}H$-dimethyl sulfate) in the presence of a base (such as NaH) to provide $^{3}H$-labeled compounds.

The present invention further provides compounds that may be classified as 1,4-benzothiazepines, including, by way of example and without limitation, S1, S2, S3, S4, S5, S6, S7, S9, S11, S12, S13, S14, S19, S20, S22, S23, S25, S26, S36, S37, S38, S40, S43, S44, S45, S46, S47, S48, S49, S50, S51, S52, S53, S54, S55, S56, S57, S58, S59, S60, S61, S62, S63, S64, S66, S67, S68, S69, S70, S71, S72, S73, S74, S75, S76, S77, S78, S79, S80, S81, S82, S83, S84, S85, S86, S87, S88, S89, S90, S91, S92, S93, S94, S95, S96, S97, S98, S99, S100, S101, S102, S103, S104, S105, S107, S108, S109, S110, S111, S112, S113, S114, S115, S116, S117, S118, S119, S120, S121, S122, and S123.

These and any other compounds of the present invention are associated with a pharmaceutically acceptable carrier, as described above, so as to form a pharmaceutical composition.

In accordance with the method of the present invention, the decrease in the level of RyR-bound FKBP is limited or prevented in the subject by decreasing the level of phosphorylated RyR in the subject. In one embodiment, the amount of the agent effective to limit or prevent a decrease in the level of RyR2-bound FKBP12.6 in the subject is an amount of the agent effective to treat or prevent heart failure, atrial fibrillation and/or exercise-induced cardiac arrhythmia in the subject. In another embodiment, the amount of the agent effective to limit or prevent a decrease in the level of RyR2-bound FKBP12.6 in the subject is an amount of the agent effective to prevent exercise-induced sudden cardiac death in the subject.

In view of the foregoing, the present invention further provides a method for treating or preventing exercise-induced cardiac arrhythmia in a subject, comprising administering to the subject a 1,4-benzothiazepine compound, as disclosed herein, in an amount effective to treat or prevent exercise-induced cardiac arrhythmia in the subject. Similarly, the present invention provides a method for preventing exercise-induced sudden cardiac death in a subject, comprising administering to the subject a 1,4-benzothiazepine compound, as disclosed herein, in an amount effective to prevent exercise-induced sudden cardiac death in the subject. Additionally, the present invention provides a method for treating or preventing atrial fibrillation or heart failure in a subject, comprising administering to the subject a compound, as disclosed herein, in an amount effective to treat or prevent the atrial fibrillation or heart failure in the subject. In each of these methods, the compound is selected from the group of compounds consisting of compounds of the formula:

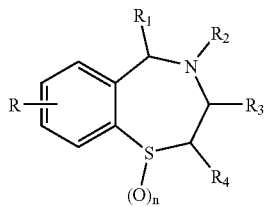

wherein, n is 0, 1, or 2;

R is located at one or more positions on the benzene ring;

each R is independently selected from the group consisting of H, halogen, —OH, —$NH_2$, —$NO_2$, —CN, —$N_3$, —$SO_3H$, acyl, alkyl, alkoxyl, alkylamino, cycloalkyl, heterocyclyl, heterocyclylalkyl, alkenyl, (hetero-)aryl, (hetero-)arylthio, and (hetero-)arylamino; wherein each acyl, alkyl, alkoxyl, alkylamino, cycloalkyl, heterocyclyl, heterocyclylalkyl, alkenyl, (hetero-)aryl, (hetero-)arylthio, and (hetero-)arylamino may be substituted with one or more radicals independently selected from the group consisting of halogen, N, O, —S—, —CN, —$N_3$, —SH, nitro, oxo, acyl, alkyl, alkoxyl, alkylamino, alkenyl, aryl, (hetero-)cycloalkyl, and (hetero-)cyclyl;

$R_1$ is selected from the group consisting of H, oxo, alkyl, alkenyl, aryl, cycloalkyl, and heterocyclyl; wherein each alkyl, alkenyl, aryl, cycloalkyl, and heterocyclyl may be substituted with one or more radicals independently selected from the group consisting of halogen, N, O, —S—, —CN, —$N_3$, —SH, nitro, oxo, acyl, alkyl, alkoxyl, alkylamino, alkenyl, aryl, (hetero-)cycloalkyl, and (hetero-)cyclyl;

$R_2$ is selected from the group consisting of H, —C=O($R_5$), —C=S($R_6$), —$SO_2R_7$, —$POR_8R_9$, —$(CH_2)_m$—$R_{10}$, alkyl, aryl, heteroaryl, cycloalkyl, cycloalkylalkyl, and heterocyclyl; wherein each alkyl, aryl, heteroaryl, cycloalkyl, cycloalkylalkyl, and heterocyclyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl;

$R_3$ is selected from the group consisting of H, $CO_2Y$, CONY, acyl, alkyl, alkenyl, aryl, cycloalkyl, and heterocyclyl; wherein each acyl, alkyl, alkenyl, aryl, cycloalkyl, and heterocyclyl may be substituted with one or more radicals independently selected from the group consisting of halogen, N, O, —S—, —CN, —$N_3$, —SH, nitro, oxo, acyl, alkyl, alkoxyl, alkylamino, alkenyl, aryl, (hetero-)cycloalkyl, and (hetero-)cyclyl; and wherein Y is selected from the group consisting of H, alkyl, aryl, cycloalkyl, and heterocyclyl;

R4 is selected from the group consisting of H, alkyl, alkenyl, aryl, cycloalkyl, and heterocyclyl; wherein each alkyl, alkenyl, aryl, cycloalkyl, and heterocyclyl may be substituted with one or more radicals independently selected from the group consisting of halogen, N, O, —S—, —CN, —$N_3$, —SH, nitro, oxo, acyl, alkyl, alkoxyl, alkylamino, alkenyl, aryl, (hetero-)cycloalkyl, and (hetero-)cyclyl;

$R_5$ is selected from the group consisting of —$NR_{16}$, $NHNHR_{16}$, NHOH, —$OR_{15}$, $CONH_2NHR_{16}$, $CO_2R_{15}$, $CONR_{16}$, $CH_2X$, acyl, alkenyl, aryl, cycloalkyl, cycloalkylalkyl, heterocyclyl, and heterocyclylalkyl; wherein each acyl, alkenyl, aryl, cycloalkyl, cycloalkylalkyl, heterocyclyl, and heterocyclylalkyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl;

$R_6$ is selected from the group consisting of —$OR_{15}$, $NHNR_{16}$, NHOH, —$NR_{16}$, $CH_2X$, acyl, alkenyl, alkyl, aryl, cycloalkyl, cycloalkylalkyl, heterocyclyl, and heterocyclylalkyl; wherein each acyl, alkenyl, alkyl, aryl, cycloalkyl, cycloalkylalkyl, heterocyclyl, and heterocyclylalkyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl;

$R_7$ is selected from the group consisting of —$OR_{15}$, —$NR_{16}$, $NHNHR_{16}$, NHOH, $CH_2X$, alkyl, aryl, cycloalkyl, cycloalkylalkyl, heterocyclyl, and heterocyclylalkyl; wherein each alkyl, aryl, cycloalkyl, cycloalkylalkyl, heterocyclyl, and heterocyclylalkyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl;

$R_8$ and $R_9$ independently are selected from the group consisting of OH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl;

$R_{10}$ is selected from the group consisting of $NH_2$, OH, —$SO_2R_{11}$, —$NHSO_2R_{11}$, C=O($R_{12}$), NHC=O($R_{12}$), —OC=O($R_{12}$), and —$POR_{13}R_{14}$;

$R_{11}$, $R_{12}$, $R_{13}$, and $R_{14}$ independently are selected from the group consisting of H, OH, $NH_2$, $NHNH_2$, NHOH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted with one or more radicals independently selected from the group consisting of halogen, —N-, —O—, —S—, —CN, —N$_3$, nitro, oxo, acyl, alkenyl, alkoxyl, alkyl, alkylamino, amino, aryl, cycloalkyl, cycloalkylalkyl, heterocyclyl, heterocyclylalkyl, and hydroxyl;

X is selected from the group consisting of halogen, CN, CO$_2$R$_{15}$, CONR$_{16}$,—NR$_{16}$, —OR$_{15}$, —SO$_2$R$_7$, and —POR$_8$R$_9$; and R$_{15}$ and R$_{16}$ independently are selected from the group consisting of H, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted with one or more radicals independently selected from the group consisting of halogen, —N—, —O—, —S—, —CN, —N$_3$, nitro, oxo, acyl, alkenyl, alkoxyl, alkyl, alkylamino, amino, aryl, cycloalkyl, cycloalkylalkyl, heterocyclyl, heterocyclylalkyl, and hydroxyl, and wherein each substituted acyl, alkenyl, alkoxyl, alkyl, alkylamino, aryl, cycloalkyl, cycloalkylalkyl, heterocyclyl, and heterocyclylalkyl radical may itself be substituted with one or more radicals independently selected from the group consisting of halogen, —N—, —O—, —S—, —CN, —N$_3$, nitro, oxo, acyl, alkenyl, alkoxyl, alkyl, alkylamino, amino, aryl, cycloalkyl, cycloalkylalkyl, heterocyclyl, heterocyclylalkyl, and hydroxy;

and salts, hydrates, solvates, complexes, and prodrugs thereof.

Examples of such compounds include, without limitation, S1, S2, S3, S4, S5, S6, S7, S9, S11, S12, S13, S14, S19, S20, S22, S23, S25, S26, S36, S37, S38, S40, S43, S44, S45, S46, S47, S48, S49, S50, S51, S52, S53, S54, S55, S56, S57, S58, S59, S60, S61, S62, S63, S64, S66, S67, S68, S69, S70, S71, S72, S73, S74, S75, S76, S77, S78, S79, S80, S81, S82, S83, S84, S85, S86, S87, S88, S89, S90, S91, S92, S93, S94, S95, S96, S97, S98, S99, S100, S101, S102, S103, S104, S105, S107, S108, S109, S110, S111, S112, S113, S14, S115, S116, S117, S118, S119, S120, S121, S122, and S123.

In an embodiment of the present invention, if R$_2$ is C=O(R$_5$) or SO$_2$R$_7$, then R is at positions 2, 3, or 5 on the benzene ring.

In another embodiment of the invention, if R$_2$ is C=O(R$_5$) or SO$_2$R$_7$, then each R is independently selected from the group consisting of H, halogen, —OH, —NH$_2$, —NO$_2$, —CN, —N$_3$, —SO$_3$H, acyl, alkyl, alkylamino, cycloalkyl, heterocyclyl, heterocyclylalkyl, alkenyl, (hetero-)aryl, (hetero-)arylthio, and (hetero-)arylamino; wherein each acyl, alkyl, alkoxyl, alkylamino, cycloalkyl, heterocyclyl, heterocyclylalkyl, alkenyl, (hetero-)aryl, (hetero-)arylthio, and (hetero-)arylamino may be substituted with one or more radicals independently selected from the group consisting of halogen, N, O, —S—, —CN, —N$_3$, —SH, nitro, oxo, acyl, alkyl, alkoxyl, alkylamino, alkenyl, aryl, (hetero-)cycloalkyl, and (hetero-)cyclyl.

In another embodiment of the invention, if R$_2$ is C=O(R$_5$) or SO$_2$R$_7$, then there are at least two R groups attached to the benzene ring. Furthermore, there are at least two R groups attached to the benzene ring, and both R groups are attached at positions 2, 3, or 5 on the benzene ring. Still further, each R is independently selected from the group consisting of H, halogen, —OH, —NH$_2$, —NO$_2$, —CN, —N$_3$, —SO$_3$H, acyl, alkyl, alkylamino, cycloalkyl, heterocyclyl, heterocyclylalkyl, alkenyl, (hetero-)aryl, (hetero-)arylthio, and (hetero-)arylamino; wherein each acyl, alkyl, alkoxyl, alkylamino, cycloalkyl, heterocyclyl, heterocyclylalkyl, alkenyl, (hetero-)aryl, (hetero-)arylthio, and (hetero-)arylamino may be substituted with one or more radicals independently selected from the group consisting of halogen, N, O, —S—, —CN, —N$_3$, —SH, nitro, oxo, acyl, alkyl, alkoxyl, alkylamino, alkenyl, aryl, (hetero-)cycloalkyl, and (hetero-)cyclyl.

In another embodiment of the invention, if R$_2$ is C=O(R$_5$), then R$_5$ is selected from the group consisting of —NR$_{16}$, NHNHR$_{16}$, NHOH, —OR$_{15}$, CONH$_2$NHR$_{16}$, CONR$_{16}$, CH$_2$X, acyl, aryl, cycloalkyl, cycloalkylalkyl, heterocyclyl, and heterocyclylalkyl; wherein each acyl, aryl, cycloalkyl, cycloalkylalkyl, heterocyclyl, and heterocyclylalkyl may be substituted with one or more radicals independently selected from the group consisting of halogen, N, O, —S—, —CN, —N$_3$, nitro, oxo, acyl, alkyl, alkoxyl, alkylamino, alkenyl, aryl, (hetero-)cycloalkyl, and (hetero-)cyclyl.

Efficacy Demonstrations

As demonstrated by FIG. 1, embodiments A, B, C, and D, S36 is more potent at increasing the binding of FKBP12.6 and RyR2 than JTV-519 and does not block the L-type Ca2+ channel (I$_{Ca,L}$) or HERG K$^+$ channel (I$_{Kr}$). In embodiment A, PKA phosphorylated RyR2 is generated as follows: cardiac SR membrane preparations (5 μl, 50 μg) are added to a total of 100 μl of kinase buffer (8 mM MgCl$_2$, 10 mM EGTA, 50 mM Tris-PIPES, pH 6.8) containing 100 μM MGATP and 40 units of PKA, and incubated at room temperature. Samples are centrifuged at 95,000 g for 10 min and the pellets are washed three times in 0.2 ml imidazole buffer. The final pellets are pooled and resuspended in imidazole buffer (final concentration ≈10 μg/μl). To test for the FKBP12.6 rebinding efficiency of JTV-519, PKA phosphorylated cardiac SR (50 mg) is incubated for 30 minutes at room temperature with the test compounds and 250 nM FKBP12.6 in 10 mM imidizol buffer, pH 7.0. Samples then are centrifuged at 100,000 g for 10 minutes and pellets washed 3 times with imidizol buffer. After washing, proteins are size-fractionated on 15% PAGE. Immunoblots are developed using an anti-FKBP antibody (1:3,000 dilution). The amount of rebinding is quantified using densitometry of Western blots and is compared to the amount of FKBP associated with RyR in non-phosphorylated SR. EC$_{50}$'s for the compounds are determined by generating FKBP binding data using concentrations of compounds ranging from 0.5-1000 nM. In embodiment B. currents through L-type Ca$^{2+}$ channels in isolated mouse cardiomyocytes are recorded using whole-cell patch clamp recording conditions with Ba$^{2+}$ as the charge carrier. The extracellular solution contains (in mM): N-methyl—D-glucamine, 125; BaCl$_2$, 20; CsCl, 5; MgCl$_2$, 1; HEPES, 10; glucose, 5; pH 7.4 (HCl). The intracellular solution contains (in mM): CsCl, 60; CaCl$_2$, 1; EGTA, 11; MgCl$_2$, 1; K$_2$ATP, 5; HEPES, 10; aspartic acid, 50; pH 7.4 (CsOH). Under these conditions, it is expected that the measured current was carried by Ba$^{2+}$ primarily through L-type calcium channels which is referred to as I$_{Ca,L}$. Drugs are applied by a local solution changer and reach the cell membrane within 1 s. The effects of nifedipine and S36 are tested with 20 ms long voltage-clamp steps to +10 or +20 mV (peak of current-voltage relation for each individual cell) from holding potentials of −80 mV or −40 mV. In embodiment C, the voltage-dependence of L-type Ca$^{2+}$ current blocked by JTV-519 (1 μM) and S36 (1 μM) are measured and presented.

Figure 2:
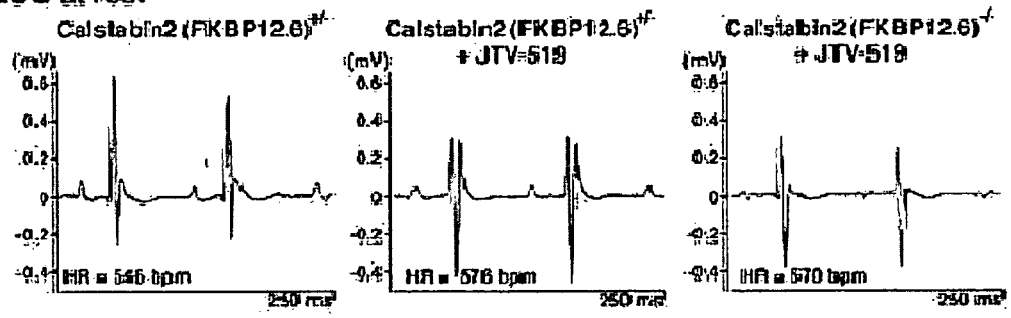
FIG. 2, embodiments A, B, C, and D demonstrate the prevention of exercise-induced ventricular arrhythmias by JTV-519 in haploinsufficient calstabin (FKBP12.6)$^{+/31}$ mice. Embodiment A are representative telemetric electrocardiograms (ECGs) of an untreated calstabin2 (FKBP12.6)$^{+/-}$ mouse (left), a JTV-519-treated calstabin2 (FKBP12.6)$^{+/-}$ mouse (middle), and a calstabin2 (FKBP12.6)$^{-/-}$ mouse (right). Embodiment B are telemetry recordings of a sustained polymorphic ventricular tachycardia (sVT) in (upper) an untreated haploinsufficient calstabin2 (FKBP12.6)$^{+/-}$ mouse and (lower) a JTV-519-treated calstabin2 (FKBP12.6)$^{+/-}$ mouse, each subjected to exercise testing immediately followed by injection with 0.5 mg epinephrine per kilogram of body weight. Embodiment C are graphs showing the numbers of mice with cardiac death (left), sustained VTs (middle), and nonsustained VTs (right) in experimental groups of mice subjected to exercise testing and injection with 0.5 mg/kg epinephrine. Embodiment D provides graphs comparing the dose dependence of pharmacological effects of JTV-519 and S36 in regard to sudden cardiac death (left), sustained VTs (middle), and nonsustained VTs (right).
Figure 2:
Figure 2:
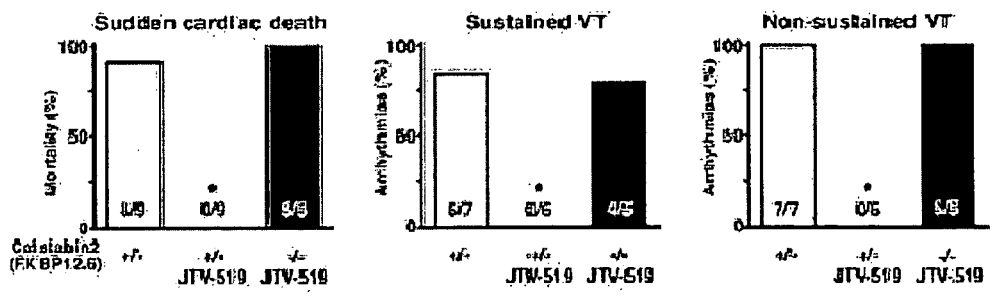
Figure 2:
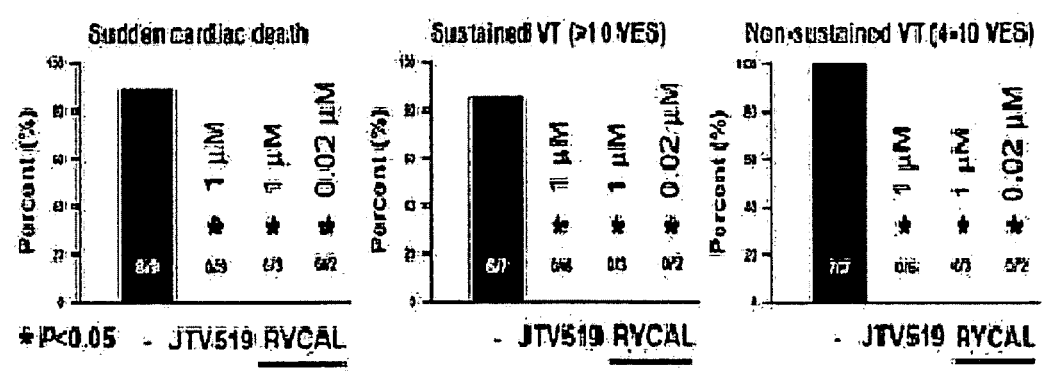

As demonstrated by FIG. 2, embodiments A, B, C, and D, S36 prevents exercise-induced sudden cardiac death at lower plasma levels compared with JTV-519. In embodiment A are shown representative ECGs of an untreated FKBP12.6$^{+/−}$ mouse and JTV519-treated FKBP12.6$^{+/−}$ and FKBP12.6$^{−/−}$ mice. Mice are treated with 0.5 mg JTV-519/per kilogram of body weight per hour for 7 days with an implanted osmotic mini-pump. JTV-519 has no effect on resting heart rate or other ECG parameters such as heart rate (HR). In embodiment B are shown sustained polymorphic ventricular tachycardia recorded by telemetry in an untreated FKBP12.6$^{+/-}$ mouse (upper tracing) subjected to exercise testing, immediately followed by injection with 0.5 mg epinephrine per kilogram of body weight. Representative telemetry ECG recording of a JTV-519-treated FKBP12.6$^{+/-}$ mouse following the same protocol is shown in the bottom tracing. In embodiment C are shown numbers of mice with cardiac death (left), sustained VTs (>10 beats, middle), and nonsustained VTs (3 to 10 arrhythmogenic beats, right) in experimental groups of mice subjected to exercise testing and injection with 0.5 mg/kg epinephrine. In embodiment D, the dose-dependence of pharmacological effects of JTV-519 and S36 is shown. Plasma levels of 1 µM JTV519 prevent cardiac arrhythmias and sudden cardiac death in FKBP12.6$^{+/-}$ mice. Plasma levels of 1 µM and 0.02 µM S36 also prevent cardiac arrhythmias and sudden cardiac death in FKBP12.6$^{+/-}$ mice.

Figure 3:
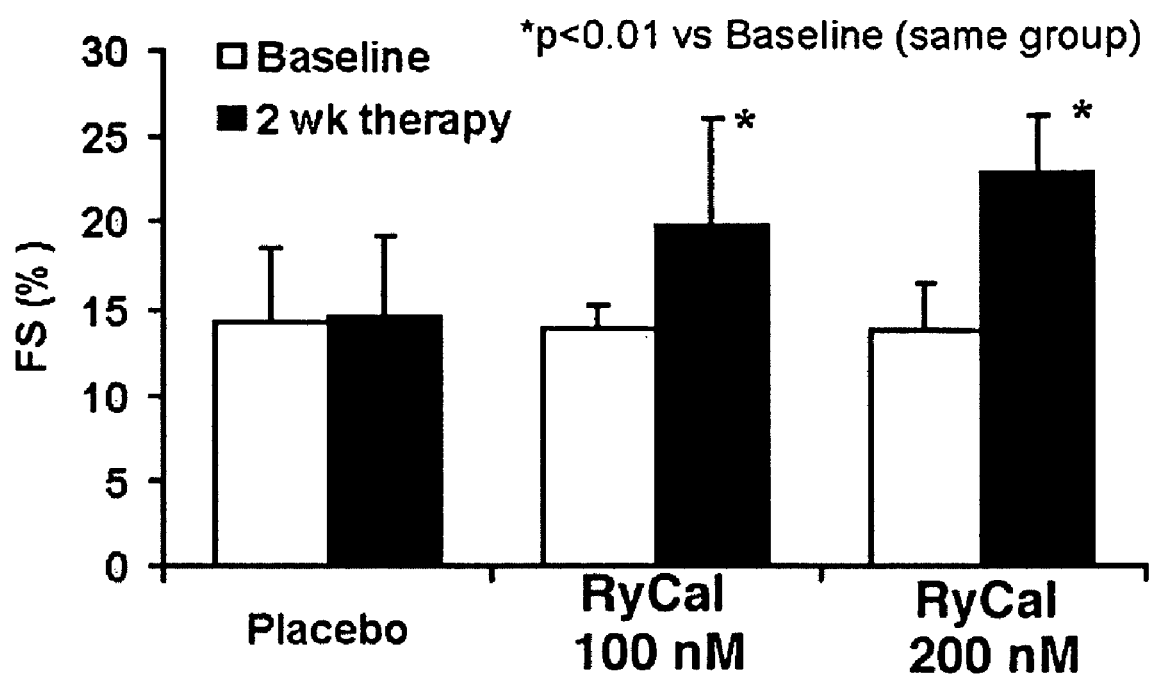
FIG. 3 is a graph showing fractional shortening (FS) of the left ventricle assessed by M-mode echocardiography 2 weeks post-myocardial infarction in mice.

FIG. 3, shows the result treated mice that are subjected to permanent ligation of the left anterior descending coronary artery resulting in myocardial infarction.

Figure 4:
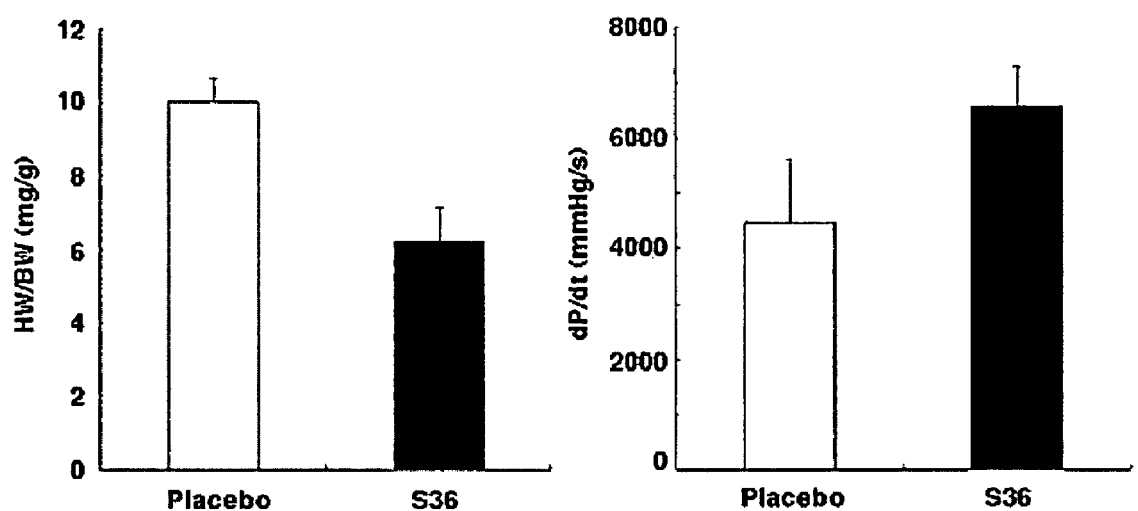
FIG. 4 is a graph showing heart weight to body weight (HW/BW) ratios and pressure-volume loops quantifications (dP/dt) one week post-myocardial infarction of placebo and S36-treated mice. S36 treatment results in a beneficial reduction of the HW/BW ratio and increased velocity of pressure development in S36 as compared to placebo treated mice.

As demonstrated by FIG. 4, S36 improves cardiac function in chronic heart failure post-myocardial infarction. Wild-type mice are subjected to permanent ligation of the left anterior descending coronary artery resulting in myocardial infarction. Seven days following myocardial infarction, mice are treated with S36 (plasma concentration 200 nM) or placebo. Heart weight to body weight (HW/BW) ratios and pressure-volume loops quantifications (dP/dt, slope of the maximum derivative of change in systolic pressure over time) show reverse remodeling and improved cardiac contractility in S36-treated mice compared with placebo.

Figure 5:
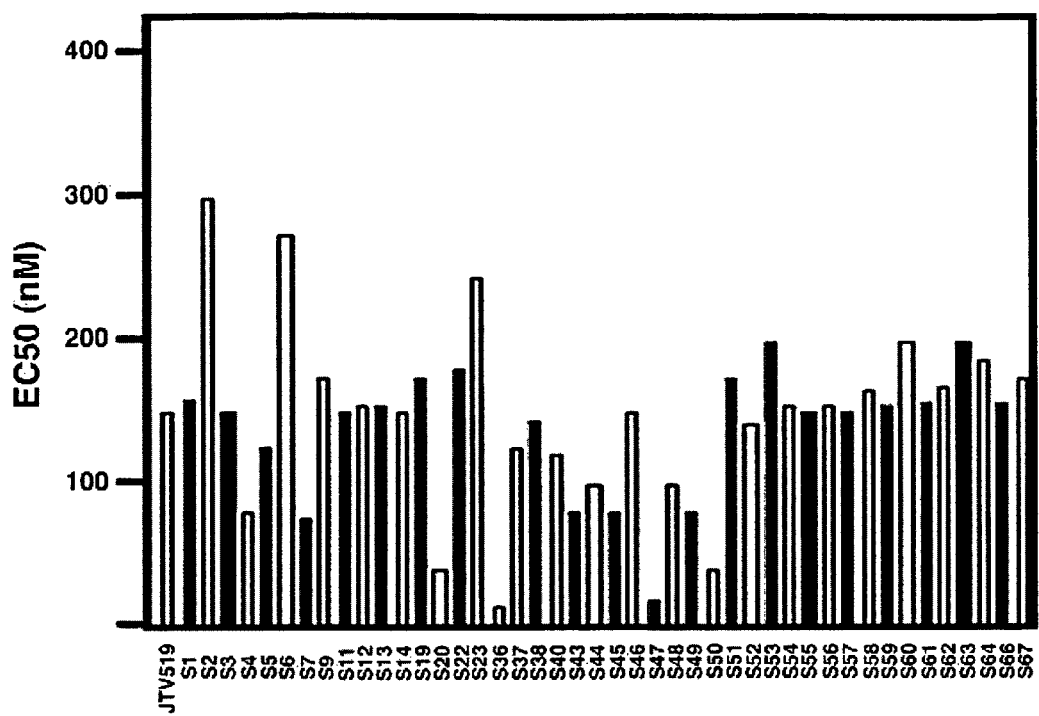
FIG. 5 is a graph summarizing $EC_{50}$ values of JTV-519 and a series of Rycal compounds indicating several compounds with a higher biologic activity as evidenced by significantly lower $EC_{50}$ values compared to JTV-519.

FIG. 5 is a summary graph of EC50 values of JTV-519 and compounds S1-S67 disclosed herein. The FKBP12.6 rebinding assay described above is used to determine the amount of FKBP12.6 binding to PKA-phosphorylated RyR2 at various concentrations (0.5-1000 nM) of the compounds shown. $EC_{50}$ values are calculated using Michaelis-Menten curve fitting.

Figure 6:
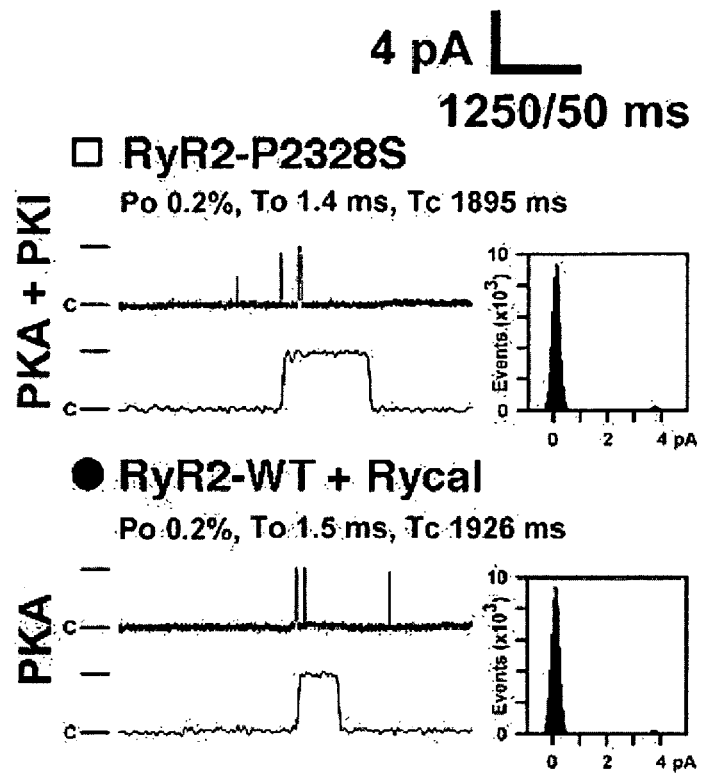
FIG. 6, embodiments A, B, and C are, respectively, (A) single-channel current traces of RyR2-P2328S and RyR2—WT; (B) single-channel current traces of RyR2-P2328S; and; (C) immunoblot analysis of calstabin-2 binding of RyR2-P2328S.
Figure 6:
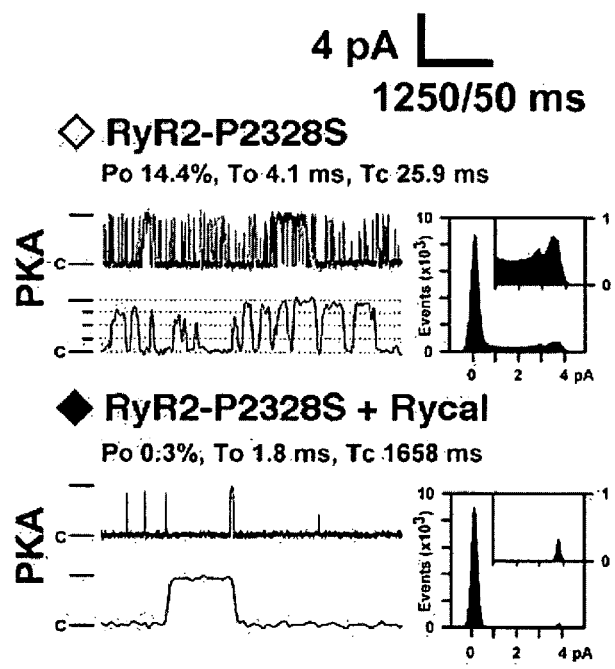
Figure 6:
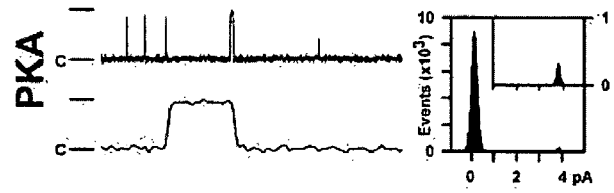
Figure 6:
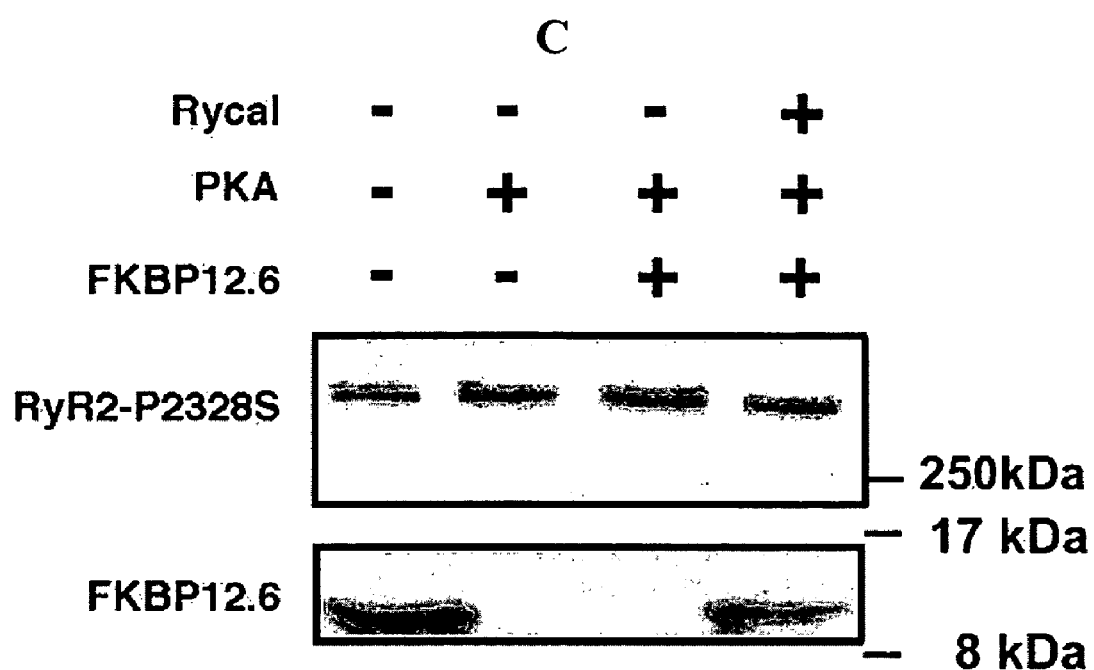

FIG. 6, embodiments A, B, and C, show CPVT-associated RyR2-P2328S channel function and structure. In embodiment A are shown representative single-channel current traces of RyR2-P2328S and RyR2-WT while embodiment B shows RyR2-P2328S Embodiment C shows immunoblot analysis of calstabin-2 binding of RyR2-P2328S.

Figure 7:
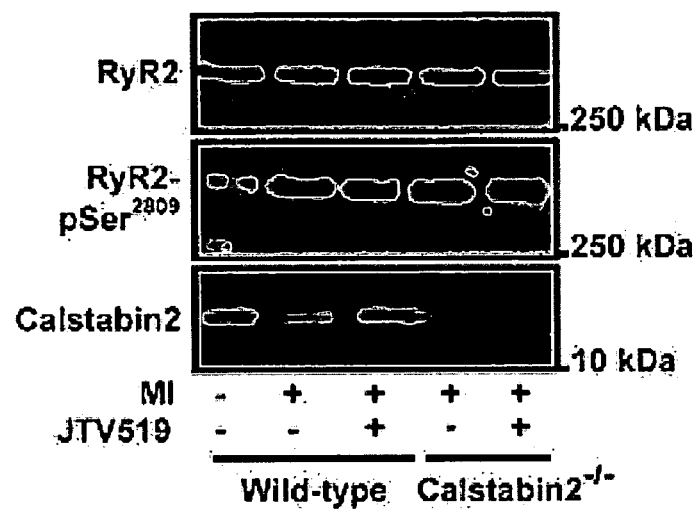
FIG. 7, embodiments A and B, are, respectively, (A) an immunoblot of RyR2 immunoprecipitated with an antibody against RyR2, and immunoblots of RyR2 PKA phosphorylation at Ser-2809 and calstabin2; and (B) a bar graph quantifying the relative amount of PKA phosphorylated RyR2 at Ser-2808 (corresponding to human Ser-2809) bound to RyR2 in wild-type (contol) and calstabin2-deficient (FKBP12.6$^{-/-}$) mice.
Figure 7:
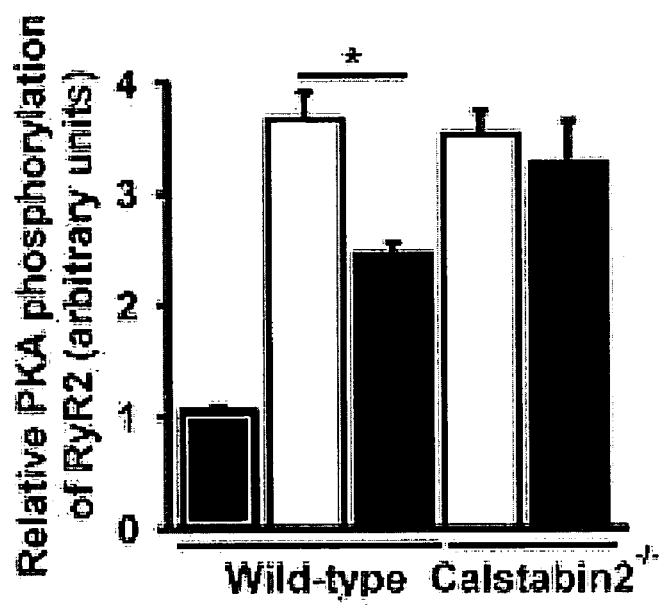

As demonstrated by FIG. 7, embodiments A and B, treatment with JTV-519 reduces PKA phosphorylation of RyR2 in mice with heart failure. Equivalent amounts of RyR2 are immunoprecipitated with an antibody against RyR2 (top blot). Representative immunoblots (embodiment A) and bar graphs (embodiment B) show the amount of PKA phosphorylated RyR2 at Ser-2808 bound to RyR2 in wild-type and calstabin2(FKBP12.6)$^{-/-}$ mice. Treatment with JTV-519 (0.5 mg/kg/h) for 28 days post-myocardial infarction reduces PKA-phosphorylation of RyR2, presumably due to reverse cardiac remodeling, in wildtype but not calstabin-2 (FKBP12.6)$^{-/-}$ mice.

Figure 8:
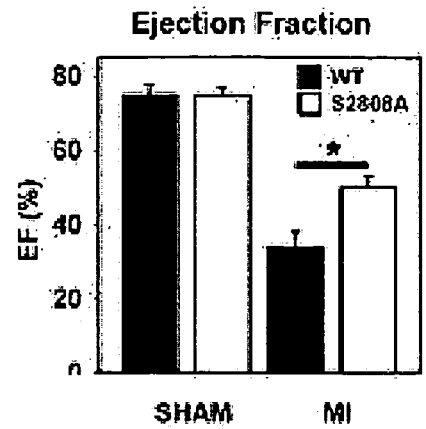
FIG. 8, embodiments A, B, and C, are, respectively, bar graphs of (A) quantitative in vivo M-mode echocardiograms comparing ejection fraction (EF) before and following sham operation or permanent left anterior descending (LAD) coronary artery ligation in wild-type and RyR2-S2808A knockin mice; (B) in vivo pressure-volume loop quantification of maximal pressure change over time (dP/dt) in wild-type and RyR2-S2808A knockin mice after sham operation or permanent left anterior descending coronary artery (LAD) ligation; and (C) quantitative M-mode echocardiographic assessment of end-systolic diameter (ESD) in wildtype and RyR2-S2808A knockin mice after sham operation or permanent left anterior descending coronary artery (LAD) ligation.
Figure 8:
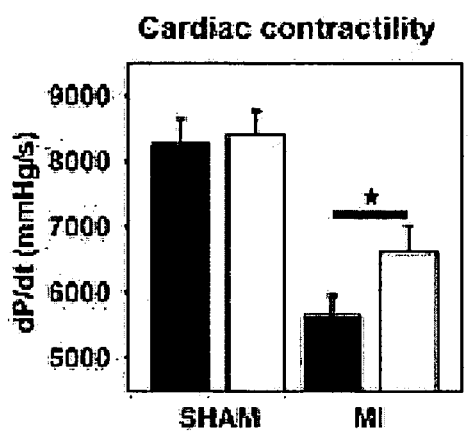
Figure 8:
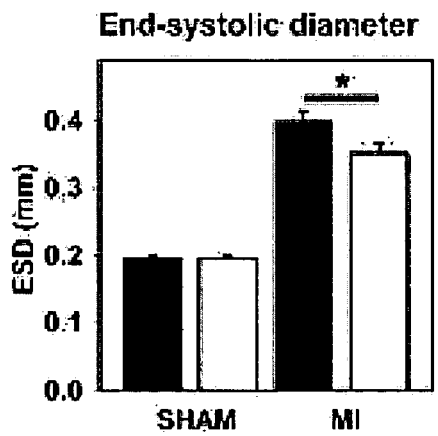

As demonstrated by FIG. 8, embodiments A and B, mice in which cardiac RyR2 cannot be PKA phosphorylated (RyR2-S2808A knockin mice) have improved cardiac function following myocardial infarction. Shown in embodiment A is the quantification of M-mode echocardiograms showing improved ejection fraction in RyR2-S2808A knockin mice compared with wildtype 28 days following permanent coronary artery ligation. Shown in embodiments B and C are pressure-volume loop quantifications showing (embodiment B) improved cardiac contractility and decreased cardiac dilation (embodiment C) in RyR2-S2808A knockin mice compared with wildtype following myocardial infarction.

Figure 9:
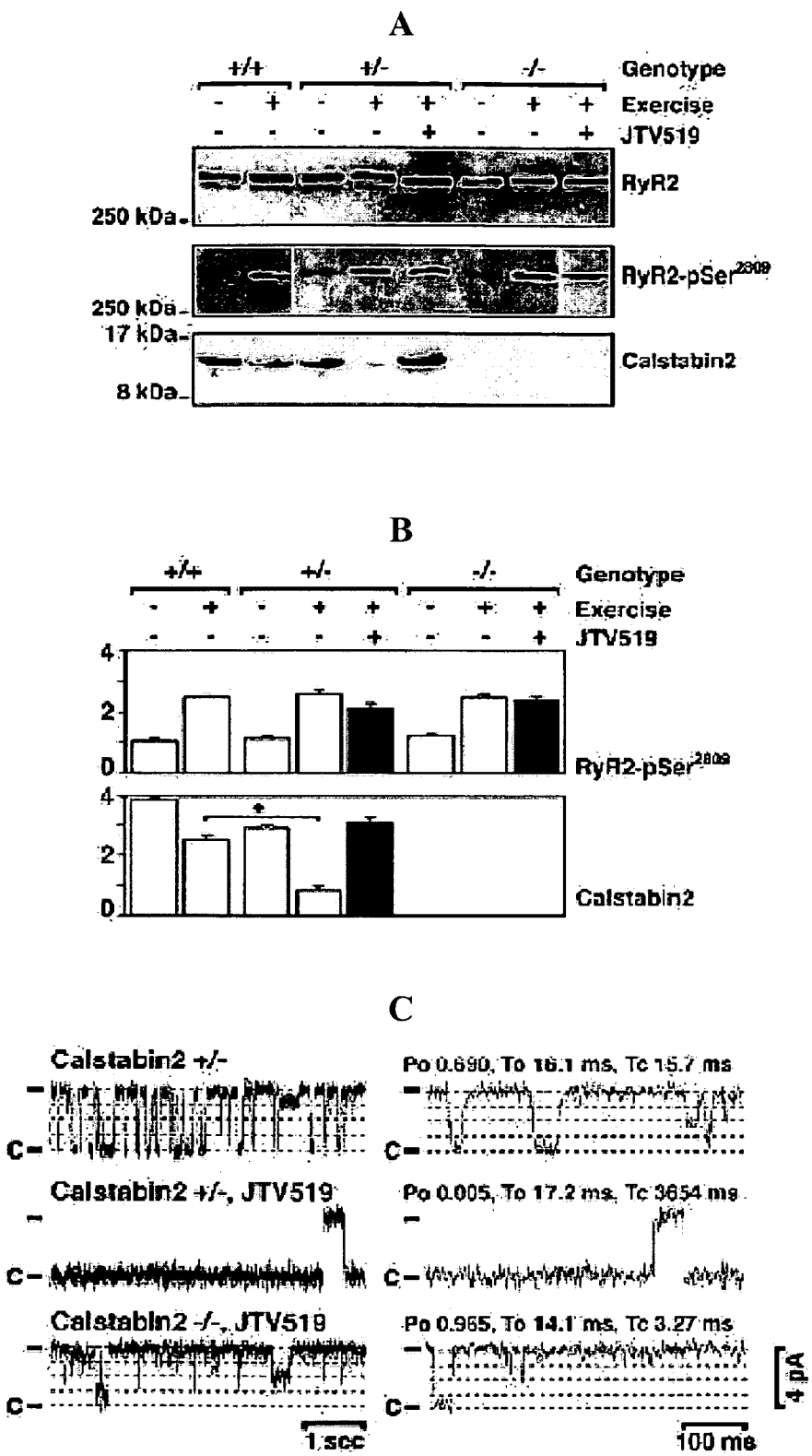
FIG. 9, embodiments A, B, C, and D demonstrate the effect of JTV-519 on calstabin2 affinity to RyR2 in haploinsufficient calstabin2 (FKBP12.6)$^{+/-}$ mice after exercise. Embodiment A is immunoblots of equivalent amounts of RyR2 immunoprecipitated with an antibody against RyR2 (top). Embodiment B are bar graphs showing the amount of PKA phosphorylation of RyR2 at Ser-2809 and the amount of calstabin2 bound to RyR2 from control animals and animals after exercise immediately followed by injection with 0.5 mg/kg epinephrine. Embodiment C are single-channel tracings of RyR2 channels isolated from hearts of haploinsufficient calstabin2$^{+/-}$ and calstabin2-1- deficient mice immediately following exercise testing and injection of 0.5 mg epinephrine per kg of body weight, both untreated (top) and after treatment (middle and bottom) with JTV-519. Average open probability (Po), open time (To) and average closed time (Tc) are as indicated; and closed state is indicated by 'c'. The dotted lines indicate subconductance levels for partial RyR2 openings. Embodiment D is a bar graph summarizing average open probabilities of single RyR2 channels from haploinsufficient calstabin2$^{+/-}$ and calstabin2$^{-/-}$ deficient mice after exercise with and without JTV-519 treatment. "*" indicates significance level P<0.05. Numbers in the bars indicate the number of single channels measured.
Figure 9:
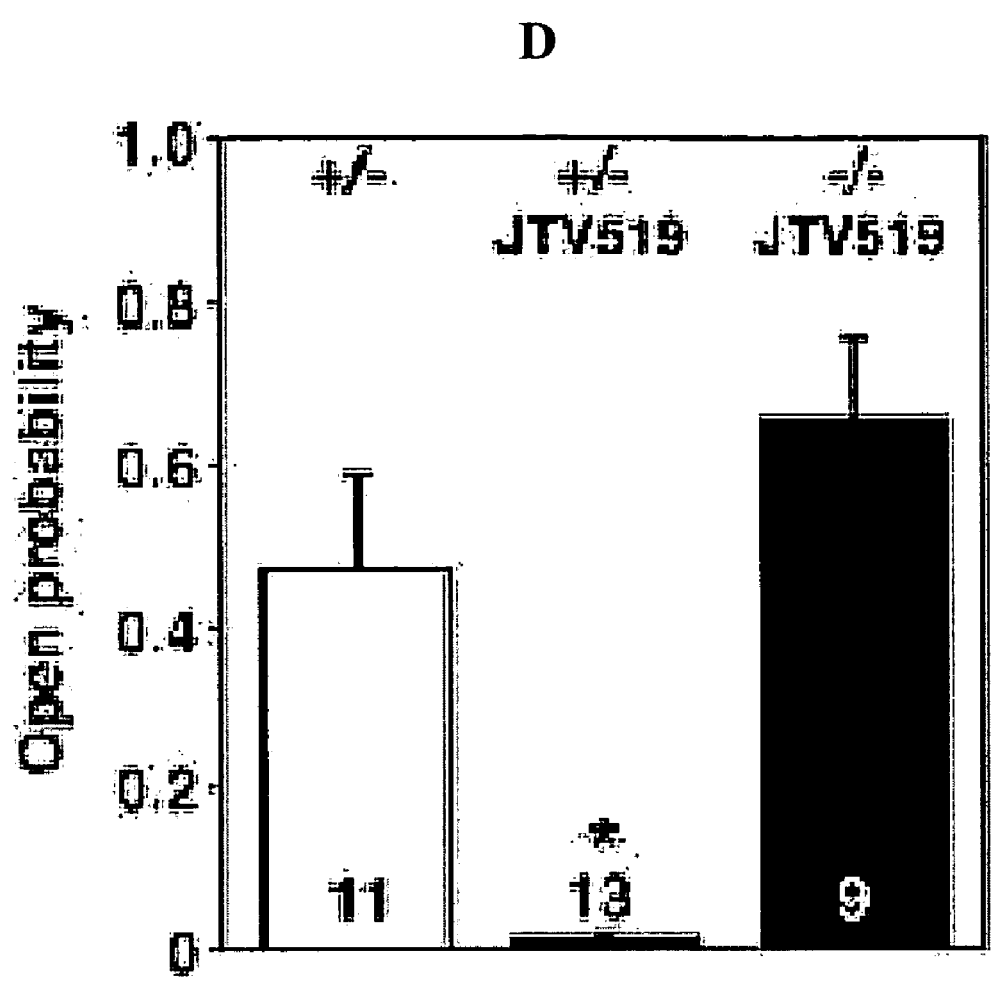

FIG. 9, embodiments A, B, C, and D demonstrate the effect of JTV-519 on calstabin2 affinity to RyR2 in haploinsufficient calstabin2 (FKBP12.6)$^{+/-}$ mice after exercise. The average probability that RyR2 channels will be open in calstabin2$^{+/-}$ mice subjected to exercise were significantly increased compared to those of channels from exercised wild type (control; calstabin2$^{+/+}$) mice, which are predominately closed under conditions that simulate diastole in the heart. As shown in embodiments C and D, treatment of exercised calstabin2$^{+/-}$ mice with JTV-519 significantly reduced the channel open probability ($P_o$) compared with that of channels from exercised mice that were not treated, consistent with increased amounts of calstabin2 in the RyR2 channel complex. Therefore, JTV-519 increases the binding affinity of calstabin2 to RyR2. In contrast, JTV-519 treatment of exercised Calstabin2$^{-/-}$ deficient mice did not result in channels with a low $P_o$, indicating that the presence of calstabin2 is necessary for JTV-519 effects which are documented as binding of calstabin2 to RyR2.

Figure 10:
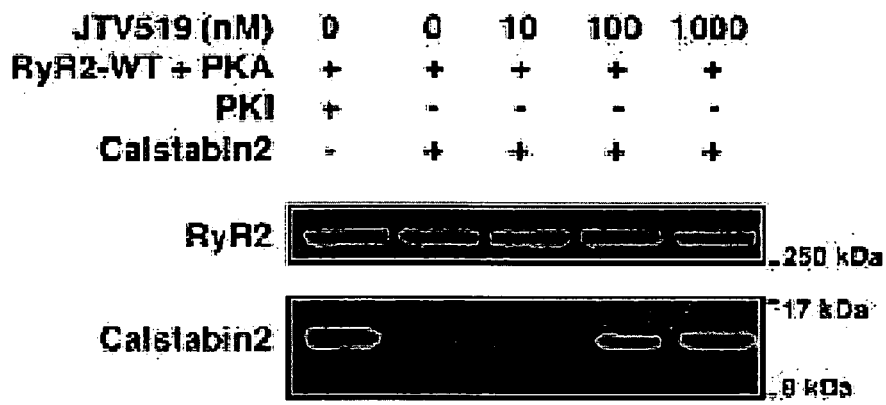
FIG. 10, embodiments A, B, C, D, E, and F demonstrate normalized RyR2 channel gating and increased calstabin2 binding to RyR2 channels after treatment with JTV-519. Embodiment A are immunoblots of immunoprecipitated wild-type RyR2 (RyR2-WT) channels phosphorylated by PKA in the absence or presence of the inhibitor peptide $PKI_{5-24}$ and incubated with calstabin2 (250 nM) at the indicated JTV-519 concentrations; the immunoblots show the amount of RyR2 (top) and the amount of calstabin2 (bottom) associated with immunoprecipitated RyR2 after incubation with or without the indicated concentrations of JTV-519. Embodiment B is immunoblots of RyR2-S2809D, which mimics constitutive PKA phosphorylation of RyR2, analyzed as in Embodiment A. Embodiment C are binding curves of $^{35}$S-radiolabeled calstabin2 to unphosphorylated or PKA phosphorylated RyR2 or to RyR2-S2809D in the presence or absence of JTV-519, documenting differences in the calstabin2 binding affinity for RyR2. Embodiments D, E, and F are single channel tracings (left) and amplitude histograms (right) of PKA-phosphorylated RyR2s (embodiments E and F) or unphosphorylated (embodiment D in presence of PKA inhibitor $PKI_4$) incubated with calstabin2 (250 nM) with (embodiment F) or without (embodiments D and E) JTV-519 (1 μM). Single-channel tracings are shown at 150 nM $[Ca^{2+}]$ which mimics the diastolic or resting phase in the heart; channel openings are upward, the dash indicates the full level of channel opening (4 pA), and "c" indicates the closed state of the channels. The amplitude histograms have amplitude represented on the x axis, and events on the y axis indicates the number of channel openings.
Figure 10:
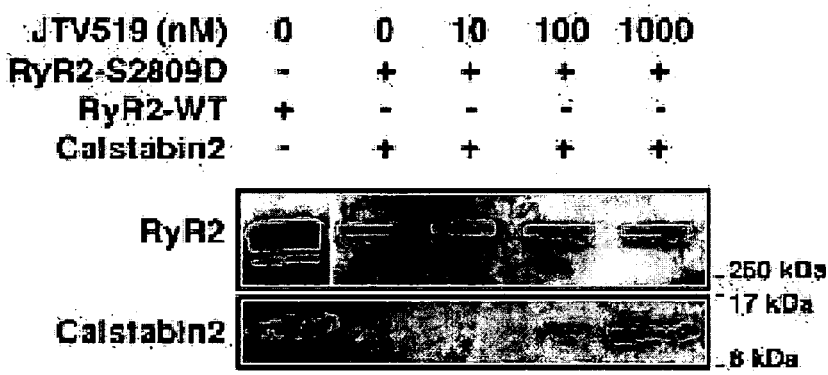
Figure 10:
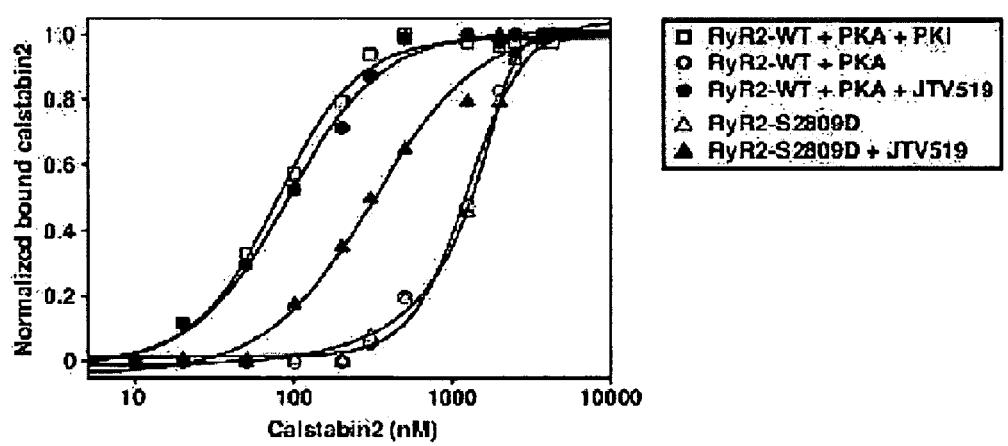
Figure 10:
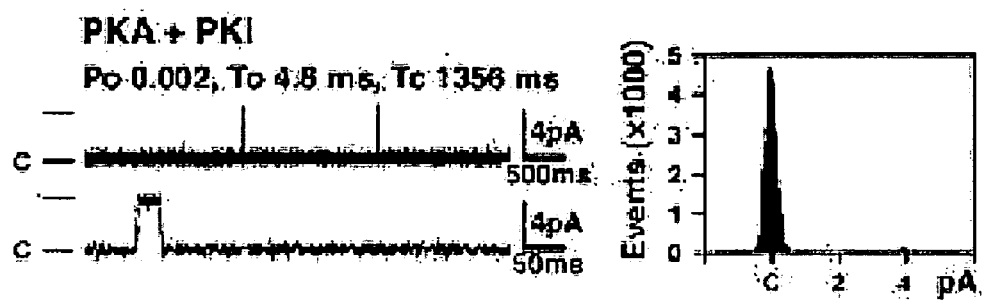
Figure 10:
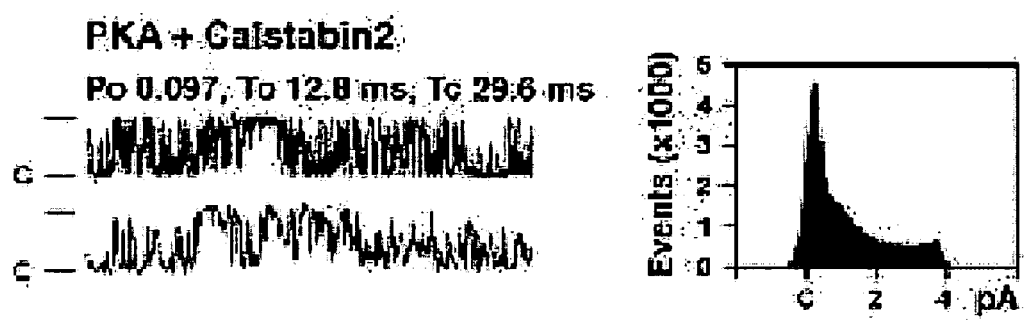
Figure 10:

FIG. 10, embodiments A, B, C, D, E, and F demonstrate, respectively, normalized RyR2 channel gating and increased calstabin2 binding to RyR2 channels after treatment with JTV-519. The immunoblots in embodiments A and B show the amounts of RyR2 and calstabin2 associated with immunoprecipitated RyR2 after incubation with the indicated concentrations of JTV-519 for, respectively, wild-type RyR2 (RyR2-WT) channels and RyR2-S2809D. The binding curves in embodiment C demonstrate that JTV-519 significantly increases the affinity of calstabin2 for PKA-phosphorylated RyR2 channels. The results also show that depletion of calstabin2 from the RyR2 macromolecular complex which is associated with increased RyR2 open probability, ventricular tachycardias, and sudden cardiac death in haploinsufficient calstabin2$^{+/-}$ mice is reversed by treatment with JTV-519. Therefore, the JTV-519 and related compounds prevent disorders and conditions associated with the RyR2 receptors.

Figure 11:
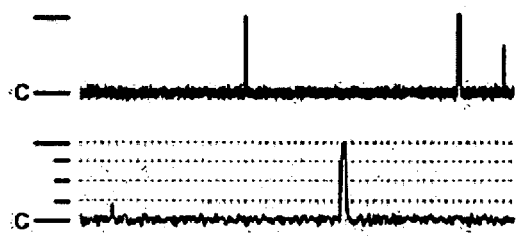
FIG. 11, embodiments A, B, C, D, E, and F demonstrate that RyR1 channel function is increased and normalized in mdx mice treated with JTV-519. Embodiments A and B are, respectively, a single channel current trace and an amplitude histogram of RyR1 from soleus muscle of a control (wild-type) mouse under resting conditions. Embodiments C and D are, respectively, a single channel current trace and an amplitude histogram of RyR1 from soleus muscle of an mdx mouse. Embodiment E and F are, respectively, a single channel current trace and an amplitude histogram of RyR1 from soleus muscle of an mdx mouse treated with JTV-519.
Figure 11:
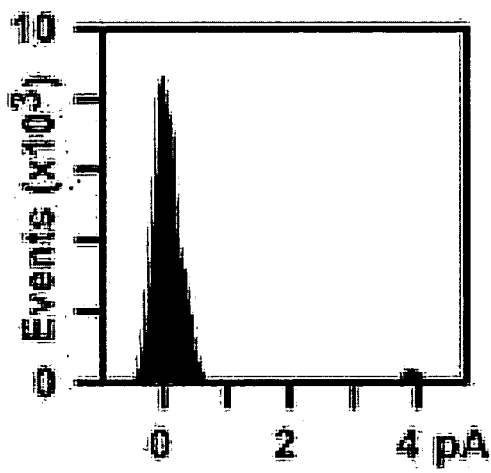
Figure 11:
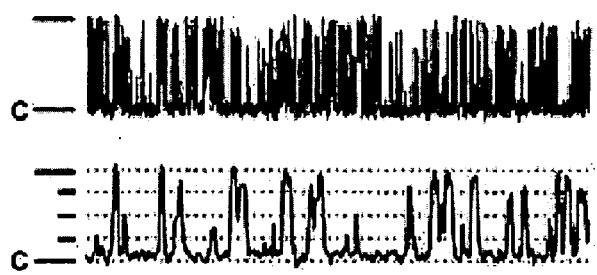
Figure 11:
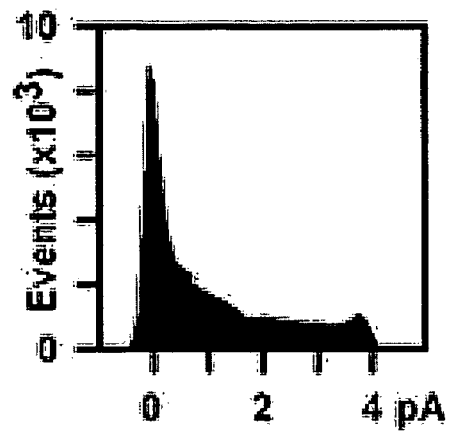
Figure 11:
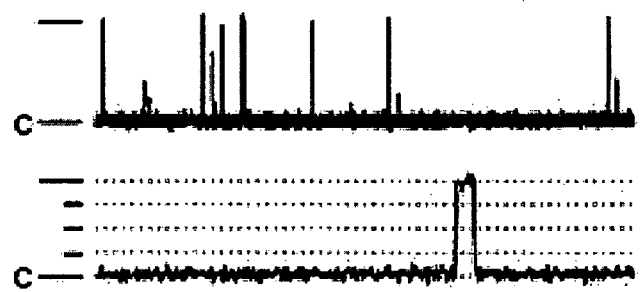
Figure 11:
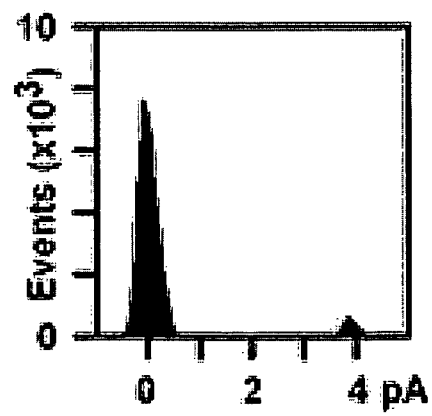

As shown in FIG. 11, embodiments A, B, C, D, and E RyR1 channel functioning is increased and normalized in mdx (dystrophin deficient) mice treated with JTV-519. In FIG. 11, channel openings are represented as upward deflections; 'c' indicates the closed state; and 4 pA current open amplitude is indicated by dash. Upper traces represent 5 secs and lower traces 500 ms; dotted lines indicate subconductance states.

Embodiment A of FIG. 11 shows a single channel current trace of RyR1 from soleus muscle of control (wild-type) mouse under resting conditions (cytoplasmic $Ca^{2+}$ 150 nM). As seen, RyR1 is predominantly closed. Embodiment C of FIG. 11 shows that RyR1 channel function in mdx mouse shows significantly increased open probability, increased average open, and decreased average closed dwell times, To and Tc, respectively. Increased Po in mdx mice is consistent with intracellular $Ca^{2+}$ leak. The amplitude histograms in embodiments B, D, and F show multiple subconductance states consistent with calstabin1 (FKBP12) depletion in RyR1 from mdx soleus muscle. Embodiment E of FIG. 11 shows an mdx mouse treated with 1.0 µM JTV-519. As seen, the RyR1 channels JTV-519-treated mouse demonstrates normal activity that is not significantly different from untreated wild-type trace, thereby indicating that JTV-519 can normalize RyR1 channel function in mdx mice.

The data of FIG. 11 are consistent with intracellular SR $Ca^{2+}$ leak via RyR1 channels as the cause of increased cytosolic $Ca^{2+}$ leak in skeletal muscles from mdx (dystrophin deficient) mice.

Figure 12:
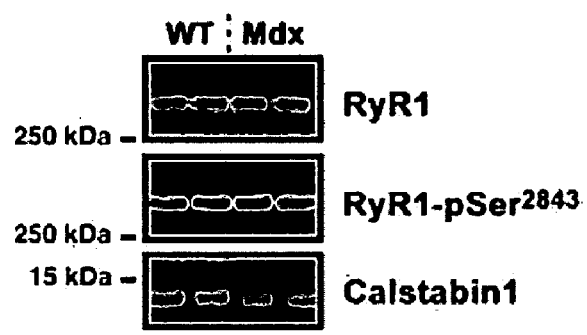
FIG. 12, embodiments A and B, are, respectively, immunoblots of RyR1, RyR1-pSer$^{2843}$, and RyR1-associated calstabin1 in mdx mice and wild-type mice; and bar graphs of the relative amounts of RyR1-pSer$^{2843}$ and calstabin1 in mdx and wild-type mice.
Figure 12:
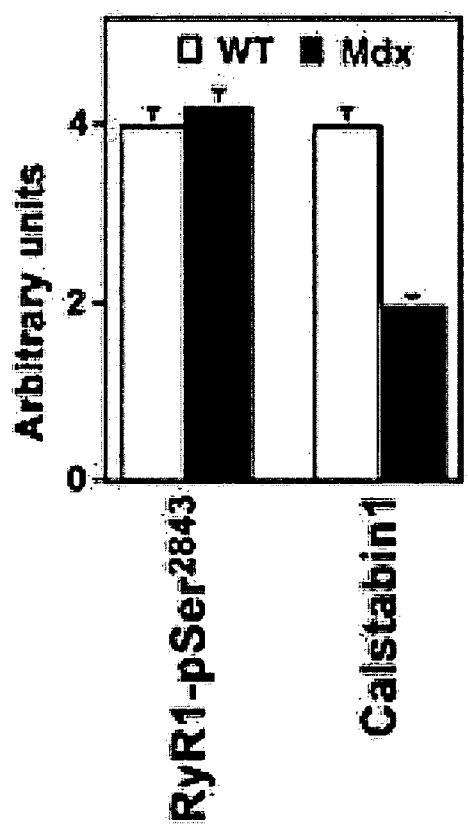

FIG. 12, embodiments A and B, demonstrate that mdx skeletal muscle has normal levels of RyR1 PKA phosphorylation, but depleted levels of calstabin1. The immunoblots in embodiment A show that mdx type mice have depeleted levels of calstabin1 compared to a control (wild-type) mouse. The summary bar graphs of embodiment B show that the mdx mouse, nevertheless, has an equivalent level of PKA-phosphorylation. Therefore, it is concluded that calstabin1 depeletion is a defect that is consistent with the intracellular $Ca^{2+}$ leak observed in skeletal muscle cells from mdx mice and myofibers from human mutation carriers. Intracellular SR $Ca^{2+}$ leak is likely to contribute to myofiber death and wasting of muscle mass by toxic intracellular $Ca^{2+}$ overload and activation of proteases.

Figure 13:
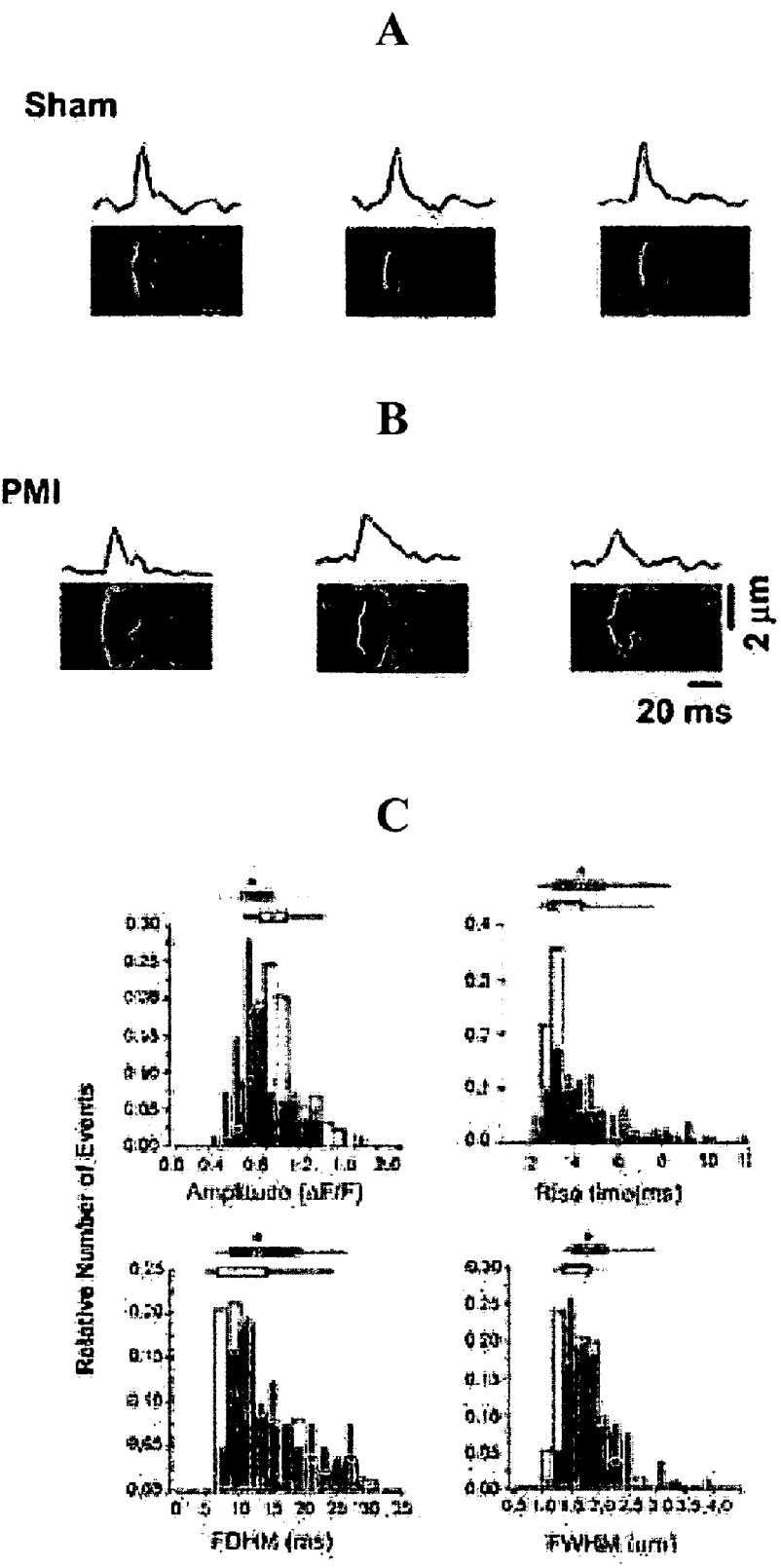
FIG. 13, embodiments A, B, and C, demonstrate that a SR $Ca^{2+}$ leak is detectable in the skeletal muscles of animals with heart failure. Embodiments A and B are fluorescence line scan images of $Ca^{2+}$ sparks in myofibers from, respectively, sham and postmyocardial infarction (PMI) rats. Embodiment C provides bar graphs summarizing the amplitude, rise time, FDHM, and FWHM of the $Ca^{2+}$ sparks for the sham (open symbols) and PMI (closed symbols) rats.

FIG. 13, embodiments A, B, and C, demonstrates that SR $Ca^{2+}$ leak at the subcellular level in skeletal muscles of animals with heart failure is detectable. Life quality and prognosis in heart failure (HF) patients is severely decreased due to skeletal muscle dysfunction (e.g., shortness of breath due to diaphragmatic weakness, and exercise intolerance due to limb skeletal muscle fatigue) in addition to depressed cardiac function. Dysregulation of intracellular SR $Ca^{2+}$ release is a pathogenic mechanism underlying skeletal muscle dysfunction in HF. HF in animals causes significantly accelerates intrinsic skeletal muscle fatigue.

Embodiments A and B of FIG. 13 are ΔF/F fluorescence line scan images of representative examples of $Ca^{2+}$ sparks in myofibers from sham and postmyocardial infarction (PMI) rats and corresponding $Ca^{2+}$ spark time course. Embodiment C shows the relative distribution of the spatio-temporal properties of the $Ca^{2+}$ sparks. Charts indicate 25, 50, 75 percentiles, the horizontal lines indicate the range from 1-99% of the distribution. Sham, open symbols (n=137, three animals); postmyocardial infarction (PMI), gray symbols (n=82, two animals). *, P<0.05. FDHM, full duration at 50% peak amplitude; FWHM, full width at 50% peak amplitude.

Figure 14:
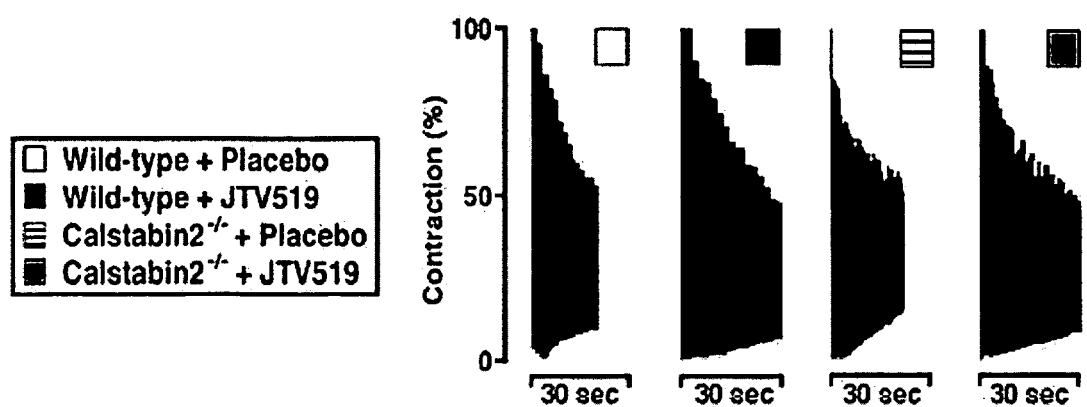
FIG. 14, embodiments A and B, demonstrate that treatment of wild-type mice with JTV-519 improves soleus muscle fatigue times. Embodiment A provides maximal tetanic force fatigue time tracings for wild-type and calstabin2$^{-/-}$ mice, treated with JTV-519 or placebo as indicated. Embodiment B are bar graphs summarizing the mean time to fatigue for wild-type and calstabin2$^{-/-}$ mice, treated with JTV-519 or placebo as indicated.
Figure 14:
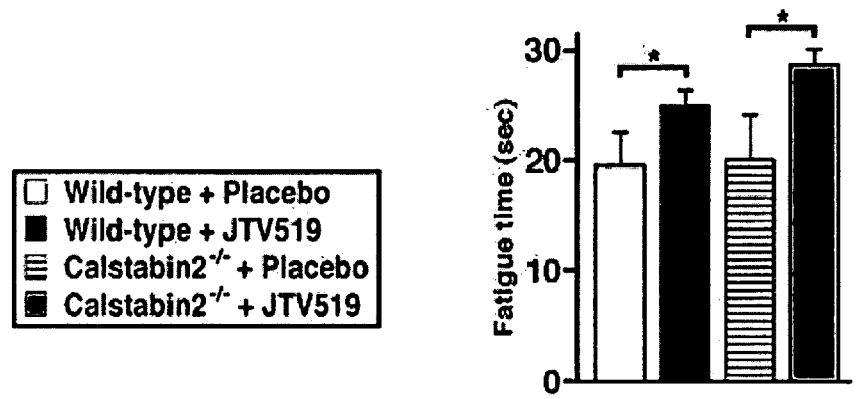

FIG. 14, embodiments A and B, demonstrate that treatment of wild-type mice with JTV-519 improved soleus muscle fatigue times compared with placebo. Soleus muscles from JTV519-treated wild-type mice or calstabin2$^{-/-}$ mice with heart failure from myocardial infarction are more resistant to fatigue (P<0.05) compared to placebo-treated mice. After completion of treatment, soleus muscle was dissected and mounted in a tissue bath to assess isolated skeletal muscle function. Representative 50% of maximal tetanic force fatigue time tracings are shown for wild-type and calstabin2$^{-/-}$ mice, treated with JTV519 or placebo, in embodiment A. In embodiment B are shown bar graph summarizing mean time to fatigue.

In summary, JTV-519 treatment improved skeletal muscle fatigability in heart failure animals in vivo. Interestingly, in calstabin2$^{-/-}$ knockout mice, fatigue times were also significantly improved in JTV519 treated mice, suggesting that the beneficial effects on isolated skeletal muscle function depend on calstabin1 and not calstabin2 binding to RyR1. Indeed, calstabin1 appears to be the only isoform of functional significance expressed in skeletal muscles.

Figure 15:
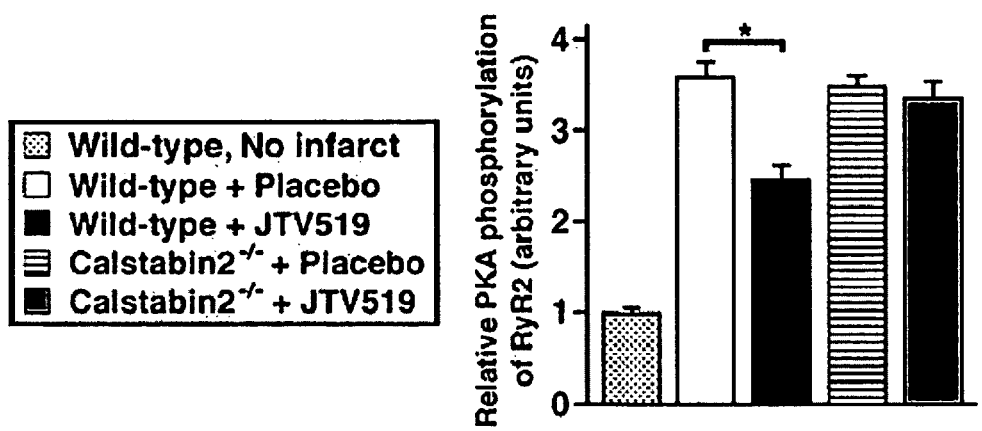
FIG. 15, embodiments A and B, demonstrate that the beneficial effects of JTV-519 treatment on skeletal muscle function depend on calstabin1 and not calstabin2 binding to RyR1. Embodiment A provides bar graphs of PKA phosphorylation of RyR1 at Ser-2844 in mice, which corresponds to Ser-2843 in humans. Embodiment B are bar graphs of the amount of calstabin1 bound to RyR1 from wild-type and calstabin2$^{-/-}$ mice treated with JTV-519 or placebo.
Figure 15:
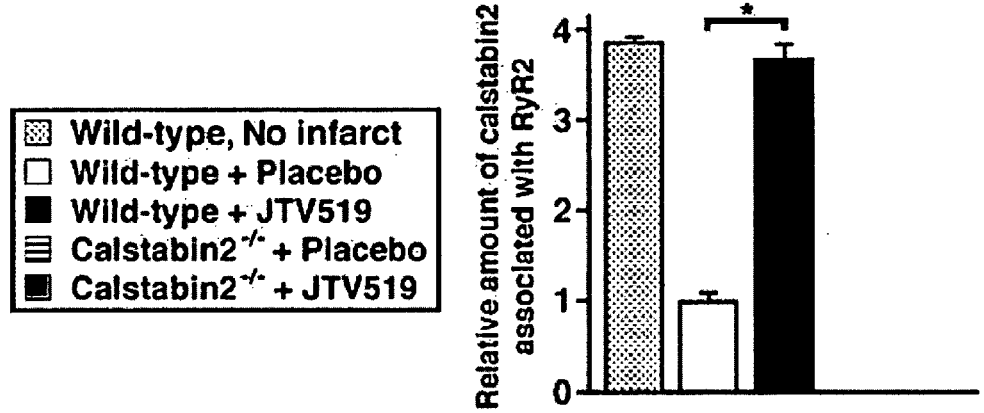

FIG. 15, embodiments A and B, demonstrates that in a mouse model of post-myocardial infarction heart failure, RyR1 in soleus muscle is also PKA-hyperphosphorylated. Both in wild-type and calstabin2$^{-/-}$ mice, JTV-519 increased binding of calstabin1 to RyR1 in soleus muscle, suggesting that JTV-519 improves skeletal muscle fatigability by normalizing calstabin1 rebinding to the channel complex. Equivalent amounts of RyR1 were immunoprecipitated with an antibody against RyR1. Embodiment A provides bar graphs show the amount of PKA phosphorylation of RyR1 at Ser-2844 in mice (corresponding to human Ser-2843). The significant decrease of RyR1 PKA phosphorylation in JTV519 treated wild-type animals is likely resulting from beneficial cardiac effects and secondary reduction of sympathetic nervous activity. Embodiment B are bar graphs showing the amount of calstabin1 bound to RyR1 from wild-type or calstabin2$^{-/-}$ mice treated with JTV519 or placebo. Mice were treated with JTV519 by implantable osmotic minipumps using a dose of 0.5 mg/kg/day. In summary, JTV-519 treatment resulted in a highly significant increase of calstabin1 in the RyR1 complex in soleus muscles in vivo.

Figure 16:
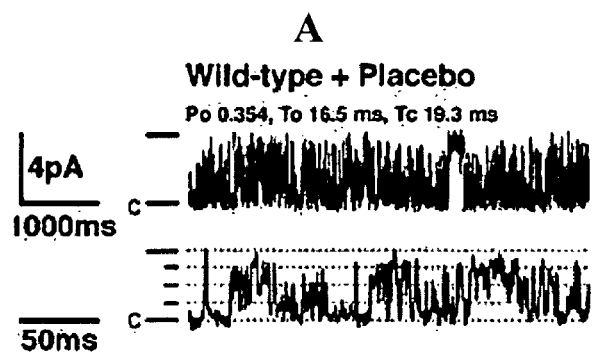
FIG. 16, embodiments A, B, C, and D demonstrate that JTV-519 normalizes abnormal or leaky RyR1 channel function in vivo. Embodiments A and C are single channel current traces of wild-type mice with heart failure treated with placebo (A) and JTV-519 (C). Embodiments B and D are amplitude histograms for wild-type mice with heart failure treated with placebo (B) and JTV-519 (D).
Figure 16:
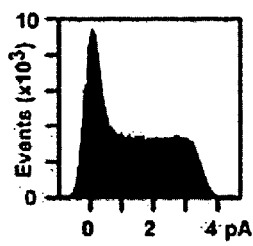
Figure 16:
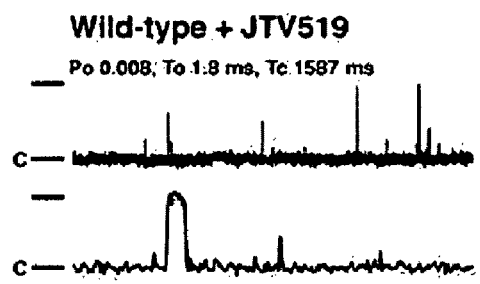
Figure 16:
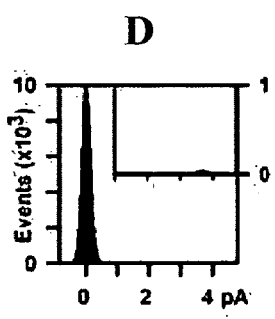

FIG. 16, embodiments A, B, C, and D demonstrates that calstabin1 rebinding to RyR1 by JTV519 normalizes abnormal or leaky RyR1 channel function in vivo. In embodiments A and C are shown RyR1 single-channel tracings at 150 nM cytoplasmic $Ca^{2+}$ representing resting conditions in skeletal muscle for wild-type mice treated with placebo and JTV-519. JTV-519 treatment of mice with heart failure and increased muscle fatigue normalized RyR1 channel gating in skeletal muscle in vivo. Channel openings are upward, the dash indicates the full level of channel opening (4 pA), the dotted lines indicate subconductance levels, and 'c' indicates the closed state of the channels. For the amplitude histograms in embodiment B and D, amplitude is represented on the x axis, and events indicates the number of channel openings. Po, To and Tc values correspond to the representative traces. Treatment as indicated on top of traces. Inset shows higher resolution of open states.

In summary, the data shows that in vivo JTV519 treatment normalizes skeletal muscle function and RyR1 channel dysfunction consistent with preventing intracellular SR $Ca^{2+}$ leak as a cause of increased skeletal muscle fatigue.

Figure 17:
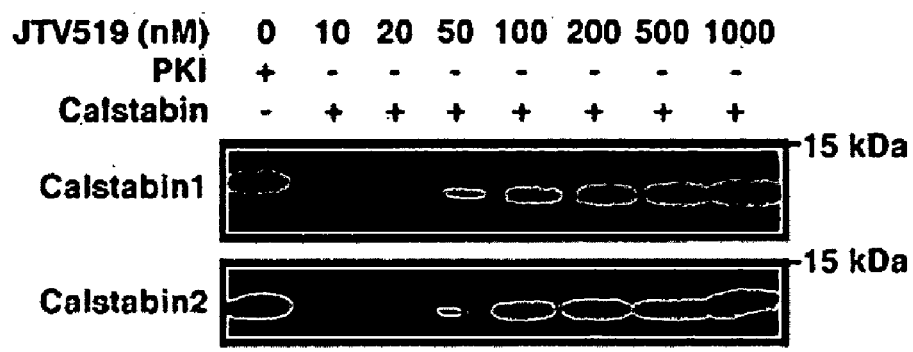
FIG. 17, embodiments A and B, demonstrate that JTV-519 increases calstabin binding to PKA phosphorylated RyR. Embodiment A are immunoblots of calstabin1 incubated and associated with RyR1 and calstabin2 incubated and associated with RyR2 at increasing concentrations of JTV-519. Embodiment B provides graphs summarizing the proportion of calstabin1 and calstabin2 bound to RyR1 and RyR2, as indicated.
Figure 17:
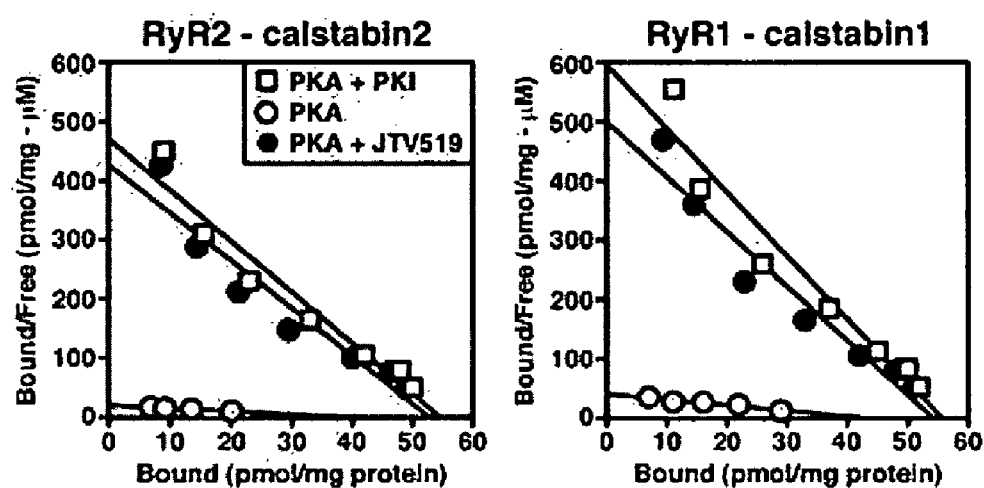

FIG. 17 demonstrate that JTV-519 also increases the binding affinity of calstabin1 for RyR1 in skeletal muscle in vivo. This probably explains why JTV519 treated mice with heart failure have increased levels of calstabin1 bound to RyR1 in soleus muscle. In embodiment A, equivalent amounts of skeletal RyR1 or cardiac RyR2 were immunoprecipitated, PKA phosphorylated and incubated with calstabin1 or calstabin2 at increasing concentrations of JTV519, respectively. Sediment represents only calstabin bound to RyR. Immunoblotting showed that ≧50 nM of JTV519 increased the binding affinity of calstabin for RyR. The graphs of embodiment B further demonstrate that PKA phosphorylation of RyR1 reduced the affinity of calstabin1 for RyR1 (open circles), whereas treatment with JTV519 (filled circles) restored the binding affinity of calstabin1 for RyR1 to that of non-PKA phosphorylated RyR1 (open squares).

Figure 18:
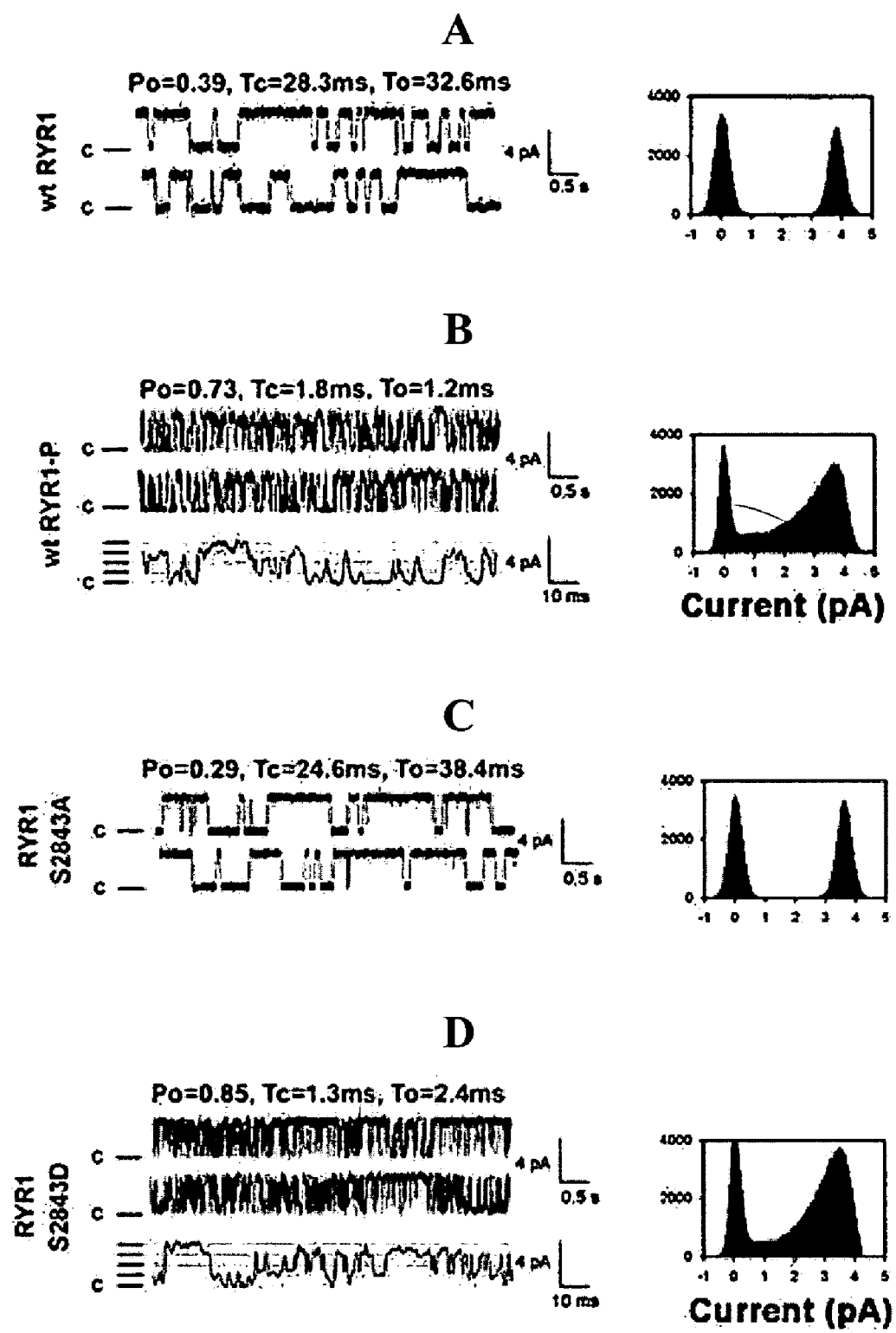
FIG. 18, embodiments A, B, C, and D, demonstrate that PKA phosphorylation of Ser-2843 increases the open probability and gating kinetics of RyR1 channels. Embodiment A provides single channel current traces and corresponding histogram of wild-type RyR1. Embodiment B provides single channel current traces and corresponding histogram of wild-type RyR1 that is PKA phosphorylated. Embodiment C provides single channel current traces and corresponding histogram of RyR1-Ser-2843A. Embodiment D provides single channel current traces and corresponding histogram of RyR1-Ser-2843D.

FIG. 18, embodiment A, B, C, and D demonstrates that Ser-2843 is the unique PKA phosphorylation site in skeletal RyR1 channels. (A) Representative single channel traces of wild-type RyR1, (B) effect of exogenous PKA phosphorylation of RyR1 (wt RyR1-P), (C) PKA does not affect RyR1-S2843A that contains a non-functional PKA phosphorylation site. Since PKA does not increase RyR1-S2843A activity, Ser-2843 appears to constitute the unique PKA phosphorylation site in RyR1 channels in skeletal muscle. Accordingly, (D) constitutively phosphorylated RyR1-S2843D mimics exogenous PKA phosphorylation shown in (B) confirming that Ser-2843 is the unique PKA phosphorylation site in skeletal RyR1 channels. RyR1 single channel recordings in planar lipid bilayers show activity of the channels at 150 nM $[Ca^{2+}]_{cis}$ (cytosolic side) with 1 mM ATP. Recordings were at 0 mV, closed state of the channels as indicated by 'c', and channel openings are upward deflections. All point amplitude histograms are shown on the right. Open probability ($P_o$) and mean closed (Tc) and open (To) dwell times are indicated above each channel tracing.

Figure 19:
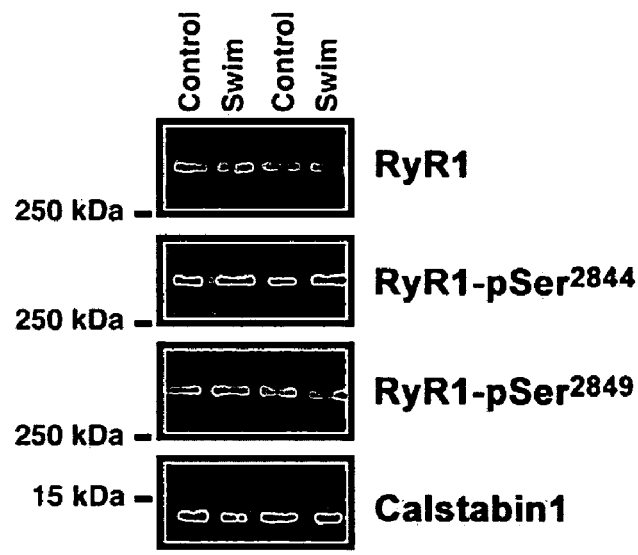
FIG. 19, embodiments A and B, demonstrate the PKA hyperphosphorylation and calstabin1 deficiency of RyR1 channels after sustained exercise. Embodiment A are immunoblots of RyR1, RyR1-pSer$^{2844}$, RyR1-pSer$^{2849}$, and calstabin1 for control and swim mice following an exercise regime. Embodiment B is a bar graph summarizing the relative amounts of the indicated compounds following the exercise regime.
Figure 19:
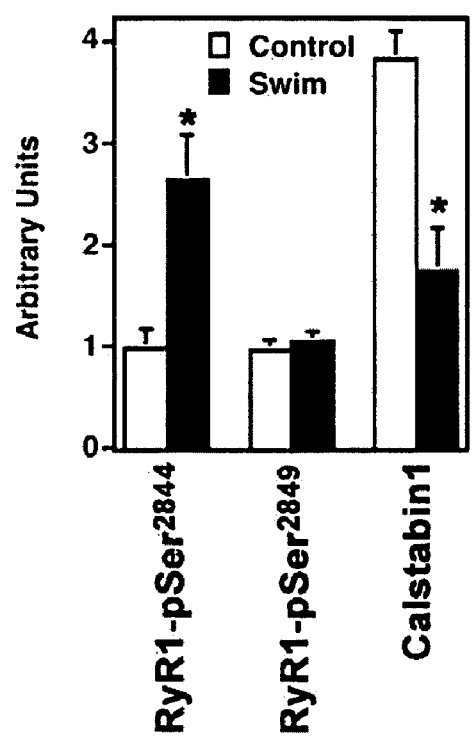

FIG. 19, embodiments A and B, demonstrates the depletion of stabilizing calstabin1 and PKA hyperphosphorylation of RyR1 channels from sustained exercise. Aerobic exercise can be defined as a form of physical exercise that increases the heart rate and enhances oxygen intake to improve performance. Examples of aerobic exercise are running, cycling, and swimming. During the study of FIG. 19, mice were challenged by aerobic exercise (forced swimming) for 90 mins twice daily. The animals were accustomed to swimming in preliminary training sessions: day —3 twice 30 mins, day —2 twice 45 mins, day —1 twice 60 mins, day 0 and following twice 90 mins. Mice were then exercised for 1, 7, or 21 additional, consecutive days for 90 mins twice daily. Between swimming sessions separated by a 4 hour rest period the mice are kept warm and given food and water. An adjustable-current water pool was used to exercise mice by swimming. An acrylic pool (90 cm long×45 cm wide×45 cm deep) filled with water to a depth of 25 cm was used. A current in the pool was generated with a pump. The current speed during the swimming session was at a constant speed of 1 l/min flow rate. The water temperature was maintained at 34° C. with an electric heater. Age- and weight-matched mice were used to exclude differences in buoyancy from body fat.

Using forced swimming as an efficient protocol to increase skeletal muscle aerobic capacity in mice, the composition and phosphorylation status of the skeletal RyR1 channel complex have been investigated. Unexpectedly, after 3 weeks of 90 mins swimming twice daily, C57Bl6 wild-type mice showed significantly increased RyR1 phosphorylation by PKA while $Ca^{2+}$-calmodulin kinase II (CaMKII) phosphorylation was not changed indicating specificity of the stress pathway RyR1 protein expression was stable, however, RyR1 channels were depleted of the stabilizing subunit calstabin1 (FKBP12). It has been shown that RyR1 hyperphosphorylation and calstabin1 depletion are consistent with leaky RyR1 channels that cause intracellular SR $Ca^{2+}$ leak.

RyR1 channels are PKA hyperphosphorylated and depleted of the stabilizing calstabin1 subunit after 3 weeks of 90 mins swimming twice daily. As seen in Embodiment A, the immunoprecipitated RyR1 macromolecular channel complex shows increased PKA phosphorylation at Ser-2844 (corresponding to human RyR1-Ser-2843) whereas CaMKII phosphorylation at Ser-2849 (corresponding to human RyR1-Ser-2848) is unchanged. Concomitant with increased RyR1-Ser-2844 PKA hyperphosphorylation, calstabin1 is depleted from the channel complex. As seen in embodiment B, normalization of phosphorylation and calstabin1 content to four subunits of the tetrameric channel complex shows a significant in increase in PKA phosphorylation and depletion of the stabilizing calstabin1 subunit. Control, non-exercised mice; swim, mice exercised 90 mins twice daily for 3 weeks (preliminary data). P<0.05.

Figure 20:
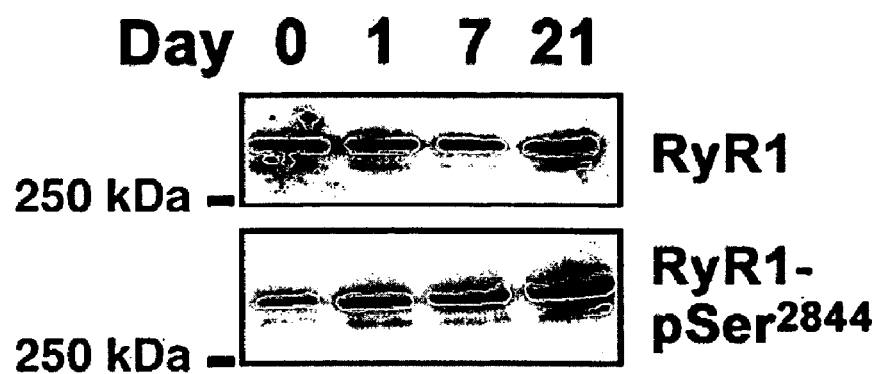
FIG. 20, embodiments A and B, demonstrate that RyR1 PKA phosphorylation increases after exposure to increasing durations of sustained exercise. Embodiment A provides immunoblots of RyR1 and RyR1-pSer$^{2844}$ following increasing durations of sustained exercise. Embodiment B is a graph showing the relative PKA phosphorylation of RyR1 for varying durations of exercise.
Figure 20:
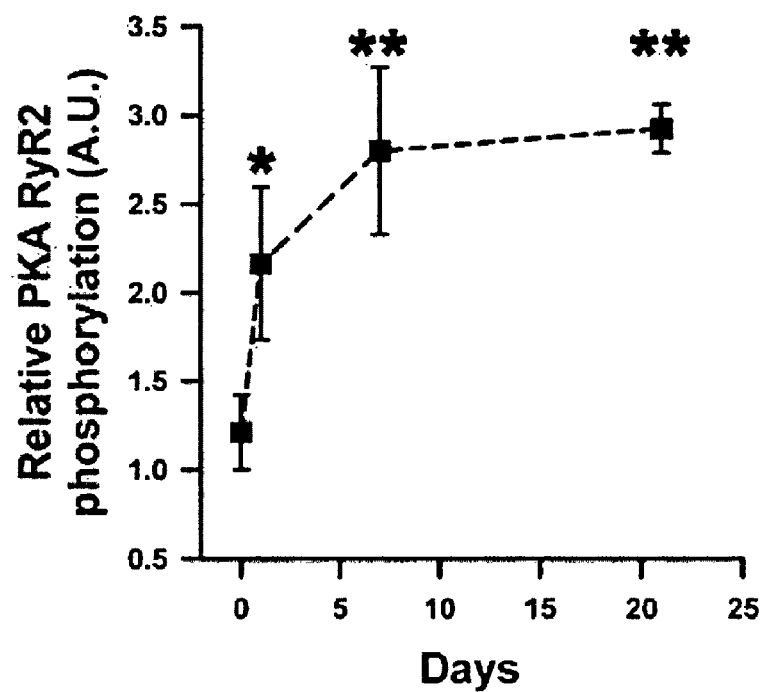

FIG. 20, embodiments A and B, demonstrate that PKA phosphorylation increases for increasing durations of sustained exercise. To investigate the influence of the duration of sustained exercise on the RyR1 $Ca^{2+}$ release channel defect, mice were exposed to swimming for 1, 7, or 21 days followed by immediate sacrifice. Longer exposure to sustained exercise results in a significant increase of RyR 1 PKA hyperphosphorylation beginning at 7 days and saturating at 21 days.

In FIG. 20, embodiment A, the immunoprecipitated RyR1 channel complex shows significantly and above physiologic levels increased PKA phosphorylation at Ser-2844 (corresponding to human RyR1-Ser-2843) after 7 days of swimming exercise. In FIG. 20, embodiment B, inormalization of RyR2-Ser-2844 phosphorylation within the tetrameric channel complex documents a significant increase in PKA phosphorylation. *, P<0.05; **, P<0.005.

In summary, the data of FIG. 20 shows that sustained exercise results in significantly increased RyR1 phosphorylation by protein kinase A (PKA) which contributes to depletion of the stabilizing calstabin1 subunit from the channel complex as the cause of a gain-of-function defect.

Figure 21:
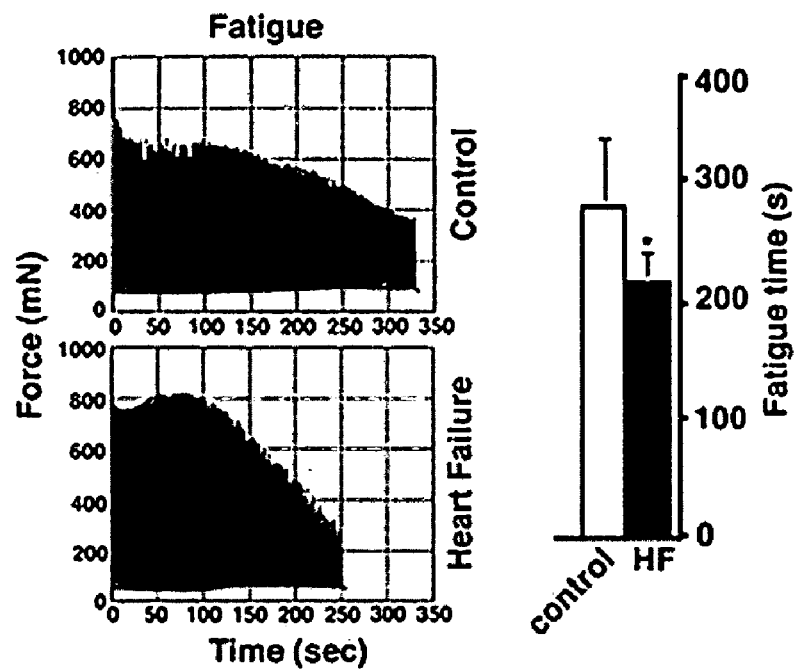
FIG. 21, embodiments A, B, and C, demonstrate that RyR1 PKA phosphorylation increases with muscle fatigue. Embodiments A and B are, respectively, fatigue time tracings and a bar graph showing mean fatigue times for rat soleus muscle of heart failure and control subjects. Embodiment C is a graph of PKA phosphorylation versus fatigue time.
Figure 21:
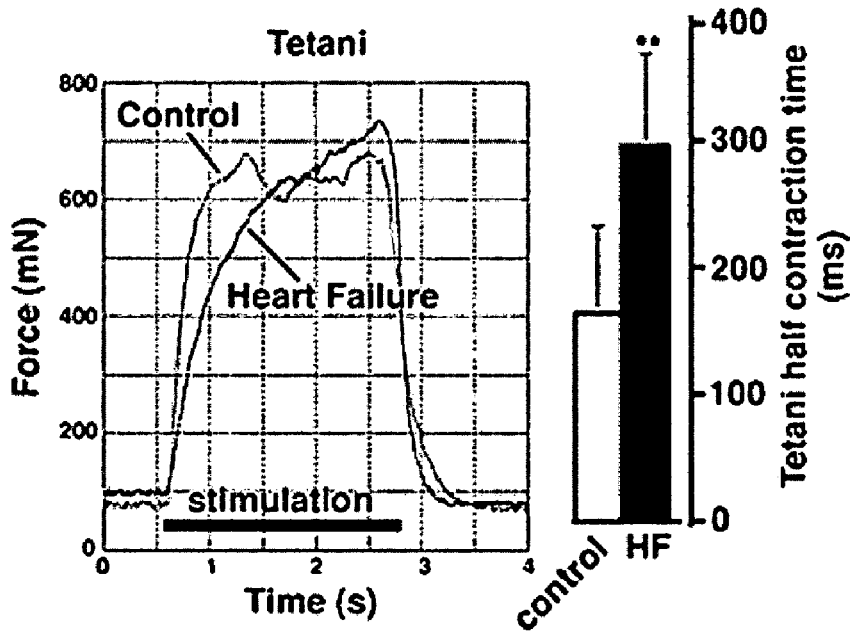
Figure 21:
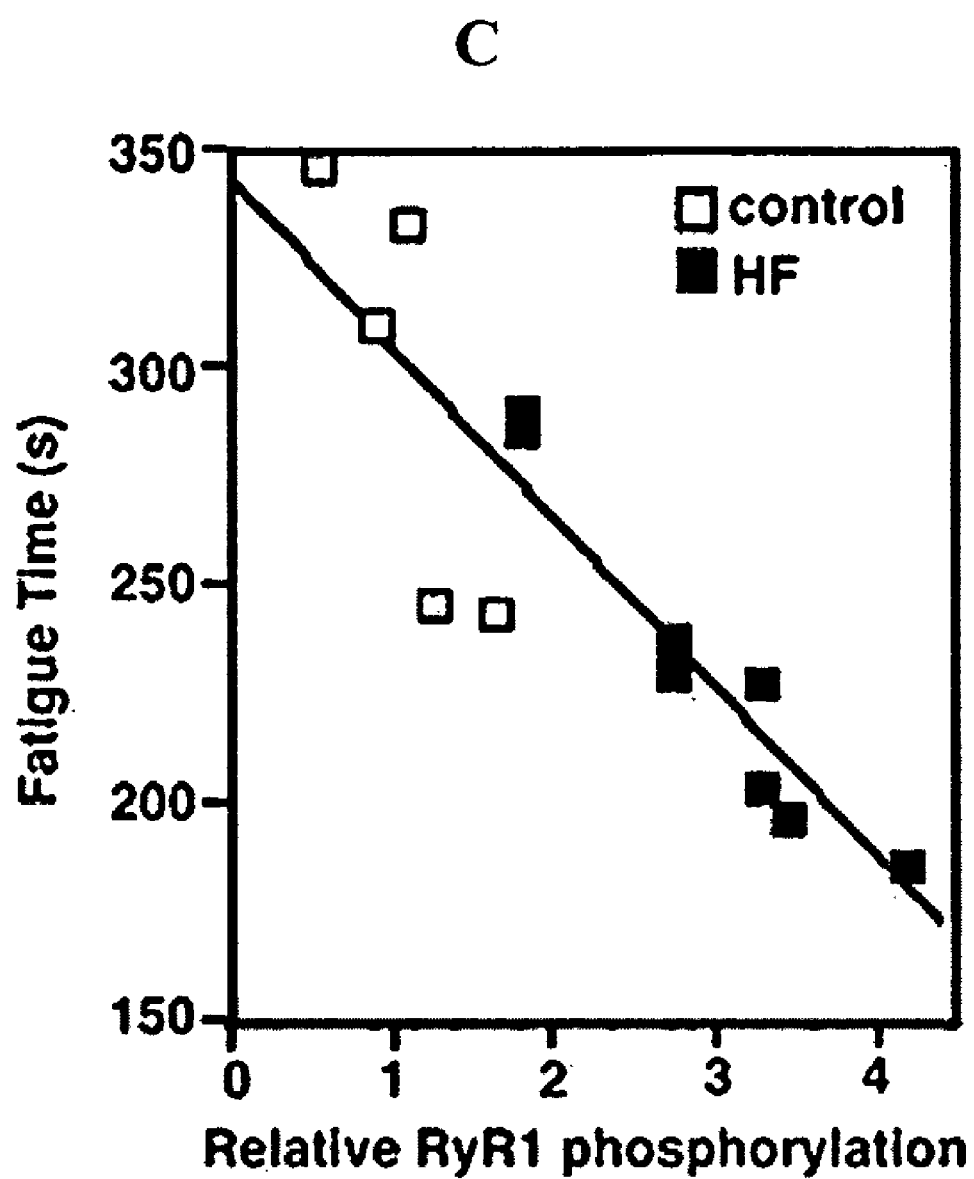

FIG. 21 provides data showing that showing that chronically increased sympathetic stimulation of skeletal muscles, results in RyR1-dependent intracellular $Ca^{2+}$ leak and significantly increased muscle fatigue. What is the functional consequence of chronically increased RyR1 PKA hyperphosphorylation? As shown in FIG. 21 for mice and rats with heart failure from myocardial infarction, chronic RyR1 PKA hyperphosphorylation results in increased muscle fatigue.

In embodiment A, it can be seen that heart failure skeletal muscle fatigues earlier than control. Rat soleus muscle (n=5 control, n=8 HF) was mounted in a tissue bath to assess contractile function. Representative fatigue time tracing is shown for control and HF skeletal muscles. Bar graph shows mean (±S.D.) time to 40% fatigue. *, P<0.05. In embodiment B, it can be seen that heart failure skeletal muscle achieved maximal tetanic force more slowly than control skeletal muscles. Tetanic force was induced by high-frequency field stimulation. Bar graph shows tetanic 50% contraction time. **, P<0.01. Embodiment C demonstrates the correlation between time to fatigue and RyR1 PKA phosphorylation (r=0.88) in rat skeletal muscle from sham and heart failure animals. Muscle function and RyR1 PKA phosphorylation were assessed using contralateral soleus muscles from each animal.

In summary, FIG. 21 provides data showing that sustained exercise causes RyR1PKA hyperphosphorylation and calstabin1 depletion, and FIG. 21 shows that the identical defect occurs in disease forms with increased sympathetic activity causing intracellular SR $Ca^{2+}$ leak and significantly accelerated skeletal muscle fatigue.

Figure 22:
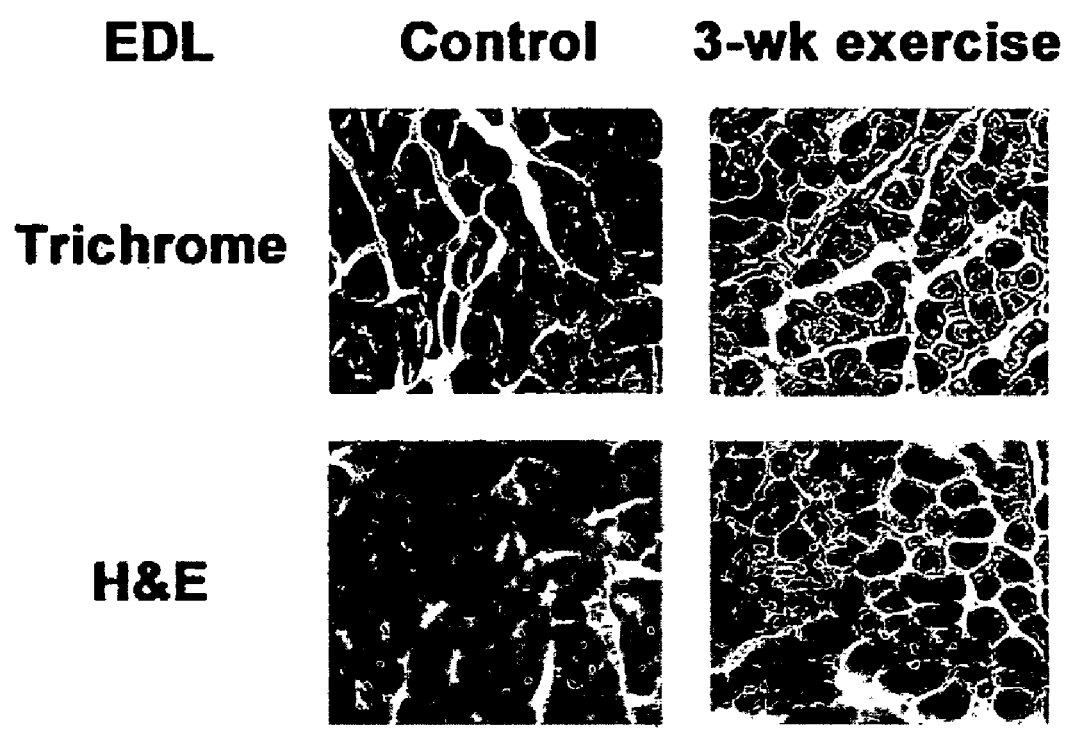
FIG. 22 are trichrome and hematoxylin-eosin stains of cross-sections of the mouse M. extensor digitorum longus, and demonstrates myofiber degeneration consistent with dystrophic remodeling following sustained exercise.

An additional problem during sustained exercise and stress is skeletal muscle degeneration further contributing to decreased skeletal muscle performance. To assess structural changes during sustained exercise, histologic changes in the fast-twitch muscles of mice exposed to 3 weeks of exercise by swimming have been characterized. Results are shown in FIG. 22. Cross-sections of the mouse *M. extensor digitorum longus* (EDL) showed histologic changes consistent with myofiber degeneration from intracellular $Ca^{2+}$ overload from defective RyR1 channels. Therefore sustained exercise for 90 mins twice daily triggers a dystrophic phenotype in EDL muscles of normal C57Bl6 mice.

Trichrome stain shows packed myofibers of similar cross-sectional dimension in non-exercised control (WT) mice (left). Three weeks swimming results in myofiber degeneration and interstitial collagen deposits with irregular fiber sizes. Hematoxylin-eosin (H&E) stain indicates nuclear changes and myofiber death. These changes are consistent with dystrophic remodeling.

The rapid delayed rectifier potassium channel (I(Kr)) is important for repolarization of the cardiac action potential. HERG is the pore-forming subunit of the I(Kr) channel. Suppression of I(Kr) function, for example as a side-effect of a drug or the result of a mutation in hERG, can lead to long-QT (LQT) syndrome, which is associated with increased risk of life-threatening arrhythmias. The compounds of the present invention exhibit a lower level of hERG blocking activity than JTV-519, as demonstrated in FIGS. 23-43. Thus, the compounds of the present invention are expected to be less toxic and/or exhibit fewer side effects than JTV-519.

FIGS. 23 to 26 illustrate the effect of the compound ARM036 (also referred to as S36) and ARM036-Na (a sodium salt of ARM036) on hERG currents.

Figure 23:
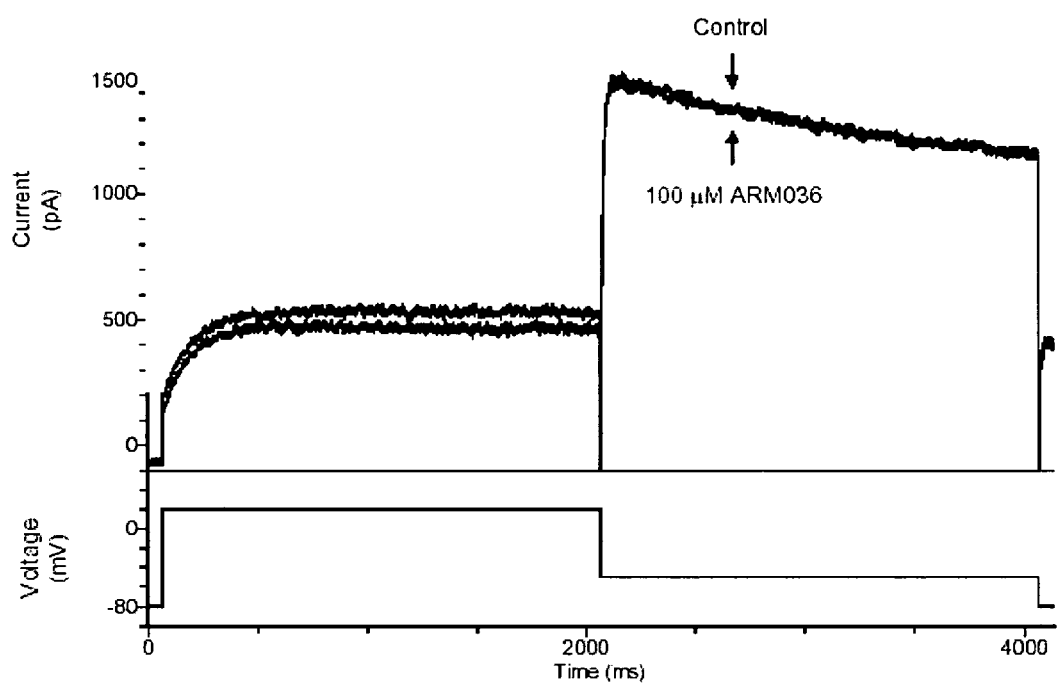
FIG. 23 shows a sample hERG current trace before (control) and after application of ARM036 at 100 μM. Also shown is the voltage pulse protocol used to evoke the hERG currents.

FIG. 23 shows a typical hERG voltage-clamp current recording before (control) and after application of ARM036 at 100 µM. The voltage pulse protocol used to activate the hERG currents is illustrated below the current trace. It can be seen that, following activation by the conditioning prepulse (to +20 mV), partial repolarization (−50 mV test pulse) of the membrane evoked a large, slowly decaying outward tail current. Application of ARM036 minimally reduced the outward tail current in a concentration- and time-dependent manner.

Figure 24:
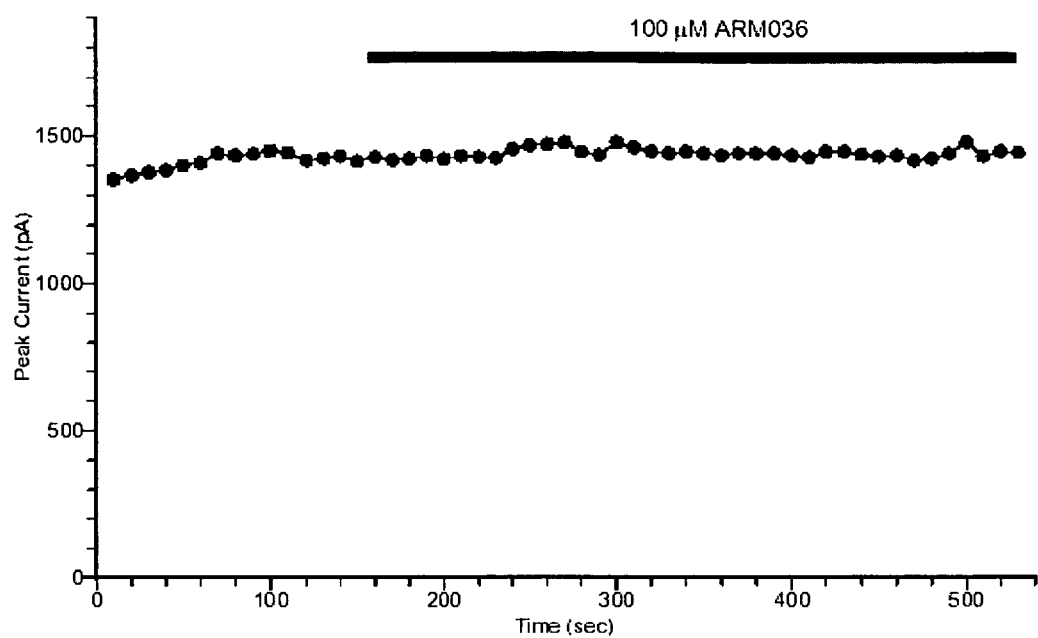
FIG. 24 shows a typical time course of the effect of ARM036 on hERG current amplitude. Application of 10 μM ARM036 is indicated by the horizontal bar.

FIG. 24 shows a typical time course of the effect of ARM036 at 100 mM on the amplitude of the hERG channel current.

Figure 25:
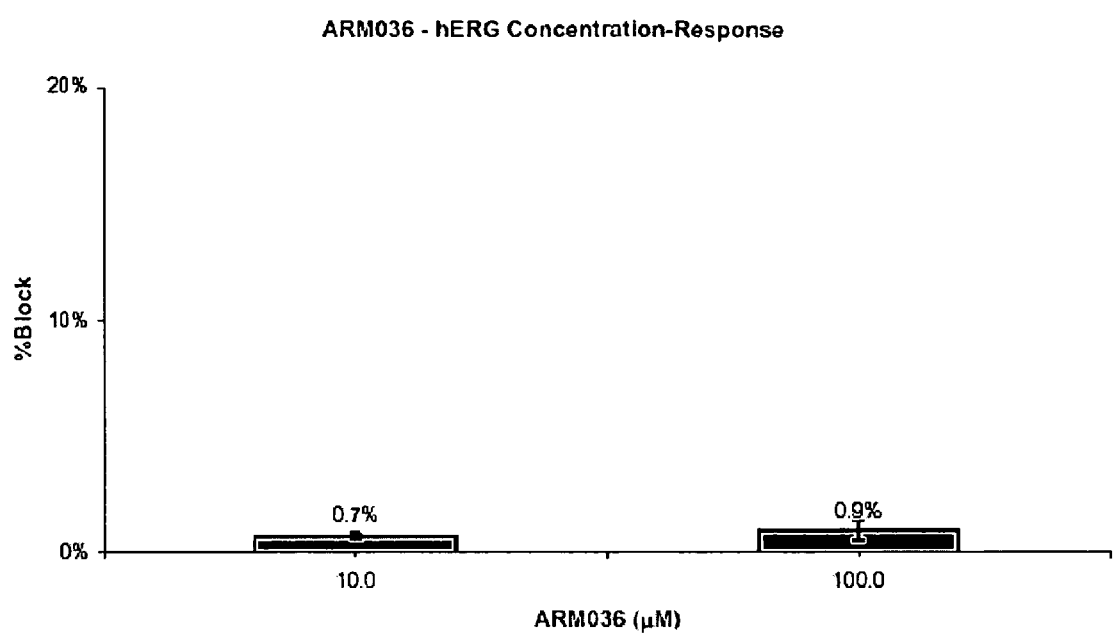
FIG. 25 is a concentration-response graph showing the percent inhibition of hERG current after application of ARM036 at various concentrations.

FIG. 25 is a graph showing the concentration-dependence of the effect of ARM036 on the hERG current. Table 1 provides the numerical data that is illustrated graphically in FIG. 25. Because the highest concentration of ARM036 tested resulted in less than 50% current inhibition, it was not possible to determine an $IC_{50}$ value for ARM036.

TABLE 1

| Concentration (µM) | Mean | SD | SEM | N |
|---|---|---|---|---|
| 10 | 0.7% | 0.3% | 0.2% | 3 |
| 100 | 0.9% | 0.7% | 0.4% | 3 |

Figure 26:
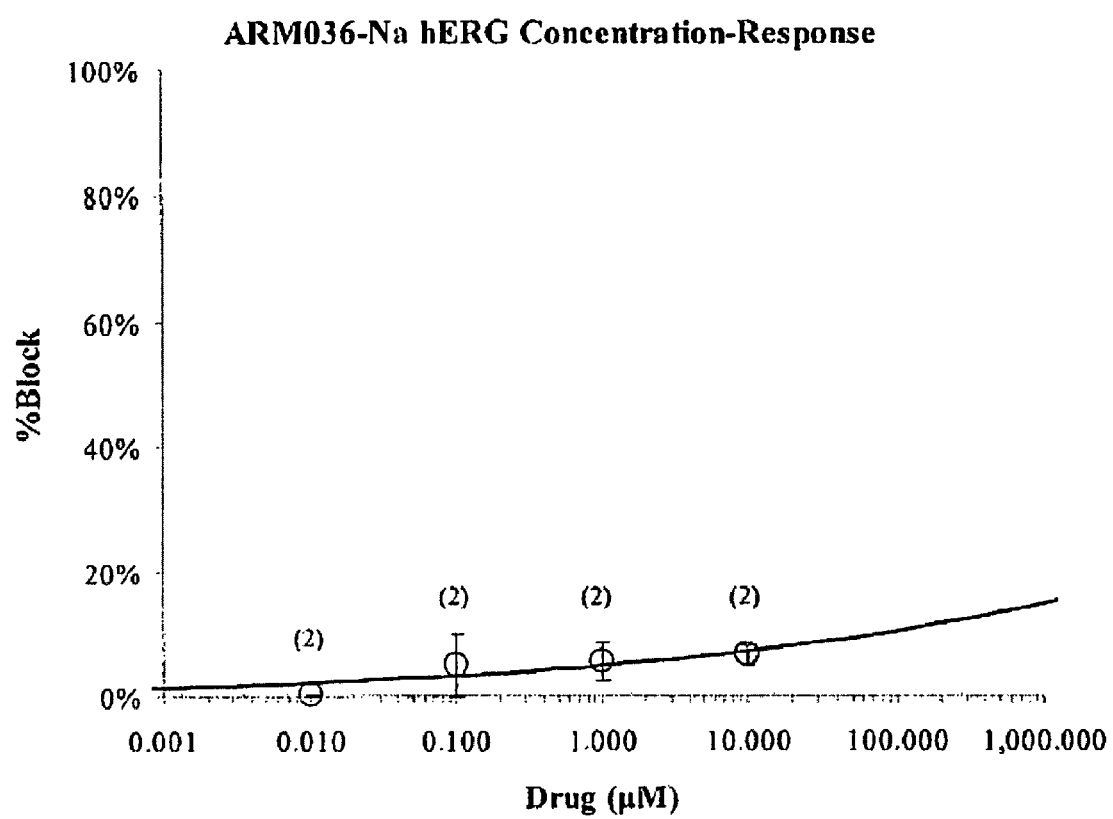
FIG. 26 is a concentration-response graph showing the percent inhibition of hERG current after application of ARM036-Na at various concentrations.

FIG. 26 is a graph showing the concentration-dependence of the effect of ARM036-Na on the hERG current. Table 2 provides the numerical data that is illustrated graphically in FIG. 26. Because the highest concentration of ARM036-Na tested resulted in less than 50% current inhibition, it was not possible to determine an $IC_{50}$ value for ARM036-NA

TABLE 2

| Test Article ID | $IC_{50}$ (µM) | Conc. (µM) | Mean % hERG Inhibition | % Standard Deviation | % Standard Error | n | Individual Data (% Inhibition) |
|---|---|---|---|---|---|---|---|
| ARM036-Na | ND | 0.01 | 0.2% | 0.2% | 0.2% | 2 | 0.0% 0.3% |
| | | 0.1 | 5.0% | 7.1% | 5.0% | 2 | 10.0% 0.0% |
| | | 1 | 5.5% | 4.4% | 3.1% | 2 | 2.4% 8.6% |
| | | 10 | 6.7% | 2.2% | 1.6% | 2 | 5.1% 8.2% |

Figure 27:
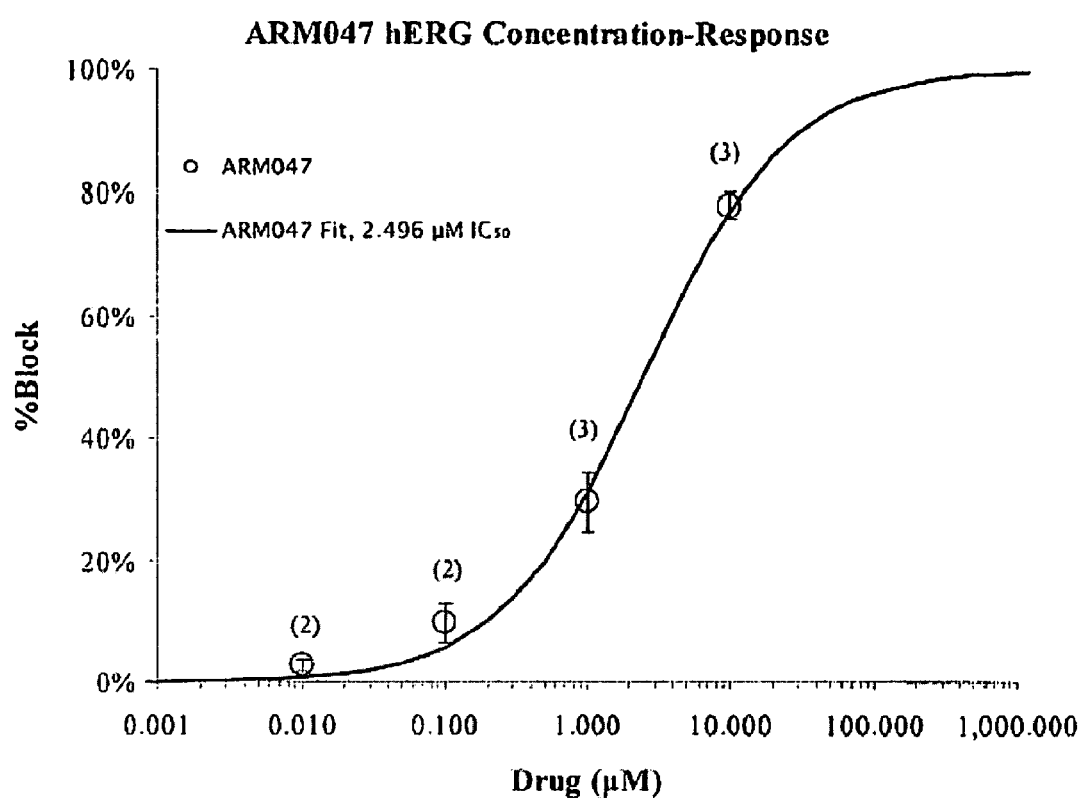
FIG. 27 is a concentration-response graph showing the percent inhibition of hERG current after application of ARM047 at various concentrations.

FIG. 27 is a graph showing the concentration-dependence of the effect of ARM047 on the HERG current. Table 3 provides the numerical data that is illustrated graphically in FIG. 27. The $IC_{50}$ value for ARM047 block of the HERG current was 2.496 µM.

TABLE 3

| Test Article ID | $IC_{50}$ (µM) | Conc. (µM) | Mean % hERG Inhibition | % Standard Deviation | % Standard Error | n | Individual Data (% Inhibition) |
|---|---|---|---|---|---|---|---|
| ARM047 | 2.496 | 0.01 | 2.7% | 1.4% | 1.0% | 2 | 1.7% 3.7% |
| | | 0.1 | 9.7% | 4.5% | 3.2% | 2 | 6.5% 12.9% |
| | | 1 | 29.6% | 8.6% | 5.0% | 3 | 30.8% 20.4% 37.5% |
| | | 10 | 78.0% | 3.6% | 2.1% | 3 | 82.1% 75.9% 75.9% |

Figure 28:
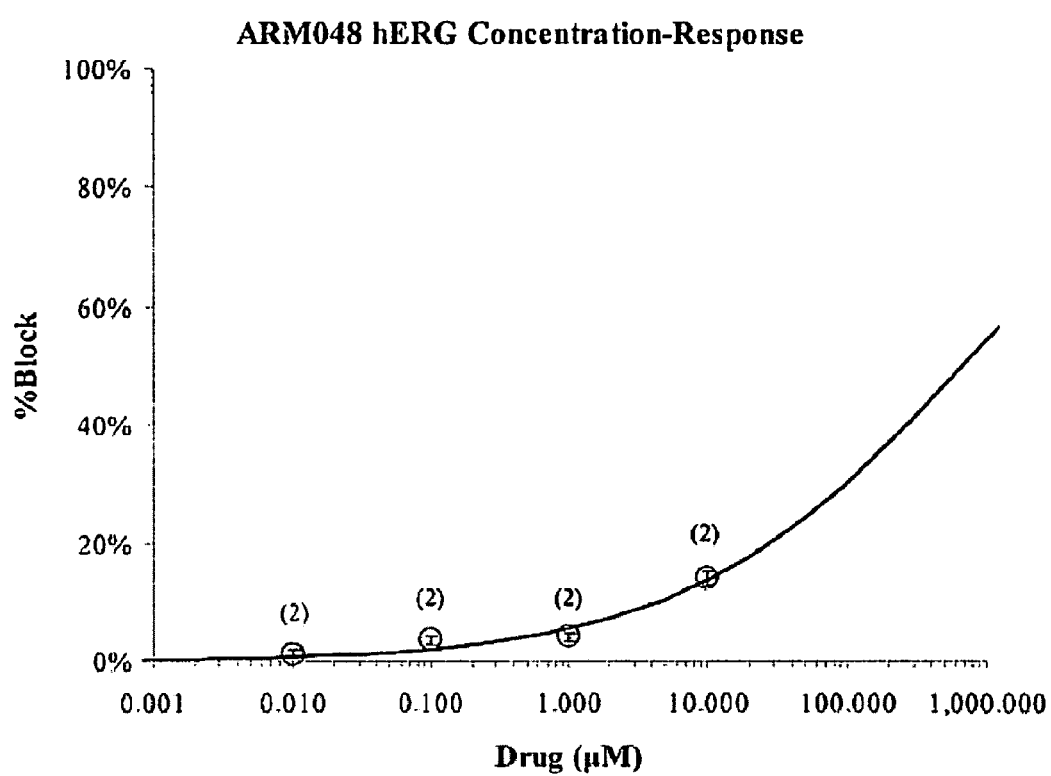
FIG. 28 is a concentration-response graph showing the percent inhibition of hERG current after application of ARM048 at various concentrations.

FIG. 28 is a graph showing the concentration-dependence of the effect of ARM048 on the HERG current. Table 4 provides the numerical data that is illustrated graphically in FIG. 28. Because the highest concentration of ARM048 tested resulted in less than 50% current inhibition, it was not possible to determine an $IC_{50}$ value for ARM048.

TABLE 4

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM048 | ND | 0.01 | 1.3% | 1.1% | 0.8% | 2 | 0.5% 2.0% |
| | | 0.1 | 3.6% | 0.9% | 0.6% | 2 | 4.2% 2.9% |
| | | 1 | 4.1% | 0.8% | 0.6% | 2 | 4.7% 3.5% |
| | | 10 | 14.0% | 1.7% | 1.2% | 2 | 15.2% 12.8% |

Figure 29:
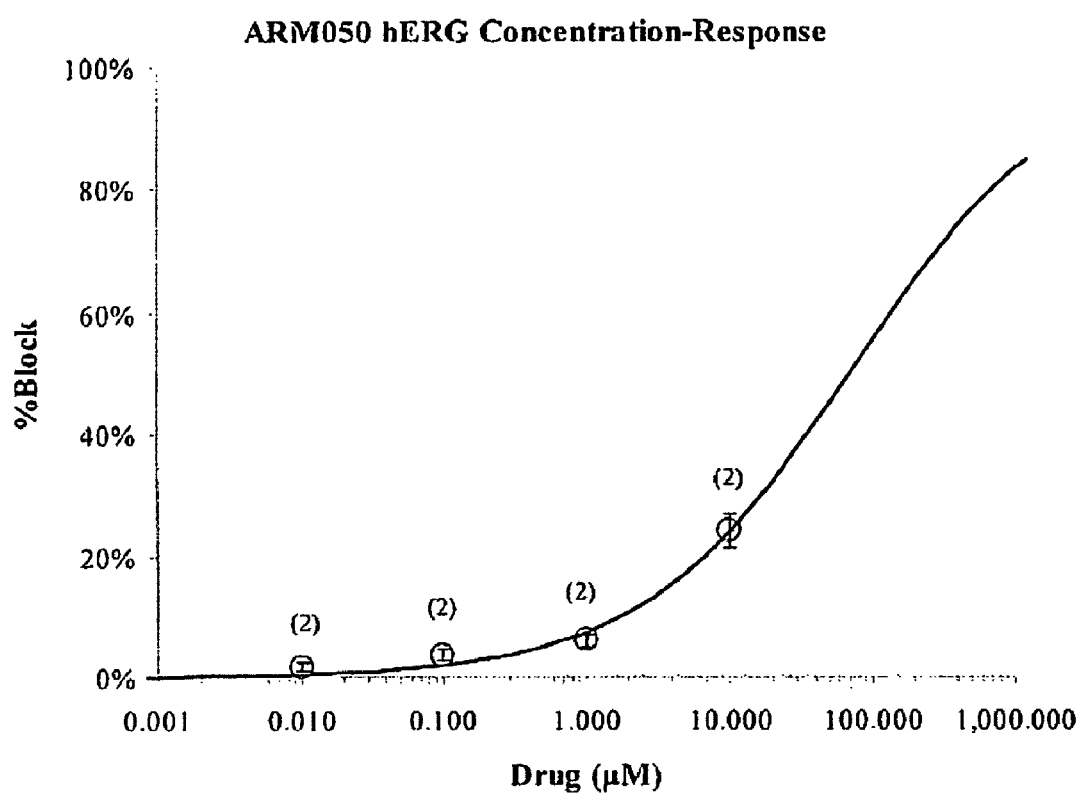
FIG. 29 is a concentration-response graph showing the percent inhibition of hERG current after application of ARM050 at various concentrations.

FIG. 29 is a graph showing the concentration-dependence of the effect of ARM050 on the hERG current. Table 5 provides the numerical data that is illustrated graphically in FIG. 29. Because the highest concentration of ARM050 tested resulted in less than 50% current inhibition, it was not possible to determine an IC$_{50}$ value for ARM050.

TABLE 5

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM050 | ND | 0.01 | 1.8% | 0.9% | 0.7% | 2 | 1.1% 2.4% |
| | | 0.1 | 3.7% | 1.4% | 1.0% | 2 | 2.7% 4.7% |
| | | 1 | 6.1% | 1.4% | 1.0% | 2 | 7.1% 5.1% |
| | | 10 | 24.2% | 4.0% | 2.9% | 2 | 27.0% 21.3% |

Figure 30:
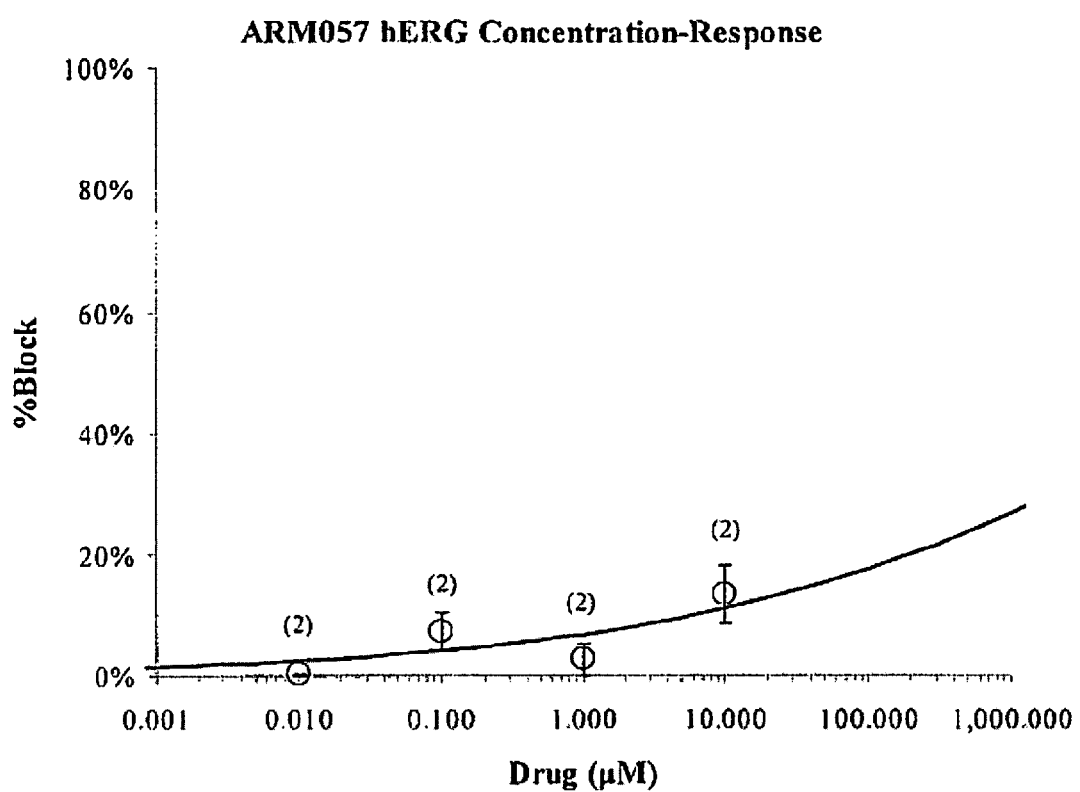
FIG. 30 is a concentration-response graph showing the percent inhibition of hERG current after application of ARM057 at various concentrations.

FIG. 30 is a graph showing the concentration-dependence of the effect of ARM057 on the hERG current. Table 6 provides the numerical data that is illustrated graphically in FIG. 30. Because the highest concentration of ARM057 tested resulted in less than 50% current inhibition, it was not possible to determine an IC$_{50}$ value for ARM057.

TABLE 6

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM057* | ND | 0.01 | 0.2% | 0.2% | 0.2% | 2 | 0.3% 0.0% |
| | | 0.1 | 7.3% | 4.5% | 3.2% | 2 | 4.1% 10.4% |
| | | 1 | 2.7% | 3.7% | 2.6% | 2 | 5.3% 0.1% |
| | | 10 | 13.6% | 6.7% | 4.8% | 2 | 18.3% 8.8% |

Figure 31:
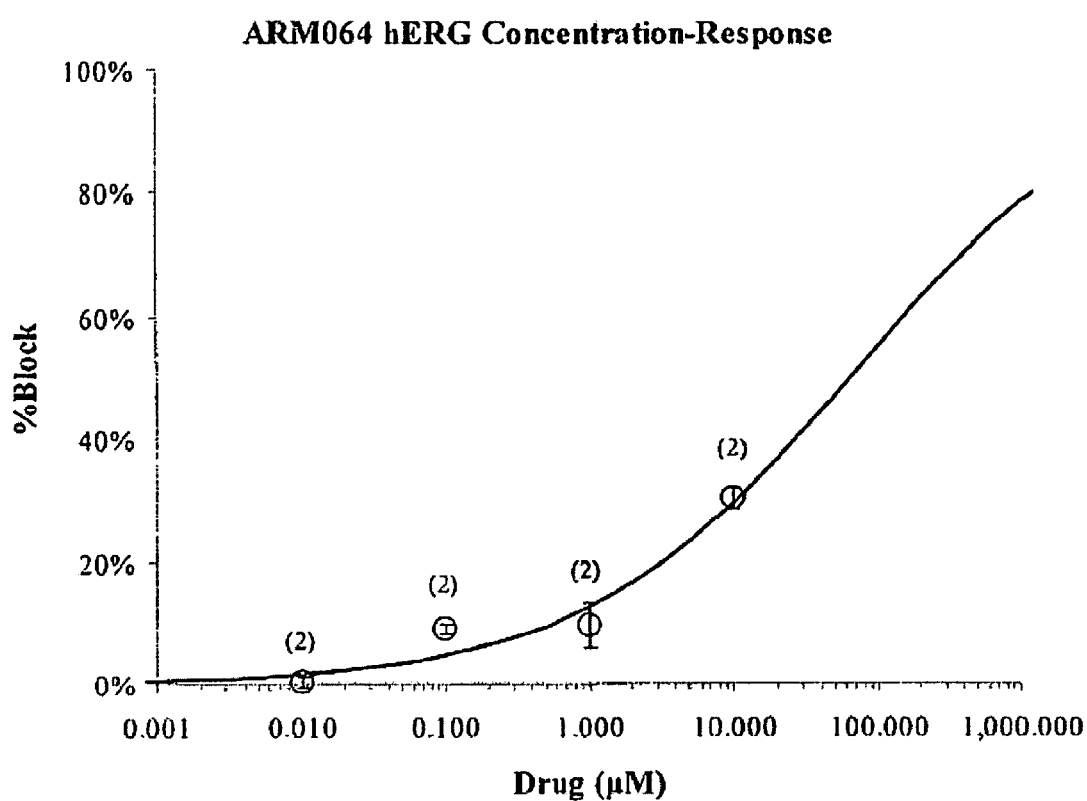
FIG. 31 is a concentration-response graph showing the percent inhibition of hERG current after application of ARM064 at various concentrations.

FIG. 31 is a graph showing the concentration-dependence of the effect of ARM064 on the hERG current. Table 7 provides the numerical data that is illustrated graphically in FIG. 31. Because the highest concentration of ARM064 tested resulted in less than 50% current inhibition, it was not possible to determine an IC$_{50}$ value for ARM064.

TABLE 7

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM064 | ND | 0.01 | 0.2% | 1.1% | 0.8% | 2 | −0.6% 1.0% |
|  |  | 0.1 | 9.0% | 1.3% | 0.9% | 2 | 9.9% 8.1% |
|  |  | 1 | 9.6% | 5.1% | 3.6% | 2 | 13.2% 6.0% |
|  |  | 10 | 30.3% | 2.5% | 1.7% | 2 | 32.0% 28.5% |

Figure 32:
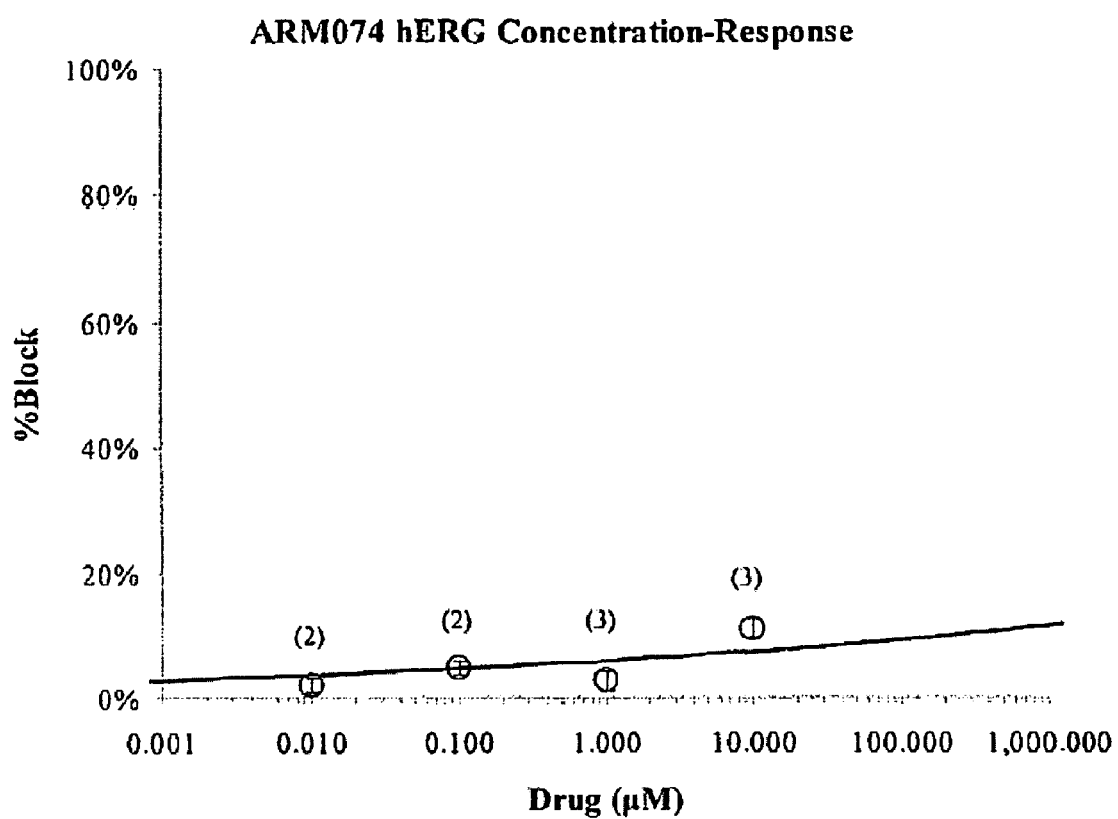
FIG. 32 is a concentration-response graph showing the percent inhibition of hERG current after application of ARM074 at various concentrations.

FIG. 32 is a graph showing the concentration-dependence of the effect of ARM074 on the hERG current. Table 8 provides the numerical data that is illustrated graphically in FIG. 32 Because the highest concentration of ARM050 tested resulted in less than 50% current inhibition, it was not possible to determine an IC$_{50}$ value for ARM074.

TABLE 8

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM074 | ND | 0.01 | 1.9% | 1.6% | 1.1% | 2 | 0.8% 3.0% |
|  |  | 0.1 | 4.8% | 1.8% | 1.1% | 2 | 5.9% 3.7% |
|  |  | 1 | 1.3% | 1.6% | 1.1% | 2 | 0.2% 2.4% 5.6% |
|  |  | 10 | 9.5% | 0.2% | 0.2% | 2 | 9.3% 9.6% 14.0% |

Figure 33:
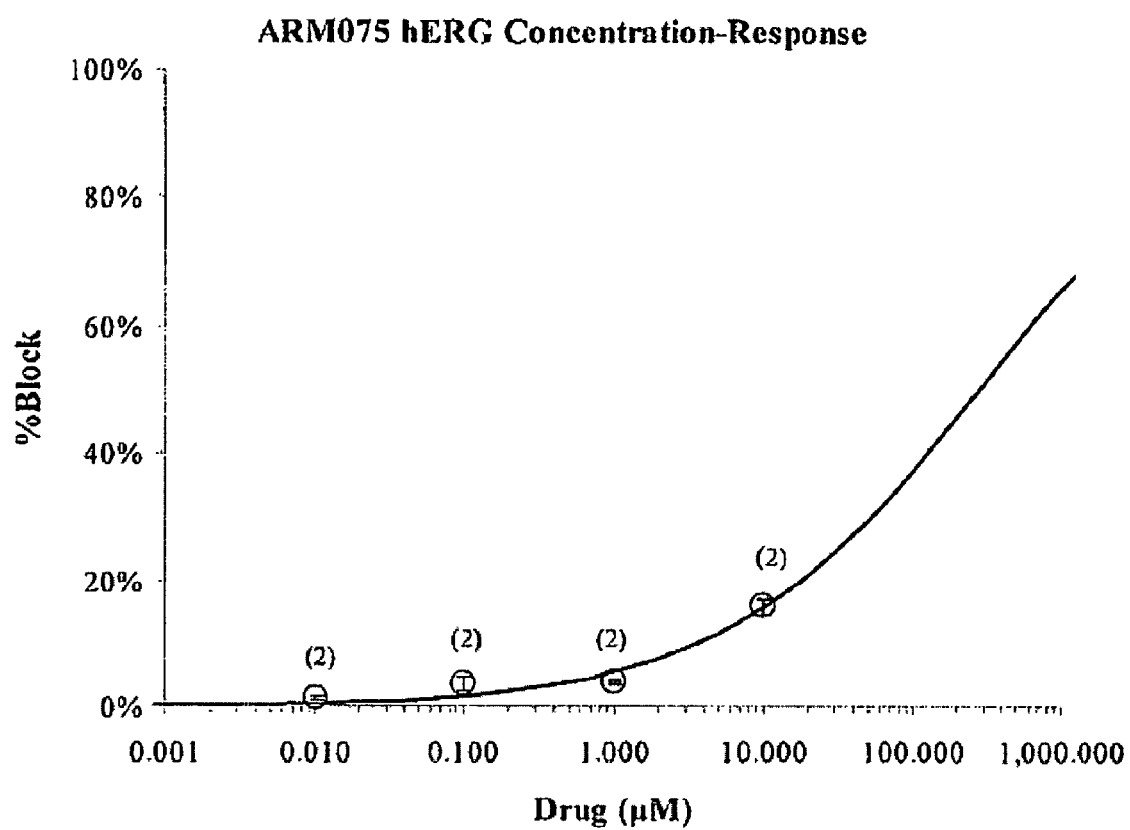
FIG. 33 is a concentration-response graph showing the percent inhibition of hERG current after application of ARM075 at various concentrations.

FIG. 33 is a graph showing the concentration-dependence of the effect of ARM075 on the hERG current. Table 9 provides the numerical data that is illustrated graphically in FIG. 33 Because the highest concentration of ARM075 tested resulted in less than 50% current inhibition, it was not possible to determine an IC$_{50}$ value for ARM075.

TABLE 9

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM075 | ND | 0.01 | 1.4% | 0.4% | 0.3% | 2 | 1.7% 1.1% |
|  |  | 0.1 | 3.7% | 1.6% | 1.1% | 2 | 2.6% 4.8% |
|  |  | 1 | 3.9% | 0.3% | 0.2% | 2 | 3.7% 4.1% |
|  |  | 10 | 16.0% | 1.8% | 1.3% | 2 | 14.7% 17.2% |

Figure 34:
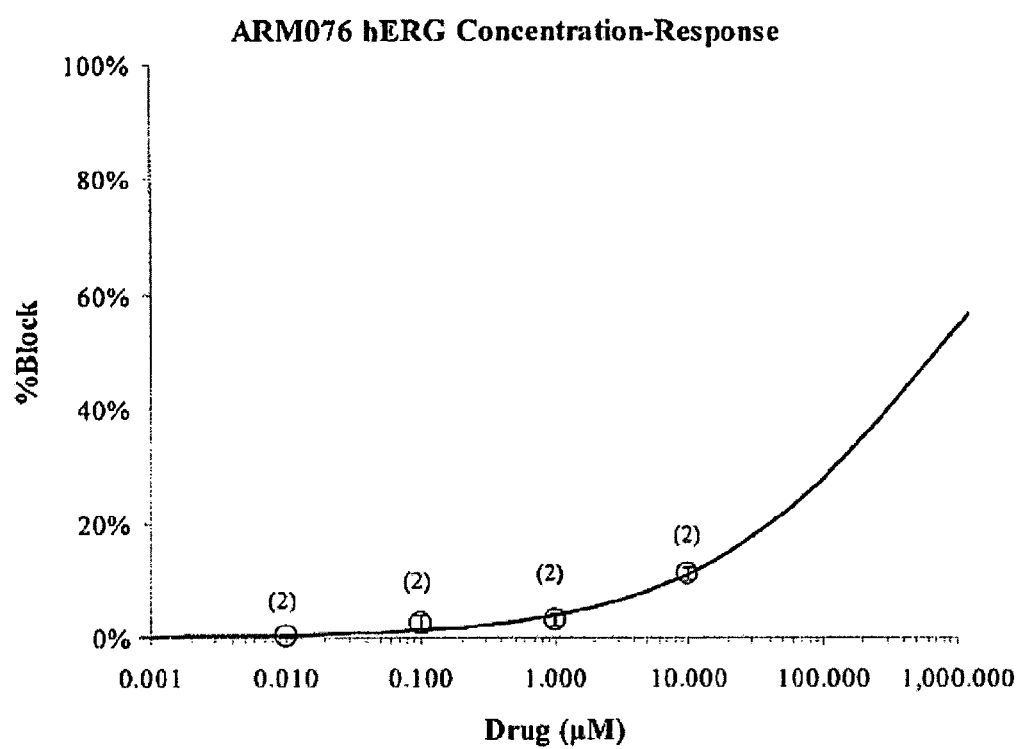
FIG. 34 is a concentration-response graph showing the percent inhibition of hERG current after application of ARM076 at various concentrations.

FIG. 34 is a graph showing the concentration-dependence of the effect of ARM076 on the hERG current. Table 10 provides the numerical data that is illustrated graphically in FIG. 34 Because the highest concentration of ARM076 tested resulted in less than 50% current inhibition, it was not possible to determine an IC$_{50}$ value for ARM076.

TABLE 10

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM076 | ND | 0.01 | 0.4% | 0.5% | 0.4% | 2 | 0.0% 0.7% |
| | | 0.1 | 2.5% | 2.2% | 1.6% | 2 | 4.0% 0.9% |
| | | 1 | 3.1% | 1.5% | 1.1% | 2 | 2.0% 4.1% |
| | | 10 | 11.2% | 1.6% | 1.2% | 2 | 10.0% 12.3% |

Figure 35:
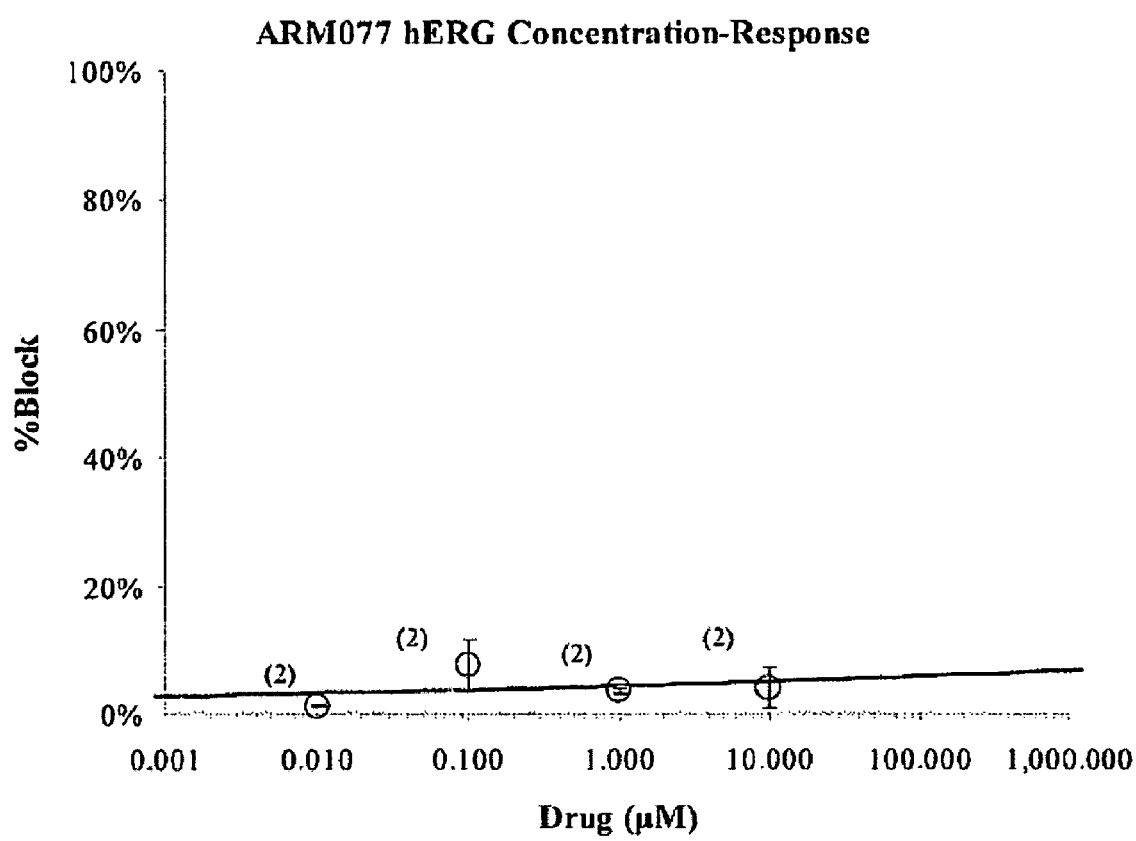
FIG. 35 is a concentration-response graph showing the percent inhibition of hERG current after application of ARM077 at various concentrations.

FIG. 35 is a graph showing the concentration-dependence of the effect of ARM077 on the hERG current. Table 11 provides the numerical data that is illustrated graphically in FIG. 35 Because the highest concentration of ARM077 tested resulted in less than 50% current inhibition, it was not possible to determine an IC$_{50}$ value for ARM077.

TABLE 11

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM077 | ND | 0.01 | 1.3% | 0.2% | 0.2% | 2 | 1.4% 1.1% |
| | | 0.1 | 7.5% | 5.5% | 3.9% | 2 | 11.4% 3.6% |
| | | 1 | 3.6% | 0.6% | 0.4% | 2 | 3.1% 4.0% |
| | | 10 | 4.1% | 4.5% | 3.2% | 2 | 0.9% 7.2% |

Figure 36:
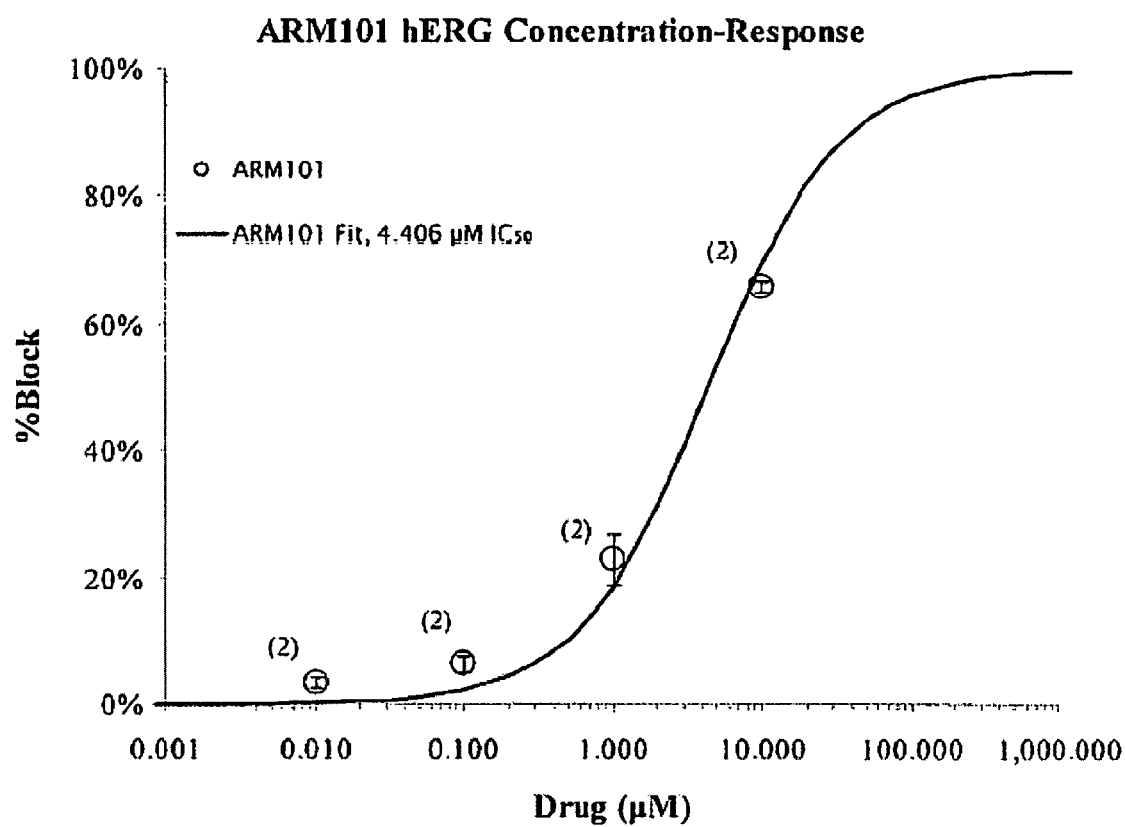
FIG. 36 is a concentration-response graph showing the percent inhibition of hERG current after application of ARM101at various concentrations.

FIG. 36 is a graph showing the concentration-dependence of the effect of ARM101 on the hERG current. Table 12 provides the numerical data that is illustrated graphically in FIG. 36 Because the highest concentration of ARM101 tested resulted in less than 50% current inhibition, it was not possible to determine an IC$_{50}$ value for ARM101.

TABLE 12

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM101 | 4.406 | 0.01 | 3.4% | 1.3% | 0.9% | 2 | 4.3% 2.5% |
| | | 0.1 | 6.4% | 1.8% | 1.3% | 2 | 5.1% 7.6% |
| | | 1 | 23.0% | 5.7% | 4.1% | 2 | 18.9% 27.0% |
| | | 10 | 65.8% | 1.3% | 0.9% | 2 | 66.7% 64.9% |

Figure 37:
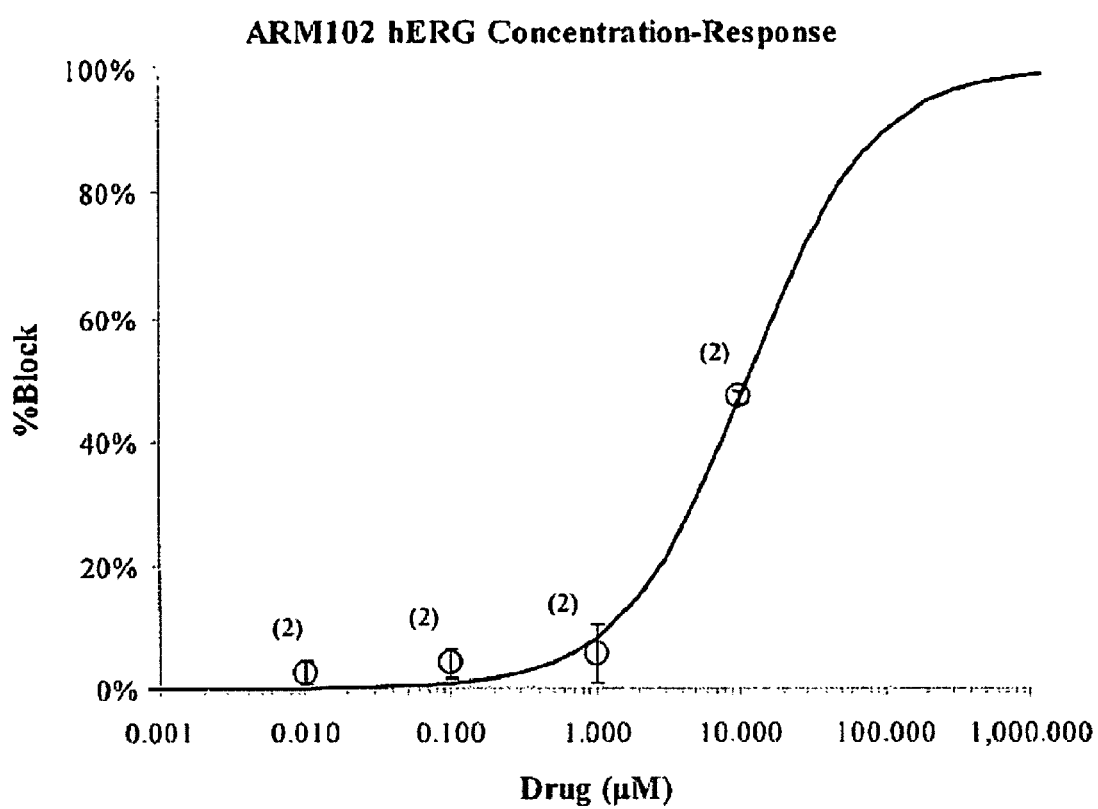
FIG. 37 is a concentration-response graph showing the percent inhibition of hERG current after application of ARM102 at various concentrations.

FIG. 37 is a graph showing the concentration-dependence of the effect of ARM102 on the hERG current. Table 13 provides the numerical data that is illustrated graphically in FIG. 37. Because the highest concentration of ARM102 tested resulted in less than 50% current inhibition, it was not possible to determine an IC$_{50}$ value for ARM102.

TABLE 13

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM102* | ND | 0.01 | 2.5% | 2.8% | 2.0% | 2 | 0.5% 4.4% |
|  |  | 0.1 | 4.2% | 3.3% | 2.4% | 2 | 1.8% 6.5% |
|  |  | 1 | 5.7% | 8.9% | 4.9% | 2 | 0.8% 10.5% |
|  |  | 10 | 47.3% | 1.5% | 1.1% | 2 | 46.2% 48.3% |

Figure 38:
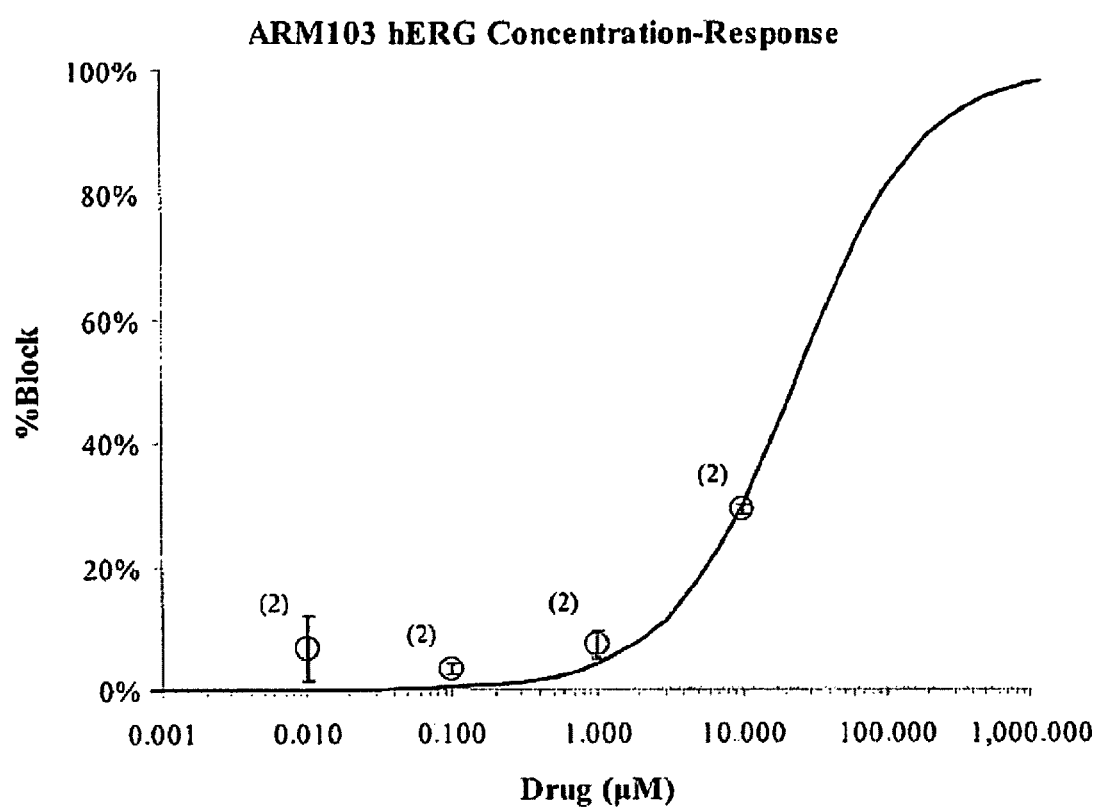
FIG. 38 is a concentration-response graph showing the percent inhibition of hERG current after application of ARM103 at various concentrations.

FIG. 38 is a graph showing the concentration-dependence of the effect of ARM103 on the hERG current. Table 14 provides the numerical data that is illustrated graphically in FIG. 38. Because the highest concentration of ARM103 tested resulted in less than 50% current inhibition, it was not possible to determine an IC$_{50}$ value for ARM103.

TABLE 14

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM103* | ND | 0.01 | 6.8% | 7.5% | 5.3% | 2 | 12.1% 1.5% |
|  |  | 0.1 | 3.3% | 1.3% | 0.9% | 2 | 4.2% 2.4% |
|  |  | 1 | 7.3% | 3.3% | 2.3% | 2 | 5.0% 9.6% |
|  |  | 10 | 29.2% | 1.1% | 0.8% | 2 | 28.4% 29.9% |

Figure 39:
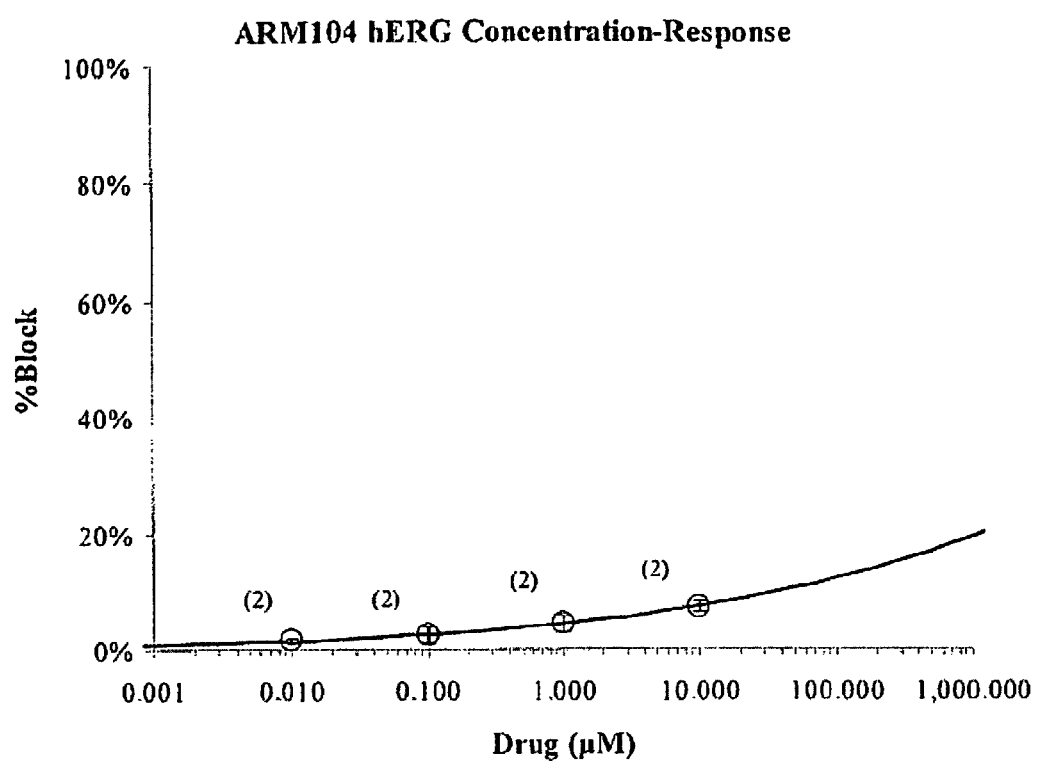
FIG. 39 is a concentration-response graph showing the percent inhibition of hERG current after application of ARM104 at various concentrations.

FIG. 39 is a graph showing the concentration-dependence of the effect of ARM104 on the hERG current. Table 15 provides the numerical data that is illustrated graphically in FIG. 39 Because the highest concentration of ARM104 tested resulted in less than 50% current inhibition, it was not possible to determine an IC$_{50}$ value for ARM104.

TABLE 15

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM104 | ND | 0.01 | 1.6% | 0.5% | 0.4% | 2 | 1.2% 1.9% |
|  |  | 0.1 | 2.5% | 2.0% | 1.4% | 2 | 1.1% 3.9% |
|  |  | 1 | 4.6% | 2.1% | 1.5% | 2 | 3.1% 6.0% |
|  |  | 10 | 7.4% | 1.3% | 0.9% | 2 | 8.3% 6.5% |

Figure 40:
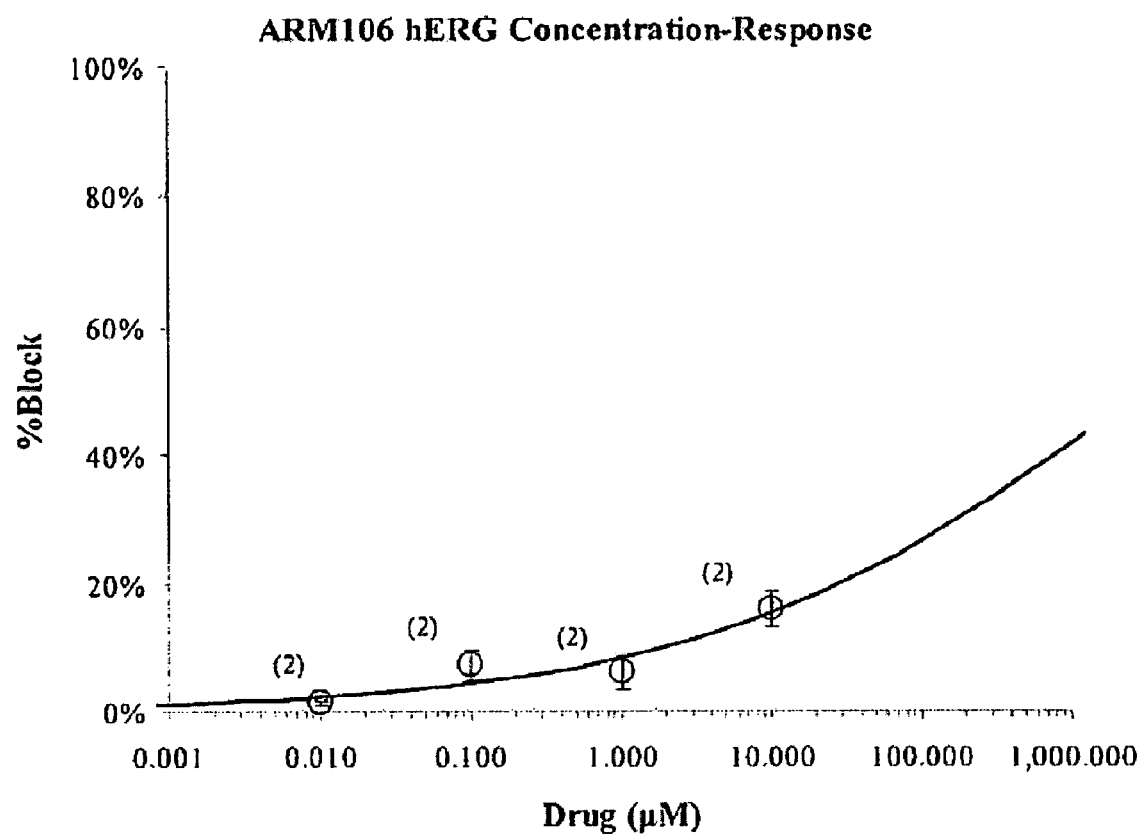
FIG. 40 is a concentration-response graph showing the percent inhibition of hERG current after application of ARM106 at various concentrations.

FIG. 40 is a graph showing the concentration-dependence of the effect of ARM106 on the hERG current. Table 16 provides the numerical data that is illustrated graphically in FIG. 40 Because the highest concentration of ARM106 tested resulted in less than 50% current inhibition, it was not possible to determine an IC$_{50}$ value for ARM106.

TABLE 16

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM106 | ND | 0.01 | 1.3% | 0.6% | 0.4% | 2 | 0.9% |
|  |  |  |  |  |  |  | 1.7% |
|  |  | 0.1 | 7.2% | 3.5% | 2.6% | 2 | 9.6% |
|  |  |  |  |  |  |  | 4.7% |
|  |  | 1 | 6.1% | 3.7% | 2.7% | 2 | 8.7% |
|  |  |  |  |  |  |  | 3.4% |
|  |  | 10 | 15.9% | 4.0% | 2.8% | 2 | 18.7% |
|  |  |  |  |  |  |  | 13.1% |

Figure 41:
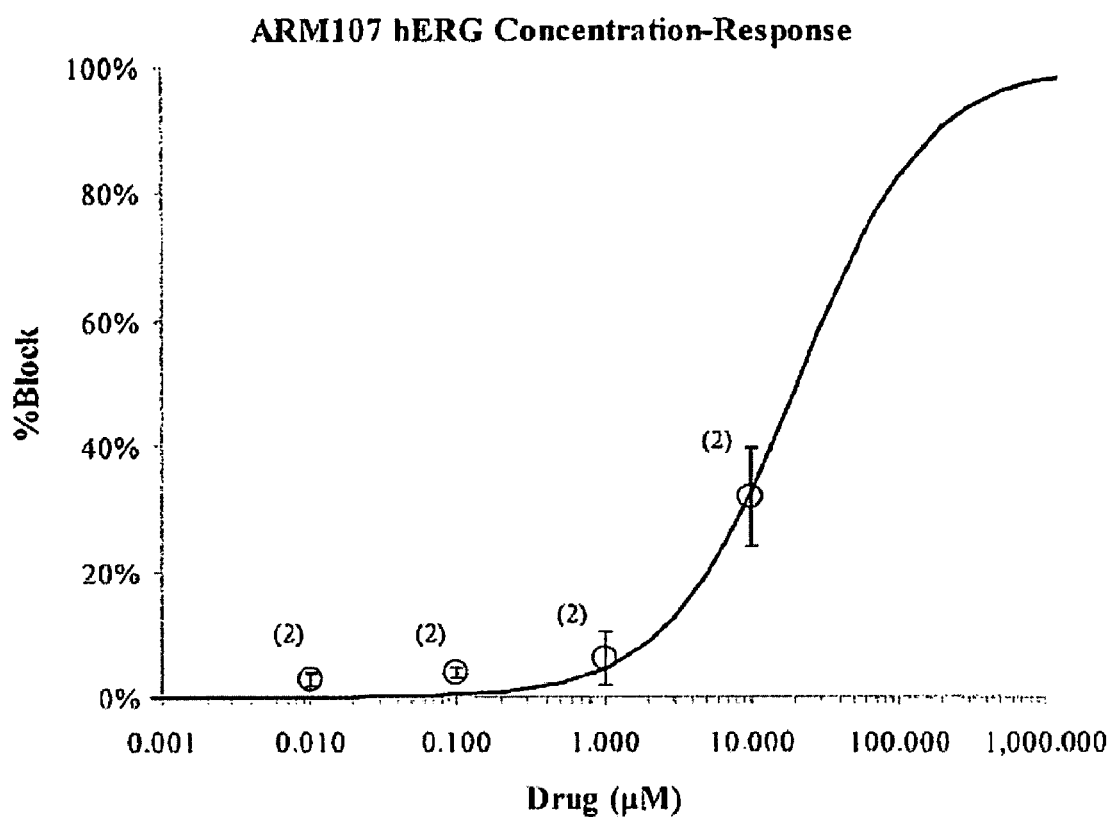
FIG. 41 is a concentration-response graph showing the percent inhibition of hERG current after application of ARM107 at various concentrations.

FIG. 41 is a graph showing the concentration-dependence of the effect of ARM107 on the hERG current. Table 17 provides the numerical data that is illustrated graphically in FIG. 41 Because the highest concentration of ARM107 tested resulted in less than 50% current inhibition, it was not possible to determine an IC$_{50}$ value for ARM107.

TABLE 17

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM107 | ND | 0.01 | 2.9% | 1.6% | 1.2% | 2 | 1.7% |
|  |  |  |  |  |  |  | 4.0% |
|  |  | 0.1 | 4.0% | 1.2% | 0.9% | 2 | 3.1% |
|  |  |  |  |  |  |  | 4.8% |
|  |  | 1 | 6.2% | 5.9% | 4.2% | 2 | 2.0% |
|  |  |  |  |  |  |  | 10.4% |
|  |  | 10 | 32.1% | 11.1% | 7.9% | 2 | 24.2% |
|  |  |  |  |  |  |  | 39.9% |

Figure 42:
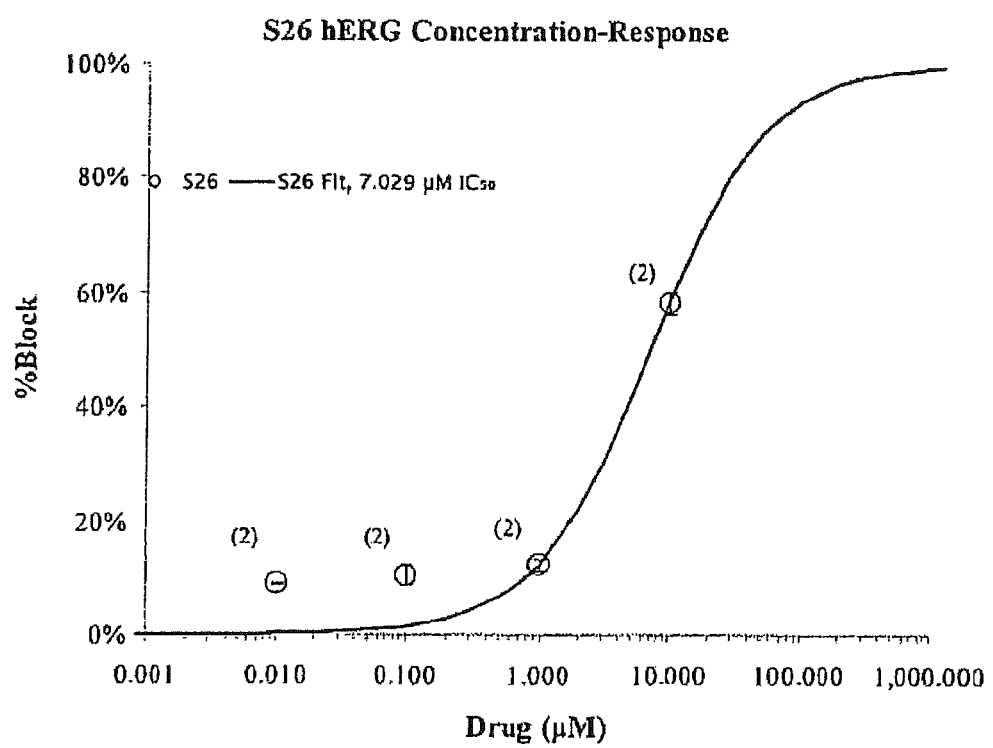
FIG. 42 is a concentration-response graph showing the percent inhibition of hERG current after application of S26 at various concentrations.

FIG. 42 is a graph showing the concentration-dependence of the effect of S26 on the hERG current. Table 18 provides the numerical data that is illustrated graphically in FIG. 42. The IC$_{50}$ value for S26 was 7.029 μM.

TABLE 18

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| S26 | 7.029 | 0.01 | 8.9% | 0.3% | 0.2% | 2 | 9.1% |
|  |  |  |  |  |  |  | 8.7% |
|  |  | 0.1 | 10.5% | 2.6% | 1.9% | 2 | 12.3% |
|  |  |  |  |  |  |  | 8.6% |
|  |  | 1 | 12.3% | 1.3% | 1.0% | 2 | 11.3% |
|  |  |  |  |  |  |  | 13.2% |
|  |  | 10 | 58.3% | 2.6% | 1.8% | 2 | 56.4% |
|  |  |  |  |  |  |  | 60.1% |

Figure 43:
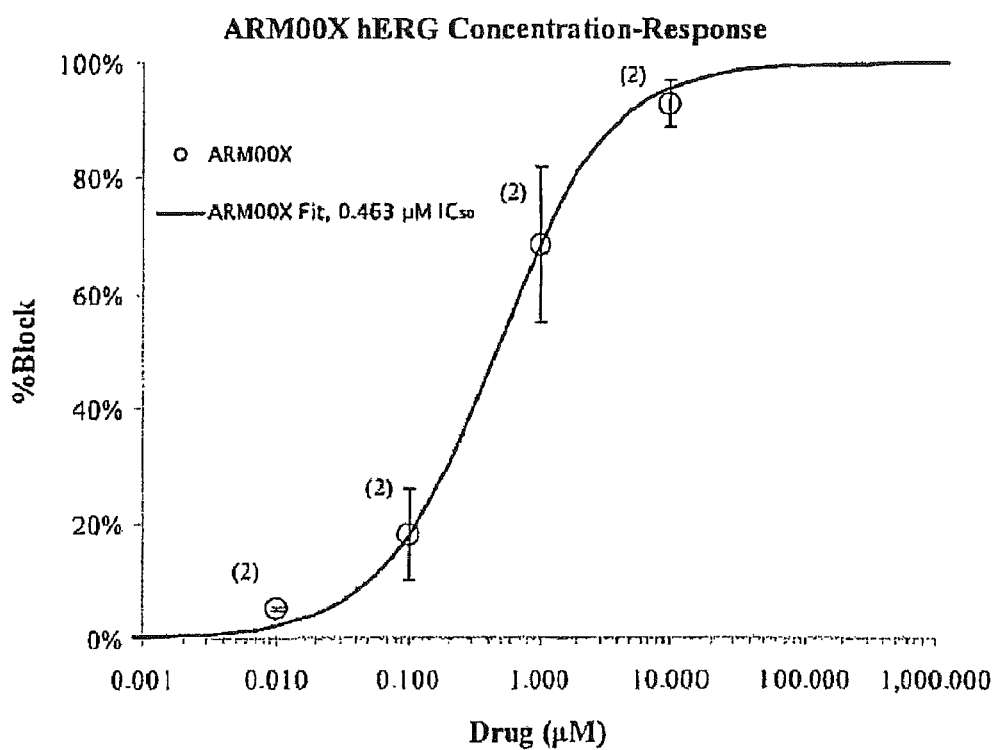
FIG. 43 is a concentration-response graph showing the percent inhibition of hERG current after application of JTV-519 ("ARM0XX") at various concentrations.

FIG. 43 is a graph showing the concentration-dependence of the effect of JTV-519 (referred to in the figure as "ARM0XX") on the hERG current. Table19 provides the numerical data that is illustrated graphically in FIG. 43. The IC$_{50}$ value for JTV-519 was 0.463 μM.

TABLE 19

| Test Article ID | $IC_{50}$ (μM) | Conc. (μM) | Mean % hERG Inhibition | % Standard Deviation | % Standard Error | n | Individual Data (% Inhibition) |
|---|---|---|---|---|---|---|---|
| ARM0XX | 0.463 | 0.01 | 5.0% | 0.3% | 0.2% | 2 | 5.2% 4.8% |
|  |  | 0.1 | 18.1% | 11.4% | 8.1% | 2 | 10.0% 26.1% |
|  |  | 1 | 68.4% | 19.1% | 13.5% | 2 | 81.9% 54.9% |
|  |  | 10 | 92.8% | 5.8% | 4.1% | 2 | 96.9% 88.7% |

The antiarrhythmic drug E-4031, a known blocker of hERG currents, was used as a positive control. E-4031 blocked the hERG current with an $IC_{50}$ of 0.5 μM (n=6).

In summary, the compounds of the present invention exhibit reduced hERG blocking activity as compared to JTV-519. Thus, the compounds of the invention are expected to be less toxic and/or exhibit fewer side effects than JTV-519.

Table 20 below provides $EC_{50}$ values for compounds S1-S107. These $EC_{50}$ data were obtained using thee FKBP12.6 rebinding assay described above to determine the amount of FKBP12.6 binding to PKA-phosphorylated RyR2 at various concentrations (0.5-1000 nM) of the compounds shown in Table 20. The $EC_{50}$ values are calculated using Michaelis-Menten curve fitting.

Table 20

| Compound No. | EC50 (nM) | Compound No. | EC50 (nM) |
|---|---|---|---|
| 1 | 150 | 48 | 100 |
| 2 | 211 | 49 | 81 |
| 3 |  | 50 | 40 |
| 4 | 102 | 51 | 175 |
| 5 | 208 | 52 | 143 |
| 6 | 252 | 53 | 200 |
| 7 | 55 | 54 | 77 |
| 9 | 205 | 55 | 111 |
| 11 | 181 | 56 | 95 |
| 12 | 197 | 57 | 73 |
| 13 | 174 | 58 | 55 |
| 14 | 182 | 59 | 102 |
| 19 | 265 | 60 | 68 |
| 20 |  | 61 | 95 |
| 22 | 355 | 62 | 45 |
| 23 | 268 | 63 | 52 |
| 25 | 40 | 64 | 44 |
| 26 | 40 | 66 | 110 |
| 27 | ca. 50 | 67 | 89 |
| 36 | 15 | 68 | ca. 100 |
| 37 |  | 74 | 220 |
| 38 | 44 | 75 | 150 |
| 40 | 100 | 76 | 25 |
| 43 | 80 | 77 | 60 |
| 44 | 121 | 101 | 105 |
| 45 | 80 | 102 | 135 |
| 46 | 150 | 104 | 111 |
| 47 | 20 | 107 | 190 |

High-throughput screening method

In addition to the compounds disclosed herein, other compounds can be discovered that are capable of modulating calcium ion channel activity, in particular those channels related to the RyR series of calcium ion channels. Provided herein is a highly-efficient assay for high-throughput screening of other compounds that are capable of modulating calcium ion channel activity.

By the way of example, and as shown in Example 5 below, a highly-efficient assay for high-throughput screening for small molecules is developed by immobilizing FKBP, either FKBP12or FKBP12.6 (e.g., wild-type FKBP12.6 or a fusion protein, such as GST-FKBP12.6) onto a 96-well plate coated with glutathione, using standard procedures. PKA-phosphorylated ryanodine receptor (RyR), specifically RyR1 or RyR3 in the case of FKBP12 and RyR2 in the case of FKBP12.6, is loaded onto the FKBP-coated plate, and incubated with compounds at various concentrations (10-100 nM) for 30 min. Thereafter, the plate is washed to remove the unbound RyR, and then incubated with anti-RyR antibody (e.g., for 30 min). The plate is washed again to remove unbound anti-RyR antibody, and then treated with fluorescent-labeled secondary antibody. The plate is read by an automatic fluorescent plate reader for binding activity.

Alternatively, RyR is PKA-phosphorylated in the presence of $^{32}$P-ATP. Radioactive PKA-phosphorylated RyR is loaded onto an FKBP-coated, 96-well plate, in the presence of JTV-519 analogues and other compounds at various concentrations (10-100 nM) for 30 min. The plate is washed to remove the unbound radiolabeled RyR, and then read by an automatic plate reader. PKA-phosphorylated RyR also is coated to the plate, and incubated with $^{-32}$S-labeled FKBP in the presence of the compounds.

The present invention is described in the following Examples, which are set forth to aid in the understanding of the invention and should not be construed to limit in any way the scope of the invention as defined in the claims which follow thereafter.

EXAMPLES

Example 1

RyR2 PKA Phosphorylation and FKBP12.6 Binding

Cardiac SR membranes are prepared, as previously described (Marx, et al., PKA phosphorylation dissociates FKBP12.6 from the calcium release channel (ryanodine receptor): defective regulation in failing hearts. *Cell*, 101: 365-76, 2000; Kaftan, et al., Effects of rapamycin on ryanodine receptor/Ca$^{(2+)}$-release channels from cardiac muscle. *Circ. Res.*, 78:990-97, 1996). $^{35}$S-labelled FKBP12.6 was generated using the TNT™ Quick Coupled Transcription/Translation system from Promega (Madison, Wis.). [$^3$H] ryanodine binding is used to quantify RyR2 levels. 100 μg of microsomes are diluted in 100 μl of 10-mM imidazole buffer (pH 6.8), incubated with 250-nM (final concentration) [$^{35}$S]-FKBP12.6 at 37° C. for 60 min, then quenched with 500 μl of ice-cold imidazole buffer. Samples are centrifuged at 100,000 g for 10 min and washed three times in imidazole buffer. The amount of bound [$^{35}$S]-FKBP12.6 is determined by liquid scintillation counting of the pellet.

Example 2

Immunoblots

Immunoblotting of microsomes (50 μg) is performed as described, with anti-FKBP12/12.6 (1:1,000), anti-RyR-5029 (1:3,000) (Jayaraman, et al., FK506 binding protein associated with the calcium release channel (ryanodine receptor). *J Biol. Chem.*, 267:9474-77, 1992), or anti-phosphoRyR2-P2809 (1:5,000) for 1 h at room temperature (Reiken, et al., Beta-blockers restore calcium release channel function and improve cardiac muscle performance in human heart failure. *Circulation*, 107:2459-66, 2003). The P2809-phospho-epitope-specific anti-RyR2 antibody is an affinity-purified polyclonal rabbit antibody, custom-made by Zymed Laboratories (San Francisco, Calif.) using the peptide, CRTRRI-(pS)-QTSQ, which corresponds to RyR2 PKA-phosphorylated at Ser$^{2809}$. After incubation with HRP-labeled anti-rabbit IgG (1:5,000 dilution; Transduction Laboratories, Lexington, Ky.), the blots are developed using ECL (Amersham Pharmacia, Piscataway, N.J.).

Example 3

Single-Channel Recordings

Single-channel recordings of native RyR2 from mouse hearts, or recombinant RyR2, are acquired under voltage-clamp conditions at 0 mV, as previously described (Marx, et al., PKA phosphorylation dissociates FKBP12.6 from the calcium release channel (ryanodine receptor): defective regulation in failing hearts. *Cell*, 101:365-76, 2000). Symmetric solutions used for channel recordings are: trans compartment—HEPES, 250 mmol/L; Ba(OH)$_2$, 53 mmol/L (in some experiments, Ba(OH)$_2$ is replaced by Ca(OH)$_2$); pH 7.35; and cis compartment—HEPES, 250 mmol/L; Tris-base, 125 mmol/L; EGTA, 1.0 mmol/L; and CaCl$_2$, 0.5 mmol/L; pH 7.35. Unless otherwise indicated, single-channels recordings are made in the presence of 150-nM [Ca$^{2+}$] and 1.0-mM [Mg$^{2+}$] in the cis compartment. Ryanodine (5 mM) is applied to the cis compartment to confirm identity of all channels. Data is analyzed from digitized current recordings using Fetchan software (Axon Instruments, Union City, Calif.). All data is expressed as mean±SE. The unpaired Student's t-testis used for statistical comparison of mean values between experiments. A value of p<0.05 is considered statistically significant.

Example 4

Compounds and Methods for Their Synthesis

Scheme 1: Synthesis of S3, S4, S5 and S54

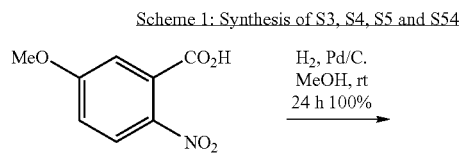

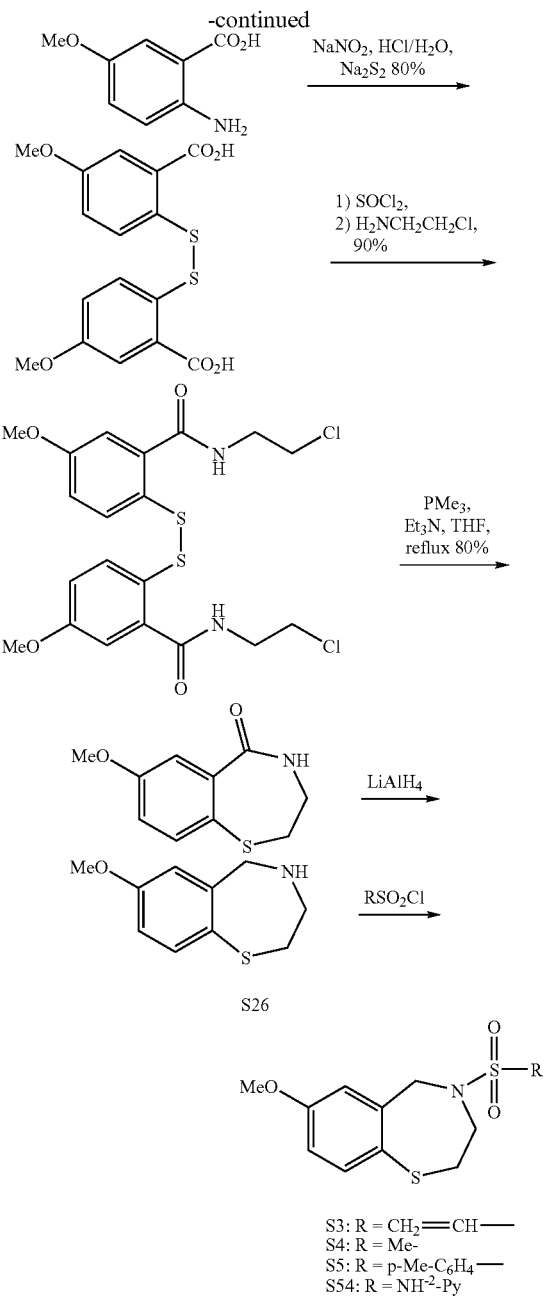

Synthon S26 was prepared according to methods described in U.S. patent application Ser. No. 10/680,988.

Synthesis of S3 (Scheme 1): To a stirred solution of vinylsulfonic acid (22 mg, 0.2 mmol) in anhydrous CH$_2$Cl$_2$ (5 ml) is added thionyl chloride (2M in CH$_2$Cl$_2$, 0.1 ml, 0.2 mmol). The reaction mixture is stirred at room temperature overnight and evaporated under vacuum. The residue is dissolved in CH$_2$Cl$_2$ (5 ml). To this solution, a solution of S26 (20 mg, 0.1 mmol) in CH$_2$Cl$_2$ (3 ml) is added drop-wise at 0° C. The reaction mixture is stirred at 0° C. for one hour and at room temperature for another hour and washed with saturated sodium bicarbonate and 1N HCl. After removal of the solvent, the product S3 is purified by SiO$_2$ column chromatography as a colorless oil (18 mg, 65%).

Synthesis of S4 (Scheme 1): To a stirred solution of S26 (20 mg, 0.1 mmol) in CH₂Cl₂ (5 ml) is added methylsulfonyl chloride (26 mg, 0.2 mmol) and triethylamine (30 mg, 0.3 mmol) at 0° C. The resulting mixture is stirred at 0° C. for one hour and at room temperature overnight. The organic phase is washed with aqueous saturated sodium bicarbonate and dried over sodium sulfate. After filtration and evaporation of the organic solvents, the product S4 is purified by SiO₂ column chromatography (25 mg oil, yield: 90%). Similarly, S5 and S54 are synthesized in 95% and 91% yields respectively.

hour and at room temperature overnight. After removal of solvent, the crude acid chloride is added to a stirred solution of S26 (20 mg, 0.1 mmol) and triethylamine (30 mg, 0.3 mmol) in CH₂Cl2 (10 ml) at 0° C. The mixture is stirred at 0° C. for one hour and at room temperature overnight. The organic phase is washed with saturated sodium bicarbonate and 1N HCl. The crude product is purified by column chromatography to give S7 as a colorless oil (34 mg, yield, 95%). Similarly, S9 is synthesized in 95% yield; synthon S27 is synthesized in 96% yield; and S40 is synthesized in 91% yield using N-hydroxysuccinimidyl 4-azidosalicylic acid (NHS-ASA).

Scheme 2: Synthesis of S1 and S2

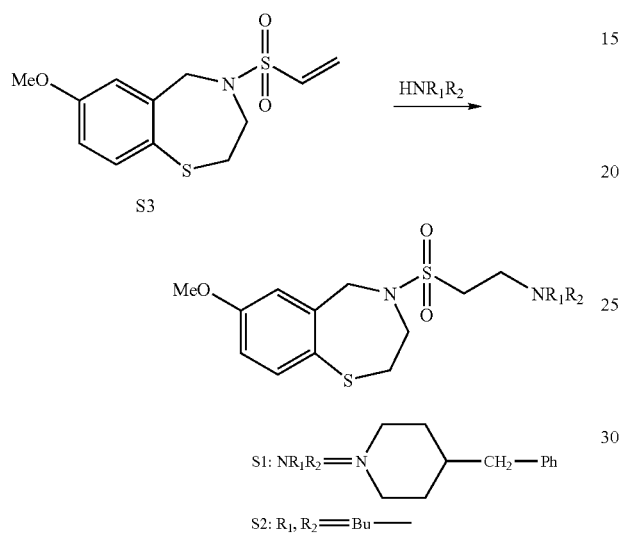

Synthesis of S1 and S2 (Scheme 2): To a solution of S3 (28 mg, 0.1 mmol) in chloroform (5 ml) is added 4-benzylpiperidine (18 mg, 0.1 mmol). The resulting mixture is stirred at room temperature for 1 day. After removal of organic solvent, the residue is purified on silica gel column. Product S1 is obtained as a colorless oil (34 mg,.yield 75%). S2 is synthesized similarly from S3 and dibutylamine in 78% yield.

Scheme 3: Synthesis of S7, S9 and S40

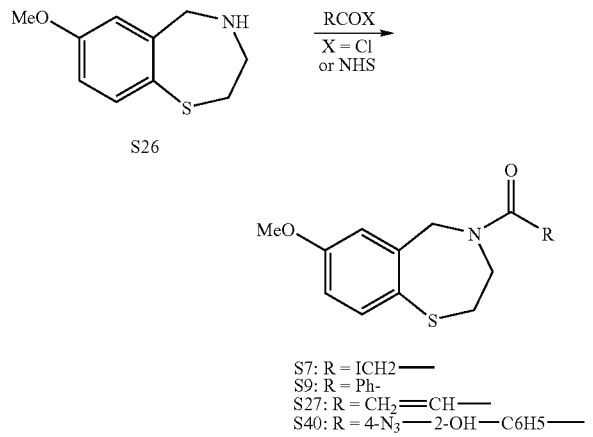

Synthesis of S7, S9,S27 and S40 (Scheme 3): To a stirred solution of iodoacetic acid (37 mg, 0.2 mmol) in CH₂Cl₂ (10 ml) is added thionyl chloride (2 M solution in CH₂Cl₂, 0.1 ml, 0.2 mmol). The resulting mixture is stirred at 0° C. for one Scheme 4: Synthesis of S11 and S12

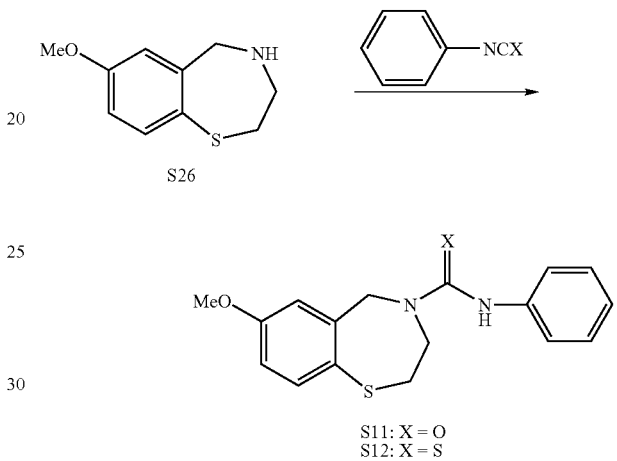

Synthesis of S11 and S12 (Scheme 4): To a solution of S26 (20 mg, 0.1 mmol) in pyridine (1 ml) is added phenyl isocyanate (18 mg, 0.15 mmol). The resulting mixture is stirred at room temperature for 24 hours. Then ethyl acetate (10 ml) is added and the organic phase is washed with 1N HCl and saturated sodium bicarbonate. The product S11 is purified by SiO₂ column chromatography as a white solid (27 mg, yield: 86%). Similarly, S12 is synthesized from S26 and phenyl isothiocyanate in 85% yield.

Scheme 5: Synthesis of S13 and S14

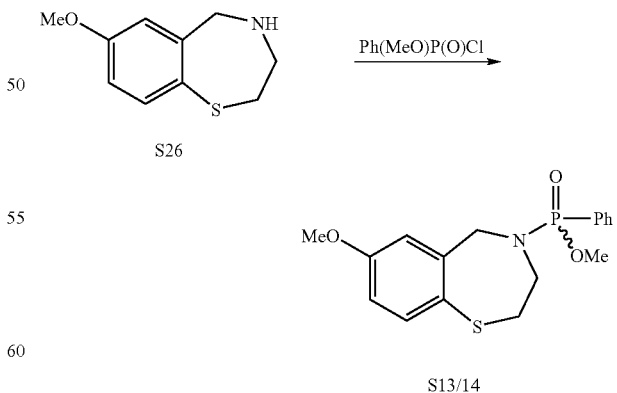

Synthesis of S13 and S14 (Scheme 5): To S26 (20 mg, 0.1 mmol) in CH₂Cl₂ (5 ml) is added triethylamine (30 mg, 0.3 mmol) and phenyl methoxyphosphonyl chloride (38 mg, 0.2 mmol) at 0° C. After stirring for 2 hours at room temperature, the reaction mixture is washed with saturated sodium bicarbonate. Isomers are separated and purified by silica gel column to yield S13 (14 mg, yield: 40%) and S14 (16 mg, yield: 45%).

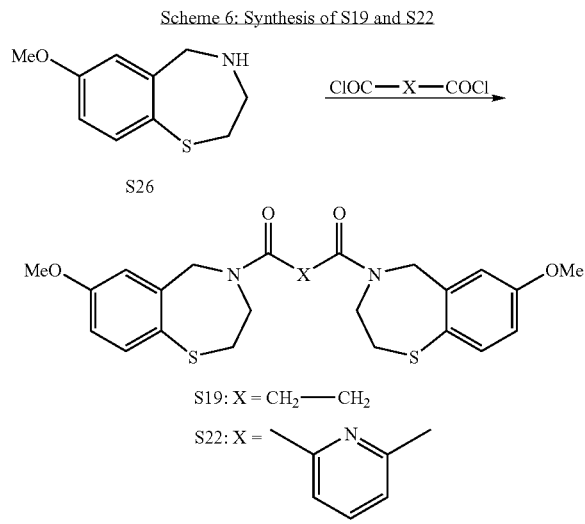

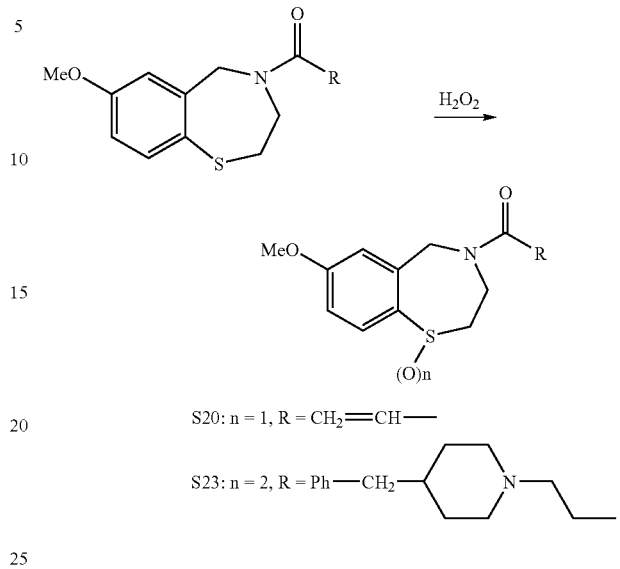

Synthesis of S19 (Scheme 6): To a stirred solution of S26 (20 mg, 0.1 mmol) and triethylamine (30 mg, 0.3 mmol) in $CH_2Cl_2$ (5 ml) is added 1,4-butyldiacid chloride (8 mg, 0.05 mmol) at 0° C. The resulting mixture is stirred at 0° C. for one hour and at room temperature overnight. The organic phase is washed with saturated sodium bicarbonate and 1N HCl and water. After removal of solvent, product S19 is purified by column chromatography (oil, 19 mg, 80% yield). Similarly S22 is prepared from 2,6 pyridyl dicarboxylic acid dichloride.

Synthesis of S20 and S23 (Scheme 7): S27 (25 mg, 0.1 mmol) in MeOH (5 ml) is treated with $H_2O_2$ (30%, 0.5 ml) at room temperature for 1 day. After treatment with sodium thiosulfate solution, methanol is removed by evaporation. The resulting residue is dissolved in ethyl acetate (10 ml) and washed with saturated sodium carbonate. After drying over sodium sulfate, solvent is evaporated to provide a crude product which is purified by silica gel column chromatography to yield S20 as colorless oil (16 mg, 60% yield). Similarly, S23 is synthesized from S10.

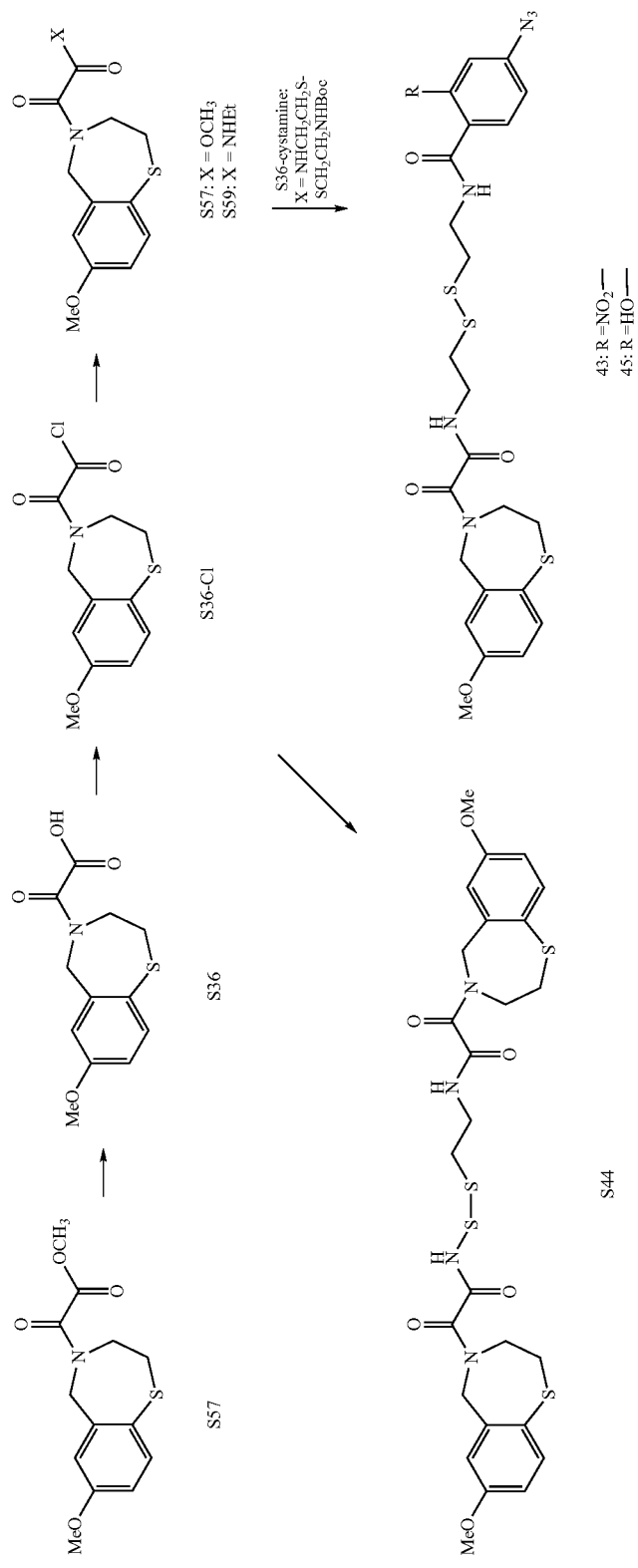

Synthesis of S36 and S57 (Scheme 8): To a stirred solution of S26 (0.85 g, 4.4 mmol) and pyridine (0.70 g, 8.8 mmol) in CH$_2$Cl$_2$ (50 ml) at 0° C. is added drop-wise methyl chlorooxoacetate (0.81 g, 6.6 mmol). The reaction mixture is stirred at 0° C. for 2 hours then washed with saturated sodium bicarbonate, 1N HCl, and water. Silica gel column chromatography provides S57 as a white solid (1.1 g, 90% yield). S57 (1.1 g, 3.9 mmol) is dissolved in methanol (10 ml) and then a solution of sodium hydroxide (0.3 g, 7.5 mmol) in water (10 ml) is added. The reaction mixture is stirred at room temperature for one hour. After solvent is removed, the residue is dissolved in water (10 ml) and washed with ether (2×10 ml). The aqueous phase is acidified with 1N HCl to pH=2. The product is extracted with CH$_2$Cl$_2$ (2×10 ml). Removal of solvent yields product S36 as a white solid (1.0 g, yield 100%). The product can be further purified by recrystalization. S38 is similarly synthesized (see Structure List).

Synthesis of S43, S44, S45 and S59 (Scheme 8): S36 (150 mg, 0.56 mmol) is treated with thionyl chloride (5 ml) at room temperature overnight. After removal of the excess thionyl chloride, the crude product S36-Cl is dissolved in CH$_2$Cl$_2$ (10 ml) and, to this solution, mono-Boc protected cystamine and pyridine (0.2 ml, 196 mg, 2.48 mmol) are added at 0° C. The reaction mixture is stirred at 0° C. for one hour and at room temperature overnight and quenched with saturated sodium bicarbonate. The organic phase is separated and the solvent is removed to give intermediate S36-cystamine, which is purified by SiO$_2$ column chromatography in 80% yield. Deprotection of the Boc-group is achieved with trifluoroacetic acid in CH$_2$Cl$_2$, and the deprotected S36-cystamine is used for the synthesis of S43 and S45 by reaction with NHS-activated ester of azido compounds. Yield is 75% for S43 and 80% for S45.

S44 is synthesized as a by-product of the following reaction: S36 (50 mg, 0.19 mmol) is treated with thionyl chloride (2 ml) at room temperature overnight. After removal of the excess of thionyl chloride, the crude product is dissolved in CH$_2$Cl$_2$ (5 ml). To this solution, cystamine (134 mg, 0.88 mmol) and pyridine (98 mg, 1.23 mmol) in CH$_2$Cl$_2$ (10 ml) is added and the reaction mixture is stirred at room temperature overnight. S44 is purified by column as a white solid (20 mg, 16%). Similarly, S57 and S59 are synthesized by reaction of S36-Cl with methanol or ethylamine (Scheme 8).

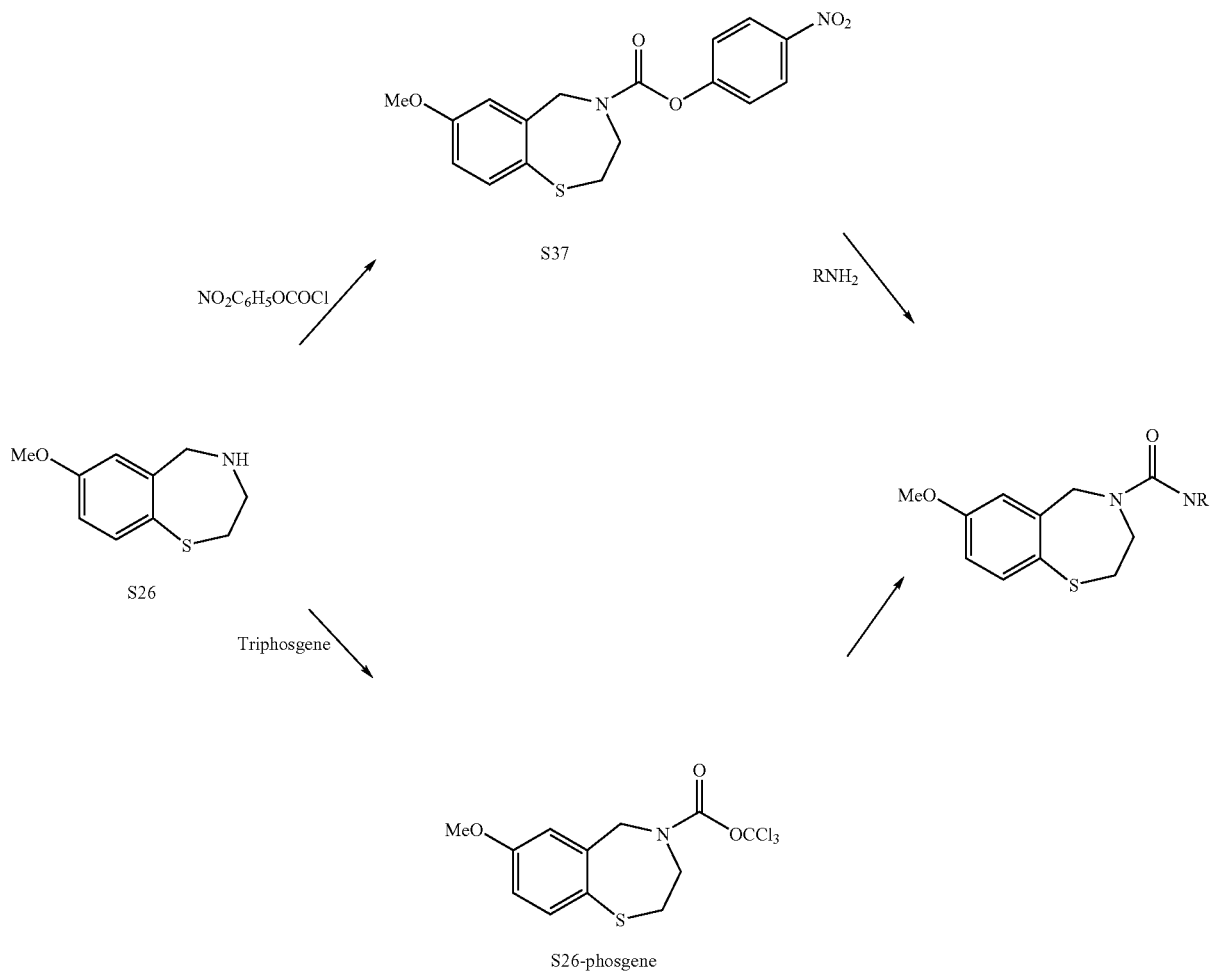

S6: NR = 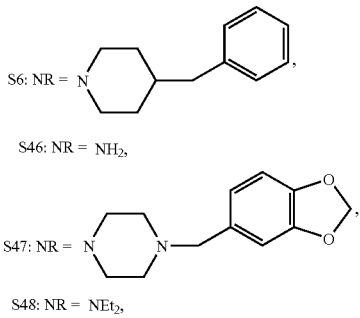

S46: NR = NH$_2$,

S47: NR = 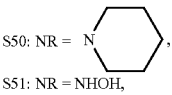

S48: NR = NEt$_2$,

S49: NR = NHCH$_2$Ph

S50: NR = 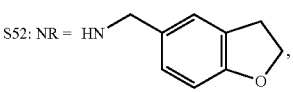

S51: NR = NHOH,

S52: NR = 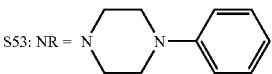

S53: NR = 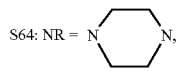

S64: NR = 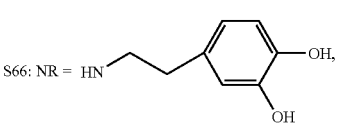

S66: NR = 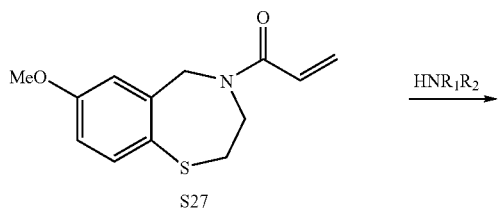

S67: NR = 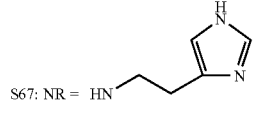

Synthesis of urea-based analogs S6, S46-S53, S64, S66, S67 (Scheme 9). S26 (195 mg, 1.0 mmol) in CH$_2$Cl$_2$ (20 ml) is added 4-nitrophenyl chloroformate (220 mg, 1.1 mmol) and triethylamine (120 mg, 1.2 mmol) at 0° C. The reaction mixture is stirred for 2 hours at room temperature and washed with water. Removal of the solvents, followed by purification using column chromatography provides compound S37 (330 mg, 91%). Reaction of S37 (36 mg, 0.1 mmole) with one equivalent of amine in DMF (3 ml) overnight provides urea-based compounds in >60% yield after purification by SiO$_2$ column chromatography. Alternatively, the urea-based compounds can be synthesized through a versatile and more reactive intermediate S26-phosgene shown in Scheme 9.

Scheme 10: Synthesis of S55, S56, S58, S60-S63

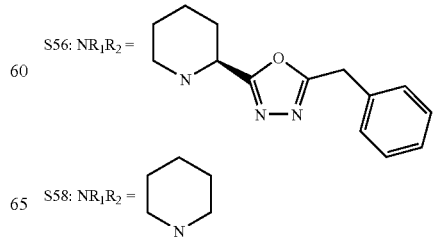

S27 → HNR$_1$R$_2$

-continued

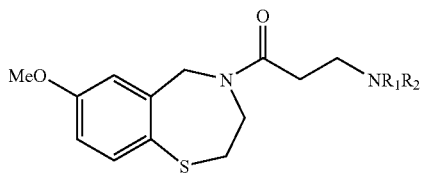

S55: NR$_1$R$_2$ = 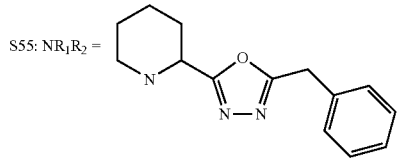

S56: NR$_1$R$_2$ =

S58: NR$_1$R$_2$ =

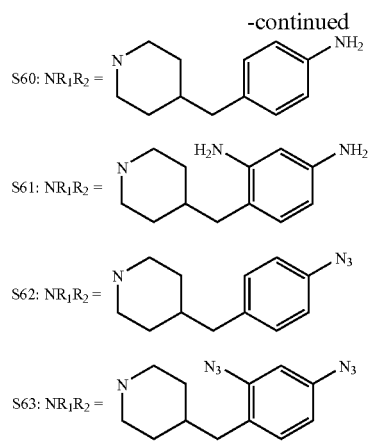

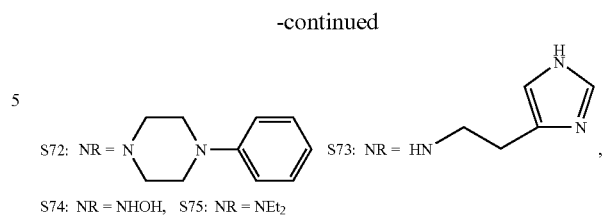

Synthesis of S55, S56, S58, S60-S63 (Scheme 10): The reaction mixture of S27 (25 mg, 0.1 mmol) and 4-(4-aminobenzyl)piperidine (19 mg, 0.1 mmol) in chloroform (5 ml) is stirred at room temperature for 2 days. After removal of solvent, the product S60 is purified by silica gel column chromatography as a white solid (36 mg, yield 90%). S55, S56, S58, and S61-S63 similarly are synthesized according to method described above.

Experimental for New Compounds

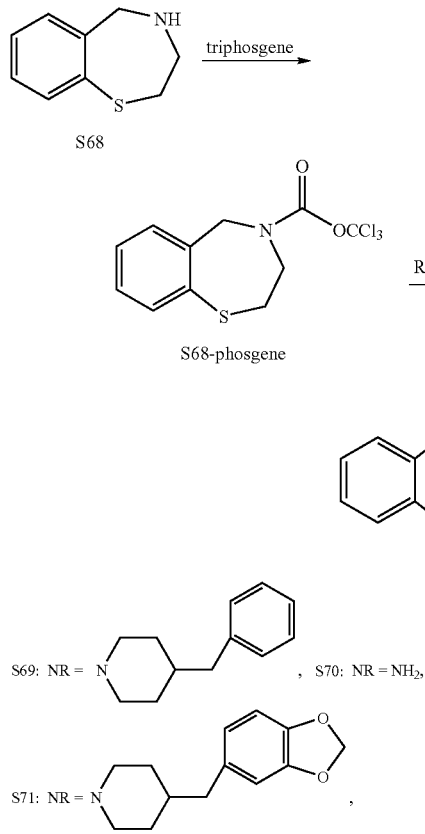

Analogs S69-S75, having no methoxyl groups on the benzene ring (R=H in Formula I), are synthesized as shown in Scheme 11 in a similar manner to that employed in the synthesis of S46-S53 (see Scheme 9). The synthesis starts with commercially available S68 and involves a versatile intermediate, S68-phosgene, to provide S69-S75 in 60-95% yield.

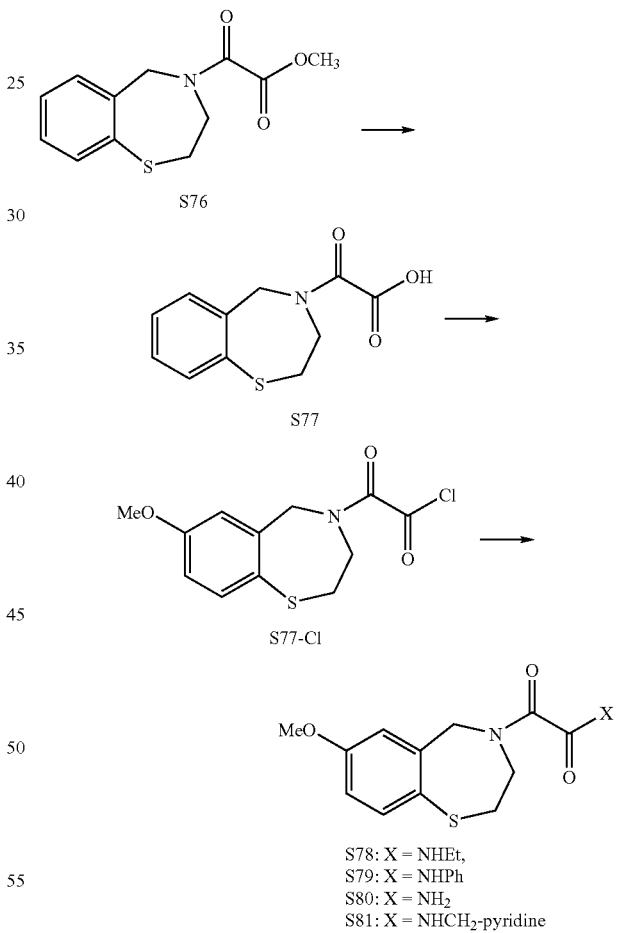

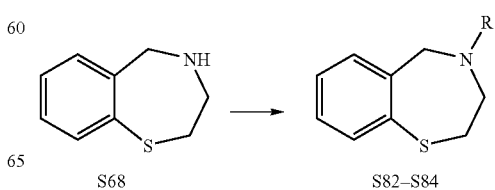

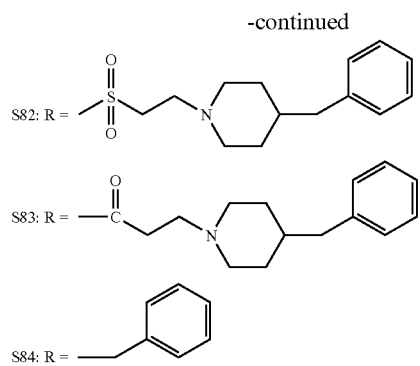

S82: R =
S83: R =
S84: R =

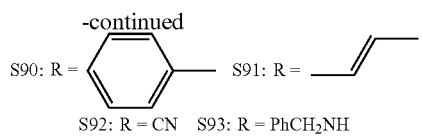

S90: R =      S91: R =
S92: R = CN   S93: R = PhCH₂NH

By analogy to the syntheses of S36, S43-S45, S57, and S59 (Scheme 8), S76-S81 are synthesized from commercially available S68 as shown in Scheme 12 in 70-95% yield. Using S68 as starting material, the compounds S82, S83, and S84, as shown in Scheme 13, also are synthesized similarly to the compounds which have a methoxy group on the benzene ring (R=4-OCH₃ in Formula I).

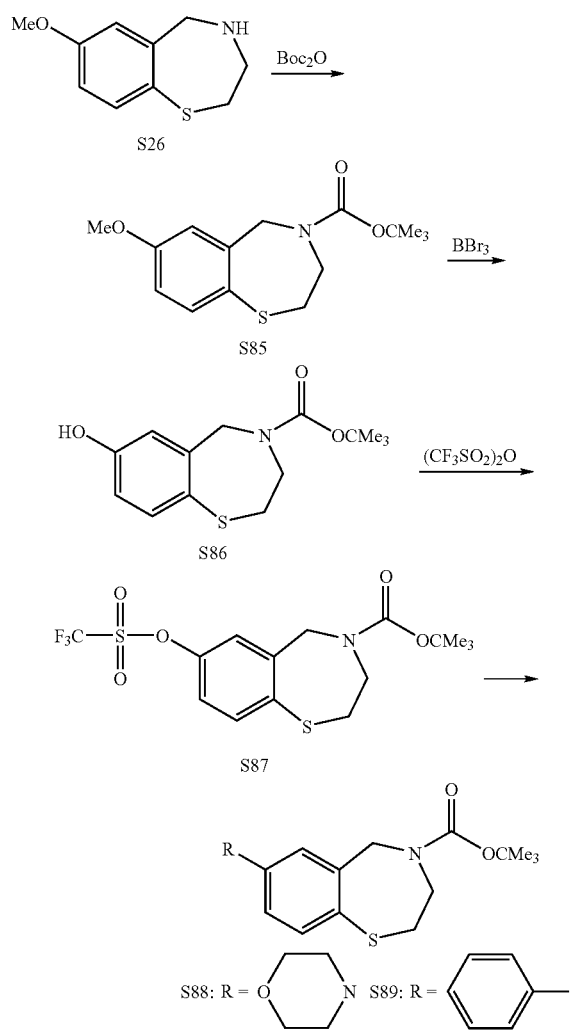

Scheme 14: Synthesis of S88-S93

S88: R = morpholinyl    S89: R = PhS-phenyl

Synthesis of S85-S93 is accomplished as shown in Scheme 14. The following are examples of the synthesis.

Synthesis of S85: A solution of S26 (10 mmol), di-tert-butyl dicarbonate (11 mmol), and triethylamine (12 mmol) in dichloromethane (100 ml) is stirred at room temperature for 5 hours. The reaction mixture is washed with saturated sodium bicarbonate solution (10 ml) and the aqueous layer is extracted with dichloromethane (2×15 ml). The combined organic layers are dried over magnesium sulfate and concentrated under vacuum to provide S85 as colorless oil (2.90 g, 98% yield).

Synthesis of S86: To a solution of S85 (2.36 g, 8 mmol) in dichloromethane (100 ml) at −78° C. is added BBr₃ (1.0 M solution in dichloromethane) (18 ml, 18 mmol) drop-wise. The solution is warmed to room temperature and the reaction mixture is quenched with methanol (100 ml) and concentrated under vacuum. The product S86 is purified by column chromatography.

Synthesis of S87: To a solution of S86 (6 mmol) in dichloromethane (40 ml) at 0° C. is added triethylamine (7 mmol) followed by trifluoromethylsulfonyl anhydride (7 mmol). The solution is stirred at room temperature for 30 minutes, and the reaction mixture is quenched with water (10 ml). The aqueous layer is extracted with dichloromethane (2×15 ml), and the combined organic layers are dried over magnesium sulfate and concentrated under vacuum. The crude product is purified by silica gel flash chromatography to provide S87 in 75% yield.

Synthesis of S88: A mixture of S87 (1 mmol), morpholine (8 ml), tris(dibenzylideneacetone)dipalladium(0) (5 mol %), 2-(di-tert-butylphosphino)-biphenyl (20 mol %), and potassium phosphate (1.2 mmol) is heated at 80° C. in a sealed tube for 12 hours. The reaction mixture is cooled to room temperature, diluted with dichloromethane (50 ml), and washed with water (10 ml). The aqueous layer is extracted with dichloromethane (2×15 ml), and the combined organic layers are dried over magnesium sulfate and concentrated under vacuum. The crude product is purified by silica gel flash chromatography to give S88 in 81% yield.

Synthesis of S89: A solution of S87 (1 mmol), benzenethiol (2 mmol) and i-Pr₂NEt (2 mmol) in CH₃CN (20 ml) is heated at 80° C. for 18 hours. After cooling, ethyl acetate (30 ml) is added and then washed with 1N HCl, water, and then 1N NaOH. After drying with Na₂SO₄, the solution was concentrated. The product S89 was purified by chromatography in 59% yield. Alternatively, S89 is synthesized by refluxing of S87 with benzenethiol in dioxane for 10 hours using i-Pr₂NEt/Pd₂(dba)₃/xantphos as catalyst.

Synthesis of S90: To a solution of S87 (1.0 mmol) in dioxane (10 mL) are added K₂CO₃ (2 mmol), phenylboronic acid (1 mmol), and (Pd(Ph₃P)₄ (0.11 mmol), and the mixture is stirred at 90° C. for 16 hours. The reaction mixture is cooled to 25° C., diluted with CH₂Cl2 (30 mL), washed with water (10 mL), and the organic phase is evaporated to dryness under vacuum. Purification by column chromatography gives S90 in 40% yield.

Synthesis of S92: To a solution of S87 (1.0 mmol) in DMF (5 mL) are added zinc cyanide (1 mmol) and Pd(Ph₃P)₄ (0.11 mmol). The reaction mixture is stirred and heated at 100° C.

for 1 hour, followed by cooling, dilution with water (50 mL) and 2 M sulfuric acid (5 mL), and extraction with EtOAc (3×). The combined organic extracts are washed with brine (2×), dried over magnesium sulfate, filtered, and evaporated under vacuum. The product S92 is purified by silica gel column chromatography in 80% yield.

centrated $HNO_3$ (2 ml) drop-wise. After 10 minutes, the reaction mixture is poured on to crushed ice (5 g) and neutralized with $Na_2CO_3$ to pH=7. The Boc-deprotected nitro intermediate is collected by extraction with EtOAc and converted back to S97 by reaction with $Boc_2O$. Purification by silica gel column chromatography provides S97 in 78% yield.

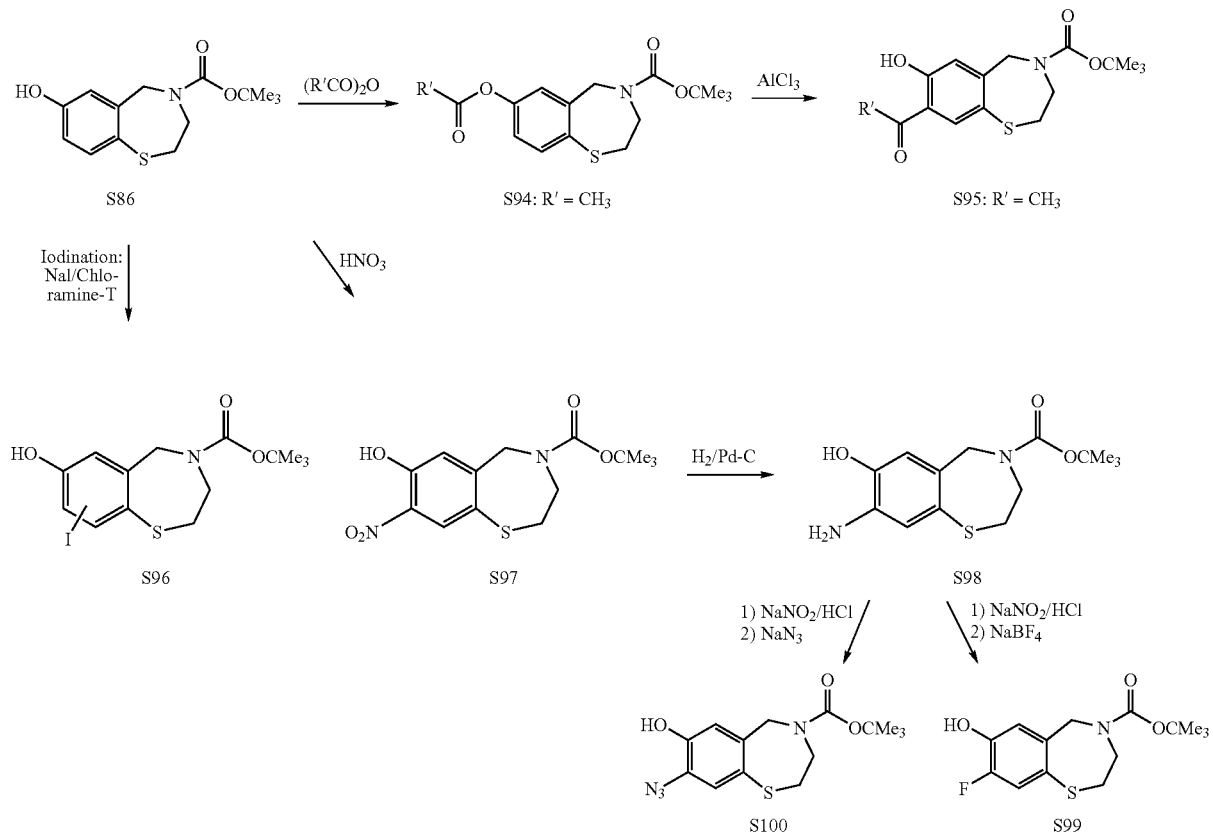

Scheme 15: Synthesis of S94-S100

Synthesis of S94: To a solution of S86 (1 mmol) in $CH_2Cl_2$ (10 ml) is added at 0° C acetic anhydride (1.2 mmol) and triethylamine (1.3 mmol). The reaction mixture is stirred at room temperature overnight, then washed with $H_2O$. After drying with $Na_2SO_4$, the solvent is evaporated and the product S94 (98% yield by NMR) is used for the next reaction without further purification.

Synthesis of S95: To a stirred solution of S84 (0.5 mmol) in benzene (20 ml) is added anhydrous $AlCl_3$ (0.6 mmol) drop-wise. The reaction mixture is refluxed for 5 hours and poured on to crushed ice (10 g). After extraction and concentration, the product S95 is purified by silica gel column chromatography in 83% yield.

Synthesis of S96: To a solution of S86 (0.1 mmol) in methanol (5 ml) is added NaI (10 mg, excess) and Chloramine-T (0.3 mmol). The reaction mixture is stirred for 30 minutes and quenched with $Na_2S_2O_3$ solution. The solvent is evaporated. The product is purified by silica gel column chromatography as a mixture of mono-iodinated or di-iodinated products in a combined yield of 60%.

Synthesis of S97: S86 (3 mmol) is added to concentrated $H_2SO_4$ (2 ml). To the stirred mixture is added, slowly, con- Synthesis of S98: A mixture of S97 (2 mmol) and 10% Pd/C (0.1 g) in methanol (20 ml) is bubbled through with $H_2$ gas for 2 hours. After filtration and concentration, the amine product is used for the next reactions without further purification.

Synthesis of S99 and S100: S98 (1 mmol) is dissolved in aqueous HCl (2 mmol HCl, 10 ml $H_2O$). To this solution is added at 0° C. slowly a solution of sodium nitrite (1 mmol) in water (5 ml). The reaction mixture is stirred at 0° C. for 1 hour, then $NaN_3$ (2 mmol) in water (2 ml) is added drop-wise at 0° C. The resulting mixture is stirred at 0° C. for 1 hour and at room temperature overnight. The product is extracted with ethyl acetate and washed with saturated sodium bicarbonate and water. The organic layer is dried over anhydrous sodium sulfate and concentrated to give crude product S98. Column purification on silica gel provide the product in 71% yield. Similarly, S99 is synthesized in 60% yield.

Synthesis of S101, S102, and S103 (also referred to as ARM101, ARM102, and ARM103, respectively) may be accomplished as shown in Scheme 16. The following are examples of the synthesis.

Scheme 16: Synthesis of ARM101, ARM102, and ARM103

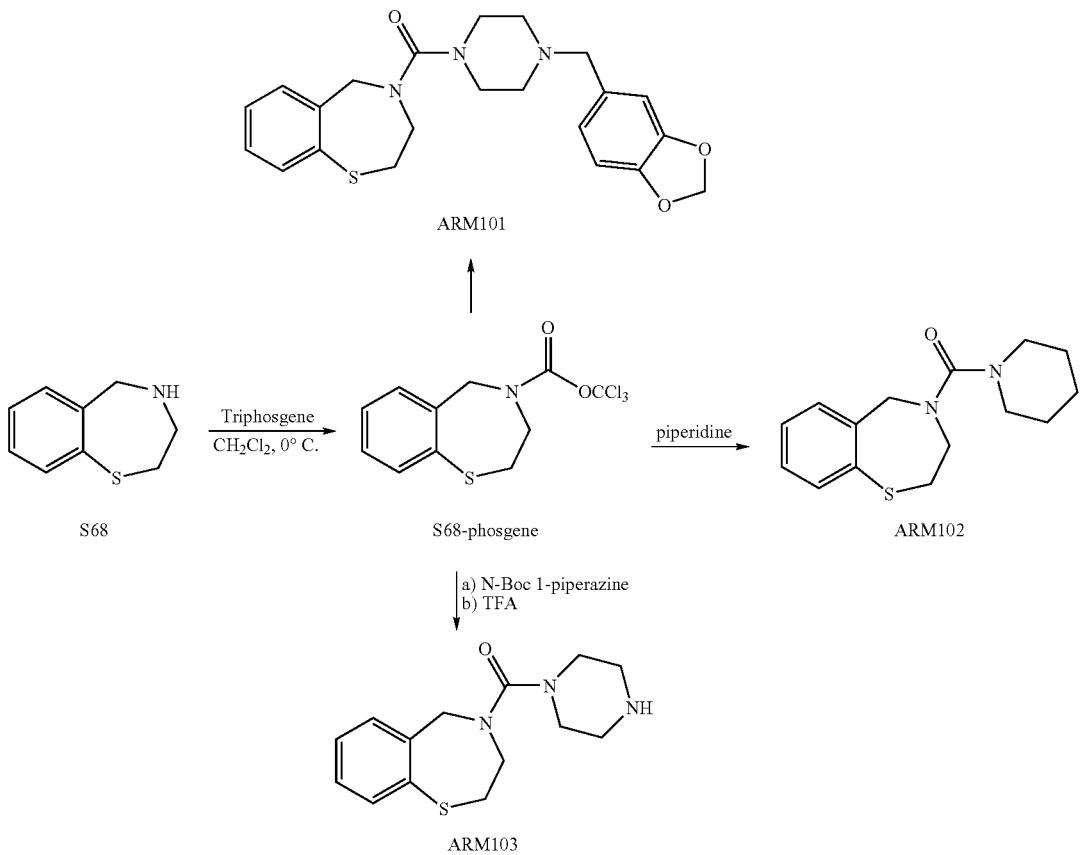

Synthesis of S101: A solution of S68 (165 mg. 1 mmol) in CH$_2$Cl$_2$ (50 ml) was cooled to 0° C. To this solution, triphosgene (150 mg, 0.5 mmol) and pyridine (0.5 ml. excess) were added and stirred at 0° C. for 1 hour. Without purification, the resulting S68-phosgene in the reaction mixture was treated with 1-piperonylpiperazine (233 mg, 1.1 mmol) at 0° C. After stirring at 0° C. for 1 hour, the reaction mixture was washed with H$_2$O (2×10 ml), 1N HCl (2×10 ml) and saturated NaHCO$_3$ (2×10 ml), and the solvents were removed under reduced pressure. Purification by SiO$_2$ column chromatography provided ARM101 having a yield of 80%. The structure of the product was confirmed by nuclear magnetic resonance (NMR), mass spectroscopy (MS) and/or by elemental analysis.

Synthesis of S102: S102 was synthesized from S68 using the same method used to synthesize S101, with the exception that piperidine was used in place of 1-piperonylpiperazine. The structure of the product was confirmed by nuclear magnetic resonance (NMR), mass spectroscopy (MS) and/or by elemental analysis.

Synthesis of S103: S103 was synthesized from S68 using the same method used to synthesize S101, with the exception that N-Boc 1-piperazine was used in place of 1-piperonylpiperazine, and in a subsequent step the Boc group was deprotected using trifluoroacetic acid (TFA). The structure of the product was confirmed by nuclear magnetic resonance (NMR), mass spectroscopy (MS) and/or by elemental analysis.

Scheme 17: Synthesis of ARM104

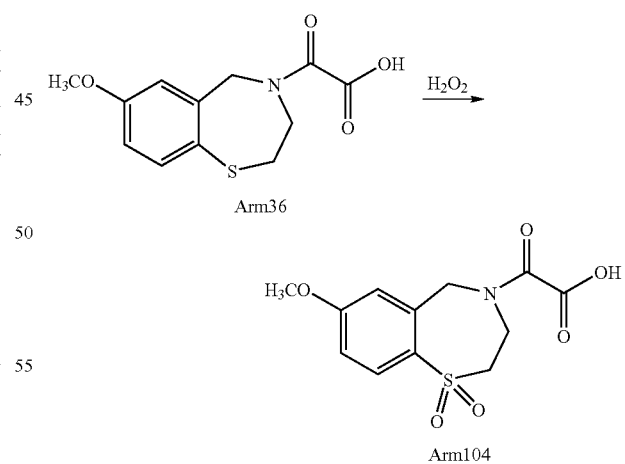

Synthesis of S104 (ARM104) may be accomplished as shown in Scheme 17. The following is an example of the synthesis. A mixture ARM036 (S36) (27 mg, 0.1 mmol), 50% H$_2$O$_2$ (1 ml), and MeOH (3 ml) was stirred at room temperature for 2 days to generate the ARM104 product. Mass spectroscopy (MS) was used to monitor the disappearance of ARM036 and the appearance of the product ARM104. The solvents were removed under reduced pressure, and the product was purified by re-crystallization. The final yield was 26 mg of ARM104 at 85% purity. The structure of the final product was determined by nuclear magnetic resonance (NMR) and/or MS.

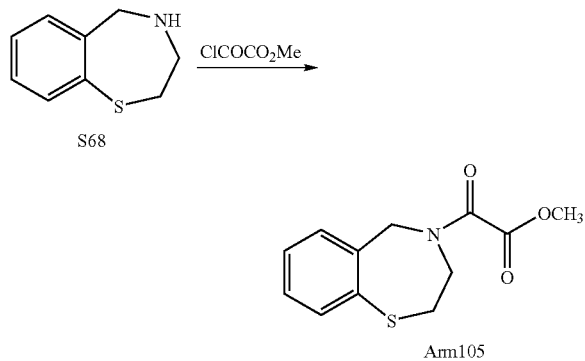

Scheme 18: Synthesis of ARM105

Synthesis of S105 (ARM105) may be accomplished as shown in Scheme 18. The following is an example of the synthesis: To a stirred solution of S68 (80 mg, 0.48 mmol) and pyridine (0.1 ml, excess) in $CH_2Cl_2$ (50 ml) at 0° C., $CH_3O$—C(O)C(O)Cl (70 mg, 0.58 mmol) was added dropwise. The reaction mixture was stirred at 0° C. for 2 hours and washed with 1N HCl, saturated sodium bicarbonate, and water. Removal of the solvents and purification by $SiO_2$ column chromatography were performed to produce the ARM105 product as a white solid (yield: 95 mg, 94%).

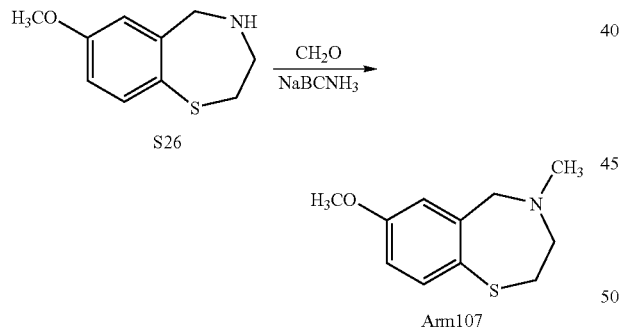

Scheme 19: Synthesis of ARM107

Synthesis of S107 (ARM107) may be accomplished as shown in Scheme 19. The following is an example of the synthesis: To S26 (180 mg, 0.92 mmol) in MeOH (20 ml) was added 30% $CH_2O$ solution (1.5 ml, excess) and sodium cyanoborohydride ($NaBCNH_3$) (0.4 g excess). The reaction mixture was stirred at room temperature, and the pH of the solution was maintained at around pH 4-5 by addition of a few drop of 1N HCl. After 3 hours, the solvents were removed under reduced pressure. The residue was dissolved in 20 ml ethyl acetate and washed with $H_2O$ and saturated $NaHCO_3$ (2×10 ml). The solvents were removed and the ARM107 was purified by $SiO_2$ column chromatography to give a yield: 170 mg, 93%.

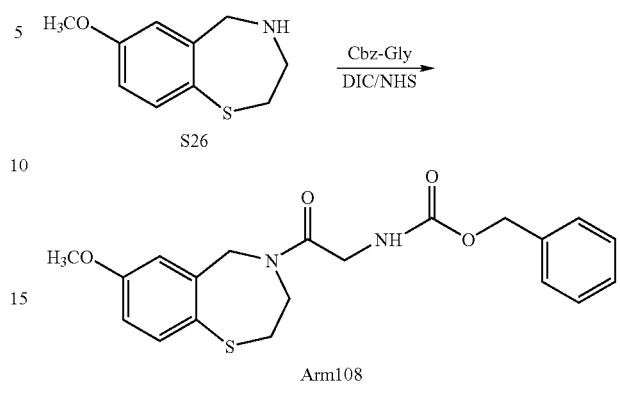

Scheme 20: Synthesis of ARM108

Synthesis of S108 (RM108) may be accomplished as shown in Scheme 20. The following is an example of the synthesis: A mixture of N-benzyloxycarbonyl-glycine (Cbz-Gly, 129 mg, 0.61 mmol), Diisopropyl-carbodiimide (DIC, 90 mg, 0.71 mmol), N-hydroxysuccinimide (NHS, 70.4 mg, 0.71 mmol) in $CH_2Cl_2$ (50 ml) was stirred for 0.5 h at room temperature. To this mixture was added S26 (100 mg, 0.51 mmol) and the mixture was stirred at room temperature for overnight. After washing with 1NCl (2×10 ml) and saturated $NaHCO_3$ solution (2×10 ml), the solvents were removed by evaporation. The product ARM108 was purified by $SiO_2$ column chromatography, to give a yield of 120 mg, 61%.

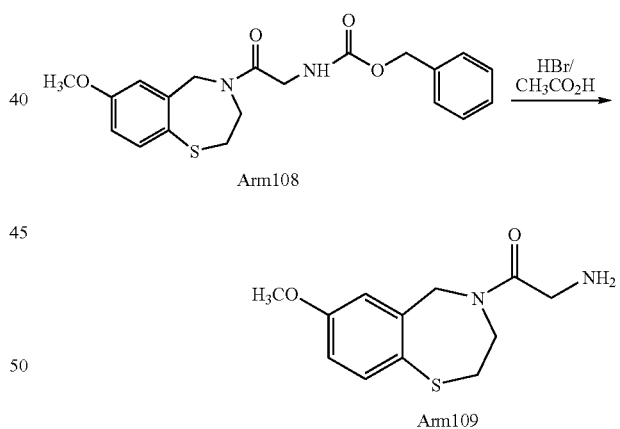

Scheme 21: Synthesis of ARM109

Synthesis of S109 (ARM109) may be accomplished as shown in Scheme 21. The following is an example of the synthesis: ARM108 (40 mg, 0.1 mmol) in $CH_2Cl_2$ (5 ml) was treated with 1 ml of 30% $HBr/CH_3CO_2H$. After stirring at room temperature overnight, the reaction mixture was evaporated under reduced pressure. The residue was dissolved in MeOH (3 ml) and treated with propylene oxide (1 ml). The solvents were removed under reduced pressure to provide crude ARM109 which was further purified by dissolving in 0.15 N HCl $H_2O$ solution (3.5 ml), followed by washing with ethyl acetate (3 ml) and evaporation. The yield of ARM109 was 28.3 mg, 95% (white powder, HCl salt).

Scheme 22: Synthesis of ARM110

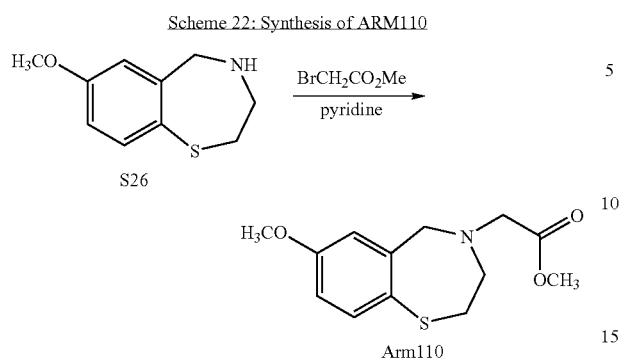

Synthesis of S110 (ARM110) may be accomplished as shown in Scheme 22. The following is an example of the synthesis: A mixture of S26 (100 mg, 0.51 mmol) and methyl 1-bromoacetate (100 mg, 1,2 eq.) and pyridine (50 mg) in DMF (what is DMF?) (5 ml) was stirred at room temperature overnight. To this mixture, ethyl aceate (50 ml) was added and washed with saturated NaHCO₃ solution (2×10 ml) and H₂O (2×10 ml). The product ARM110 as an oil was purified by SiO₂ column chromatography, to give a yield of 32 mg, 23%.

Scheme 23: Synthesis of ARM111

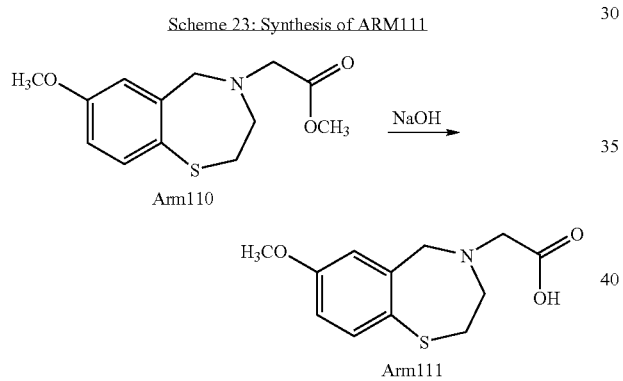

Synthesis of S111 (ARM111) may be accomplished as shown in Scheme 23. The following is an example of the synthesis: To a mixture of ARM110 (16 mg, 0.06 mmol) in MeOH (2 ml) was added 1N NaOH (0.1 ml) and the mixture was stirred at room temperature overnight. The solvents were removed under reduced pressure and the residue was dissolved in H₂O (10 ml). The aqueous phase was washed with ethyl acetate (2×5 ml) and acidified with 1N HCl to pH=4. Removal of the solvents under reduced pressure provided crude ARM111. The NaCl was removed using ethanol to yield pure ARM111 as solid, having a yield of 1 3 mg, 87%.

Scheme 24: Synthesis of Arm112

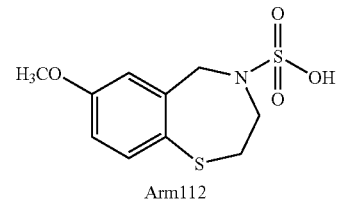

-continued

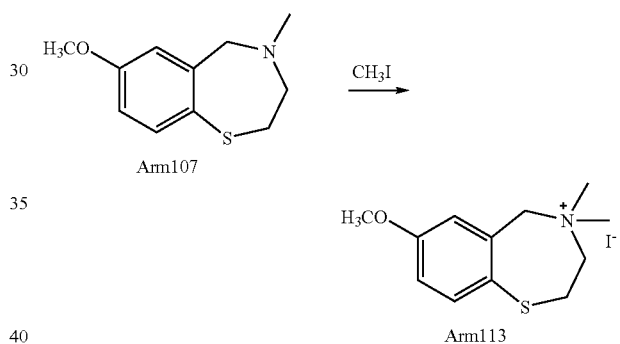

Synthesis of S112 (ARM112) may be accomplished as shown in Scheme 24. The following is an example of the synthesis: To a mixture of S26 (100 mg, 0.51 mmol) and pyridine (100 mg) in CH₂Cl₂ (20 ml), SO₂Cl₂ (89 mg, 1.2 eq.) was added drop-wise at 0° C. and stirred at room temperature overnight. The solvents were removed under reduced pressure and the residue was dissolved in 5.5 ml NaOH solution (5 ml H₂O+0.5 ml 1N NaOH). The water solution was washed with ethyl acetate (2×5 ml), and acidified with 1N HCl to pH 4. The aqueous phase was extracted with ethyl acetate (3×5 ml) and the ethyl acetate phase was evaporated under reduced pressure to provide ARM112, as powder, with a yield of 9 mg.

Scheme 25: Synthesis of ARM113

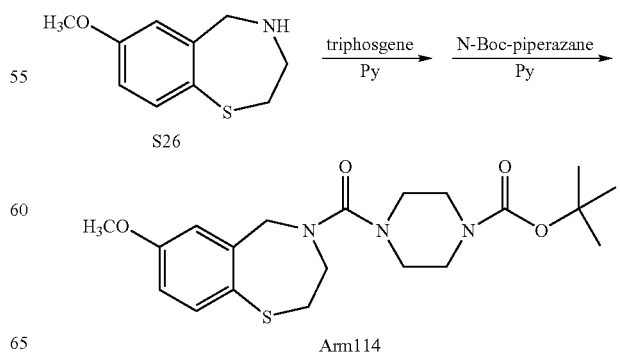

Synthesis of S113 (ARM113) may be accomplished as shown in Scheme 25. The following is an example of the synthesis: ARM107 (45 mg, 0.21 mmol) in ethyl acetate (2 ml) was treated with CH₃I (200 mg, excess). The mixture was stirred at room temperature overnight and the product ARM113, as white solid, was collected by filtration to give a yield of 69 mg, 97%.

Scheme 25A: Synthesis of Arm114

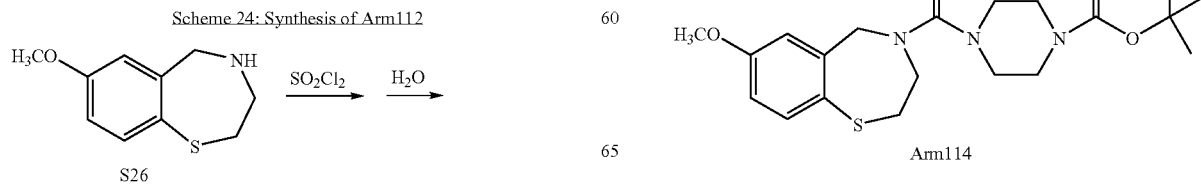

Synthesis of S114 (ARM114) may be accomplished as shown in Scheme 25A. The following is an example of the synthesis. S26 (195 mg, 1 mmol) in $CH_2Cl_2$ (50 ml) was cooled to 0° C. To this solution, triphosgene (150 mg, 0.5 mmol) and pyridine (0.5 ml. excess) was added and stirred at 0° C. for 1 hour. Without purification, the resulting S26-phosgene in the reaction mixture was treated with N-Boc 1-piperazine (200 mg, 1.1 mmol) at 0° C. After stirring at 0° C. for 1 hour, the reaction mixture was washed with $H_2O$ (2×10 ml), 1N HCl (2×10 ml), and saturated $NaHCO_3$ (2×10 ml), and the solvents were removed under reduced pressure. Purification by $SiO_2$ column chromatography provided ARM114 with a yield of 80%.

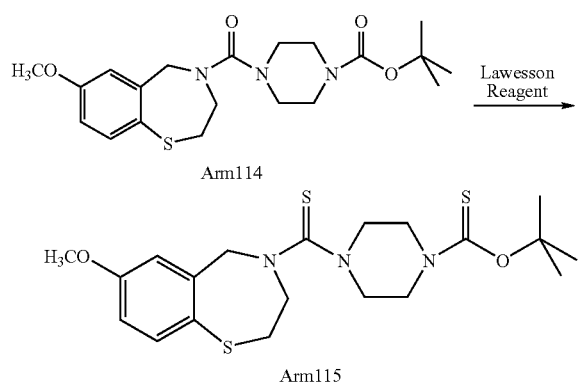

Synthesis of S115 (ARM115) may be accomplished as shown in Scheme 26. The following is an example of the synthesis: A mixture of ARM114 (200 mg, 0.49 mmol) and Lawesson Reagent (400 mg) in toluene (50 ml) was stirred at 90° C. for 5 hours. The mixture was cooled to room temperature and washed with saturated $NaHCO_3$ (2×20 ml). The product ARM115 was purified by $SiO_2$ column chromatography to give a yield of 160 mg, 75%.

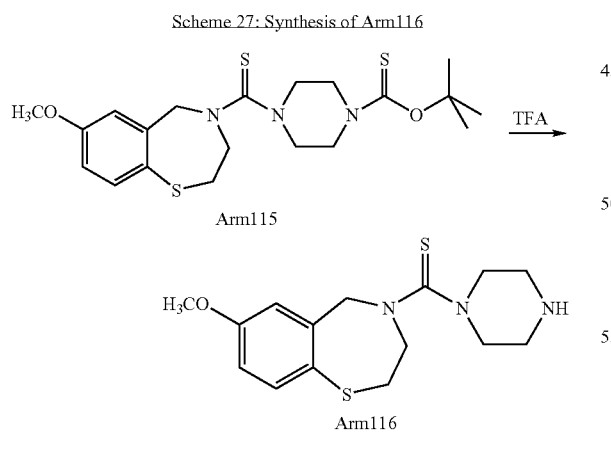

Synthesis of S116 (ARM116) may be accomplished as shown in Scheme 27. The following is an example of the synthesis: A mixture of ARM115 (10 mg, 0.02 mmol) and trifluoroacetic acid (TFA, 0.5 ml) in $CH_2Cl_2$ (10 ml) was stirred at room temperature for 2 hours. Evaporation of the solvents under reduced pressure produced ARM116 with yield of 6 mg, 92%.

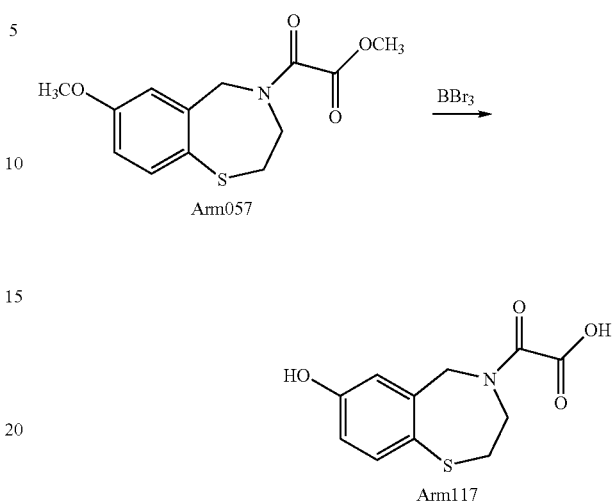

Synthesis of S117 (ARM117) may be accomplished as shown in Scheme 28. The following is an example of the synthesis: A solution of ARM057 (200 mg, 0.71 mmol) in $CH_2Cl_2$ (20 ml) was cooled to −78° C. To this, 1M $BBr_3$ in $CH_2Cl_2$ (1 ml) was added, and the mixture was stirred at −78° C. for 3 hours and then warmed to room temperature overnight. The mixture was washed with 1N HCl (2×10 ml) and $H_2O$ (1×10 ml). After removal of the solvents, the product ARM117 was purified by $SiO_2$ column chromatography to give a yield of 60 mg, 33%.

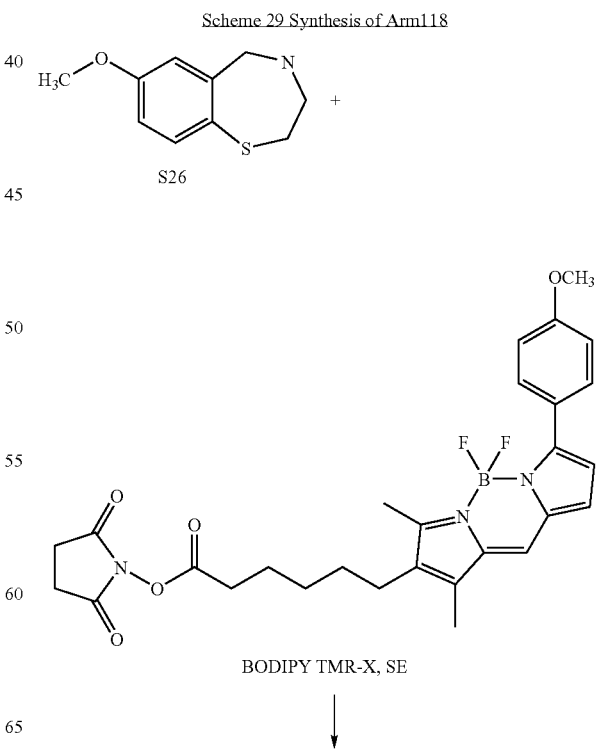

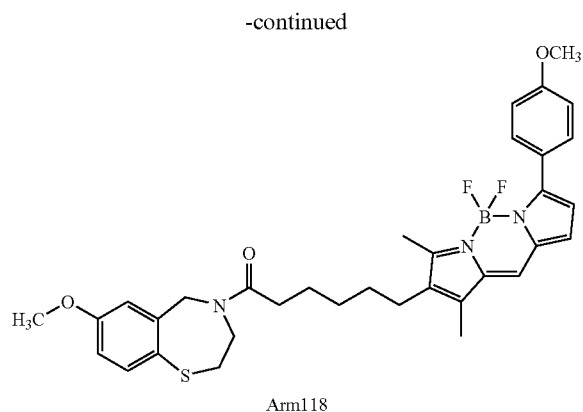

Arm118

Synthesis of S118 (ARM118) may be accomplished as shown in Scheme 29. The following is an example of the synthesis: S26 (3.6 mg, 0.018 mmol) in $CH_2Cl_2$ (3 ml) was treated with BODIPY TMR-X, SE (Molecular Probes Inc.) (4 mg, 0.006 mmol) for 3 hours. The mixture was washed with 0.01 N HCl (2×1 ml) and saturated $NaHCO_3$ (2×1 ml). Removal of the solvents under reduced pressure yielded pure ARM118 (98%).

Scheme 30: Synthesis of ARM119

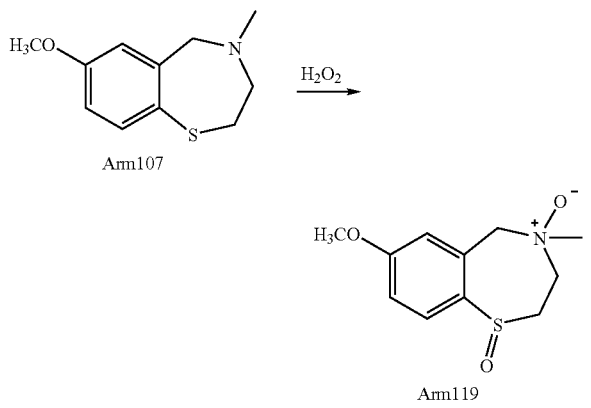

Arm119

Synthesis of S119 (ARM119) maybe accomplished as shown in Scheme 30. The following is an example of the synthesis: A mixture ARM107 (50 mg, 0.24 mmol), 50% $H_2O_2$ (1 ml), MeOH (3 ml) was stirred at room temperature for 2 days (mass spectrometry was used to monitor the disappearance of ARM107 and the formation of the product). The solvents were removed under reduced pressure to give ARM110, having a yield of 26 mg, 45%.

Scheme 31: Synthesis of ARM120 and ARM121

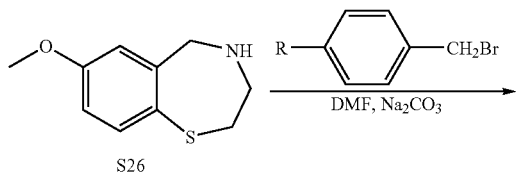

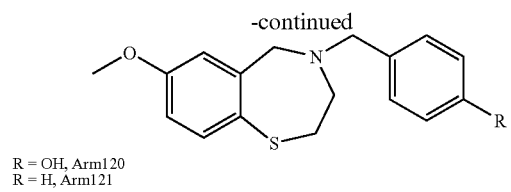

R = OH, Arm120
R = H, Arm121

Synthesis of S120 (ARM120) and S121 (ARM121) may be accomplished as shown in Scheme 31. The following is an example of the synthesis: A mixture S26 (195 mg, 1 mmol), benzyl bromide (1.1 mmol) and $Na_2CO_3$ (10 mmol) in DMF (10 ml) was stirred overnight. Ethyl acetate (30 ml) was added to the reaction, and then the reaction was washed with $H_2O$ (4×10 ml). The organic phase was concentrated under reduced pressure and the residue was purified by column chromatography to give S121 as a white powder, with a yield of 280 mg, at 98%. S120 was similarly synthesized, but using 4-OH-benzyl bromide instead of benzyl bromide.

Synthesis of S122 (ARM122) (LB21300-30). The following is an example of the synthesis: To a cold solution of compound S26 (250 mg, 1.28 mmol, 1 equivalent) in $CH_2Cl_2$ (50 mL) at 0° C. was added DIEA (0.67 mL, 3.8 mmol, 3.0 equivalent), followed by acetoxyacetyl chloride (0.17 mL, 1.58 mmol, 1.24 equivalent). Then, the reaction mixture was stirred at 0° C. for 20 min, diluted with 1.0 M HCl aqueous solution (100 mL) and extracted by $CH_2Cl_2$ (3×50 mL). The combined organic layers were washed ($H_2O$, brine), dried ($Na_2SO_4$), filtered, and evaporated to dry. The crude product was purified by chromatography on a silica gel column, eluting with a gradient increasing in polarity from 0 to 50% petroleum in ethyl acetate. Relevant fractions were combined to give the desired compound (350 mg, 93%).

Synthesis of S123 (ARM123) (LB21300-34). The following is an example of the synthesis: To a solution of compound S122 (287 mg, 0.97 mmol, I equivalent) in MeOH (5 mL) and THF (8 mL) at 23° C. was added LiOH (140 mg, 3.33 mmol, 3.44 equivale in $H_2O$ 5 mL). The reaction mixture was stirred at 23° C. for 20 minutes, diluted with 1.0 M HCl aqueous solution (100 mL) and extracted by $CH_2Cl_2$ (3×50 mL). The combined organic layers were washed ($H_2O$, brine), dried ($Na_2SO_4$), filtered and evaporated to dry. The crude product was purified by chromatography on a silica gel column, eluting with a gradient increasing in polarity from 0 to 70% petroleum in ethyl acetate. Relevant fractions were combined to give S123 (244 mg, 100%).

Example 5

High-Throughput Screening Method

Assays for screening biologically-active small molecules have been developed. These assays are based on rebinding of FKBP12 protein to RyR.

A highly-efficient assay for high-throughput screening for small molecules is developed by immobilization of FKBP12.6 (GST-fusion protein) onto a 96-well plate coated with glutathione. PKA-phosphorylated ryanodine receptor type 2 (RyR2) is loaded onto the FKBP12.6-coated plate, and incubated with JTV-519 analogues at various concentrations (10-100 nM) for 30 min. Thereafter, the plate is washed to remove the unbound RyR2, and then incubated with anti-RyR2 antibody for 30 min. The plate is again washed to remove unbound anti-RyR2 antibody, and then treated with fluorescent-labeled secondary antibody. The plate is read by an automatic fluorescent plate reader for binding activity.

In an alternative assay, RyR2 is PKA-phosphorylated in the presence of 32P-ATP. Radioactive PKA-phosphorylated RyR2 is loaded onto an FKBP12.6-coated, 96-well plate, in the presence of JTV-519 analogues at various concentrations (10-100 nM) for 30 min. The plate is washed to remove the unbound radiolabeled RyR2, and then read by an automatic plate reader.

Example 6

Effect of ARM036 Compounds of hERG Currents

The effects of the compounds of the invention on hERG currents were studied using cultured human embryonic kidney 293 (HEK 293) cells which had been stably tranfected with hERG cDNA. HEK 293 cells do not express endogenous hERG. HEK293 cells were transfected with a plasmid containing the hERG cDNA and a neomycin resistance gene. Stable transfectants were selected by culturing the cells in the presence of G418. The selection pressure was maintained by continued culture in the presence of G418. Cells were cultures in Dulbecco's Modified Eagle Medium/Nutreint Mizture F-12 (D-MEM/F-12) supplemented with 10% fetal bovin serum, 199U/ml penicillin G sodium, 10 µg/mL streptomycin sulfate and 500 µg/mL G418. Cells for use in electrophysiology were cultured in 35 mm dishes.

Electrophysiological recordings (using the whole-cell patch clamp method) were performed at room temperature (18° C.-24° C.). Each cell acted as its own control. The effect Of ARM0036 was evaluated at two concentrations: 10 and 100 µM. Each concentration was tested in at least three cells (n≧3). 90 nM Cisapride (commercially available from TOCRIS Bioscience) was used as a positive control for hERG blockade. For recording, cells were transferred to the recording chamber and superfused with vehicle control solution. The patch pipette solution for whole cell recording contained 130 mM potassium aspartate, 5 mM MgCl2, 5 mM EGTA, 4 mM ATP and 10 mM HEPES. The pH was adjusted to 7.2 with KOH. The pipette solution was prepared in batches, aliquoted, and stored frozen. A fresh aliquot was thawed and used each day. Patch pipettes were made from glass capillary tubing using a P-97 micropipette puller (Sutter Instruments, Novato, Calif.). A commercial patch clamp amplifier was used for whole cell recordings. Before digitization, current records were low-pass filtered at one-fifth of the sampling frequency.

Onset and steady state block of hERG current was measured using a pulse pattern with fixed amplitudes (conditioning prepulse: +20 mV for 2 seconds; test pulse: −50 mV for 2 seconds) repeated at 10 second intervals, from a holding potential of −80 mV. Peak tail current was measured during the 2 second step to −50 mV. A steady state was maintained for at least 30 seconds before applying the test compound or the positive control. Peak tail current was monitored until a new steady state was achieved. Test compound concentrations were applied cumulatively in ascending order without washout between applications.

Data acquisition and analysis was performed using the suite of pCLAMP (Vre. 8.2) programs (Axon Instruments, Union City, Calif.). Steady state was defined by the limiting constant rate of change with time (linear time dependence). The steady state before and after application of the test or control compounds was used to calculate the percentage of current inhibited at each concentration. Concentration-response data were fit to an equation of the form:

% Block={1-1/[Test]/IC$_{50}$)N]}×100 where [Test] is the concentration of the test compound, IC$_{50}$ (inhibitory concentration 50) is the concentration of the test compound producing half-maximal inhibition, N is the Hill coefficient, and % Block is the percentage of hERG current inhibited at each concentration of the test compound. Nonlinear squares fits were solved with the Solver add-in for Excel 2000 (Microsoft, Redmond, Wash.). For some compounds it was not possible to determine the IC$_{50}$ because the highest concentration of the test compound used did not block the hERG channel by 50% or more.

Example 7

Effect of Various Compounds on hERG Currents

Multiple compounds of the invention were tested for their effects on hERG currents. The compounds tested were: ARM036-Na ARM047, ARM048, ARM050, ARM057, ARM064, ARM074, ARM075, ARM076, ARM077, ARM101, ARM102, ARM103, ARM104, ARM106, ARM107 and ARM26. By way of comparison, the effect of JTV-519 (referred to in the figures as ARM0XX) on hERG currents was also tested. Electrophysiological recordings were made using the PatchXpress 7000A (Molecular Devices) automatic parallel patch clamp system. Each compound was tested at 0.01, 0.1, 1 and 10 mM, with each concentration tested in 2 cells (n>2). The duration of exposure to each test concentration was 5 minutes. Other aspects of the experimental protocols were essentially similar to those described in Example 6. For some compounds it was not possible to determine the IC$_{50}$ because the highest concentration of the test compound used did not block the hERG channel by 50% or more.

All publications, references, patents and patent applications cited herein are incorporated by reference in their entirety to the same extent as if each individual application, patent or patent application was specifically and individually indicated to be incorporated by reference in its entirety.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A compound having the formula of I-i:

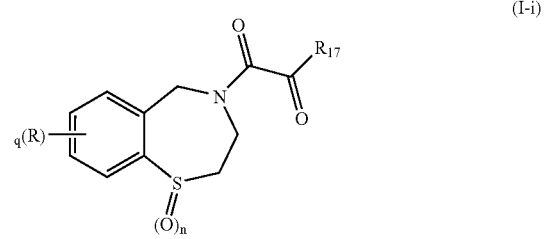

wherein n is 0, 1, or 2;
q is 0, 1, 2, 3, or 4;
each R is located at position 6, 7, 8 or 9 on the benzothiazepine ring;
each R is independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-) arylamino; wherein each acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino may be substituted or unsubstituted;

$R_{17}$ is selected from the group consisting of —$NR_{15}R_{16}$, —$NHNR_{15}R_{16}$, —NHOH, —$OR_{15}$, —$CH_2X$, alkenyl, aryl, cycloalkyl, cycloalkylalkyl, heterocyclyl, and heterocyclylalkyl; wherein each alkenyl, aryl, cycloalkyl, cycloalkylalkyl, heterocyclyl, and heterocyclylalkyl may be substituted or unsubstituted;

X is selected from the group consisting of halogen, —CN, —$CO_2R_{15}$, —C(=O)$NR_{15}R_{16}$, —$NR_{15}R_{16}$, —$OR_{15}$, —$SO_2R_7$, and —P(=O)$R_8R_9$;

$R_7$ is selected from the group consisting of H, —$OR_{15}$, —$NR_{15}R_{16}$, —$NHNR_{15}R_{16}$, —NHOH, —$CH_2X$, alkyl, alkenyl, alkynyl, aryl, cycloalkyl, cycloalkylalkyl, heterocyclyl, and heterocyclylalkyl; wherein each alkyl, alkenyl, alkynyl, aryl, cycloalkyl, cycloalkylalkyl, heterocyclyl, and heterocyclylalkyl may be substituted or unsubstituted;

$R_8$ and $R_9$ independently are selected from the group consisting of —OH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and $R_{15}$ and $R_{16}$ independently are selected from the group consisting of H, acyl, alkenyl, alkoxyl, OH, $NH_2$, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; optionally $R_{15}$ and $R_{16}$ together with the N to which they are bonded may form a heterocycle which may be substituted or unsubstituted;

or an enantiomer, diastereomer, tautomer, or a pharmaceutically acceptable salt thereof.

2. The compound of claim 1, wherein each R is independently selected from the group consisting of H, halogen, —OH, —OMe, —$NH_2$, —$NO_2$, —CN, —$CF_3$, —$OCF_3$, —$N_3$, —S(=O)$_2C_1$-$C_4$alkyl, —S(=O)$C_1$-$C_4$alkyl, —OS(=O)$_2CF_3$, Ph, —$NHCH_2$Ph, —C(=O)Me, morpholinyl and propenyl; and n is 0.

3. The compound of claim 2, wherein $R_{17}$ is —$NR_{15}R_{16}$, or —$OR_{15}$.

4. The compound of claim 2, wherein $R_{17}$ is —OH, —OMe, —$NEt_2$, —NHEt, —NHPh, —$NH_2$, or —$NHCH_2$pyridyl.

5. The compound of claim 1, wherein each R is independently selected from the group consisting of H, halogen, —OH, —OMe, —$NH_2$, —$NO_2$, —CN, —$CF_3$, —$OCF_3$, —$N_3$, —S(=O)$_2C_1$-$C_4$alkyl, —S(=O)$C_1$-$C_4$alkyl, —S—$C_1$-$C_4$alkyl, —OS(=O)$_2CF_3$, Ph, —$NHCH_2$Ph, —C(=O)Me, morpholinyl and propenyl; and n is 1 or 2.

6. The compound of claim 5, wherein $R_{17}$ is —$NR_{15}R_{16}$, or —$OR_{15}$.

7. The compound of claim 5, wherein $R_{17}$ is —OH, —OMe, —$NEt_2$, —NHEt, —NHPh, —$NH_2$, or —$NHCH_2$pyridyl.

8. The compound of claim 1, having the formula I-j:

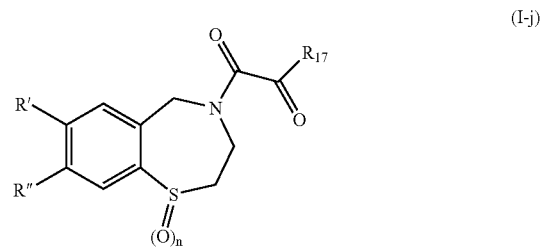

(I-j)

wherein R' and R" are independently selected from the group consisting of H, halogen, —OH, —$NH_2$, —$NO_2$, —CN, —$CF_3$, —$OCF_3$, —$N_3$, —$SO_3H$, —S(=O)$_2$alkyl, —S(=O)alkyl, —OS(=O)$_2CF_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted; and $R_{17}$ and n are as defined in claim 1;

or an enantiomer, diastereomer, tautomer or pharmaceutically acceptable salt thereof.

9. The compound of claim 1, wherein the compound is selected from the group consisting of:

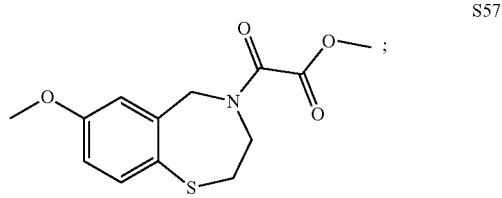

S57

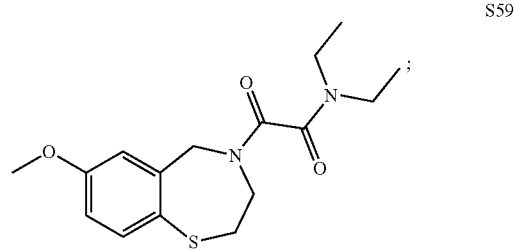

S59

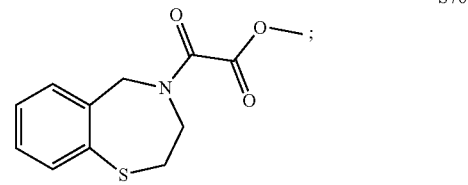

S76

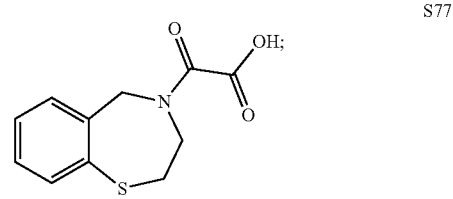

S77

-continued

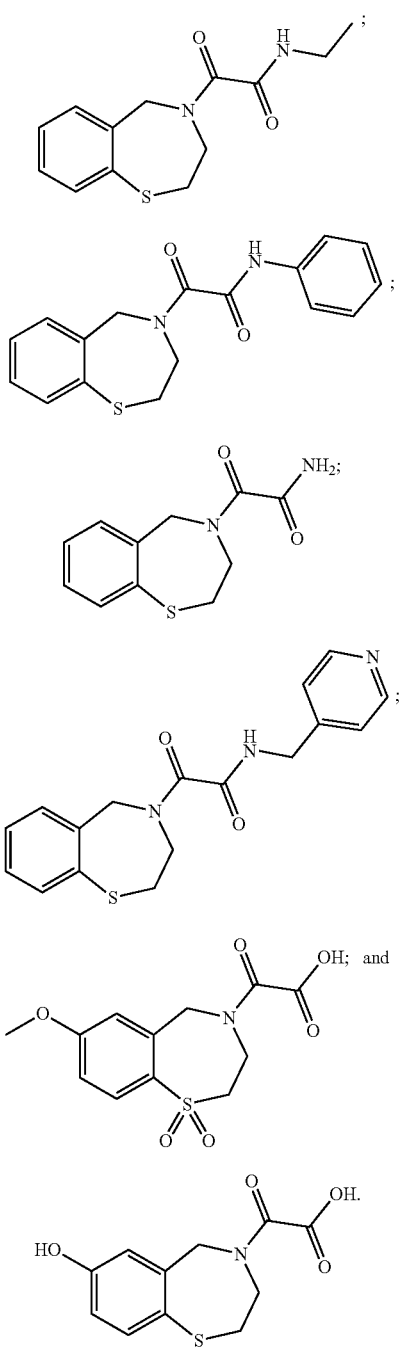

10. A pharmaceutical composition comprising a compound according to claim 1 and a pharmaceutically acceptable carrier.

11. The pharmaceutical composition of claim 10, wherein the composition is presented in a form selected from the group consisting of capsules, granules, powders, solutions, suspensions, and tablets.

12. The pharmaceutical composition of claim 10, wherein the composition is administered by a method selected from the group consisting of oral, sublingual, buccal, parenteral, intravenous, transdermal, inhalation, intranasal, vaginal, intramuscular, and rectal modes of administration.

13. A method of treating a disorder or a disease in a subject, comprising administering to the subject a therapeutically effective amount of a compound according to claim 1 to effectuate the treatment, wherein the disorder or disease is selected from the group consisting of cardiac disorders and diseases, skeletal muscular disorders and diseases, cognitive disorders and diseases, malignant hyperthermia, diabetes, and sudden infant death syndrome; wherein the cardiac disorders and diseases are selected from the group consisting of irregular heartbeat disorders and diseases; exercise-induced irregular heartbeat disorders and diseases; congestive heart failure; chronic obstructive pulmonary disease; and high blood pressure; wherein the skeletal muscular disorders and diseases are selected from the group consisting of skeletal muscle fatigue, exercise-induced skeletal muscle fatigue, muscular dystrophy, bladder disorders, and incontinence; and wherein the cognitive disorders and diseases are selected from the group consisting of Alzheimer's Disease, forms of memory loss, and age-dependent memory loss.

14. The method of claim 13, wherein the compound is administered to the subject to treat cardiac disorders and diseases selected from the group consisting of irregular heartbeat disorders and diseases; exercise-induced irregular heartbeat disorders and diseases; congestive heart failure; chronic obstructive pulmonary disease; and high blood pressure.

15. The method of claim 14, wherein the irregular heartbeat disorders and diseases and exercise-induced irregular heartbeat disorders and diseases are selected from the group consisting of atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof.

16. The method of claim 13, wherein the compound is administered to the subject to treat skeletal muscular disorders and diseases selected from the group consisting of skeletal muscle fatigue, exercise-induced skeletal muscle fatigue, muscular dystrophy, bladder disorders, and incontinence.

17. The method of claim 13 wherein the compound is administered to the subject to treat cognitive disorders and diseases selected from the group consisting of Alzheimer's Disease, forms of memory loss, and age-dependent memory loss.

18. The method of claim 13, wherein the compound modulates calcium-ion channels in cells of the subject.

19. The method of claim 13, wherein the subject is an in vitro or in vivo system.

20. The method of claim 13, wherein the subject is a human.

21. A method of reducing the risk of sudden cardiac death in a subject who is considered to be subject to such risk, comprising administering to the subject a therapeutically effective amount of a pharmaceutically acceptable salt of S36, wherein S36 is represented by the structure:

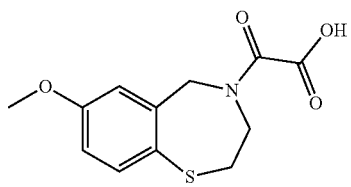

to thus reduce the subject's risk of sudden cardiac death.

22. The method of claim 21, wherein the risk of sudden cardiac death is an exercise-induced risk.

23. The method of claim 21, wherein the compound is a sodium salt of S36, which is represented by the structure:

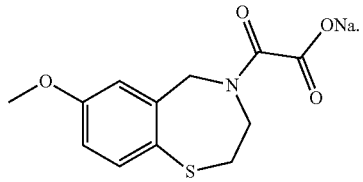

24. The method of claim 21, wherein the compound modulates calcium-ion channels in cells of the subject.

25. A pharmaceutically acceptable salt of the compound S36, wherein S36 is represented by the structure

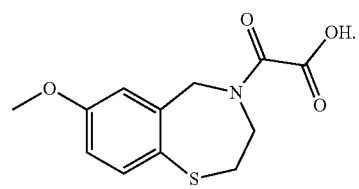

S36

26. The compound of claim 25, wherein the salt is a sodium salt, and the compound is represented by the structure:

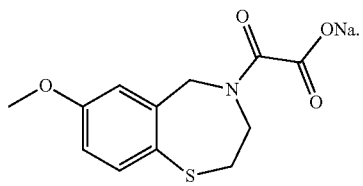

27. A pharmaceutical composition comprising a compound according to claim 25, and a pharmaceutically acceptable carrier.

28. The pharmaceutical composition of claim 27, wherein the composition is presented in a form selected from the group consisting of capsules, granules, powders, solutions, suspensions, and tablets.

29. The pharmaceutical composition of claim 27, wherein the composition is administered by a method selected from the group consisting of oral, sublingual, buccal, parenteral, intravenous, transdermal, inhalation, intranasal, vaginal, intramuscular, and rectal modes of administration.

30. A method of treating a disorder or a disease in a subject, comprising administering to the subject a therapeutically effective amount of the compound S36

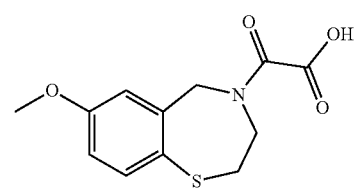

S36 or a pharmaceutically acceptable salt, to effectuate the treatment, wherein the disorder or disease is selected from the group consisting of cardiac disorders and diseases, skeletal muscular disorders and diseases, cognitive disorders and diseases, malignant hyperthermia, diabetes, and sudden infant death syndrome; wherein the cardiac disorders and diseases are selected from the group consisting of irregular heartbeat disorders and diseases; exercise-induced irregular heartbeat disorders and diseases; congestive heart failure; chronic obstructive pulmonary disease; and high blood pressure; wherein the skeletal muscular disorders and diseases are selected from the group consisting of skeletal muscle fatigue, exercise-induced skeletal muscle fatigue, muscular dystrophy, bladder disorders, and incontinence; and wherein the cognitive disorders and diseases are selected from the group consisting of Alzheimer's Disease, forms of memory loss, and age-dependent memory loss.

31. The method of claim 30, wherein the compound is administered to the subject to treat cardiac disorders and diseases selected from the group consisting of irregular heartbeat disorders and diseases; exercise-induced irregular heartbeat disorders and diseases; congestive heart failure; chronic obstructive pulmonary disease; and high blood pressure.

32. The method of claim 30, wherein the irregular heartbeat disorders and diseases and exercise-induced irregular heartbeat disorders and diseases are selected from the group consisting of atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof.

33. The method of claim 30, wherein the compound is administered to the subject to treat skeletal muscular disorders and diseases selected from the group consisting of skeletal muscle fatigue, exercise-induced skeletal muscle fatigue, muscular dystrophy, bladder disorders, and incontinence.

34. The method of claim 30, wherein the compound is administered to the subject to treat cognitive disorders and diseases selected from the group consisting of Alzheimer's Disease, forms of memory loss, and age-dependent memory loss.

35. The method of claim 30, wherein the compound modulates calcium-ion channels in cells of the subject.

36. The method of claim 30, wherein the subject is an in vitro or in vivo system.

37. The method of claim 30, wherein the subject is a human.

38. The method of claim 30, wherein the compound is a sodium salt of S36, which is represented by the structure:

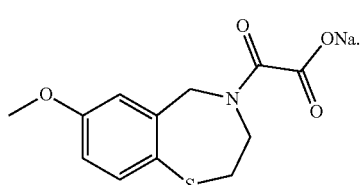

* * * * *

UNITED STATES PATENT AND TRADEMARK OFFICE
CERTIFICATE OF CORRECTION

PATENT NO. : 7,879,840 B2
APPLICATION NO. : 11/506285
DATED : February 1, 2011
INVENTOR(S) : Marks et al.

It is certified that error appears in the above-identified patent and that said Letters Patent is hereby corrected as shown below:

Title Page:
Item (56) References Cited, U.S. Patent Documents:
  After "6,495,544 B2  12/2002, change "Moormann et al." to -- Hansen, Jr. et al. --.
  After "6,649,366 B2  11/2003, change "Tavares et al." to -- Chubinskaya et al. --.
Item (56) References Cited, Other Publications:
  International Preliminary Report on Patentability from International Application
     PCT/US2005/045914: after "mailed Jun. 28", change "20073" to -- 2007 --.
  Mackenzie et all reference: change "all" to -- al., --.
  Zahradka et al. reference: change "MT1 Mmp," to -- MT1 MMP --.
  International Search Report an Written Opinion mailed Aug. 14, 2008, for International
     Application no. PCT/US07/09289 filed Apr. 13, 2007: change "an" to -- and --.
  Supplementary European Search Report for European Patent Application No. 04756121.2: add
     -- mailed Dec. 21, 2007 --.
  Bangur et al. reference: change "IIb" to -- IIB --.
  Brillantes et al. reference (second occurrence): change "cardiab" to -- cardiac --.
  Dietz et al. reference: change "Glydogen" to -- Glycogen --.
  Doi et al. reference: change "Develepment" to -- Development --.
  Drexler et al. reference: change "Coverting" to -- Converting --.
  Gretarsdottir et al. reference: change "encodina" to -- encoding --.
  Haut, Donahue, et al. reference: change "Osteoblistic" to -- Osteoblastic --.
  Jiang, D. et al. reference: change "Asssociated" to -- Associated --.
  Katz et al. reference: change "Excercise" to -- Exercise --.
  Kukin, M.L. et al. reference: change "Excercise" to -- Exercise --.
  Marks et al. reference (second occurrence): change "Rvanodine" to -- Ryanodine --; and change
     "Catecholaminegric" to -- Catecholaminergic --.
  Marx, S.O. et al. reference (third occurrence): change "(Rvanodine" to -- Ryanodine --.
  McPhie, et al. reference: change "is is" to -- is it --.
  Merit HF Study Group reference: change "Merit HF" to -- MERIT-HF --; and change "Chrohic" to
     -- Chronic --.

Signed and Sealed this
Eleventh Day of October, 2011

David J. Kappos
*Director of the United States Patent and Trademark Office*

Title Page (continued):
 Minotti et al. reference: change "Excercise" to -- Exercise --.
 Mongillo, et al. reference: change "revelas" to -- reveals --.
 Packer, et al. reference: change "Promise" to -- PROMISE --.
 Perry, et al. reference: change "betaarrestins" to -- beta-arrestins --.
 Reiner, G. et al. reference: change "Regulation' And" to -- Regulation And --.
 Ruehr, et al. reference: after "kinase" change "a" to -- A --; and after "muscle" change "a" to
  -- A --.
 Sen, L.Y. et al. reference: change "Isloated" to -- Isolated --.
 Sorensen et al. reference: change "Excercised" to -- Exercised --.
 Suissa, et al. reference: change "Grit." to -- Crit. --.
 Szabo et al. reference (second occurrence): change "derviatives" to -- derivatives --.
 Tasken, et al. reference: change "constitue" to -- constitute --.
 Tester, et al. reference (second occurrence): change "authopsy" to -- autopsy --.
 Wellen et al. reference: change "Wellen" to -- Wellens --.
 Yamamoto, et al. reference (second occurrence): change "peptice" to -- peptide --.
 Yamamoto Nino, M. et al. reference: change "Yamamoto-Nino" to -- Yamamoto Hino --.
 Lehnart et al. reference: change "caridac" to -- cardiac --.
 Wehrens et al. reference (first occurrence): change "Pka" to -- PKA --.
 The Cardiac Arrhythmia Suppression Trial (CAST) reference: change "Encload" to -- England --.
 Harrison's Principles of Internal Midicinae reference: change "Midicinae" to -- Medicine --.
 Non-Final Office Action (Restriction Requirement) mailed May 13, 2008 for U.S. Appl. No.
  11/212,143: after "filed Aug." change "23" to -- 25 --.

Column 19:
Line 29, change "and;" to -- and --.

Column 85:
Line 22, change "result" to -- results of --.
Line 47, after "RyR2-P2328S" insert -- . --.

Column 133:
Line 30, change "Of" to -- of --.

Line 32, change "(n≧3)" to -- (n≥3) --.

Line 37, change "MgCl2" to -- $MgCl_2$ --.

Column 135:
Line 48 (claim 2, line 4), after "—S(=O)$C_1$-$C_4$alkyl," insert -- —S—$C_1$-$C_4$alkyl, --.